US009676802B2

(12) United States Patent
Qiu et al.

(10) Patent No.: US 9,676,802 B2
(45) Date of Patent: Jun. 13, 2017

(54) HEPATITIS C VIRUS INHIBITORS

(71) Applicant: ENANTA PHARMACEUTICALS, INC., Watertown, MA (US)

(72) Inventors: Yao-Ling Qiu, Andover, MA (US); Hui Cao, Belmont, MA (US); Xiaowen Peng, Cambridge, MA (US); Zhigang Chen, Acton, MA (US); Yat Sun Or, Watertown, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 14/254,265

(22) Filed: Apr. 16, 2014

(65) Prior Publication Data
US 2014/0308243 A1   Oct. 16, 2014

Related U.S. Application Data

(63) Continuation of application No. PCT/US2012/060556, filed on Oct. 17, 2012.

(60) Provisional application No. 61/547,880, filed on Oct. 17, 2011.

(51) Int. Cl.
| | | |
|---|---|---|
| A01N 43/56 | (2006.01) | |
| A61K 31/415 | (2006.01) | |
| C07F 9/6561 | (2006.01) | |
| A61K 31/426 | (2006.01) | |
| C07D 498/08 | (2006.01) | |
| C07D 498/18 | (2006.01) | |
| C07D 519/00 | (2006.01) | |
| A61K 38/21 | (2006.01) | |
| A61K 31/13 | (2006.01) | |
| A61K 31/7056 | (2006.01) | |
| A61K 38/55 | (2006.01) | |
| A61K 31/4188 | (2006.01) | |
| A61K 31/4196 | (2006.01) | |
| A61K 31/422 | (2006.01) | |
| A61K 31/4245 | (2006.01) | |
| A61K 31/427 | (2006.01) | |
| A61K 31/428 | (2006.01) | |
| A61K 31/4439 | (2006.01) | |
| A61K 31/454 | (2006.01) | |
| A61K 31/4709 | (2006.01) | |
| A61K 31/496 | (2006.01) | |
| A61K 31/506 | (2006.01) | |
| A61K 31/5377 | (2006.01) | |
| A61K 31/675 | (2006.01) | |
| A61K 45/06 | (2006.01) | |

(52) U.S. Cl.
CPC .......... *C07F 9/65616* (2013.01); *A61K 31/13* (2013.01); *A61K 31/4188* (2013.01); *A61K 31/4196* (2013.01); *A61K 31/422* (2013.01); *A61K 31/426* (2013.01); *A61K 31/427* (2013.01); *A61K 31/428* (2013.01); *A61K 31/4245* (2013.01); *A61K 31/4439* (2013.01); *A61K 31/454* (2013.01); *A61K 31/4709* (2013.01); *A61K 31/496* (2013.01); *A61K 31/506* (2013.01); *A61K 31/5377* (2013.01); *A61K 31/675* (2013.01); *A61K 31/7056* (2013.01); *A61K 38/21* (2013.01); *A61K 38/55* (2013.01); *A61K 45/06* (2013.01); *C07D 498/08* (2013.01); *C07D 498/18* (2013.01); *C07D 519/00* (2013.01)

(58) Field of Classification Search
CPC .... A61K 31/7056; A61K 38/00; A61K 39/12; A61K 31/426; A61K 31/415; A61K 31/433
See application file for complete search history.

(56) References Cited

U.S. PATENT DOCUMENTS

| 2011/0137633 A1 | 6/2011 | Hutchins et al. |
| 2011/0189129 A1 | 8/2011 | Qiu et al. |
| 2011/0250172 A1 | 10/2011 | Qiu et al. |

*Primary Examiner* — Hasan Ahmed
*Assistant Examiner* — Kaipeen Yang
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, esters, or prodrugs thereof:

$$Q\text{-}G\text{-}A\text{-}L\text{-}B\text{---}Z\text{---}W \qquad (I),$$

which inhibit RNA-containing virus, particularly the hepatitis C virus (HCV). Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

31 Claims, No Drawings

HEPATITIS C VIRUS INHIBITORS

RELATED APPLICATIONS

This application is a continuation of International Application No. PCT/US2012/060556, which designated the United States and was filed on Oct. 17, 2012, published in English, which claims the benefit of U.S. Provisional Application No. 61/547,880, filed on Oct. 17, 2011. The entire teachings of the above applications are incorporated herein by reference.

TECHNICAL FIELD

The present invention relates to novel antiviral agents. More specifically, the present invention relates to compounds which can inhibit the function of the NS5A protein encoded by Hepatitis C virus (HCV), compositions comprising such compounds, methods for inhibiting HCV viral replication, methods for treating or preventing HCV infection, and processes for making the compounds.

BACKGROUND OF THE INVENTION

Infection with HCV is a major cause of human liver disease throughout the world. In the U.S., an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the U.S. in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of responders, 50-70% relapse within 6 months of cessation of treatment. Recently, with the introduction of pegylated interferon (Peg-IFN), both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). There are three structural proteins, C, E1 and E2. The P7 protein is of unknown function and is comprised of a highly variable sequence. There are several nonstructural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. The NS5B protein (591 amino acids, 65 kDa) of HCV (Behrens, S. E. et at (1996) *EMBO J.* 151 2-22) encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) *Journal of Virology,* 74(4): 2046-2051). Thus, inhibition of NS5B RdRp activity (inhibition of RNA replication) is predicted to be useful to treat HCV infection.

Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et at (1996) J. Virology 70:3363-3371; Tanaka, T. et at (1995) Biochem Biophys. Res. Commun. 215744-749; Tanaka, T. et at (1996) J. Virology 70:3307-3312; Yamada, N. et at (1996) Virology 223:255-261). The 3' NTR is predicted to form a stable secondary structure which is essential for HCV growth in chimps and is believed to function in the initiation and regulation of viral RNA replication.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1; and in Rice, C. M. *Nature* 2005, 435, 374.

Based on the foregoing, there exists a significant need to identify compounds with the ability to inhibit HCV.

SUMMARY OF THE INVENTION

The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are also useful as antiviral agents.

In its principal aspect, the present invention provides a compound of Formula (I):

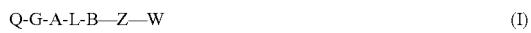

Q-G-A-L-B—Z—W    (I)

or a pharmaceutically acceptable salt thereof, wherein:

A and B are each independently absent or a monocyclic or polycyclic group independently selected from the group consisting of aryl, heteroaryl, heterocyclic, $C_3$-$C_8$ cycloalkyl and $C_3$-$C_8$ cycloalkenyl, each optionally substituted; preferably, A and B are each independently optionally substituted aryl or optionally substituted heteroaryl;

L is absent or an aliphatic group; preferably, L is selected from the group consisting of O, —NH—, —C(O)—, —C(O)NH—, $C_1$-$C_4$ alkyl, $C_2$-$C_4$ alkenyl, $C_2$-$C_4$ alkynyl, —($C_1$-$C_4$ alkyl)-N(R)—($C_1$-$C_4$ alkyl)- and heterocyclic, each optionally substituted;

wherein at least one of A, B and L is present;

Z is —C(O)NH—, an optionally substituted 5-membered heteroaryl containing one or more nitrogen atoms, or an optionally substituted 5-membered heteroaryl fused to a mono- or bicyclic ring, wherein the mono- or bicyclic ring is aromatic or non-aromatic, wherein the mono- or bicyclic ring is attached to one of groups A, L and B and wherein the 5-membered heteroaryl contains one or more nitrogen atoms; preferably, Z is an optionally substituted imidazolyl, an optionally substituted benzimidazolyl or an optionally substituted imidazopyridyl;

G is absent, —C(O)NH—, an optionally substituted 5-membered heteroaryl containing one or more nitrogen atoms, or an optionally substituted 5-membered heteroaryl fused to a mono- or bicyclic ring, wherein the mono- or bicyclic ring is aromatic or non-aromatic, wherein the mono- or bicyclic ring is attached to one of groups A, L and B and wherein the 5-membered heteroaryl contains one or more nitrogen atoms; preferably, G is an optionally substituted imidazolyl, an optionally substituted benzimidazolyl or an optionally substituted imidazopyridyl;

W is

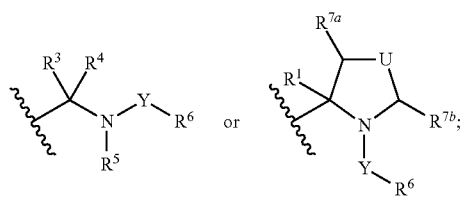

Q is hydrogen,

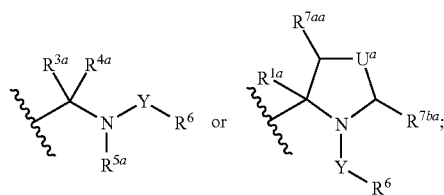

Y at each occurrence is independently C(O) or S(O)$_2$; preferably, Y is C(O);

$R^1$ and $R^{1a}$ at each occurrence are independently hydrogen, hydroxy, O($C_1$-$C_4$ alkyl) or optionally substituted $C_1$-$C_4$ alkyl;

$R^3$, $R^{3a}$, $R^4$ and $R^{4a}$ are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; preferably, hydrogen or optionally substituted $C_1$-$C_4$ alkyl; alternatively, $R^3$ and $R^4$ or $R^{3a}$ and $R^{4a}$ can be taken together with the carbon atom to which they are attached to form optionally substituted $C_3$-$C_8$ cycloalkyl or optionally substituted heterocyclic;

$R^5$ and $R^{5a}$ are each independently hydrogen, optionally substituted $C_1$-$C_8$ alkyl, or optionally substituted $C_3$-$C_8$ cycloalkyl; preferably, $R^5$ and $R^{5a}$ are hydrogen or optionally substituted $C_1$-$C_4$ alkyl;

wherein one of $R^3$, $R^4$ and $R^5$ is connected to group Z via a linker of -$L^1$-$L^2$-$L^3$- or alternatively one of $R^3$, $R^4$ and $R^5$ is connected to group B via a linker of -$L^1$-$L^2$-$L^3$-, wherein group B is present;

alternatively, wherein one of $R^{3a}$, $R^{4a}$ and $R^{5a}$ is connected to group G via a linker of -$L^1$-$L^2$-$L^3$, wherein group G is present; or alternatively, wherein one of $R^{3a}$, $R^{4a}$ and $R^{5a}$ is connected to group A via a linker of -$L^1$-$L^2$-$L^3$-, wherein group A is present;

Yet alternatively, wherein one of $R^3$, $R^4$ and $R^5$ is connected to group Z or group B via a linker of -$L^1$-$L^2$-$L^3$- and one of $R^{3a}$, $R^{4a}$ and $R^{5a}$ is connected to group G or group A via a linker of -$L^1$-$L^2$-$L^3$;

$L^1$ and $L^3$ at each occurrence are each independently an aliphatic group, or one of $L^1$ and $L^3$ is absent and the other of $L^1$ and $L^3$ is an aliphatic group; preferably, $L^1$ and $L^3$ at each occurrence are independently a linear aliphatic group, or one of $L^1$ and $L^3$ is absent and the other of $L^1$ and $L^3$ is a linear aliphatic group;

$L^2$ at each occurrence is independently absent, or selected from the group consisting of aryl, heteroaryl, heterocyclic, $C_3$-$C_8$ cycloalkyl, and $C_3$-$C_8$ cycloalkenyl, each optionally substituted;

wherein -$L^1$-$L^2$-$L^3$- together form a linker; preferably, -$L^1$-$L^2$-$L^3$- together form a linker of from 6 to 16 bond lengths;

$R^6$ at each occurrence is independently selected from the group consisting of $O(C_1-C_8$ alkyl), amino, $C_1-C_8$ alkyl, $C_2-C_8$ alkenyl, $C_2-C_8$ alkynyl, $C_3-C_8$ cycloalkyl, $C_3-C_8$ cycloalkenyl, heterocyclic, aryl, and heteroaryl, each optionally substituted; preferably, $R^6$ at each occurrence is independently optionally substituted $C_1-C_8$ alkyl; more preferably, $R^6$ at each occurrence is independently $C_1-C_8$ alkyl optionally substituted with amino, hydroxy, protected amino or $O(C_1-C_4$ alkyl);

U and $U^a$ are each independently absent or selected from O, S, S(O), $SO_2$, NC(O)—$(C_1-C_4$ alkyl), C(O), protected carbonyl, $OCH_2$, $OCH_2CH_2$, $SCH_2$, $SCH_2CH_2$, $C(R^7)_2$, $Si(R^7)_2$, $C(R^7)_2C(R^7)_2$, and $C=C(R^2)_2$; preferably, U and $U^a$ are $C(R^7)_2$, $Si(R^7)_2$, C=N—OMe, or $C=CH_2$;

$R^2$ at each occurrence is independently hydrogen, halogen, optionally substituted $C_1-C_4$ alkyl, optionally substituted aryl, or optionally substituted heteroaryl;

$R^7$ at each occurrence is independently selected from the group consisting of hydrogen, halogen, cyano, hydroxy, optionally substituted $O(C_1-C_4$ alkyl), $S(C_1-C_4$ alkyl), amino optionally substituted with one or two $C_1-C_4$ alkyl, optionally substituted aryl, optionally substituted heteroaryl, optionally substituted $C_1-C_4$ alkyl, and optionally substituted $C_3-C_8$ cycloalkyl; preferably, $R^7$ is hydrogen, halogen, methyl, or cyclopropyl;

alternatively two geminal $R^7$ groups are taken together with the carbon atom to which they are attached to form a spiro, optionally substituted 3- to 7-membered cyclic group selected from the group consisting of $C_3-C_7$ cycloalkyl, $C_3-C_7$ cycloalkenyl or 3- to 7-membered heterocyclic; preferably, two geminal $R^7$ groups are taken together with the carbon atom to which they are attached to form a spiro, optionally substituted cyclopropyl;

$R^{7a}$, $R^{7aa}$, $R^{7b}$, and $R^{7ba}$ at each occurrence are each independently selected from the group consisting of hydrogen, optionally substituted aryl, optionally substituted $C_1-C_4$ alkyl, and optionally substituted $C_3-C_8$ cycloalkyl; preferably, $R^{7a}$, $R^{7aa}$, $R^{7b}$, and $R^{7ba}$ at each occurrence are each independently hydrogen, cyclopropyl, or methyl;

alternatively, $CHR^{7a}$—U, $CHR^{7b}$—U, $CHR^{7aa}$—$U^a$ or $CHR^{7ba}$—$U^a$ can be taken together to form a group selected from CH=CH, fused and optionally substituted $C_3-C_8$ cycloalkyl, fused and optionally substituted aryl, or fused and optionally substituted heterocyclic; preferably, $CHR^{7a}$—U or $CHR^{7b}$—U are taken together to form a fused and optionally substituted cyclopropyl;

Yet alternatively, U, $R^{7a}$, and $R^{7b}$ are taken together with the carbon atoms to which they are attached to form a bridged, optionally substituted 4- to 7-membered cyclic group selected from the group consisting of $C_4-C_7$ cycloalkyl, $C_4-C_7$ cycloalkenyl and 4- to 7-membered heterocyclic; preferably, U, $R^{7a}$, and $R^{7b}$ are taken together with the carbon atoms to which they are attached to form a bridged cyclopentyl; and wherein one of $R^{7a}$, $R^{7b}$ and U is connected to group Z via a linker of -$L^1$-$L^2$-$L^3$-; or alternatively wherein one of $R^{7a}$, $R^{7b}$ and U is connected to group B via a linker of -$L^1$-$L^2$-$L^3$; wherein group B is present;

alternatively, wherein one of $R^{7aa}$, $R^{7ba}$, and $U^a$ is connected to group G via a linker of -$L^1$-$L^2$-$L^3$- wherein group G is present; or alternatively, one of $R^{7aa}$, $R^{7ba}$, and $U^a$ is connected to group A via a linker of -$L^1$-$L^2$-$L^3$- wherein group A is present;

Yet alternatively, wherein one of $R^{7a}$, $R^{7b}$ and U is connected to group Z or group B via a linker of -$L^1$-$L^2$-$L^3$- and one of $R^{7aa}$, $R^{7ba}$, and $U^a$ is connected to group G or group A via a linker of -$L^1$-$L^2$-$L^3$-;

alternatively, U is connected to group $R^6$ via a linker of -$L^1$-$L^2$-$L^3$-; and Yet alternatively, $U^a$ is connected to group $R^6$ via a linker of -$L^1$-$L^2$-$L^3$.

Each preferred group stated above can be taken in combination with one, any or all other preferred groups.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

In yet another aspect, the present invention provides a method of inhibiting the replication of a RNA-containing virus comprising contacting said virus with a therapeutically effective amount of a compound or a combination of compounds of the present invention, or a pharmaceutically acceptable salt thereof. Particularly, this invention is directed to methods of inhibiting the replication of HCV.

In still another aspect, the present invention provides a method of treating or preventing infection caused by an RNA-containing virus comprising administering to a patient in need of such treatment a therapeutically effective amount of a compound or combination of compounds of the present invention, or a pharmaceutically acceptable salt thereof. Particularly, this invention is directed to methods of treating or preventing infection caused by HCV.

Yet another aspect of the present invention provides the use of a compound or combination of compounds of the present invention, or a therapeutically acceptable salt thereof, as defined hereinafter, in the preparation of a medicament for the treatment or prevention of infection caused by RNA-containing virus, specifically HCV.

DETAILED DESCRIPTION OF THE INVENTION

The present invention relates to compounds of Formula (I) as illustrated above, or a pharmaceutically acceptable salt thereof The compounds of the invention have utility in inhibiting the replication of RNA-containing virus, including, for example, HCV. Other compounds useful for inhibiting the replication of RNA-containing viruses and/or for the treatment or prophylaxis of HCV infection have been described in copending U.S. application Ser. No. 12/702,673 filed Feb. 9, 2010 entitled "Linked Dibenzimidazole Antivirals"; U.S. application Ser. No. 12/702,692 filed Feb. 9, 2010 entitled "Linked Dibenzimidazole Derivatives"; U.S. application Ser. No. 12/702,802 filed Feb. 9, 2010 entitled "Linked Dibenzimidazole Derivatives"; U.S. application Ser. No. 12/707,190 filed Feb. 17, 2010 entitled "Linked Diimidazole Antivirals"; U.S. application Ser. No. 12/707,200 filed Feb. 17, 2010 entitled "Linked Diimidazole Derivatives"; U.S. application Ser. No. 12/707,210 filed Feb. 17, 2010 entitled "Hepatitis C Virus Inhibitors"; U.S. application Ser. No. 12/714,583 filed Mar. 1, 2010 entitled "Novel Benzimidazole Derivatives"; U.S. application Ser. No. 12/714,576 filed Mar. 1, 2010 entitled "Hepatitis C Virus Inhibitors"; U.S. application Ser. No. 12/816,148 filed Jun. 15, 2010 entitled "Hepatitis C Virus Inhibitors"; U.S. application Ser. No. 12/816,171 filed Jun. 15, 2010 entitled "Hepatitis C Virus Inhibitors"; U.S. application Ser. No. 12/879,025 filed Sep. 10, 2010 entitled "Hepatitis C Virus Inhibitors"; U.S. application Ser. No. 12/879,026 filed Sep. 10, 2010 entitled "Hepatitis C Virus Inhibitors"; U.S. application Ser. No. 12/879,027 filed Sep. 10, 2010 entitled "Hepatitis C Virus Inhibitors"; U.S. application Ser. No. 12/879,028 filed Sep. 10, 2010 entitled "Hepatitis C Virus Inhibitors"; U.S. application Ser. No. 12/879,029 filed Sep. 10, 2010 entitled "Hepatitis C Virus Inhibitors"; U.S. application Ser. No. 12/879,031 filed Sep. 10, 2010 entitled "Hepatitis C Virus Inhibitors"; U.S. application Ser. No. 12/851,350 filed Aug. 5, 2010 entitled "Combination Pharmaceutical Agents As Inhibitors Of HCV Replication"; U.S. application Ser. No. 12/967,486 filed Dec. 14, 2010 entitled "Hepatitis C Virus Inhibitors"; U.S. application Ser. No. 13/013,212 filed Jan. 25, 2011 entitled "Hepatitis C Virus Inhibitors"; U.S. application Ser. No. 13/082,621 filed Apr. 8, 2011 entitled "Hepatitis C Virus Inhibitors" U.S. application Ser. No. 13/152,377 filed Jun. 3, 2011 entitled "Hepatitis C Virus Inhibitors;" and U.S. application Ser. No. 13/207,910 filed Aug. 11, 2011 entitled "Hepatitis C Virus Inhibitors".

As discussed above, a general strategy for the development of antiviral agents is to inactivate virally encoded proteins, including NS5A, that are essential for the replication of the virus. The relevant patent disclosures describing the synthesis of HCV NS5A inhibitors are: US 2009/0202478; US 2009/0202483; US 2010/0233120; US 2010/0260708; WO 2004/014852; WO 2006/079833; WO 2006/133326; WO 2007/031791; WO 2007/070556; WO 2007/070600; WO 2007/082554; WO 2008/021927; WO 2008/021928; WO 2008/021936; WO 2008/048589; WO 2008/064218; WO 2008/070447; WO 2008/144380; WO 2008/154601; WO 2009/020825; WO 2009/020828; WO 2009/034390; WO 2009/102318; WO 2009/102325; WO 2009/102694; WO 2010/017401; WO 2010/039793; WO 2010/065668; WO 2010/065674; WO 2010/065681; WO 2010/091413; WO 2010/096777; WO 2010/096462; WO 2010/096302; WO2010/099527; WO 2010/111483; WO 2010/111534; WO 2010/117635; WO 2010/111673; WO 2010/117704; WO 2010/132538; WO 2010/132601; WO 2010/138488; WO 2010/138368; WO 2010/138790; WO 2010/138791; WO 2010/148006; US 2010/0215618; WO 2011/004276; WO 2011/009084; WO 2011/015657; WO 2011/015658; WO 2011/026920; WO 2011/028596; WO 2011/031904; WO 2011/031934; WO 2011/046811; WO 2011/050146 and WO 2011/054834, WO2011/05988, WO2011/060000, WO2011/066241, WO2011/1075439, WO2011/075615, WO2011/079327, WO2011/082077, WO2011/087740, WO2011/091446, WO2011/112429, WO2011/119853, WO2011/119858, WO2011/119860, WO2011/119870, WO2011/127350, WO2011/149856, WO2011/150243, WO2011/153396, WO2011/154871, WO2011/156543, WO2011/156578, WO2011/156757A, WO2012/003642, WO2012/009394, WO2012/013643, WO2012/018325, WO2012/018534, WO2012/020036, WO2012/021591, WO2012/021704, WO2012/027712, WO2012/039717, WO2012/040389, WO2012/040923, WO2012/040924, WO2012/041014, WO2012/041227, WO2012/048421, WO2012/050848, WO2012/050850, WO2012050918, WO2012/051361, WO2012/061552, WO2012/068234, WO2012/074437, WO2012/083043, WO2012/083048, WO2012/083053, WO2012/083058, WO2012/083059, WO2012/083061, WO2012/083164, WO2012/083170, WO2012/087976, WO2012/109080, WO2012/116257, WO2012/122716, WO2012/123298, and WO2012/125926.

It is to be understood that when one of $R^3$, $R^4$ and $R^5$ is connected to group Z via a linker of $-L^1-L^2-L^3-$, or when one of $R^3$, $R^4$ and $R^5$ is connected to group B via a linker of $-L^1-L^2-L^3-$, $R^3$, $R^4$ or $R^5$ is not hydrogen. In certain embodiments, when one of $R^3$, $R^4$ and $R^5$ is connected to one of groups Z and B via a linker of $-L^1-L^2-L^3-$, the linker is attached to a ring atom of one of groups Z and B.

Similarly, it is to be understood that when one of $R^{3a}$, $R^{4a}$ and $R^{5a}$ is connected to group G via a linker of $-L^1-L^2-L^3-$ or when one of $R^{3a}$, $R^{4a}$ and $R^{5a}$ is connected to group A via a linker of $-L^1-L^2-L^3-$, $R^{3a}$, $R^{4a}$ or $R^{5a}$ is not hydrogen. In certain embodiments, when one of $R^{3a}$, $R^{4a}$ and $R^{5a}$ is connected to one of groups G and A via a linker of $-L^1-L^2-L^3-$, the linker is attached to a ring atom of one of groups G and A.

It is also to be understood that when one of $R^{7a}$, $R^{7b}R^{7aa}$, or $R^{7ba}$ is connected to groups Z, B, G or A, $R^{7a}$, $R^{7b}R^{7aa}$, or $R^{7ba}$ is not hydrogen. In certain aspects, when one of $R^{7a}$, $R^{7b}$ or U is connected to group Z or group B via a linker of $-L^1-L^2-L^3-$, the linker is connected to a ring atom of one of groups Z and B. In certain additional aspects, when one of groups $R^{7aa}$, $R^{7ba}$ and $U^a$ is connected to group G or group A via a linker of $-L^1-L^2-L^3$, the linker is connected to a ring atom of one of groups G and A. In certain additional aspects, when U is connected to one of groups Z and B, U is $C(R^7)$ and the ring carbon of U is connected to the linker of $-L^1-L^2-L^3$. In further embodiments, when $U^a$ is connected to one of groups G and A, $U^a$ is $C(R^7)$ and the ring carbon of $U^a$ is connected to the linker of $-L^1-L^2-L^3$.

In one embodiment, the present invention relates to compounds represented by Formula (Ia), (Ib), (Ic), or (Id) and pharmaceutically acceptable salts thereof:

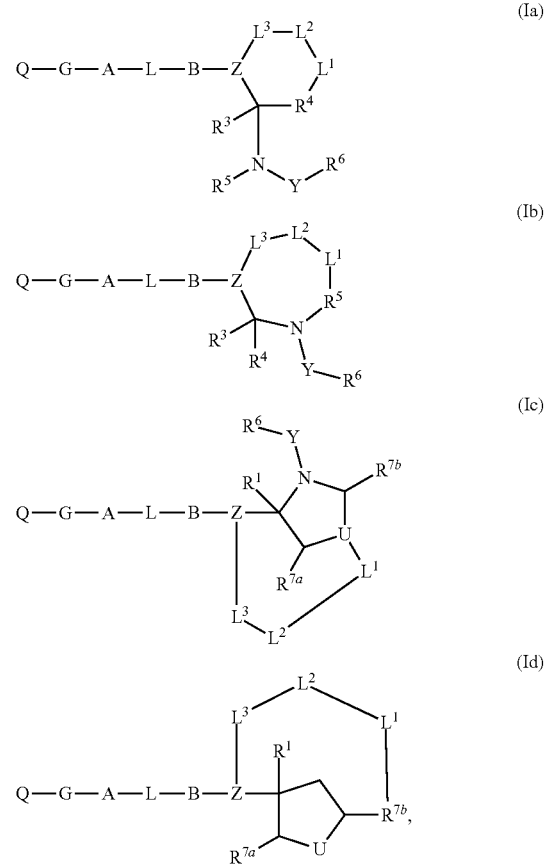

wherein A, B, G, L, Q, U, Y, $L^1$, $L^2$, $L^3$, $R^1$, $R^3$, $R^4$, $R^5$, $R^6$, $R^{7a}$, and $R^{7b}$ are as previously defined.

In another embodiment, the present invention relates to compounds represented by Formula (Ie) and pharmaceutically acceptable salts thereof:

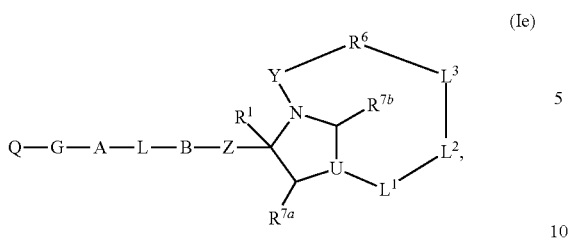
(Ie)

wherein A, B, G, L, Q, U, Y, L$^1$, L$^2$, L$^3$, R$^1$, R$^3$, R$^4$, R$^5$, R$^6$, R$^{7a}$, and R$^{7b}$ are as previously defined.

In another embodiment, the present invention relates to compounds represented by Formula (Ie) and pharmaceutically acceptable salts thereof; wherein -L$^1$-L$^2$-L$^3$- together form a linker of from 6 to 10 bond lengths; A, B, G, L, Q, U, Y, R$^1$, R$^3$, R$^4$, R$^5$, R$^6$, R$^{7a}$, and R$^{7b}$ are as previously defined.

In yet another embodiment, the present invention relates to compounds of Formula (Ia), (Ib), (Ic), or (Id) and pharmaceutically acceptable salts thereof; wherein Z is —C(O)NH— and the linker -L$^1$-L$^2$-L$^3$- is connected to one of groups B, G or A.

In yet another embodiment, the present invention relates to compounds of Formula (Ia), (Ib), (Ic), or (Id) and pharmaceutically acceptable salts thereof; wherein Z is an optionally substituted 5-membered heteroaryl containing one or more nitrogen atoms.

In yet another embodiment, the present invention relates to compounds of Formula (Ia), (Ib), (Ic), or (Id) and pharmaceutically acceptable salts thereof; wherein Z is an optionally substituted 5-membered heteroaryl fused to a mono- or bicyclic ring, wherein the mono- or bicyclic ring is aromatic or non-aromatic, wherein the mono- or bicyclic ring is attached to one of groups A, L and B and wherein the 5-membered heteroaryl contains one or more nitrogen atoms.

In yet another embodiment, the present invention relates to compounds of Formula (Ia), (Ib), (Ic), or (Id) and pharmaceutically acceptable salts thereof; wherein Z is an optionally substituted imidazolyl or optionally substituted benzimidazolyl.

In still another embodiment, the present invention relates to compounds of Formula (Ia), (Ib), (Ic), (Id), or a pharmaceutically acceptable salt thereof; wherein Y is C(O); R$^6$ is C$_1$-C$_8$ alkyl optionally substituted with amino, halogen, hydroxy, aryl, heteroaryl, heterocyclic, C$_3$-C$_8$ cycloalkyl, protected amino or O(C$_1$-C$_4$ alkyl).

In one embodiment, the present invention relates to compounds represented by Formula (Ia-1), (Ia-2), (Ib-1), (Ib-2), (Ic-1), or (Ic-2) and pharmaceutically acceptable salts thereof:

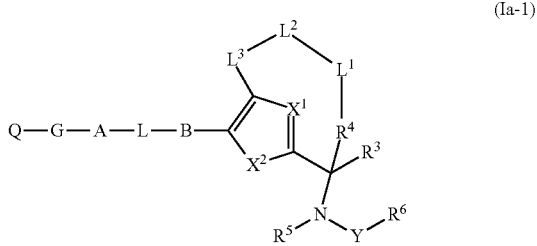
(Ia-1)

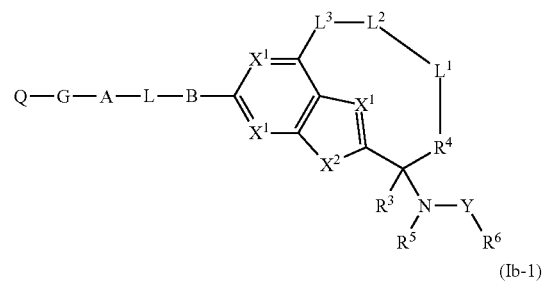
(Ia-2)

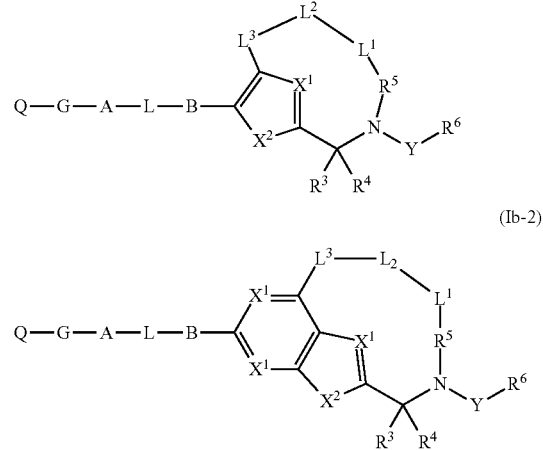
(Ib-1)

(Ib-2)

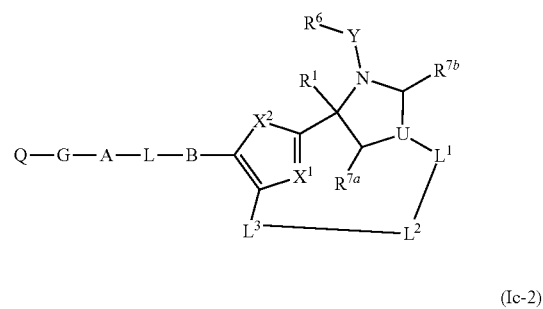
(Ic-1)

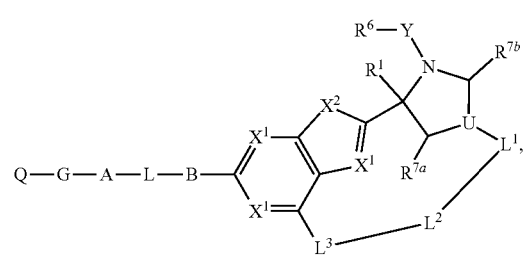
(Ic-2)

wherein X$^1$ at each occurrence are each independently N or C(R$^{11}$); preferably, X$^1$ is N or CH; R$^{11}$ at each occurrence is independently hydrogen, halogen or optionally substituted C$_1$-C$_4$ alkyl; preferably, R$^{11}$ is hydrogen; X$^2$ at each occurrence is independently N(R$^1$), O or S; preferably, X$^2$ is NH; and A, B, G, L, Q, Y, L$^1$, L$^2$, L$^3$, R$^1$, R$^3$, R$^4$, R$^5$, R$^6$, R$^{7a}$, and R$^{7b}$ are as previously defined; and in Formulae (Ic-1) and (Ic-2), U is C(R$^7$).

In one embodiment, the present invention relates to compounds represented by Formula (IIa), (IIb), (IIc), or (IId) and pharmaceutically acceptable salts thereof:

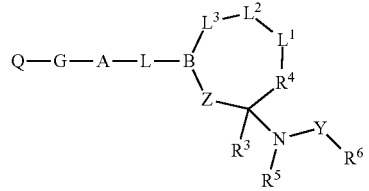
(IIa)

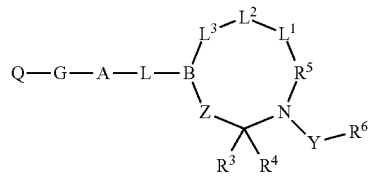
(IIb)

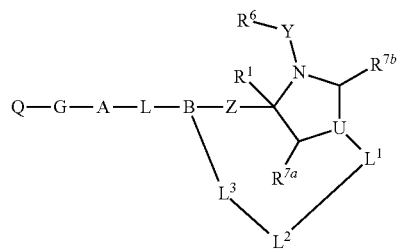
(IIc)

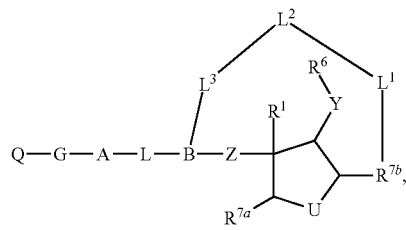
(IId)

wherein A, B, G, L, Q, U, Y, L$^1$, L$^2$, L$^3$, R$^1$, R$^3$, R$^4$, R$^5$, R$^6$, R$^{7a}$, and R$^{7b}$ are as previously defined; and U in Formula (IIc) is C(R$^7$).

In an additional embodiment, the present invention relates to compounds represented by Formula (IIa-1), (IIa-2), (IIa-3), (IIa-4), (IIa-5), or (IIa-6) and pharmaceutically acceptable salts thereof:

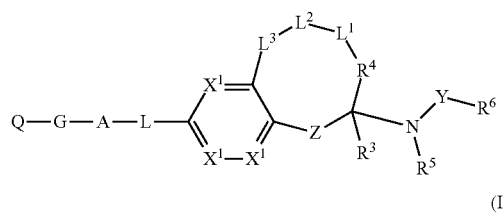
(IIa-1)

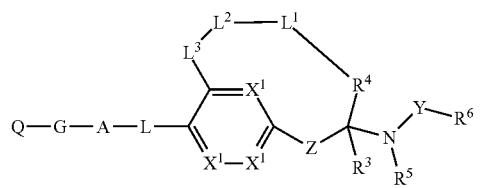
(IIa-2)

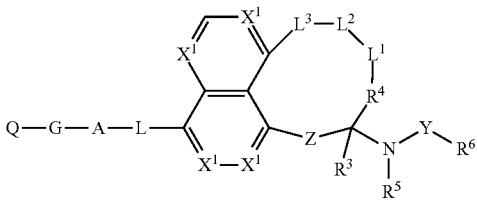
(IIa-3)

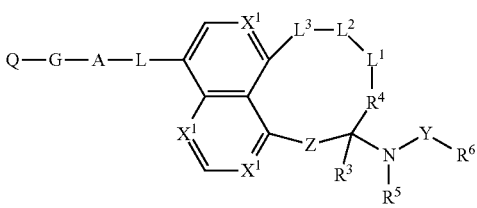
(IIa-4)

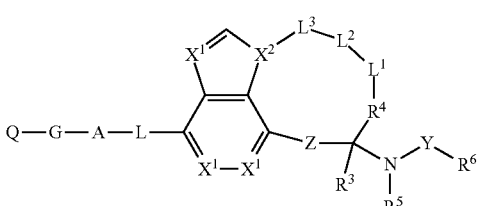
(IIa-5)

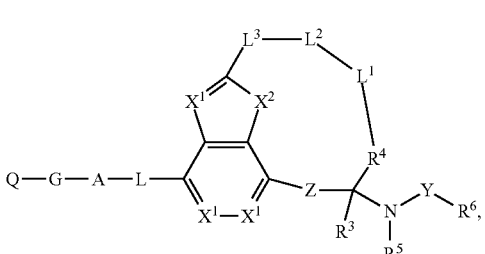
(IIa-6)

wherein A, G, L, Q, Y, Z, L$^1$, L$^2$, L$^3$, R$^3$, R$^4$, R$^5$, R$^6$, X$^1$, and X$^2$ in Formula (IIa-6) are as previously defined; and X$^2$ in Formula (IIa-5) is N.

In an additional embodiment, the present invention relates to compounds represented by Formula (IIb-1), (IIb-2), (IIb-3), (IIb-4), (IIb-5), or (IIb-6) and pharmaceutically acceptable salts thereof:

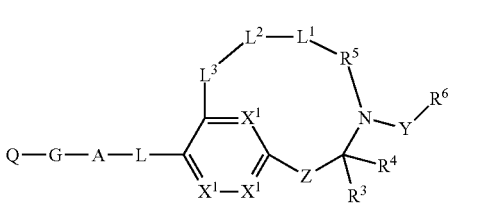
(IIb-1)

(IIb-2)

-continued (IIb-3)
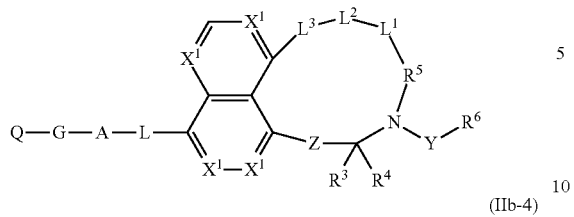

(IIb-4)
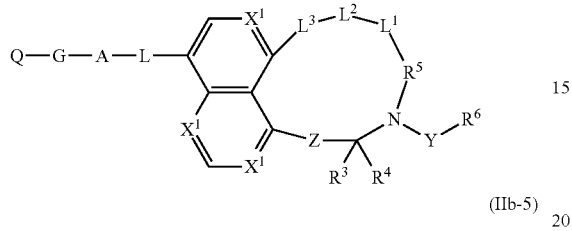

(IIb-5)
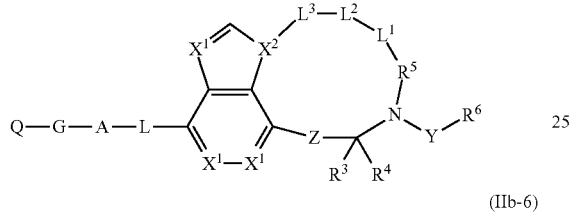

(IIb-6)
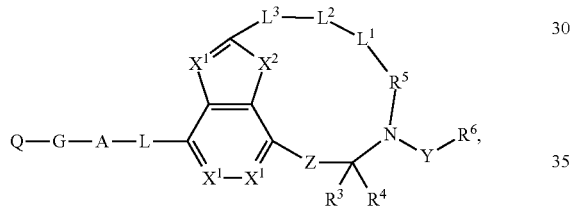

wherein A, G, L, Q, Y, Z, $L^1$, $L^2$, $L^3$, $R^3$, $R^4$, $R^5$, $R^6$, $X^1$, and $X^2$ in (IIb-6) are as previously defined; and $X^2$ in (IIb-5) is N.

In an additional embodiment, the present invention relates to compounds represented by Formula (IIc-1), (IIc-2), (IIc-3), (IIc-4), (IIc-5), or (IIc-6) and pharmaceutically acceptable salts thereof:

(IIc-1)
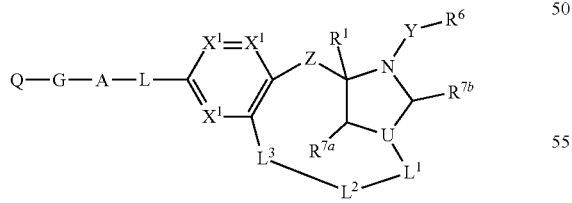

(IIc-2)
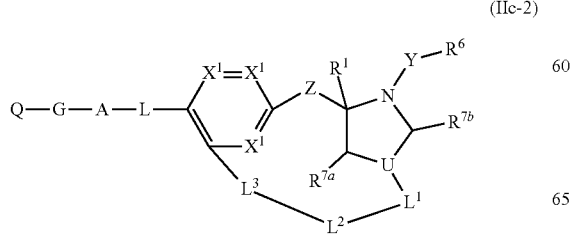

-continued (IIc-3)
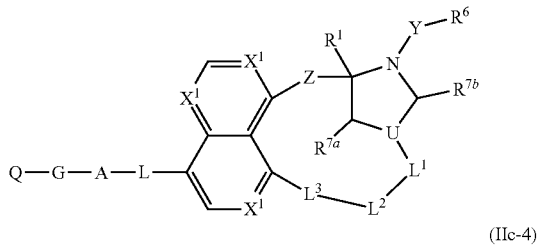

(IIc-4)
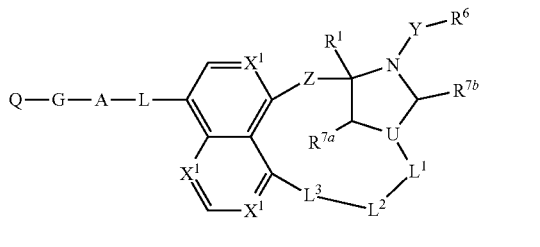

(IIc-5)
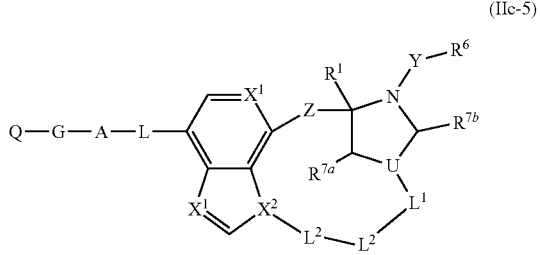

(IIc-6)
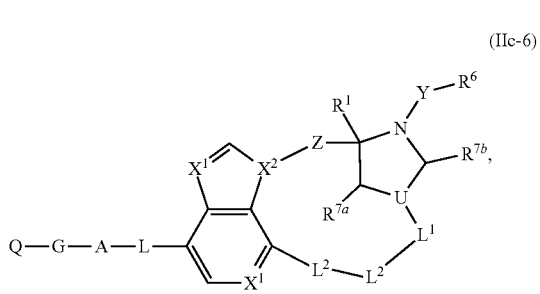

wherein A, G, L, Q, Y, Z, $L^1$, $L^2$, $L^3$, $R^3$, $R^4$, $R^5$, $R^6$, and $X^1$ are as previously defined; U is $C(R^7)$; and $X^2$ in (IIc-5) and (IIc-6) are N.

In an additional embodiment, the present invention relates to compounds represented by Formula (IIIa), (IIIb), (IIIc), or (IIId), and pharmaceutically acceptable salts thereof:

(IIIa)
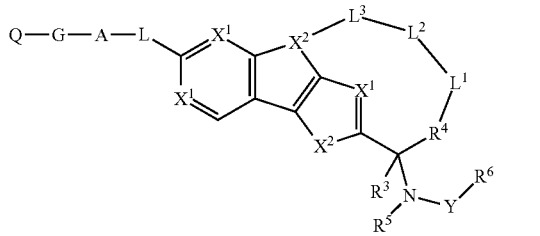

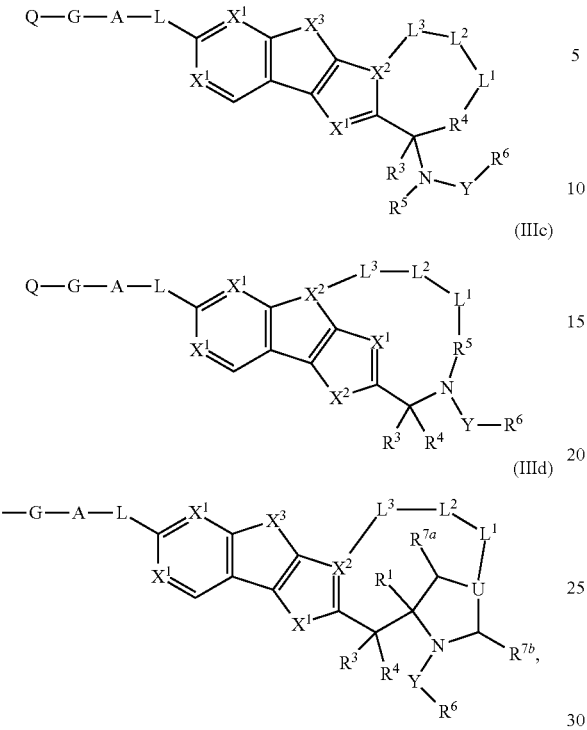

wherein A, G, L, Q, Y, $L^1$, $L^2$, $L^3$, $R^3$, $R^4$, $R^5$, $R^6$, $R^{7a}$, and $R^{7b}$ are as previously defined; $X^2$ is N or NH; $X^3$ is O, S, CH=CH or CH=N.

In yet another embodiment, the present invention relates to compounds of Formula (I), and pharmaceutically acceptable salts thereof; wherein $L^1$ and $L^3$ at each occurrence are each independently a linear aliphatic group, or one of $L^1$ and $L^3$ at each occurrence is a linear aliphatic group and the other of $L^1$ and $L^3$ is absent.

In yet another embodiment, the present invention relates to compounds of Formula (I) and pharmaceutically acceptable salts thereof; wherein one of $L^1$ and $L^3$ is a linear aliphatic group, and the other of $L^1$ and $L^3$ is an aliphatic group containing an optionally substituted cycloalkyl, heterocyclic or cycloalkenyl.

In yet another embodiment, the present invention relates to compounds of Formula (I), and pharmaceutically acceptable salts thereof; wherein the linker -$L^1$-$L^2$-$L^3$- is a linear aliphatic group and wherein said linker is from 8 to 14 bond lengths.

In yet another embodiment, the present invention relates to compounds of Formula (I), and pharmaceutically acceptable salts thereof; wherein the linker -$L^1$-$L^2$-$L^3$- together is a combination of a linear aliphatic group(s) and a cyclic group, and wherein said linker is from 6 to 16 bond lengths. In another aspect of the invention, the linker -$L^1$-$L^2$-$L^3$- together is a combination of a linear aliphatic group(s) and a cyclic group, and -$L^1$-$L^2$-$L^3$- together form a linker of from 8 to 14 bond lengths.

In still another embodiment, the present invention relates to compounds of Formula (I), and pharmaceutically acceptable salts thereof; wherein the linker -$L^1$-$L^2$-$L^3$- is selected from the following groups:

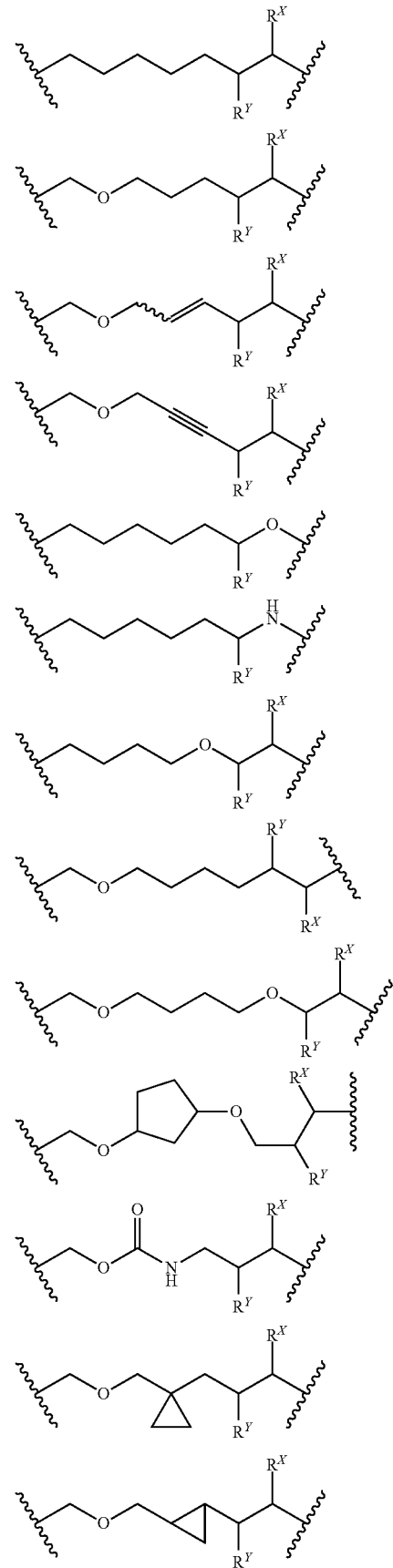

-continued

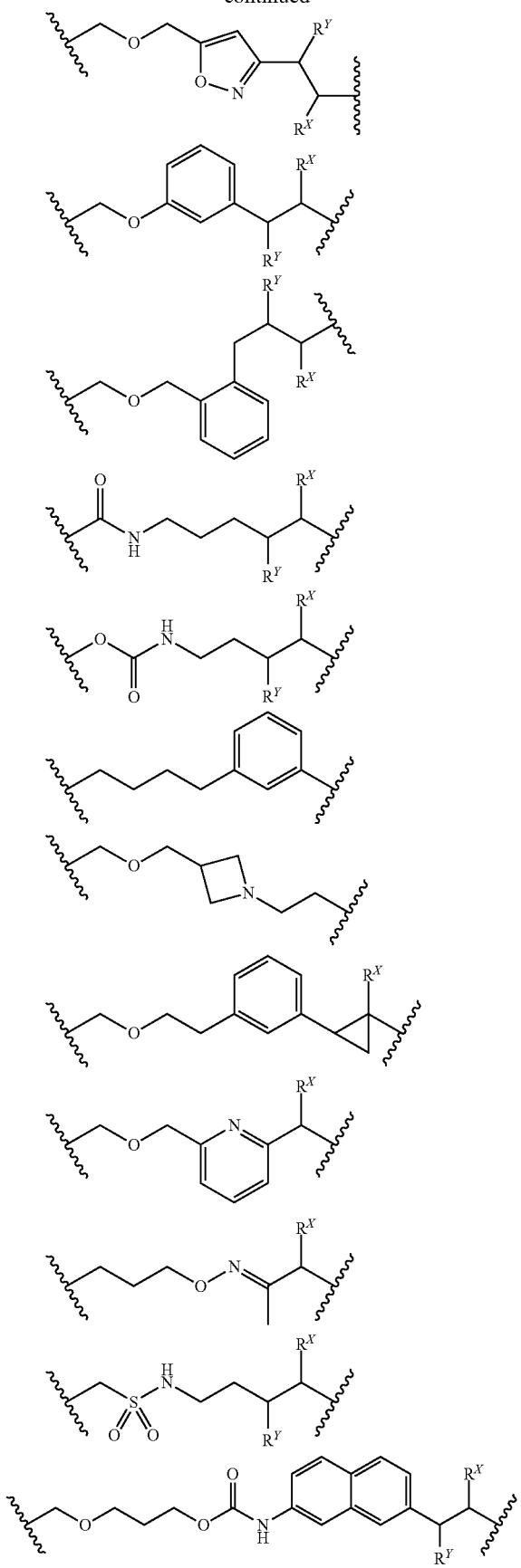

-continued

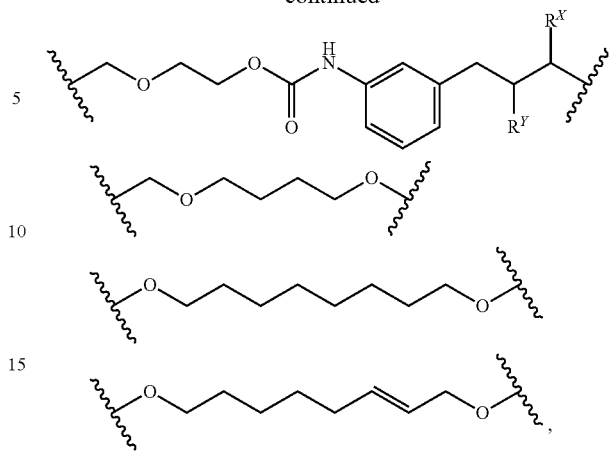

wherein $R^X$ is hydrogen, amino, hydroxy, protected amino or $O(C_1$-$C_4$ alkyl); $R^Y$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, or heteroaryl, each optionally substituted; preferably optionally substituted $C_1$-$C_8$ alkyl; and wherein each of the above shown groups is further optionally substituted.

In still another embodiment, the present invention relates to compounds of Formula (I) and pharmaceutically acceptable salts thereof; wherein G is optionally substituted five-membered heteroaryl containing one or more nitrogen atoms, and is each C-attached to Q and to one of groups A, L and B.

In still another embodiment, the present invention relates to compounds of Formula (I) and pharmaceutically acceptable salts thereof; wherein G is optionally substituted 5/6-membered ring fused heteroaryl, wherein the 5-membered ring of said 5/6-membered fused heteroaryl is a heteroaryl containing one or more nitrogen atoms and wherein the 5-membered ring is C-attached, and wherein the 6-membered ring of said 5/6-membered fused heteroaryl is aryl or heteroaryl and is C-attached to one of groups A, L and B.

In still another embodiment, the present invention relates to compounds of Formula (I) and pharmaceutically acceptable salts thereof; wherein G and Z are each independently illustrated by the following heteroaryl groups:

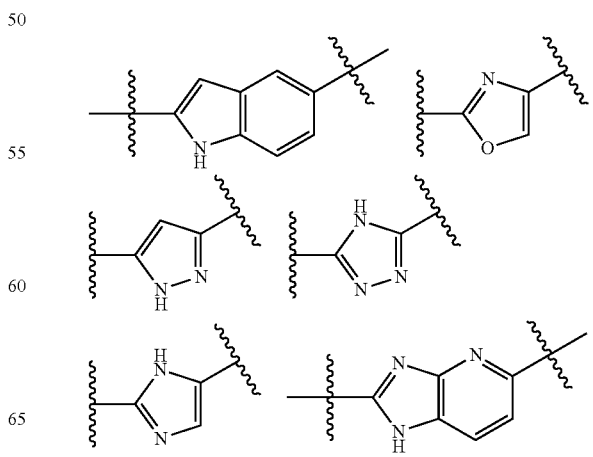

-continued

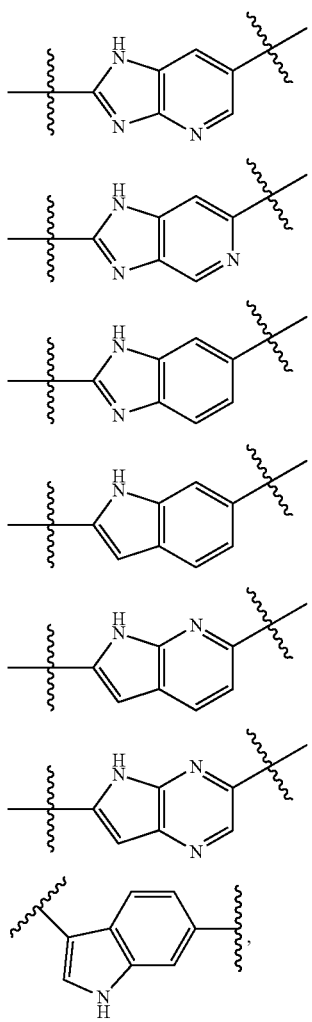

wherein each of the above shown heteroaryl groups is optionally substituted, wherein a ring atom of one of groups G and Z can be bonded to -$L_1$-$L_2$-$L_3$-.

In still another embodiment, the present invention relates to compounds of Formula (I) and pharmaceutically acceptable salts thereof; wherein G and Z are each independently selected from the following heteroaryl groups:

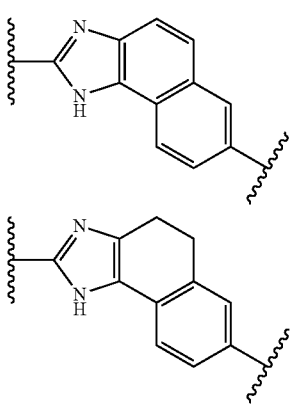

-continued

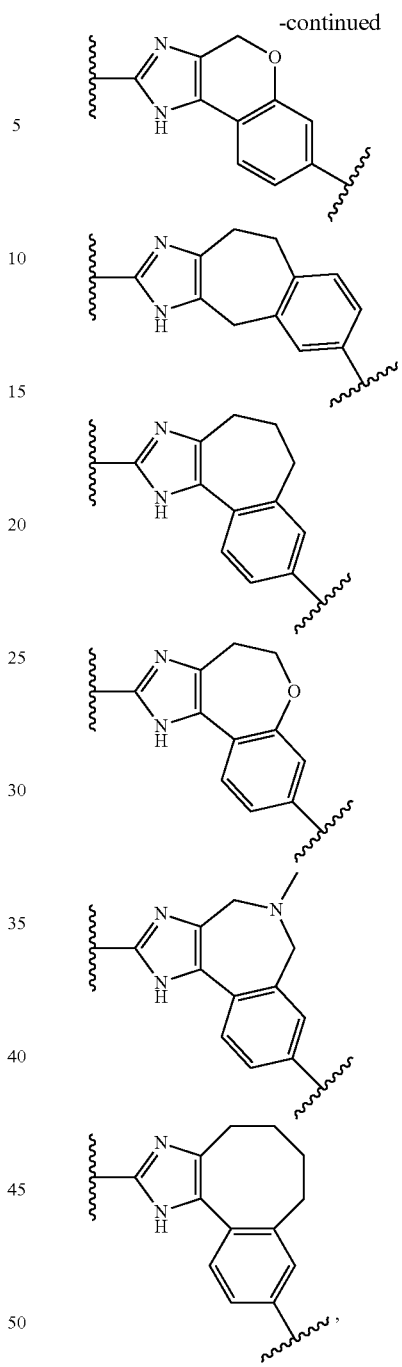

wherein each of the above shown heteroaryl groups is optionally substituted, wherein a ring atom of one of groups G and Z can be bonded to -$L_1$-$L_2$-$L_3$-.

In still another embodiment, the present invention relates to compounds of Formula (I) and pharmaceutically acceptable salts thereof; wherein L is a linear aliphatic group, A and B are each independently optionally substituted phenyl, monocyclic heteroaryl, naphthyl, or bicyclic heteroaryl.

In still another embodiment, the present invention relates to compounds of Formula (I), Formulae (Ia~Id), and pharmaceutically acceptable salts thereof; wherein A and B are each independently optionally substituted phenyl; L is —$CH_2N(R)CH_2$—, wherein R is optionally substituted aryl or heteroaryl; preferably, optionally, A and B are each optionally substituted phenyl.

In still another embodiment, the present invention relates to compounds of Formula (I), Formulae (Ia~Id), and pharmaceutically acceptable salts thereof; wherein L is an optionally substituted heterocyclic, A and B are each independently optionally substituted phenyl, monocyclic heteroaryl, naphthyl, or bicyclic heteroaryl.

In still another embodiment, the present invention relates to compounds of Formula (I), Formulae (Ia~Id), and pharmaceutically acceptable salts thereof; wherein A and B are each independently optionally substituted phenyl; L is a pyrrolidinyl group substituted with a phenyl or heteroaryl, wherein said phenyl or heteroaryl may be optionally further substituted.

In still another embodiment, the present invention relates to compounds of Formula (I), Formulae (Ia~Id), and pharmaceutically acceptable salts thereof; wherein L is absent, A and B are each independently optionally substituted phenyl, monocyclic heteroaryl, naphthyl, or bicyclic heteroaryl.

In still another embodiment, the present invention relates to compounds of Formula (I), Formulae (Ia~Id), and pharmaceutically acceptable salts thereof; wherein L is absent, one of A and B is a $C_3$-$C_8$ cycloalkyl, and the other of A and B is an optionally substituted aryl or heteroaryl.

In still another embodiment, the present invention relates to compounds of Formula (I), Formulae (Ia~Id), and pharmaceutically acceptable salts thereof; wherein L is absent, one of A and B is a heterocyclic, and the other of A and B is an optionally substituted aryl or heteroaryl.

In still another embodiment, the present invention relates to compounds of Formula (I), Formulae (Ia~Id), and pharmaceutically acceptable salts thereof; wherein L is a linear aliphatic group, A is optionally substituted phenyl, monocyclic heteroaryl, naphthyl, or bicyclic heteroaryl.

In still another embodiment, the present invention relates to compounds of Formula (I), Formulae (Ia~Id) and pharmaceutically acceptable salts thereof; wherein A is optionally substituted phenyl; L is —CH$_2$N(R)CH$_2$—, wherein R is optionally substituted aryl or heteroaryl.

In still another embodiment, the present invention relates to compounds of Formula (I), Formulae (Ia~Id) and pharmaceutically acceptable salts thereof; wherein L is an optionally substituted heterocyclic, A is independently optionally substituted phenyl, monocyclic heteroaryl, naphthyl, or bicyclic heteroaryl.

In still another embodiment, the present invention relates to compounds of Formula (I), Formulae (Ia~Id) and pharmaceutically acceptable salts thereof; wherein A is optionally substituted phenyl; L is a pyrrolidinyl group substituted with a phenyl or heteroaryl, wherein said phenyl or heteroaryl may be optionally further substituted.

In still another embodiment, the present invention relates to compounds of Formula (I), Formulae (Ia~Id) and pharmaceutically acceptable salts thereof; wherein L is absent, A is a $C_3$-$C_8$ cycloalkyl, a heterocyclic, optionally substituted phenyl, monocyclic heteroaryl, naphthyl, or bicyclic heteroaryl, optionally substituted aryl or heteroaryl.

In still another embodiment, the present invention relates to compounds of Formula (I), and pharmaceutically acceptable salts thereof; A, L and B or A and L are taken together to form a linker selected from the following groups:

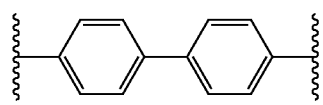

-continued

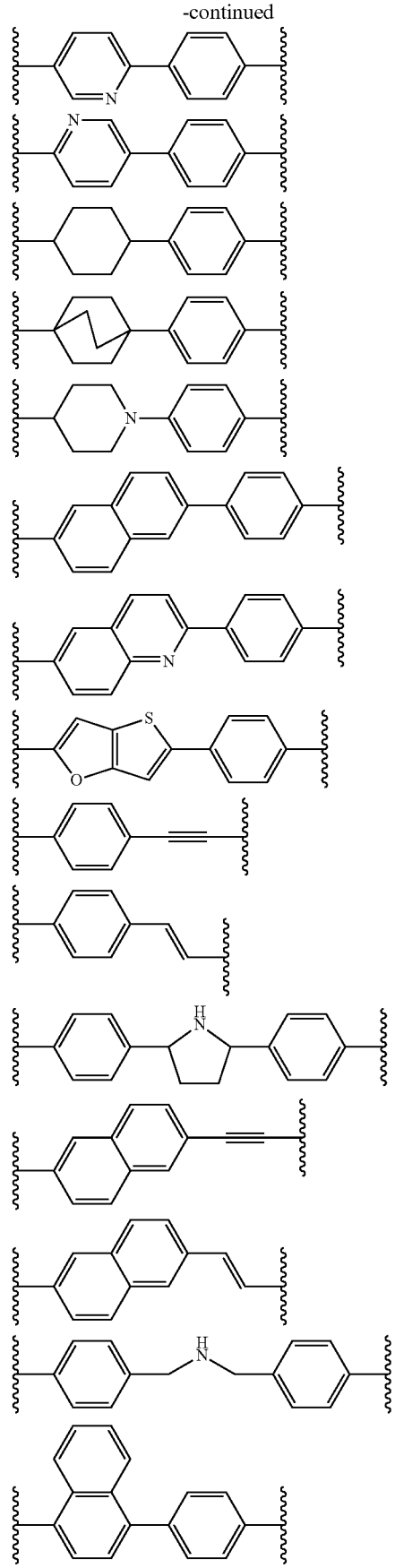

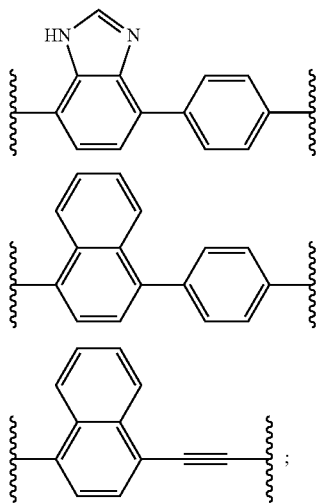

wherein each of the above shown cyclic groups is optionally substituted and wherein a ring atom of each of said A groups can be bonded to the linker -$L_1$-$L_2$-$L_3$-.

In still another embodiment, the present invention relates to compounds of Formula (I) and pharmaceutically acceptable salts thereof; wherein A or B is a fused polycyclic aryl or heteroaryl selected from the following groups:

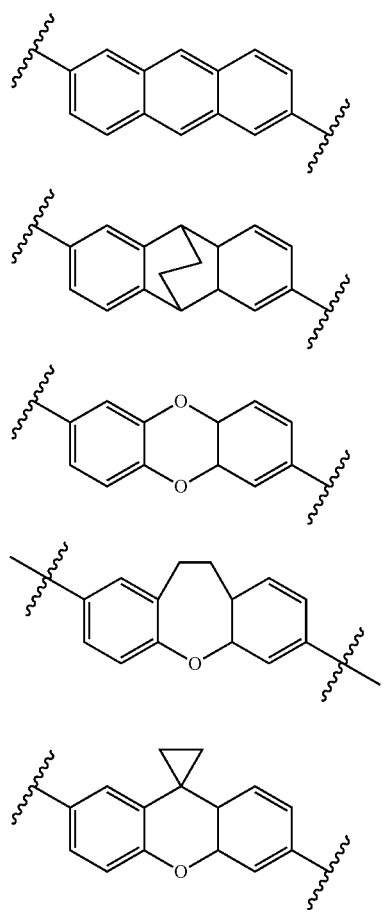

wherein each of the above shown cyclic groups is optionally substituted and wherein a ring atom of each of said groups can be bonded to the linker -$L^1$-$L^2$-$L^3$-.

In still another embodiment, the present invention relates to compounds of Formula (I) and pharmaceutically acceptable salts thereof; wherein A or B is a fused polycyclic aryl or heteroaryl selected from the following groups:

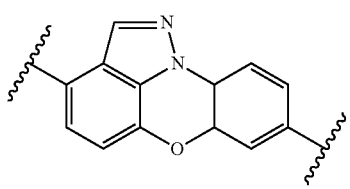

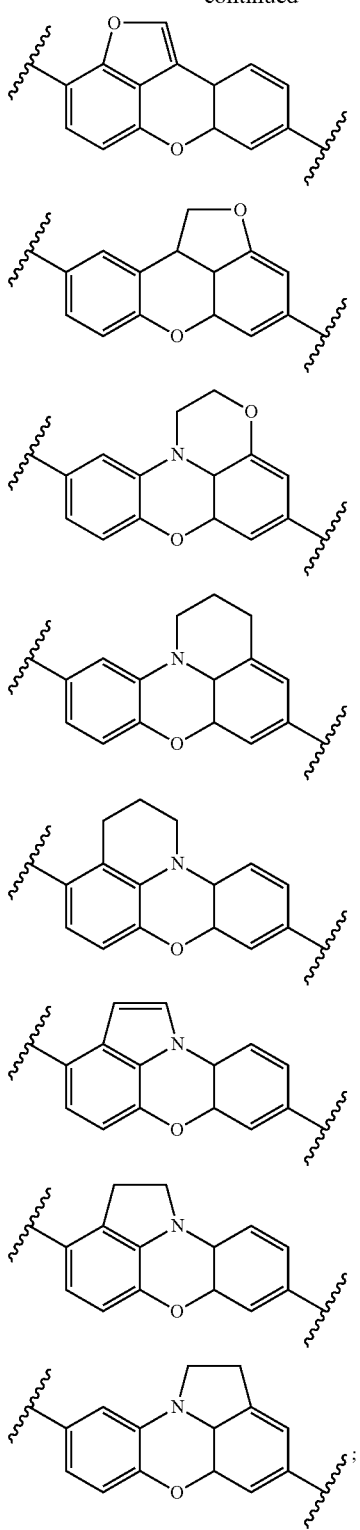

wherein each of the above shown cyclic groups is optionally substituted and wherein a ring atom of each of said groups can be bonded to the linker -L$^1$-L$^2$-L$^3$-.

In still another embodiment, the present invention relates to compounds of Formula (I), and pharmaceutically acceptable salts thereof; wherein W is

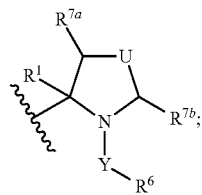

Q is

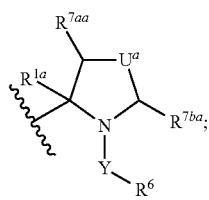

wherein U, R$^1$, R$^{1a}$, R$^{7a}$, R$^{7aa}$, R$^{7b}$, R$^{7ba}$, and Y are as previously defined.

In still another embodiment, the present invention relates to compounds of Formulae (IVa~IVd) or a pharmaceutically acceptable salt thereof;

(IVa)

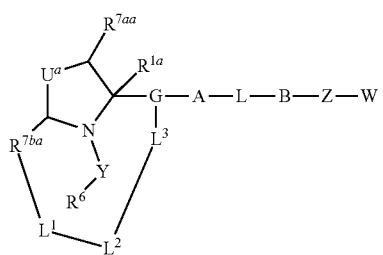

(IVb)

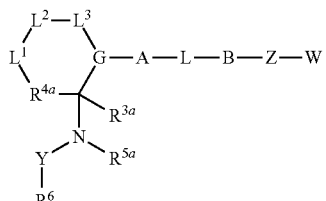

(IVc)

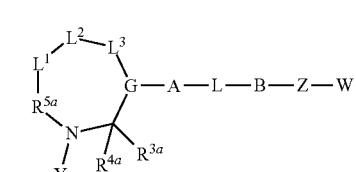

(IVd)

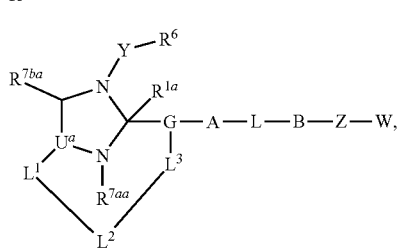

wherein A, B, G, L, U$^a$, W, Y, Z, R$^{1a}$, R$^{3a}$, R$^{4a}$, R$^{5a}$, R$^6$, R$^{7aa}$, and R$^{7ba}$ are as previously defined.

In still another embodiment, the present invention relates to compounds of Formulae (IVa~IVd), or a pharmaceutically acceptable salt thereof; wherein Y is C(O); $R^6$ is $C_1$-$C_8$ alkyl optionally substituted with amino, halogen, hydroxy, aryl, heteroaryl, heterocyclic, $C_3$-$C_8$ cycloalkyl, protected amino or O($C_1$-$C_4$ alkyl).

In still another embodiment, the present invention relates to compounds of Formulae (Va~Va), or a pharmaceutically acceptable salt thereof;

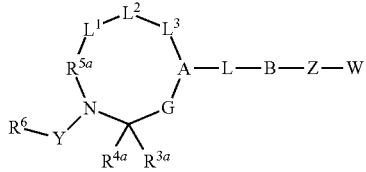

(Va)

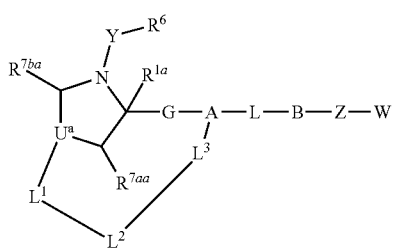

(Vb)

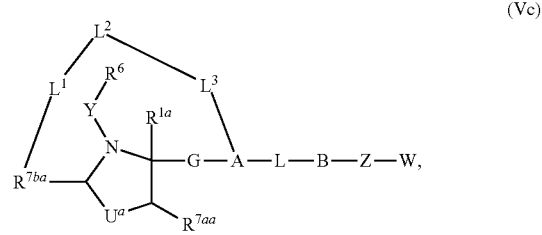

(Vc)

wherein A, B, G, L, $U^a$, W, Y, Z, $R^{1a}$, $R^{3a}$, $R^{4a}$, $R^{5a}$, $R^6$, $R^{7aa}$, and $R^{7ba}$ are as previously defined.

In still another embodiment, the present invention relates to compounds of Formulae (Va~Vc), or a pharmaceutically acceptable salt thereof; wherein Y is C(O); $R^6$ is $C_1$-$C_8$ alkyl optionally substituted with amino, halogen, hydroxy, aryl, heteroaryl, heterocyclic, $C_3$-$C_8$ cycloalkyl, protected amino or O($C_1$-$C_4$ alkyl).

In still another embodiment, the present invention relates to compounds of Formulae (VIa~VId), or a pharmaceutically acceptable salt thereof;

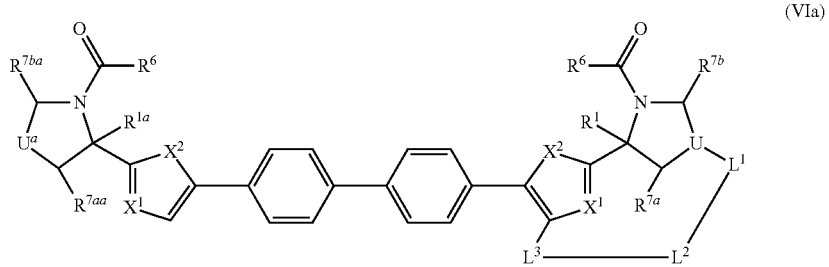

(VIa)

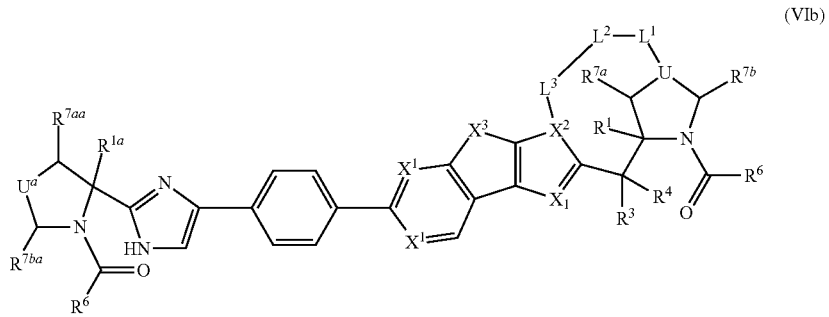

(VIb)

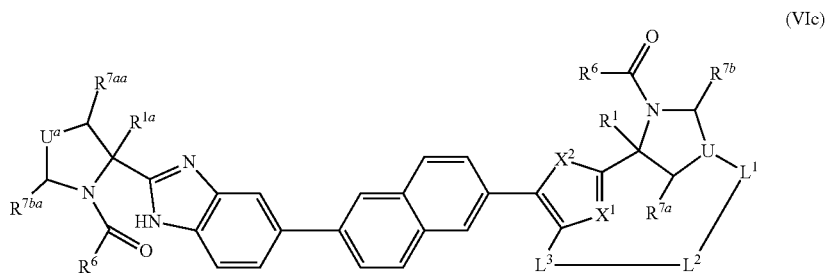

(VIc)

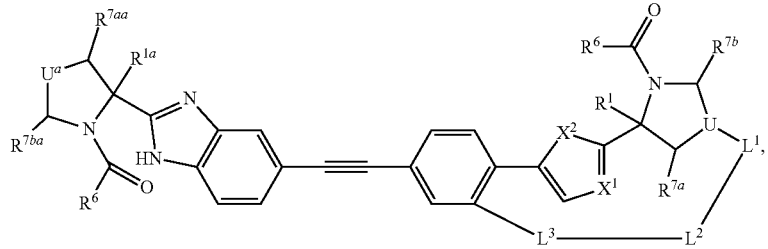
(VId)
wherein $L^1$, $L^2$, $L^3$, U, $U^a$, Y, $X^1$, $X^2$, $X^3$, $R^1$, $R^{1a}$, $R^6$, $R^{7a}$, $R^{7b}$, $R^{7aa}$, and $R^{7ba}$ are as previously defined.
In still another embodiment, the present invention relates to compounds of Formula (I) and a pharmaceutically acceptable salt thereof; wherein
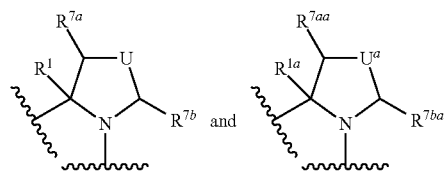
at each occurrence are each independently illustrated by the following groups:
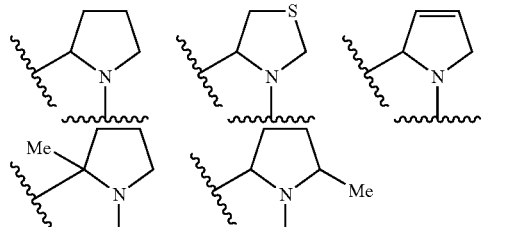
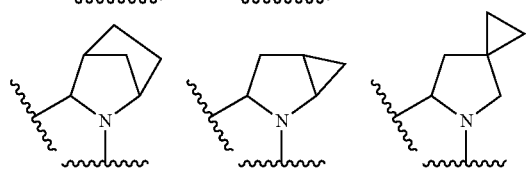
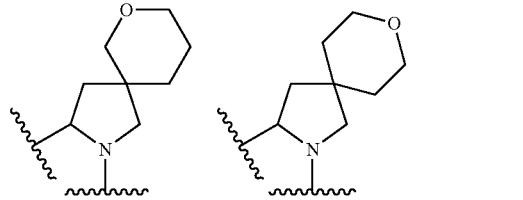
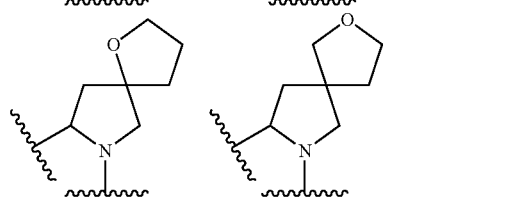
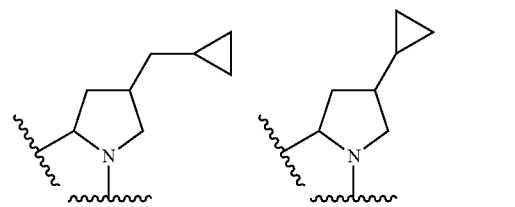
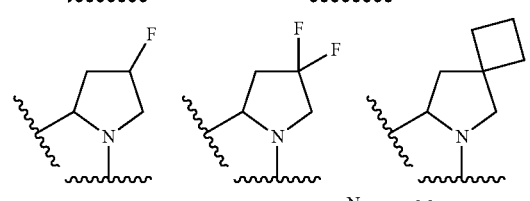
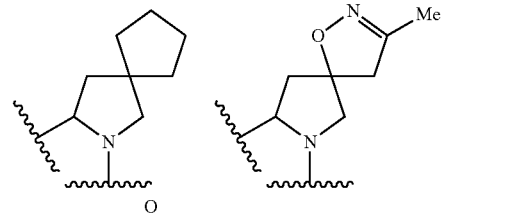
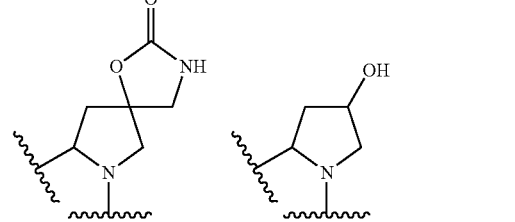

-continued

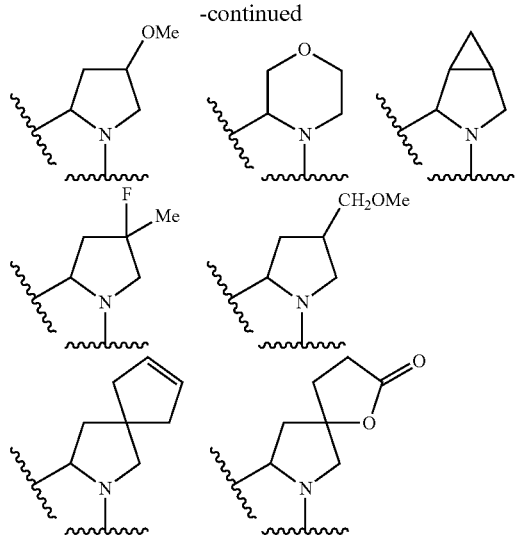

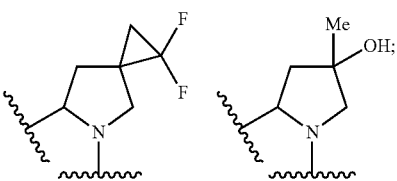

wherein each of said groups is optionally substituted and wherein a hydrogen atom or a group at the position corresponding to U can be replaced or extended with a linker -L$^1$-L$^2$-L$^3$- which is connected to one of groups Z, B, G or A.

Representative compounds of the present invention are those selected from compounds 1-345 compiled in Tables 1-11:

TABLE 1

Compounds 1-219.

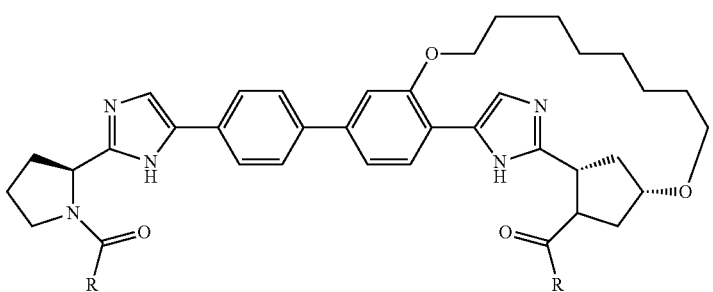

| Entry |  |
|---|---|
| 1 | 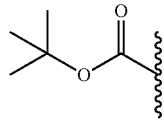 [SMILES: *C(=O)OC(C)(C)C] |
| 2 | 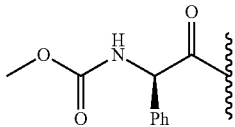 [SMILES: *C(=O)[C@H](NC(=O)OC)c1ccccc1] |
| 3 | 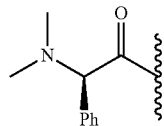 |
| 4 | 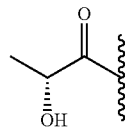 [SMILES: *C(=O)[C@@H](C)O] |

TABLE 1-continued

Compounds 1-219.

| Entry | R group |
|-------|---------|
| 5 | 3-hydroxy-1-oxopentyl (ethyl, CH(OH), C(=O)–) |
| 6 | propanoyl (CH₃CH₂C(=O)–) |
| 7 | methoxyacetyl (CH₃OCH₂C(=O)–) |
| 8 | N,N-dimethylcarbamoyl ((CH₃)₂NC(=O)–) |
| 9 | methoxycarbonyl (CH₃OC(=O)–) |
| 10 | 4-oxopentanoyl (acetyl-CH₂CH₂C(=O)–) |
| 11 | 3-hydroxy-4-methyl-1-oxopentyl (isopropyl-CH(OH)-C(=O)–) |
| 12 | pent-4-enoyl (CH₂=CHCH₂CH₂C(=O)–) |

TABLE 1-continued
Compounds 1-219.
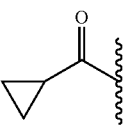 [SMILES: *C(=O)C1CC1]

| Entry | |
|---|---|
| 13 |  |
| 14 | 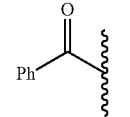 |
| 15 | 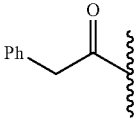 [SMILES: *C(=O)Cc1ccccc1] |
| 16 | 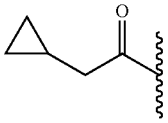 [SMILES: *C(=O)CC1CC1] |
| 17 |  |
| 18 |  |
| 19 | |
| 20 | |

TABLE 1-continued

Compounds 1-219.

| Entry | R |
|---|---|
| 21 | (S)-PhCH(OH)C(O)- |
| 22 | (pyridin-3-yl)CH₂C(O)- |
| 23 | (pyridin-4-yl)CH₂C(O)- |
| 24 | (S)-PhCH₂CH(OH)C(O)- |
| 25 | (S)-tetrahydrofuran-2-yl-C(O)- |
| 26 | (R)-tetrahydrofuran-2-yl-C(O)- |
| 27 | tetrahydrofuran-3-yl-C(O)- |
| 28 | (1-methylpiperidin-4-yl)-C(O)- |

TABLE 1-continued

Compounds 1-219.

| Entry | R group structure |
|-------|-------------------|
| 29 | tetrahydropyran-4-yl carbonyl |
| 30 | morpholine-4-carbonyl |
| 31 | trans-4-(Boc-amino)cyclohexylcarbonyl |
| 32 | cis-4-(Boc-amino)cyclohexylcarbonyl |
| 33 | 1-Boc-piperidine-4-carbonyl |
| 34 | 4-(diethylamino)cyclohexylcarbonyl |

TABLE 1-continued

Compounds 1-219.

| Entry | |
|---|---|
| 35 | (methyl carbamate-NH-cyclohexyl-C(O)-) |
| 36 | (4-methylpiperazine-1-carbonyl-) |
| 37 | (2-(piperidin-1-ylmethyl)phenyl-CH2-C(O)-) |
| 38 | (2-(pyrrolidin-1-ylmethyl)phenyl-CH2-C(O)-) |
| 39 | (2-((dimethylamino)methyl)phenyl-CH2-C(O)-) |

TABLE 1-continued

Compounds 1-219.

| Entry | R-C(O)- group |
|---|---|
| 40 | 2-((4-methylpiperazin-1-yl)methyl)phenylacetyl |
| 41 | 2-(morpholinomethyl)phenylacetyl |
| 42 | trans-4-(methoxycarbonylamino)cyclohexanecarbonyl |
| 43 | thiazole-4-carbonyl |
| 44 | oxazole-2-carbonyl |
| 45 | oxazole-5-carbonyl |

TABLE 1-continued

Compounds 1-219.

| Entry | R group |
|-------|---------|
| 46 | (1H-imidazol-5-yl)methyl-C(=O)- |
| 47 | 1H-imidazol-5-yl-C(=O)- |
| 48 | (1-methyl-1H-imidazol-5-yl)-C(=O)- |
| 49 | (1H-tetrazol-5-yl)methyl-C(=O)- |
| 50 | (2-fluorophenyl)-C(=O)- |
| 51 | (4-(dimethylamino)phenyl)-C(=O)- |
| 52 | pyridin-4-yl-C(=O)- |

TABLE 1-continued
Compounds 1-219.
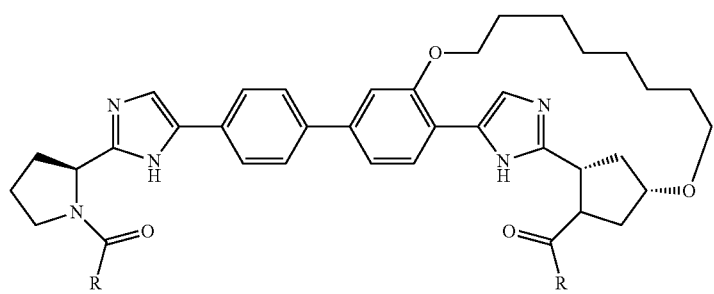
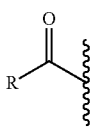
| Entry | |
|---|---|
| 53 | 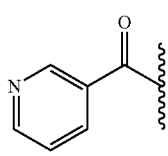 |
| 54 | 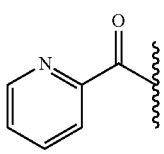 |
| 55 | 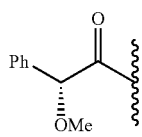 |
| 56 | 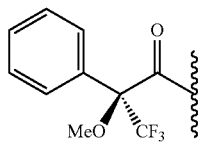 |
| 57 | 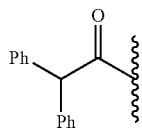 |
| 58 | 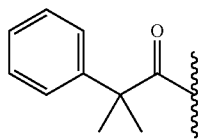 [SMILES: *C(=O)C(C)(C)c1ccccc1] |
| 59 | 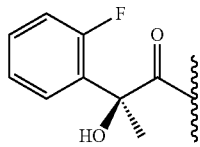 [SMILES: *C(=O)[C@@](C)(O)c1ccccc1F] |

TABLE 1-continued
Compounds 1-219.
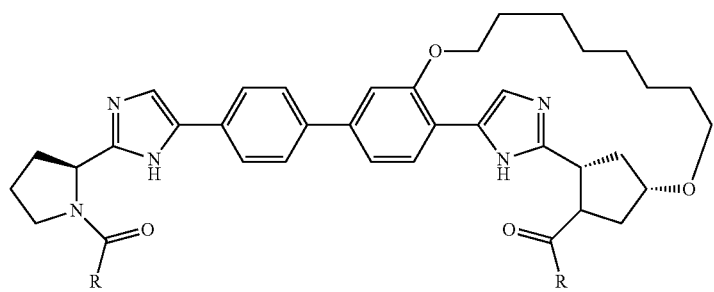
| Entry | |
|---|---|
| 60 |  |
| 61 | 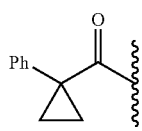 |
| 62 | 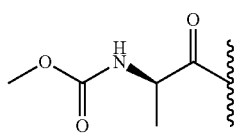 [SMILES: *C(=O)[C@@H](C)NC(=O)OC] |
| 63 | 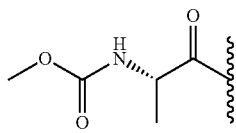 [SMILES: *C(=O)[C@H](C)NC(=O)OC] |
| 64 | 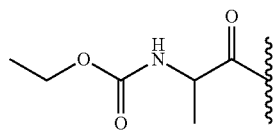 [SMILES: *C(=O)C(C)NC(=O)OCC] |
| 65 | 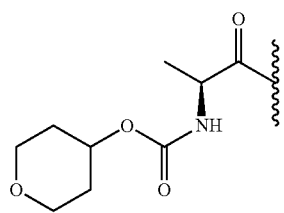 [SMILES: *C(=O)[C@H](C)NC(=O)OC1CCOCC1] |

TABLE 1-continued

Compounds 1-219.

| Entry | R group structure |
|-------|------|
| 66 | methyl carbamate-NH-CH(CH2OMe)-C(O)- |
| 67 | methyl carbamate-NH-CH(CH2CH3)-C(O)- |
| 68 | methyl carbamate-NH-CH(CH2CH3)-C(O)- |
| 69 | methyl carbamate-NH-CH(CH2CH2OMe)-C(O)- |
| 70 | methyl carbamate-NH-CH(CH(OH)CH3)-C(O)- |
| 71 | methyl carbamate-NH-CH(CH(OH)CH3)-C(O)- |

TABLE 1-continued
Compounds 1-219.
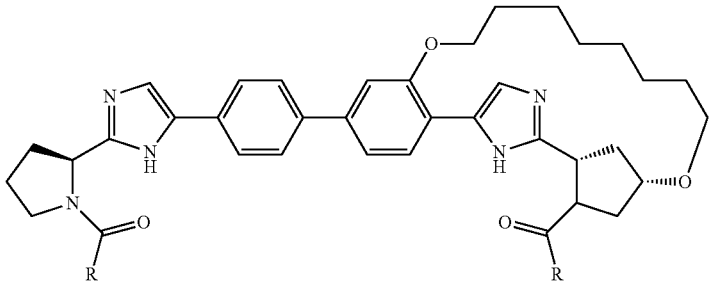
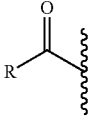
| Entry | |
|---|---|
| 72 | 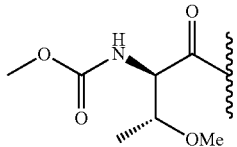 [SMILES: *C(=O)[C@H](NC(=O)OC)[C@@H](C)OC] |
| 73 | 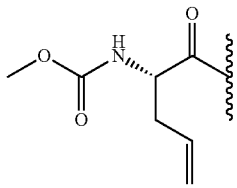 [SMILES: *C(=O)[C@H](CC=C)NC(=O)OC] |
| 74 | 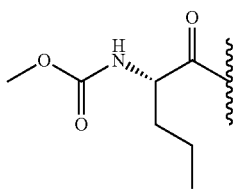 [SMILES: *C(=O)[C@H](CCC)NC(=O)OC] |
| 75 | 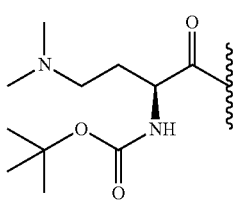 [SMILES: *C(=O)[C@H](CCN(C)C)NC(=O)OC(C)(C)C] |
| 76 | 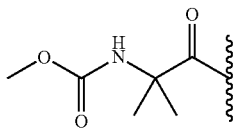 [SMILES: *C(=O)C(C)(C)NC(=O)OC] |
| 77 | 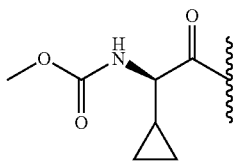 [SMILES: *C(=O)[C@H](NC(=O)OC)C1CC1] |

TABLE 1-continued
Compounds 1-219.
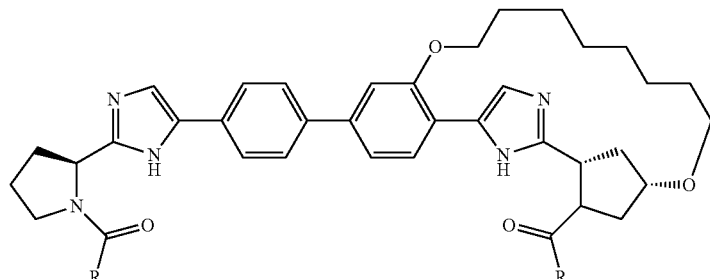
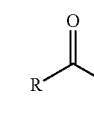
| Entry | |
|---|---|
| 78 | 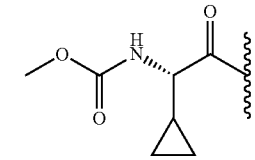 [SMILES: *C(=O)[C@@H](NC(=O)OC)C1CC1] |
| 79 | 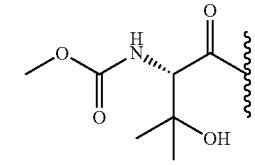 [SMILES: *C(=O)[C@@H](NC(=O)OC)C(C)(C)O] |
| 80 | 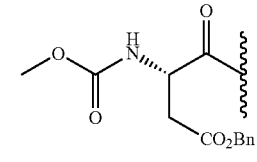 [SMILES: *C(=O)[C@H](CC(=O)OCc1ccccc1)NC(=O)OC] |
| 81 | 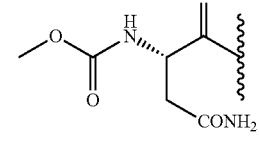 |
| 82 | 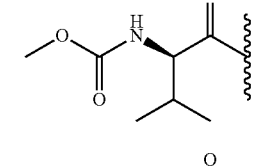 |
| 83 | 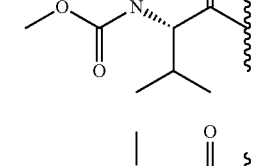 |
| 84 | 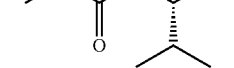 |

TABLE 1-continued
Compounds 1-219.
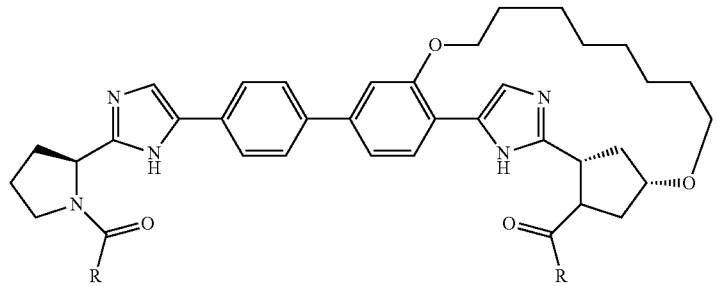
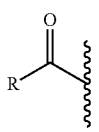
| Entry | |
|---|---|
| 85 | 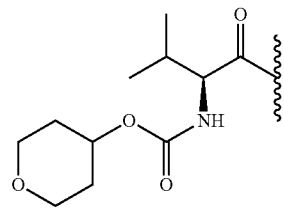 [SMILES: *C(=O)[C@@H](NC(=O)OC1CCOCC1)C(C)C] |
| 86 | 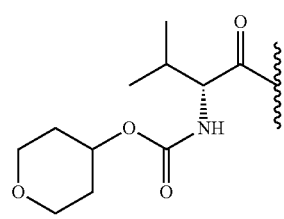 [SMILES: *C(=O)[C@H](NC(=O)OC1CCOCC1)C(C)C] |
| 87 | 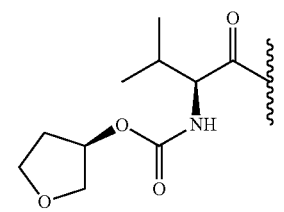 [SMILES: *C(=O)[C@@H](NC(=O)O[C@@H]1CCOC1)C(C)C] |
| 88 | 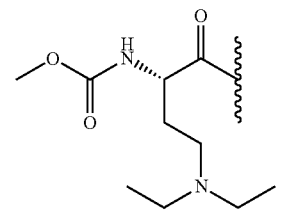 [SMILES: *C(=O)[C@H](CCN(CC)CC)NC(=O)OC] |
| 89 | 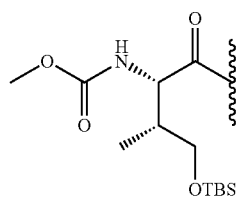 [SMILES: *C(=O)[C@@H](NC(=O)OC)[C@@H](C)CO[Si](C)(C)C(C)(C)C] |

TABLE 1-continued

Compounds 1-219.

| Entry | |
|---|---|
| 90 | methyl carbamate, CH(CH(CH3)CH2OTBS) |
| 91 | methyl carbamate, CH(CH2CH2N(Et)2) |
| 92 | methyl carbamate, CH(tetrahydropyran-4-yl) |
| 93 | methyl carbamate, CH(tetrahydropyran-4-yl) (epimer) |
| 94 | methyl carbamate, 1-aminocyclopropyl |
| 95 | methyl carbamate, 1-aminocyclobutyl |

TABLE 1-continued
Compounds 1-219.
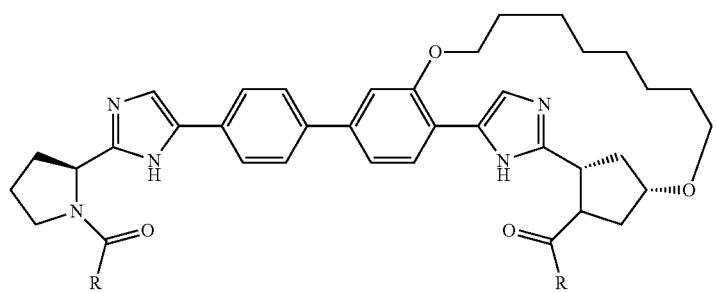
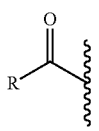
| Entry | |
|---|---|
| 96 | 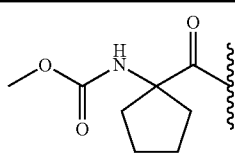 |
| 97 | 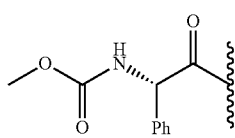 [SMILES: *C(=O)[C@@H](NC(=O)OC)c1ccccc1] |
| 98 | 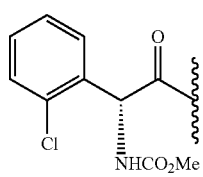 |
| 99 | 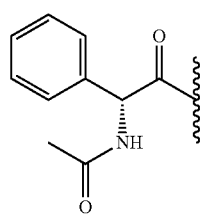 [SMILES: *C(=O)[C@H](NC(C)=O)c1ccccc1] |
| 100 | 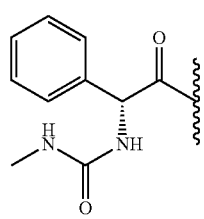 [SMILES: *C(=O)[C@H](NC(=O)NC)c1ccccc1] |
| 101 | 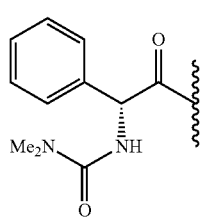 [SMILES: *C(=O)[C@H](NC(=O)N(C)C)c1ccccc1] |

TABLE 1-continued

Compounds 1-219.

| Entry | R group structure |
|---|---|
| 102 | phenyl-CH(NH-C(=O)-NH-Et)-C(=O)- |
| 103 | phenyl-CH(NH-C(=O)-NH-cyclopentyl)-C(=O)- |
| 104 | (2S)-1-(methoxycarbonyl)azetidine-2-carbonyl- (MeO₂C-N-azetidinyl-C(=O)-) |
| 105 | 1-Boc-azetidin-3-yl-C(=O)- |
| 106 | (S)-2-(NHCO₂Me)-3-(pyridin-2-yl)propanoyl- |
| 107 | (S)-2-(NHCO₂Me)-3-(pyridin-3-yl)propanoyl- |

TABLE 1-continued
Compounds 1-219.
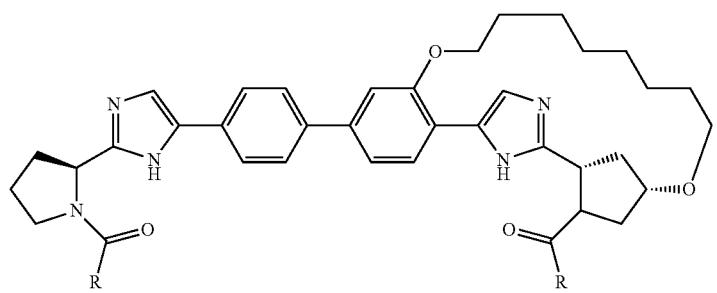
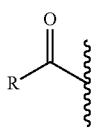
| Entry | |
|---|---|
| 108 |  |
| 109 |  |
| 110 |  |
| 111 | 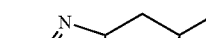 |
| 112 | 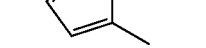 |
| 113 | 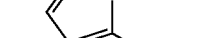 |

TABLE 1-continued
Compounds 1-219.
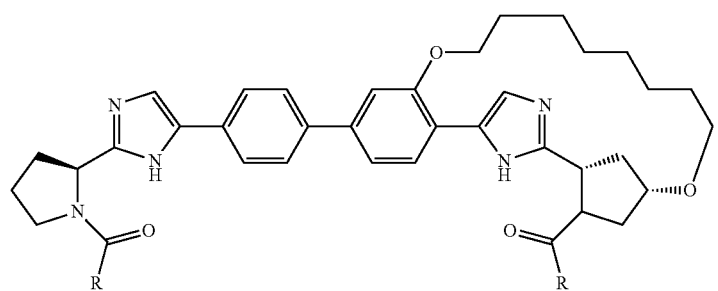
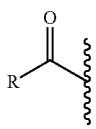
| Entry | |
|---|---|
| 114 | 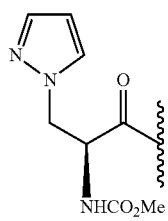 |
| 115 | 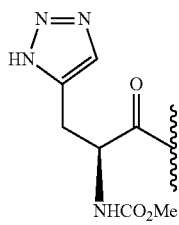 |
| 116 | 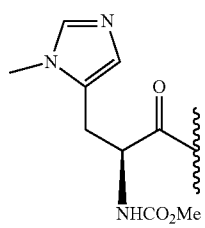 |
| 117 | 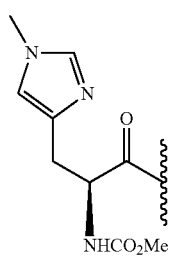 |

TABLE 1-continued

Compounds 1-219.

| Entry | |
|---|---|
| 118 | (S)-2-(methoxycarbonylamino)-3-phenylpropanoyl |
| 119 | (R)-2-(methoxycarbonylamino)-3-phenylpropanoyl |
| 120 | (S)-2-(methoxycarbonylamino)-3-(4-((hydroxy(methoxy)phosphoryl)oxy)phenyl)propanoyl |
| 121 | (S)-2-(methoxycarbonylamino)-3-(1H-indol-3-yl)propanoyl |

TABLE 1-continued
Compounds 1-219.
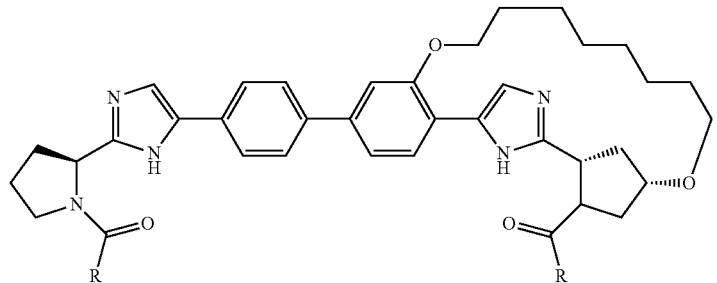
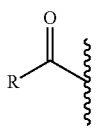
| Entry | |
|---|---|
| 122 | 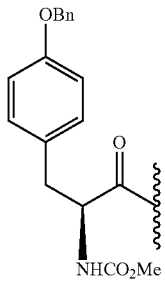 |
| 123 | 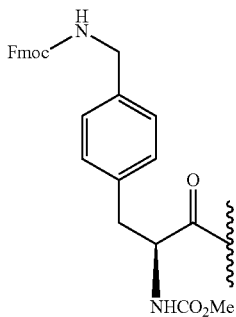 |
| 124 | 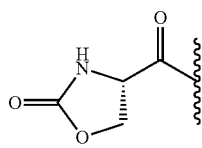 [SMILES: *C(=O)[C@@H]1COC(=O)N1] |
| 125 | 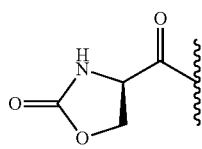 [SMILES: *C(=O)[C@H]1COC(=O)N1] |
| 126 | 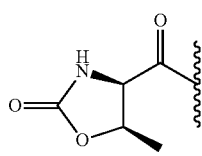 [SMILES: *C(=O)[C@@H]1NC(=O)O[C@@H]1C] |

TABLE 1-continued

Compounds 1-219.

| Entry | R group |
|-------|---------|
| 127 | methyl carbamate on cyclopentane with ketone |
| 128 | methyl carbamate on cyclopentane with ketone (stereoisomer) |
| 129 | methyl carbamate on cyclohexane with ketone |
| 130 | methyl carbamate on cyclopentane (1,3-disubstituted) with ketone |
| 131 | methyl carbamate on cyclopentane (1,3-disubstituted) with ketone (stereoisomer) |
| 132 | methyl carbamate on cyclohexane with ketone (stereoisomer) |

TABLE 1-continued
Compounds 1-219.
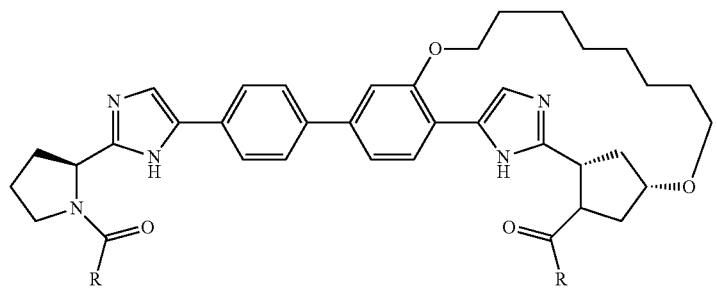
| Entry | |
|---|---|
| 133 | 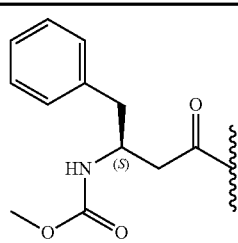 |
| 134 | 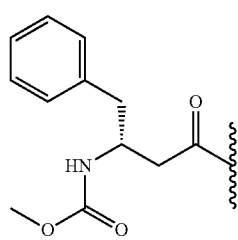 [SMILES: *C(=O)C[C@@H](Cc1ccccc1)NC(=O)OC] |
| 135 | 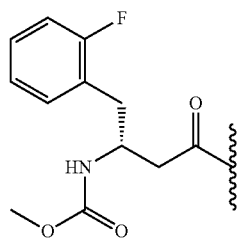 [SMILES: *C(=O)C[C@@H](Cc1ccccc1F)NC(=O)OC] |
| 136 | 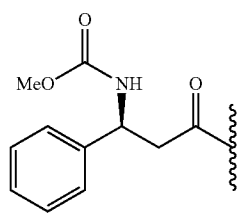 [SMILES: *C(=O)C[C@H](NC(=O)OC)c1ccccc1] |
| 137 | 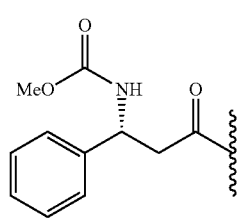 [SMILES: *C(=O)C[C@@H](NC(=O)OC)c1ccccc1] |

TABLE 1-continued

Compounds 1-219.

| Entry | |
|---|---|
| 138 | |
| 139 | |
| 140 | |
| 141 | |
| 142 | |
| 143 | |

TABLE 1-continued
Compounds 1-219.
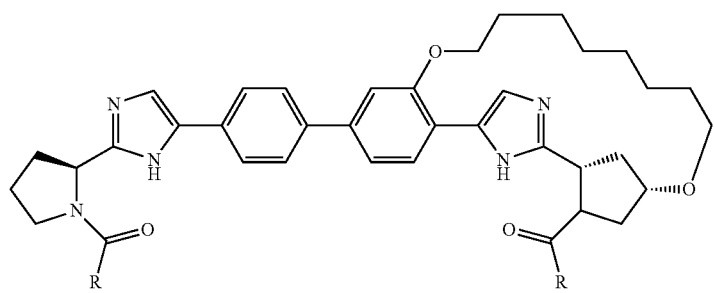
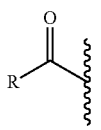
| Entry | |
|---|---|
| 144 | 4-methylpiperazine-N-CH(Ph)-C(O)- |
| 145 | pyrrolidine-N-CH(Ph)-C(O)- |
| 146 | (3S)-3-fluoropyrrolidine-N-CH(Ph)-C(O)- |
| 147 | (3R)-3-fluoropyrrolidine-N-CH(Ph)-C(O)- |
| 148 | 4-phenylpiperidine-N-CH(Ph)-C(O)- |
| 149 | 4-hydroxy-4-methylpiperidine-N-CH(Ph)-C(O)- |
| 150 | 4-hydroxypiperidine-N-CH(Ph)-C(O)- |

TABLE 1-continued

Compounds 1-219.

| Entry | R-C(O)- group |
|---|---|
| 151 | 3-oxopiperazin-1-yl, α-Ph (S) |
| 152 | morpholin-4-yl, α-Ph (S) |
| 153 | piperidin-1-yl, α-Ph (S) |
| 154 | 4-(Cbz)piperazin-1-yl, α-Ph (S) |
| 155 | 2-(trifluoromethyl)phenyl, α-NMe₂ |
| 156 | 3-(trifluoromethyl)phenyl, α-NMe₂ |

TABLE 1-continued

Compounds 1-219.

| Entry | R group |
|---|---|
| 157 | 3-pyridyl-CH(NMe₂)-C(=O)- |
| 158 | 2-pyridyl-CH(NMe₂)-C(=O)- |
| 159 | 4-pyridyl-CH(NMe₂)-C(=O)- |
| 160 | 3-chlorophenyl-CH(NMe₂)-C(=O)- |
| 161 | 2-chlorophenyl-CH(NMe₂)-C(=O)- |
| 162 | 6-chloro-3-pyridyl-CH(NMe₂)-C(=O)- |

TABLE 1-continued
Compounds 1-219.
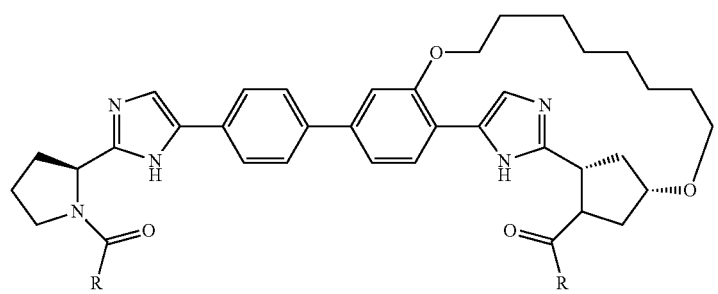
| Entry | 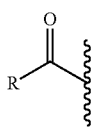 |
|---|---|
| 163 | 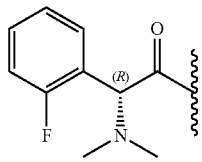 |
| 164 | 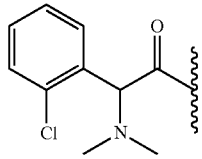 [SMILES: *C(=O)C(c1ccccc1Cl)N(C)C] |
| 165 | 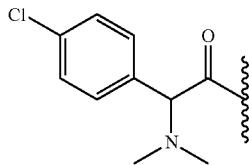 [SMILES: *C(=O)C(c1ccc(Cl)cc1)N(C)C] |
| 166 | 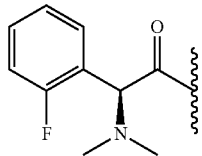 [SMILES: *C(=O)[C@H](c1ccccc1F)N(C)C] |
| 167 | 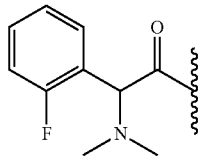 [SMILES: *C(=O)C(c1ccccc1F)N(C)C] |
| 168 | 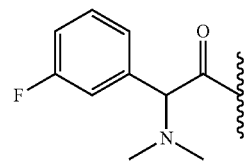 [SMILES: *C(=O)C(c1cccc(F)c1)N(C)C] |

US 9,676,802 B2
TABLE 1-continued
Compounds 1-219.
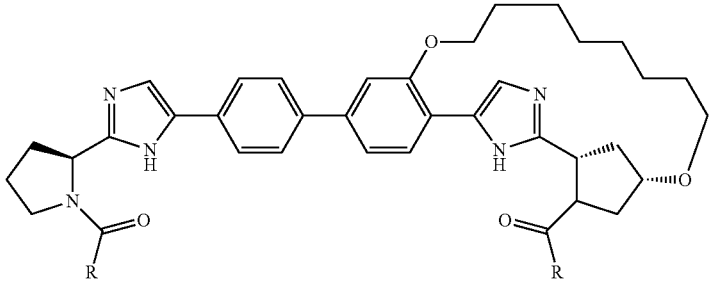
| Entry | |
|---|---|
| 169 | 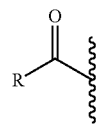 |
| 170 | 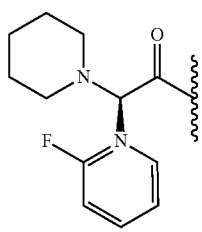 |
| 171 | 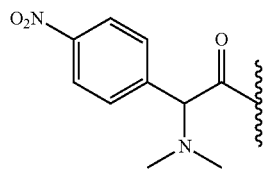 [SMILES: *C(=O)C(c1ccc([N+](=O)[O-])cc1)N(C)C] |
| 172 | 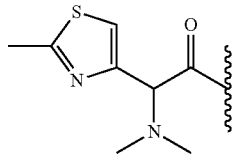 |
| 173 | 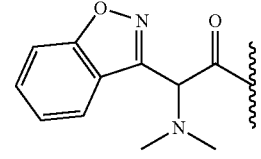 [SMILES: *C(=O)C(c1noc2ccccc12)N(C)C] |
| 174 | 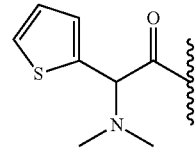 [SMILES: *C(=O)C(c1cccs1)N(C)C] |

TABLE 1-continued
Compounds 1-219.
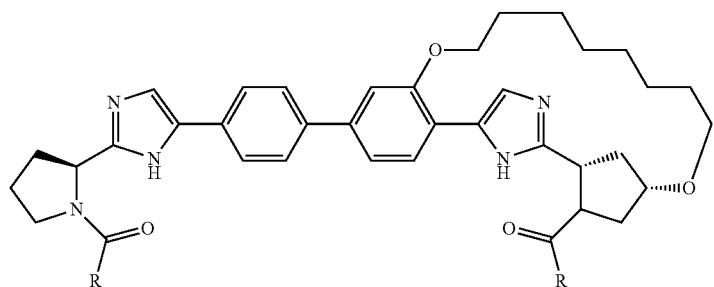
| Entry | |
|---|---|
| 175 | 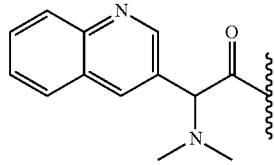 [SMILES: *C(=O)C(c1cnc2ccccc2c1)N(C)C] |
| 176 | 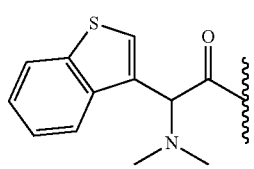 [SMILES: *C(=O)C(c1csc2ccccc12)N(C)C] |
| 177 | 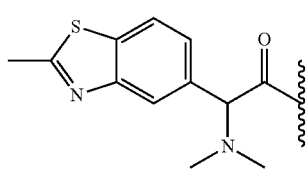 [SMILES: *C(=O)C(c1ccc2sc(C)nc2c1)N(C)C] |
| 178 | 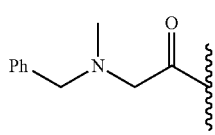 [SMILES: *C(=O)CN(C)Cc1ccccc1] |
| 179 | 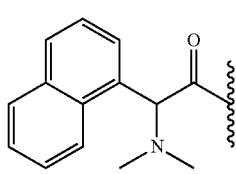 [SMILES: *C(=O)C(c1cccc2ccccc12)N(C)C] |
| 180 | 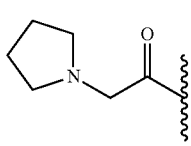 [SMILES: *C(=O)CN1CCCC1] |
| 181 | 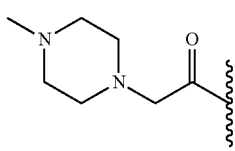 [SMILES: *C(=O)CN1CCN(C)CC1] |

TABLE 1-continued
Compounds 1-219.
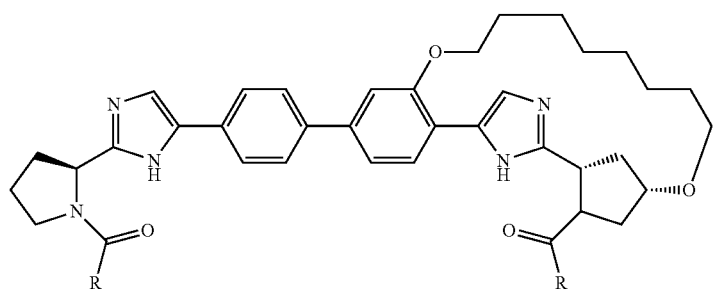
| Entry | R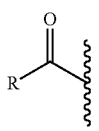 |
|---|---|
| 182 | 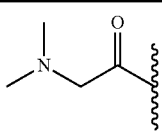 |
| 183 | 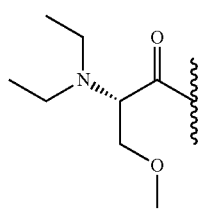 [SMILES: *C(=O)[C@H](COC)N(CC)CC] |
| 184 | 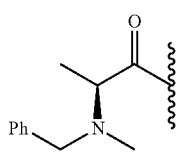 [SMILES: *C(=O)[C@H](C)N(C)Cc1ccccc1] |
| 185 | 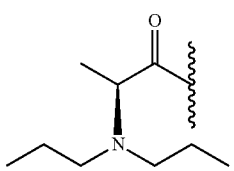 [SMILES: *C(=O)[C@H](C)N(CCC)CCC] |
| 186 | 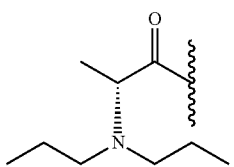 [SMILES: *C(=O)[C@@H](C)N(CCC)CCC] |
| 187 | 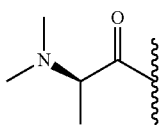 |
| 188 | 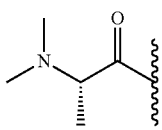 |

TABLE 1-continued

Compounds 1-219.

| Entry | R group |
|---|---|
| 189 | acetamido-alanyl |
| 190 | N,N-diethylamino-alanyl |
| 191 | N,N-diethylamino-alanyl (epimer) |
| 192 | acetamido-D-alanyl |
| 193 | N,N-diethylamino-O-methylseryl |
| 194 | N,N-diethylamino-2-aminobutanoyl |

TABLE 1-continued

Compounds 1-219.

| Entry | |
|---|---|
| 195 | (structure: 2-(diethylamino)-3-methylpentanoyl) |
| 196 | (structure: 2-(N-benzyl-N-methylamino)-3-methylbutanoyl) |
| 197 | (structure: 2-(dimethylamino)propanoyl) |
| 198 | (structure: 2-(diethylamino)-3-carbamoylpropanoyl) |
| 199 | (structure: 2-(diethylamino)-3-methylbutanoyl) |
| 200 | (structure: 2-((4,5-dihydro-1H-imidazol-2-yl)amino)-3-methylbutanoyl) |

US 9,676,802 B2
TABLE 1-continued
Compounds 1-219.
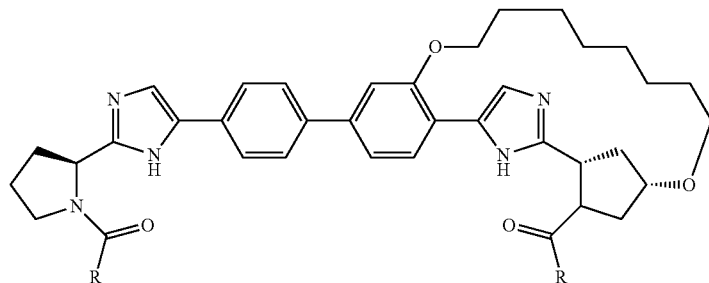
| Entry | |
|---|---|
| 201 | 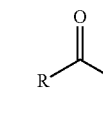 |
| 202 | 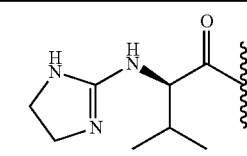 |
| 203 | 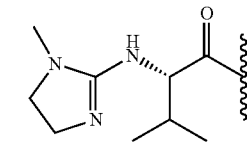 [SMILES: *C(=O)[C@@H](NC1=NCCN1C)C(C)C] |
| 204 | 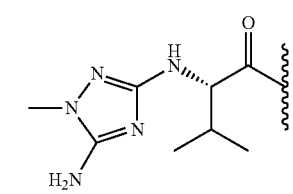 [SMILES: *C(=O)[C@@H](Nc1nc(N)n(C)n1)C(C)C] |
| 205 | 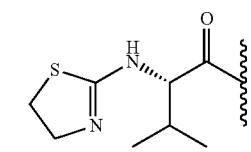 [SMILES: *C(=O)[C@@H](NC1=NCCS1)C(C)C] |
| 206 | 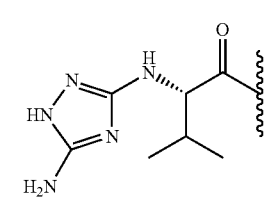 [SMILES: *C(=O)[C@@H](Nc1n[nH]c(N)n1)C(C)C] |
| 207 | 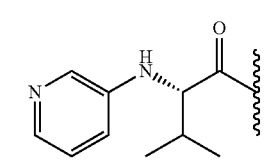 [SMILES: *C(=O)[C@@H](Nc1cccnc1)C(C)C] |

TABLE 1-continued
Compounds 1-219.
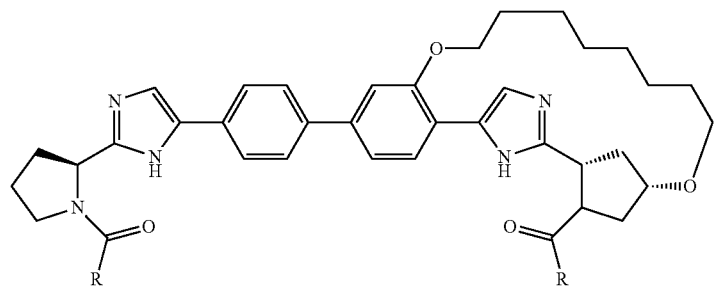
Entry
208 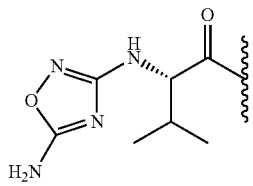 [SMILES: *C(=O)[C@@H](Nc1noc(N)n1)C(C)C]
209 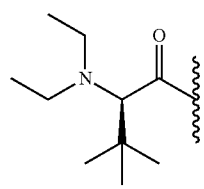 [SMILES: *C(=O)[C@H](N(CC)CC)C(C)(C)C]
210 
211 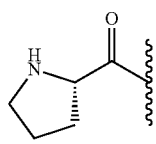 [SMILES: *C(=O)[C@@H]1CCCN1]
212 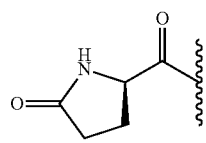 [SMILES: *C(=O)[C@H]1CCC(=O)N1]
213 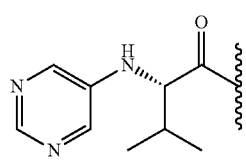 [SMILES: *C(=O)[C@@H](Nc1cncnc1)C(C)C]

TABLE 1-continued

Compounds 1-219.

| Entry | |
|---|---|
| 214 | (pyrrolidine with gem-difluoro at 4-position, C(=O)- attachment) |
| 215 | (pyrrolidine with 4-fluoro, C(=O)- attachment) |
| 216 | (bicyclic pyrrolidine-cyclopropane fused, C(=O)- attachment) |
| 217 | (N-methyl pyrrolidine, C(=O)- attachment) |
| 218 | (N-methyl-4-fluoropyrrolidine, C(=O)- attachment) |
| 219 | (4-fluoropyrrolidine, C(=O)- attachment) |

TABLE 2
Compounds 220-229.
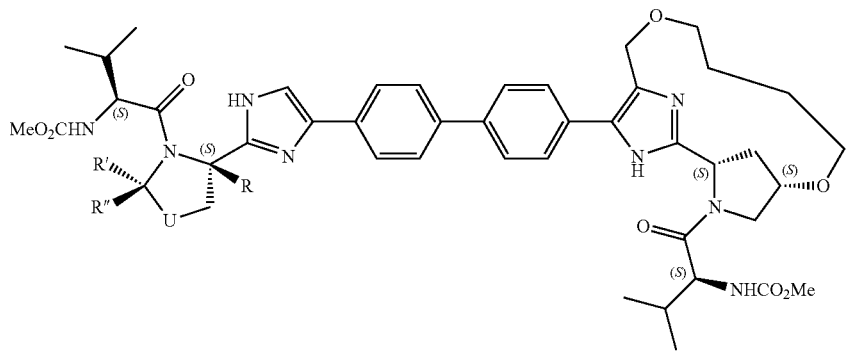
| Entry | R | R' | R" | U |
|---|---|---|---|---|
| 220 | Me | H | H | CH$_2$ |
| 221 | H | H | H | CF2 |
| 222 | Me | H | H | S |
| 223 | H | H | H | 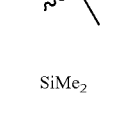 |
| 224 | H | H | H | SiMe$_2$ |
| 225 | H | H | H | 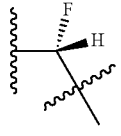 |
| 226 | H | Ph | H | CH$_2$ |
| 227 | H | H | H | 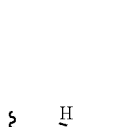 |
| 228 | H | H | Ph | CH$_2$ |
| 229 | H | H | H | 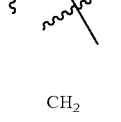 |

TABLE 3
Compounds 230-239.
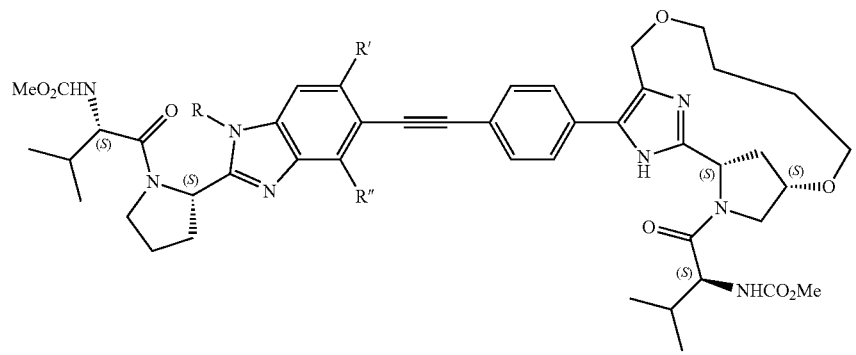
| Entry | R | R' | R" |
|---|---|---|---|
| 230 | Me | H | H |
| 231 | H | CO$_2$Me | H |
| 232 | H | F | H |
| 233 | H | H | CO$_2$Me |
| 234 | H | H | F |
| 235 | H | OMe | H |
| 236 | H | Cl | H |
| 237 | H | H | OMe |
| 238 | H | H | Cl |
| 239 | H | CF$_3$ | H |
TABLE 4
Compounds 240-253.
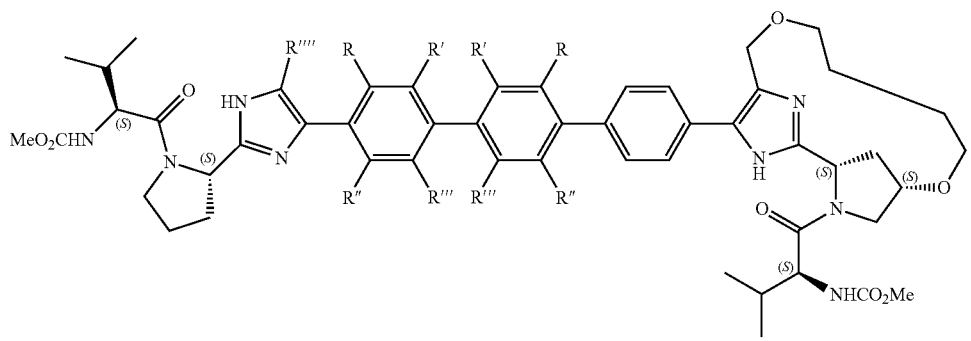
| Entry | R | R' | R" | R''' | R'''' |
|---|---|---|---|---|---|
| 240 | F | H | H | H | H |
| 241 | F | F | H | H | H |
| 242 | Me | H | H | H | H |
| 243 | Me | Me | H | H | H |
| 244 | H | H | Me | Me | H |
| 245 | H | H | Et | Et | H |
| 246 | CF$_3$ | H | H | H | H |
| 247 | CF$_3$ | H | CF$_3$ | H | H |
| 248 | Cl | H | H | H | H |
| 249 | Cl | H | Cl | H | H |
| 250 | H | H | H | H | Br |
| 251 | H | H | H | H | Cl |
| 252 | H | H | H | H | F |
| 253 | H | H | H | H | CF$_3$ |

TABLE 5
Compounds 254-268.
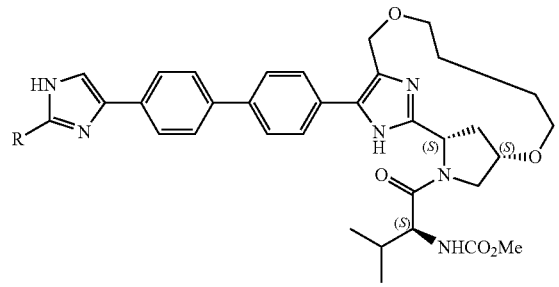
| Entry | R |
|---|---|
| 254 | 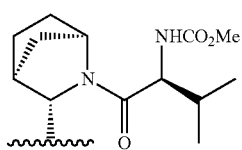 |
| 255 | 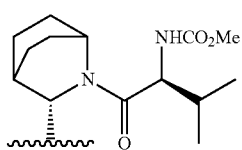 |
| 256 | 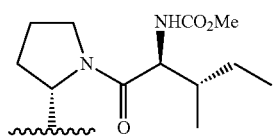 |
| 257 | 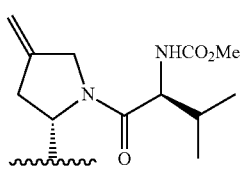 |
| 258 | 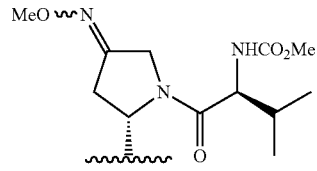 |
| 259 | 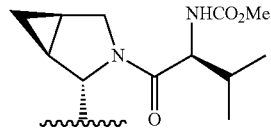 |
| 260 | 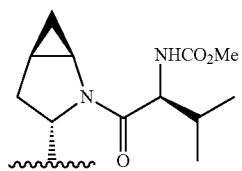 |
TABLE 5-continued
Compounds 254-268.
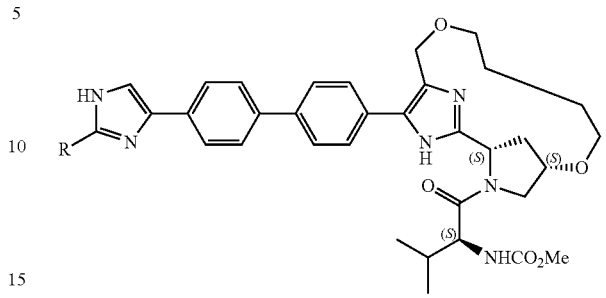
| Entry | R |
|---|---|
| 261 | 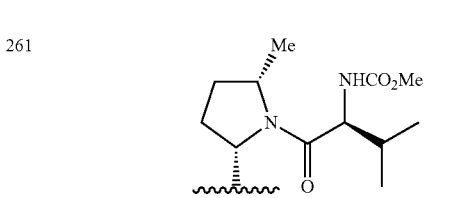 |
| 262 | 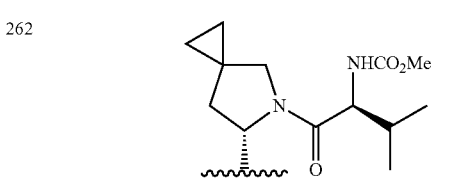 |
| 263 | 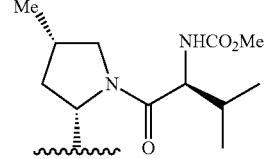 |
| 264 | 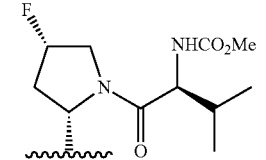 |
| 265 | 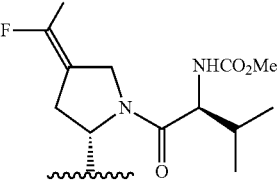 |
| 266 | 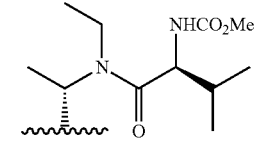 |

TABLE 5-continued

Compounds 254-268.

| Entry | R |
|---|---|
| 267 | (cyclopropyl-CH(N(Me)C(O)-CH(iPr)-NHCO₂Me)-) |
| 268 | (CH₂=CHCH₂-CH(NHC(O)-CH(iPr)-NHCO₂Me)-) |

TABLE 6

Compounds 269-286.

| Entry | Aᵃ |
|---|---|
| 269 | 2,6-naphthalenediyl |
| 270 | quinoline-2,6-diyl |
| 271 | 2,6-anthracenediyl |

TABLE 6-continued
Compounds 269-286.
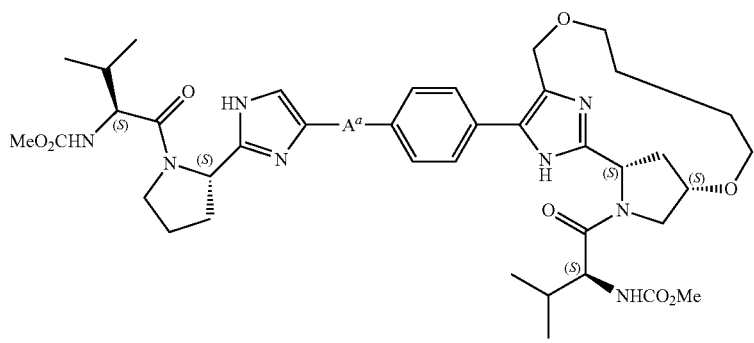
| Entry | $A^a$ |
|---|---|
| 272 | 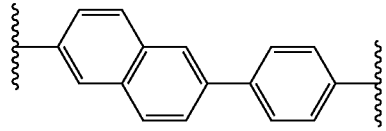 [SMILES: *c1ccc(-c2ccc3cc(*)ccc3c2)cc1] |
| 273 | 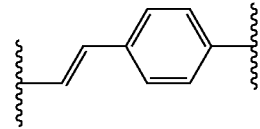 |
| 274 | 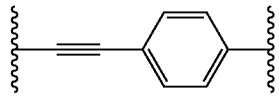 |
| 275 | 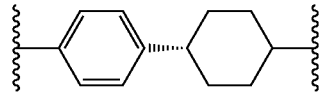 |
| 276 | 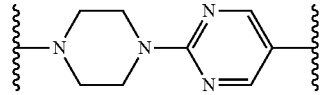 [SMILES: *c1cnc(N2CCN(*)CC2)nc1] |
| 277 | 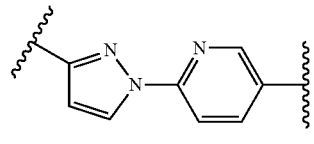 [SMILES: *c1ccc(-n2ccc(*)n2)nc1] |
| 278 | 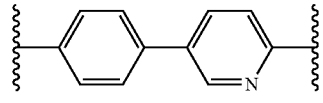 [SMILES: *c1ccc(-c2ccc(*)nc2)cc1] |
| 279 | 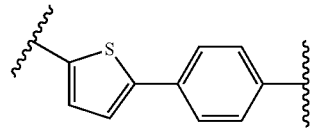 [SMILES: *c1ccc(-c2ccc(*)s2)cc1] |
| 280 | 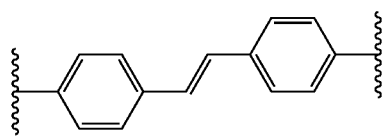 [SMILES: *c1ccc(/C=C/c2ccc(*)cc2)cc1] |

TABLE 6-continued
Compounds 269-286.
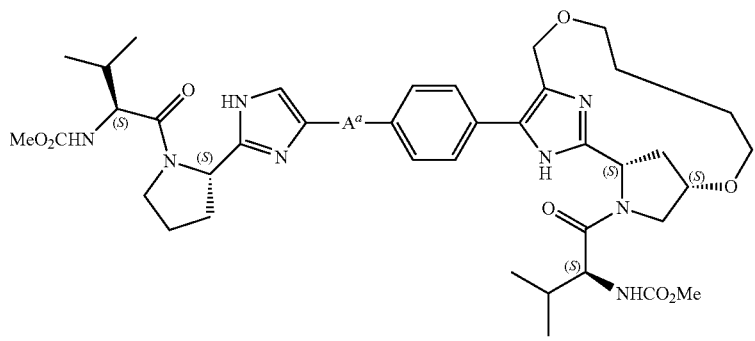
| Entry | $A^a$ |
|---|---|
281
![structure: phenyl-alkyne-thiazole linker]
282
![structure: thiophene-thiazole linker]
283
![structure: vinyl-pyridine linker]
284
![structure: ethyl-naphthalene linker]
285
![structure: vinyl-naphthalene linker]
286
![structure: alkyne-naphthalene linker]

TABLE 7
Compounds 287-307.
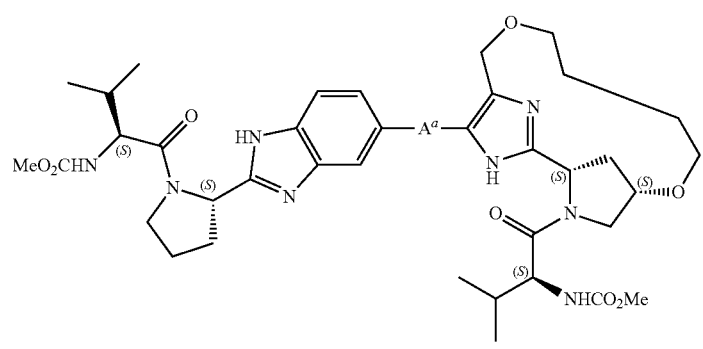
| Entry | $A^a$ |
|---|---|
| 287 | |
| 288 | |
| 289 | |
| 290 | |
| 291 | |
| 292 | |
| 293 | |
| 294 | |
| 295 | |

TABLE 7-continued
Compounds 287-307.
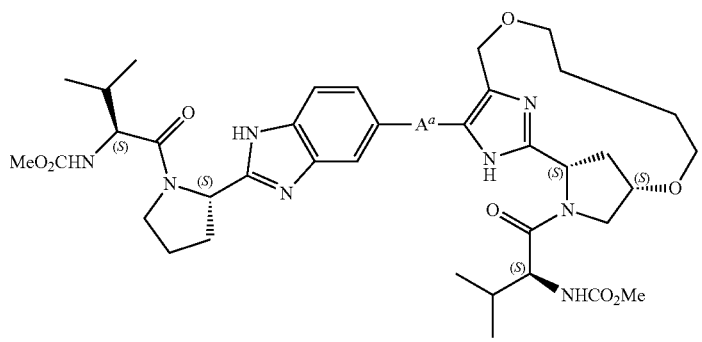
| Entry | $A^a$ |
|---|---|
| 296 | 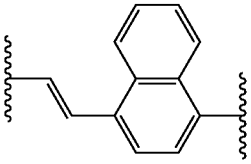 [SMILES: */C=C/c1ccc(*)c2ccccc12] |
| 297 | 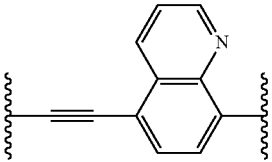 |
| 298 | 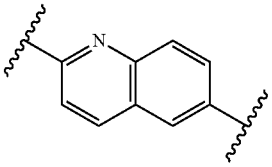 [SMILES: *c1ccc2nc(*)ccc2c1] |
| 299 | 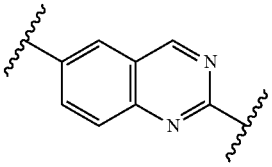 [SMILES: *c1ccc2nc(*)ncc2c1] |
| 300 | 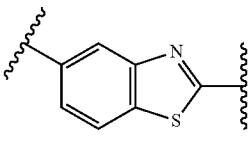 [SMILES: *c1ccc2sc(*)nc2c1] |
| 301 |  |
| 302 | 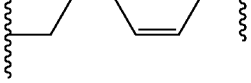 |

TABLE 7-continued
Compounds 287-307.
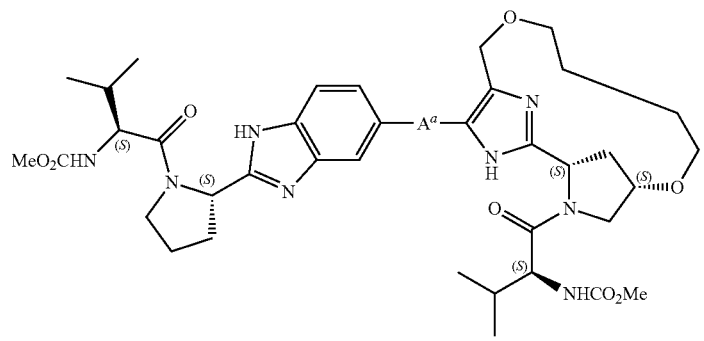
| Entry | $A^a$ |
|---|---|
| 303 | 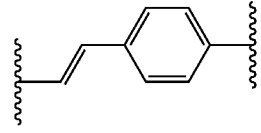 |
| 304 | 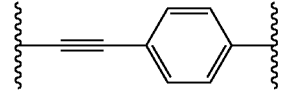 [SMILES: *C#Cc1ccc(*)cc1] |
| 305 | 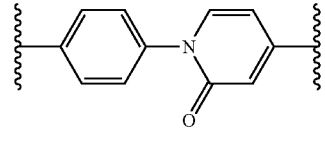 [SMILES: *c1ccc(-n2ccc(*)cc2=O)cc1] |
| 306 | 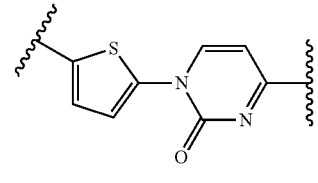 [SMILES: *c1ccn(-c2ccc(*)s2)c(=O)n1] |
| 307 | 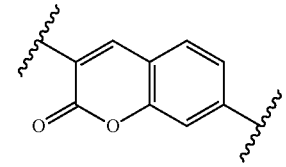 [SMILES: *c1ccc2cc(*)c(=O)oc2c1] |

TABLE 8
Compounds 308-319.
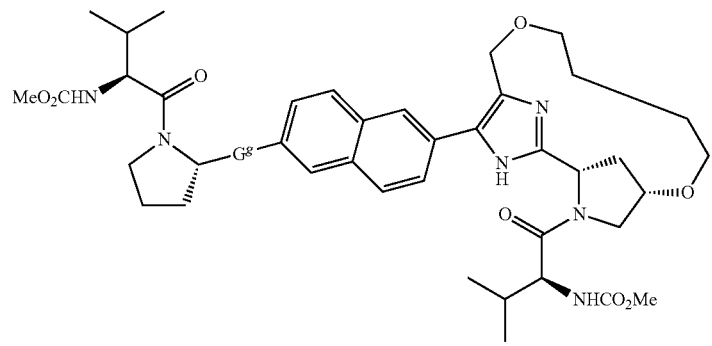
| Entry | G$^g$ |
|---|---|
| 308 | 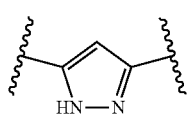 |
| 309 | 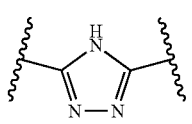 |
| 310 | 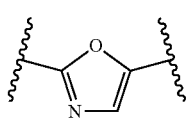 |
| 3117 | 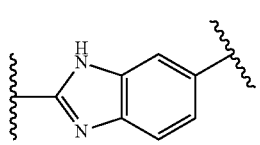 |
| 312 | 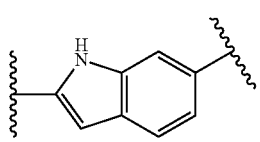 [SMILES: *c1ccc2cc(*)[nH]c2c1] |
| 313 | 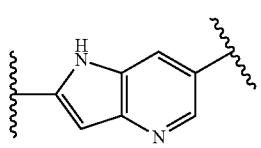 [SMILES: *c1cnc2cc(*)[nH]c2c1] |
| 314 | 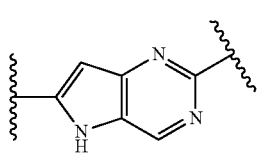 [SMILES: *c1ncc2[nH]c(*)cc2n1] |
| 315 | 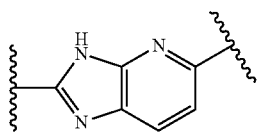 [SMILES: *c1ccc2nc(*)[nH]c2n1] |

TABLE 8-continued
Compounds 308-319.
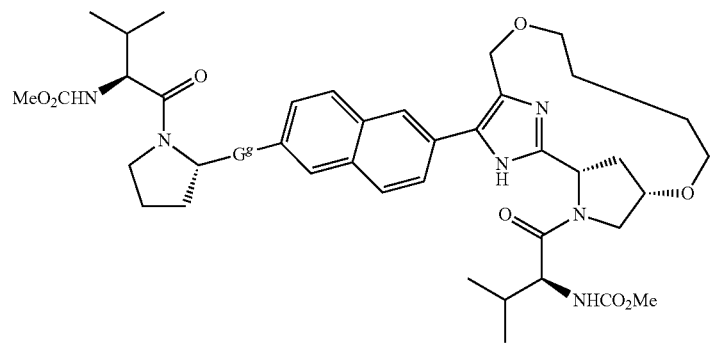
| Entry | G$^g$ |
|---|---|
| 316 | 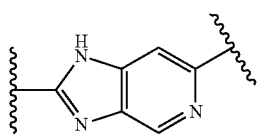 |
| 317 | 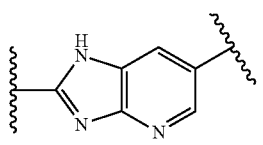 [SMILES: *c1cnc2nc(*)[nH]c2c1] |
| 318 | 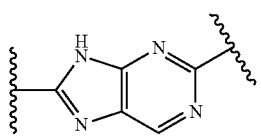 |
| 319 | 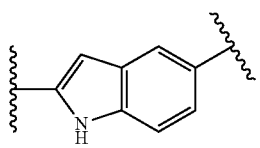 [SMILES: *c1ccc2[nH]c(*)cc2c1] |
TABLE 9
Compounds 320-337.
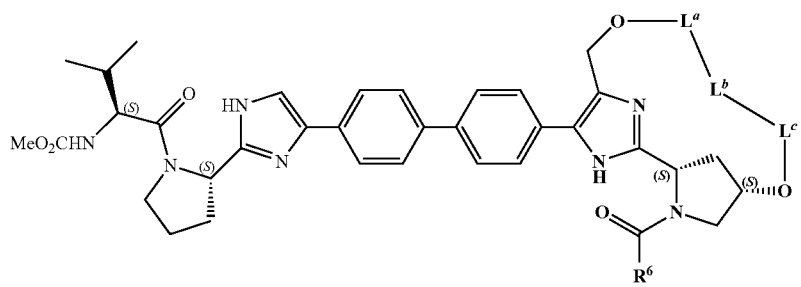
| Entry | L$^a$—L$^b$—L$^c$ |
|---|---|
| 320 | 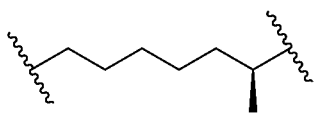 [SMILES: *CCCCC[C@@H](*)C] |

TABLE 9-continued
Compounds 320-337.
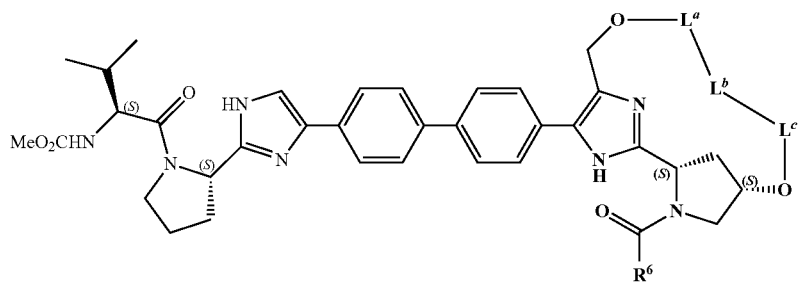
| Entry | $L^a$—$L^b$—$L^c$ |
|---|---|
| 321 | ~CH₂-O-CH₂CH₂CH₂-CH(•)~ |
| 322 | ~CH₂-O-CH₂-CH=CH-CH(•)~ |
| 323 | ~CH₂-O-C(O)-NH-CH₂CH₂~ |
| 324 | ~CH₂-S(O)₂-NH-CH₂CH₂CH₂~ |
| 325 | ~C(O)-NH-CH₂CH₂-O-CH(•)~ |
| 326 | ~CH₂-O-CH₂CH₂CH₂CH₂~ |
| 327 | ~CH₂-O-CH₂CH₂CH₂CH₂-O-CH(•)~ |
| 328 | ~CH₂-O-CH₂CH₂-N=C(CH₃)~ |
| 329 | ~CH₂-O-CH₂-C≡C-CH(•)~ |

TABLE 9-continued
Compounds 320-337.
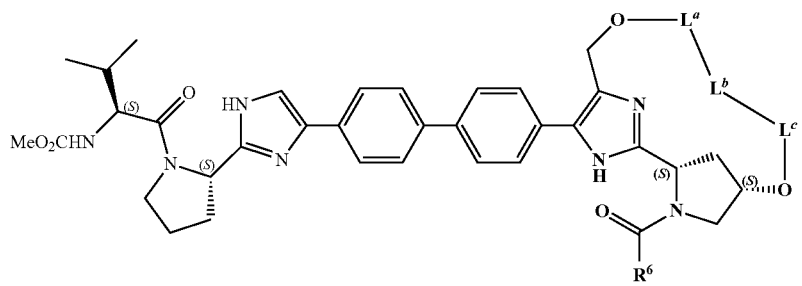
| Entry | $L^a$—$L^b$—$L^c$ |
|---|---|
| 330 | 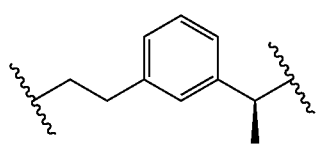 [SMILES: *CCc1cccc([C@@H](*)C)c1] |
| 331 | 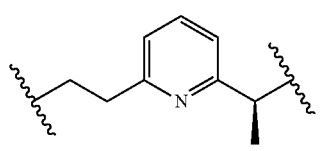 [SMILES: *CCc1cccc([C@@H](*)C)n1] |
| 332 | 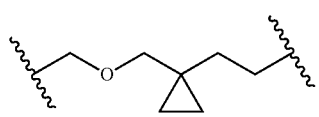 [SMILES: *CCC1(COC*)CC1] |
| 333 | 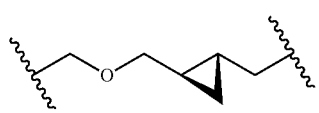 [SMILES: *COC[C@@H]1C[C@H]1C*] |
| 334 | 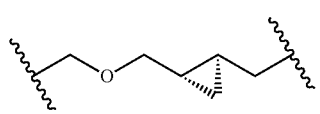 [SMILES: *COC[C@H]1C[C@@H]1C*] |
| 335 | 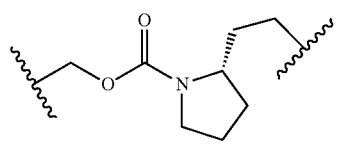 [SMILES: *CC[C@@H]1CCCN1C(=O)OC*] |
| 336 | 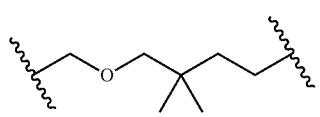 [SMILES: *CCC(C)(C)COC*] |
| 337 | 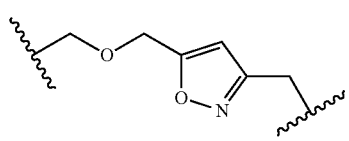 [SMILES: *COCc1cc(C*)no1] |

TABLE 10
Compounds 334-341.
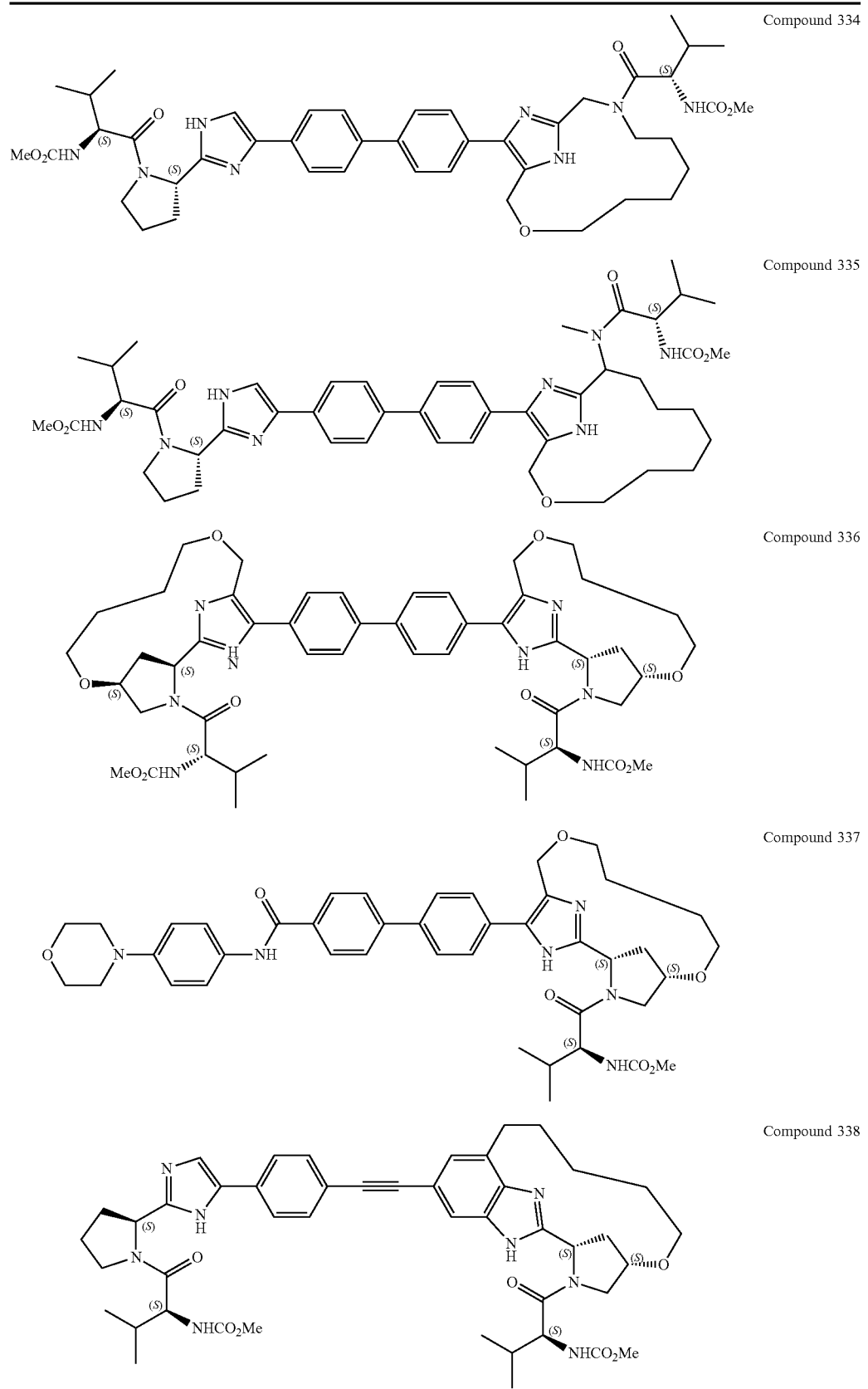
Compound 334
Compound 335
Compound 336
Compound 337
Compound 338

TABLE 10-continued
Compounds 334-341.
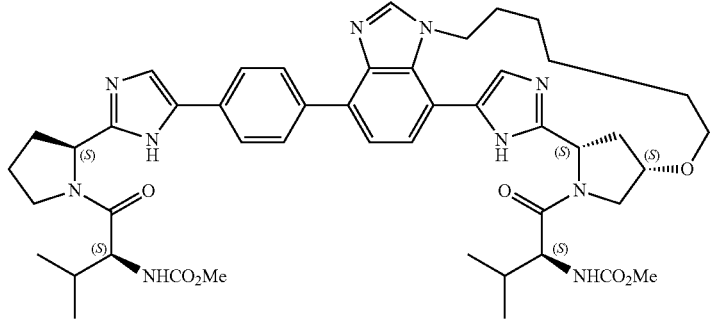
Compound 339
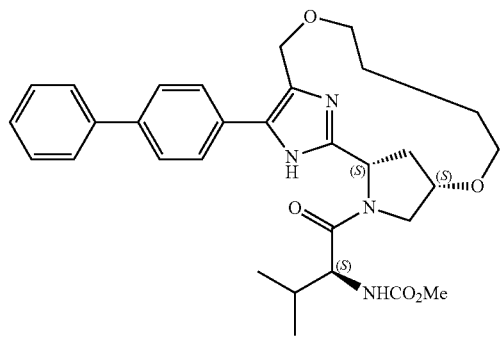
Compound 340
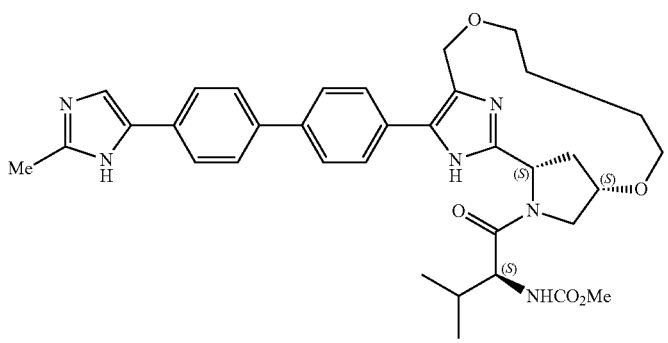
Compound 341
TABLE 11
Compounds 342-346.
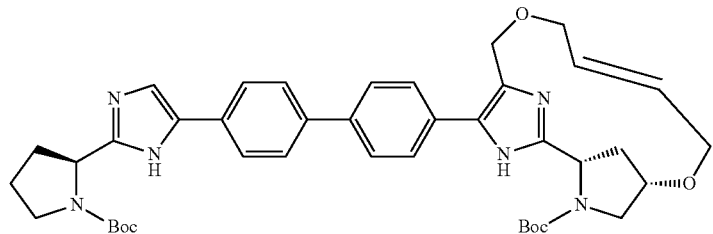 [SMILES: CC(C)(C)OC(=O)N1CCC[C@H]1c1ncc(-c2ccc(-c3ccc(-c4[nH]c5nc4COC/C=C/CO[C@H]4C[C@@H]5N(C(=O)OC(C)(C)C)C4)cc3)cc2)[nH]1]
Compound 342

TABLE 11-continued

Compounds 342-346.

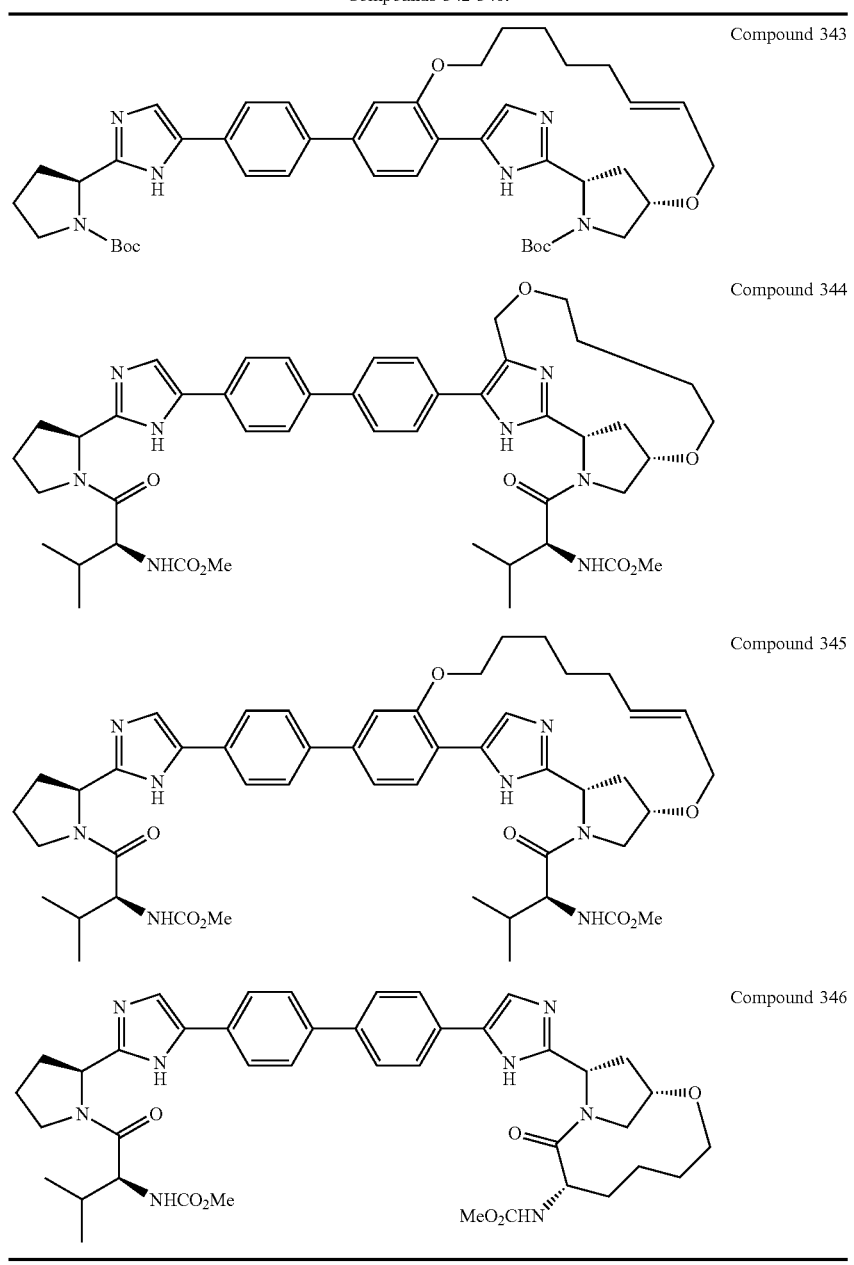

Compound 343

Compound 344

Compound 345

Compound 346

It will be appreciated that the description of the present invention herein should be construed in congruity with the laws and principals of chemical bonding. In some instances it may be necessary to remove a hydrogen atom in order to accommodate a substitutent at any given location.

It is intended that the definition of any substituent or variable (e.g., $R^1$, $R^2$, X, u, m, etc.) at a particular location in a molecule be independent of its definitions elsewhere in that molecule. For example, each of the two $R^6$ groups may be the same or may be different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to, prevention, retardation, prophylaxis, therapy and/or cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising any single compound or a combination of two or more compounds delineated herein, or a pharmaceutically acceptable salt thereof, with a pharmaceutically acceptable carrier or excipient.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for disease caused by HCV infection that suppresses HCV viral replication by direct or indirect mechanisms. These agents include, but are not limited to, host immune modulators (for example, interferon-alpha, pegylated interferon-alpha, consensus interferon, interferon-beta, interferon-gamma, CpG oligonucleotides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, or a pharmaceutically acceptable salt thereof. Examples of the host immune modulator include, but are not limited to, interferon-alpha, pegylated-interferon-alpha, interferon-beta, interferon-gamma, a cytosine, a vaccine, and a vaccine comprising an antigen and an adjuvant, and said second antiviral agent inhibits replication of HCV either by inhibiting host cellular functions associated with viral replication or by targeting proteins of the viral genome. A non-limiting example of the RNA-containing virus is hepatitis C virus (HCV).

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, or a pharmaceutically acceptable salt thereof. A non-limiting example of the RNA-containing virus is hepatitis C virus (HCV).

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, or a pharmaceutically acceptable salt thereof. An agent that treats patients for disease caused by hepatitis B (HBV) infection may be for example, but not limited thereto, L-deoxythymidine, adefovir, lamivudine or tenfovir, or any combination thereof. A non-limiting example of the RNA-containing virus is hepatitis C virus (HCV).

A further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, or a pharmaceutically acceptable salt thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. A non-limiting example of the RNA-containing virus is hepatitis C virus (HCV).

It can occur that a patient may be co-infected with hepatitis C virus and one or more other viruses, including but not limited to human immunodeficiency virus (HIV), hepatitis A virus (HAV) and hepatitis B virus (HBV). Thus also contemplated herein is combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, or a therapeutically acceptable salt thereof, and one or more agents selected from the group consisting of a host immune modulator and one or more additional antiviral agents, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytosine, a vaccine, and a vaccine comprising an antigen and an adjuvant. Preferably said additional antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, or as a pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined herein above, with a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including, but not limited to, agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents that can be administered in combination with a compound of the present invention include a cytochrome P450 monooxygenase inhibitor (also referred to herein as a CYP inhibitor), which is expected to inhibit metabolism of the compounds of the invention. Therefore, the cytochrome P450 monooxygenase inhibitor would be in an amount effective to inhibit metabolism of the compounds of this invention. Accordingly, the CYP inhibitor is administered in an amount sufficient to improve one or more pharmacokinetic (PK) features including, but not limited to, plasma concentration, bioavailiablity, area under the plasma concentration time curve (AUC), elimination half-life, and systemic clearance, of a compound of the invention when one or more of its PK features of said compound is improved in comparison to that in the absence of the CYP inhibitor.

In one embodiment, the invention provides methods for improving the pharmacokinetics of compounds of the invention. The advantages of improving the pharmacokinetics of drugs are recognized in the art (see, for example, US Pat. Publication No's. US 2004/0091527; US 2004/0152625; and US 2004/0091527). Accordingly, one embodiment of this invention provides a method comprising administering an inhibitor of CYP3A4 and a compound of the invention. Another embodiment of this invention provides a method comprising administering a compound of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant compound of the invention may be used in a method of this invention. These CYP inhibitors include, but are not limited to, ritonavir (see, for example, WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, ditiazem, erythromycin, VX-944, and VX-497. Preferred CYP inhibitors include ritonavir, ketoconazole, troleandomycin, 4-methyl pyrazole, cyclosporin, and clomethiazole.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack comprising at least a compound of the invention and a CYP inhibitor and an information insert containing directions on the use of the combination of the invention. In an alternative embodiment of this invention, the pack further comprises one or more of additional agent as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a compound of the invention and a CYP inhibitor (and optionally an additional agent) or derivatives thereof are prepared in a conventional manner. Typically, such a kit will comprise, e. g. a composition of a compound of the invention and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The terms "$C_1$-$C_4$ alkyl," "$C_1$-$C_6$ alkyl," "$C_1$-$C_8$ alkyl," "$C_2$-$C_4$ alkyl," or "$C_3$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$ cycloalkyl", or "$C_4$-$C_7$ cycloalkyl," as used herein, refers to a monocyclic or polycyclic saturated carbocyclic ring compound, and the carbon atoms may be optionally oxo-substituted. Examples of $C_3$-$C_8$ cycloalkyl include, but not limited to, cyclopropyl, cyclobutyl, cyclopentyl, cyclohexyl, cyclopentyl and cyclooctyl; and examples of $C_4$-$C_7$ cycloalkyl include, but not limited to, cyclopentyl, cyclohexyl, bicyclo[2.2.1]heptyl, and the like.

The term "$C_3$-$C_8$ cycloalkenyl" or "$C_5$-$C_7$ cycloalkenyl," as used herein, refers to monocyclic or polycyclic carbocyclic ring compound having at least one carbon-carbon double bond and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

The term "arylalkyl," as used herein, refers to an aryl-substituted alkyl group. More preferred arylalkyl groups are aryl-$C_1$-$C_6$-alkyl groups.

The term "heteroarylalkyl," as used herein, refers to a heteroaryl-substituted alkyl group. More preferred heteroarylalkyl groups are heteroaryl-$C_1$-$C_6$-alkyl groups.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the linear aliphatic group can be selected from one or more of the specified functional groups or a combination thereof, or a group wherein one or more carbons of a non-aromatic hydrocarbon (optionally substituted) is replaced by a specified functional group. In some examples, the linear aliphatic group can be represented by the formula M-V-M', where M and M' are each independently absent or an alkyl, alkenyl or alkynyl, each optionally substituted, and V is a functional group. In some examples, V is selected from the group consisting of C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{11})C(O)C(O)N(R^{11})$, $N(R^{11})S(O)_2N(R^{11})$, $C(O)N(R^{11})S(O)_2$ or $C(O)N(R^{11})S(O)_2N(R^{11})$; wherein $R^{11}$ is as previously defined. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any —C(O)—NH—, alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, —NO$_2$, —N$_3$, —CN, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, CO$_2$—C$_3$-C$_{12}$-cycloalkyl, —CO$_2$— aryl, CO$_2$-heteroaryl, CO$_2$-heterocyloalkyl, —OCONH$_2$, —NH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$— C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O) NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH— C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthio-methyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

As described above, -L$^1$-L$^2$-L$^3$- taken together is a linker group of preferably from 6 to 16, 8 to 12, 8 to 16 or 6 to 14 bond lengths. The preferred 6 to 16, 8 to 12, 8 to 16 or 6 to 14 bond lengths is inclusive of the bonds between the linker and an atom of one of groups Z, B, G and A and between the linker and R$^3$, R$^4$, R$^5$, R$^{7a}$, R$^{7b}$, U, R$^{7aa}$, R$^{7ba}$ or U$^a$. It is to be understood that when the linker includes a cyclic group, the preferred 6 to 16, 8 to 12, 8 to 16 or 6 to 14 bond length is the shortest possible distance, as measured in bond lengths, between an atom of one of groups Z, B, G and A, and R$^3$, R$^4$, R$^5$, R$^{7a}$, R$^{7b}$, U, R$^{7aa}$, R$^{7ba}$ or U$^a$.

The term "hydroxy activating group," as used herein, refers to a labile chemical moiety which is known in the art to activate a hydroxyl group so that it will depart during synthetic procedures such as in a substitution or an elimination reaction. Examples of hydroxy activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenylmethyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenylmethoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, _luminu, acetates, propionates, butyrates, acrylates and ethylsuccinates.

The term "pharmaceutically acceptable prodrugs," as used herein, refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug," as used herein, means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs," Textbook of Drug Design and Development, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, _luminum or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, _luminum or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free _luminum groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of _luminum and amino groups are also included, as are carbonate prodrugs, sulfonate esters and sulfate esters of _luminum groups. Derivatization of _luminum groups as (acyloxy) methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and _luminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery). A discussion of pulmonary delivery of antibiotics is also found in U.S. Pat. No. 6,014,969, incorporated herein by reference.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula (I) described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (e.g. Interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

A compound of the present invention can also be administered in combination or alternation with antiviral agent. Exemplary antiviral agents include ribavirin, interferon, interleukin or a stabilized prodrug of any of them. More broadly described, the compound can be administered in combination or alternation with any of the anti-HCV drugs listed in Table 12 below.

TABLE 12

Table of anti-Hepatitis C Compounds in Current Clinical Development

| Drug name | Drug category | Pharmaceutical Company |
|---|---|---|
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |

TABLE 12-continued

Table of anti-Hepatitis C Compounds in Current Clinical Development

| Drug name | Drug category | Pharmaceutical Company |
|---|---|---|
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HepX™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) | protease inhibitor | InterMune |
| Narlaprevir (SCH 900518) | Protease inhibitor | Schering/Merck |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| INX-189 | Polymerase Inhibitor | Inhibitex |
| PSI-7977 | Polymerase Inhibitor | Pharmasset |
| PSI-938 | Polymerase Inhibitor | Pharmasset |
| R1626 | Polymerase inhibitor | Roche |
| MK-3281 | Polymerase inhibitor | Merck |
| PSI-7851 | Polymerase inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase Inhibitor | Gilead |
| VCH-759 | Polymerase Inhibitor | Vertex |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| BMS-824393 | NS5A inhibitor | Bristol-Myers-Squibb |
| GS-5885 | NS5A inhibitor | Gilead |
| ITX5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-antimiR™-122) | microRNA | Santaris Pharma |
| Debio 025 | Cyclophilin inhibitor | Debiopharm |
| SCY-635 | Cyclophilin inhibitor | Scynexis |

Unless otherwise defined, all technical and scientific terms used herein are accorded the meaning commonly known to one of ordinary skill in the art.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; BtOH for 1-hydroxybenzotriazole; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phosphonium Hexafluorophosphate; Brine for sodium chloride solution in water; Cbz for carbobenzyloxy; CDI for carbonyldiimidazole; CH$_2$Cl$_2$ for dichloromethane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; dppb for diphenylphosphino butane; DBU for 1,8-diazabicyclo[5.4.0]undec-7-ene; DCC for N,N'-dicyclohexylcarbodiimide; DEAD for diethylazodicarboxylate; DIAD for diisopropyl azodicarboxylate; DIBAL-H for diisobutylaluminium hydride; DIPEA or (i-Pr)$_2$EtN for N,N-diisopropylethyl amine; Dess-Martin periodinane for 1,1,1-tris(acetyloxy)-1,1-dihydro-1, 2-benziodoxol-3-(1H)-one; DMAP for 4-dimethylaminopyridine; DME for 1,2-dimethoxyethane; DMF for N,N-dimethylformamide; DMSO for dimethyl sulfoxide; DMT for di(p-methoxyphenyl)phenylmethyl or dimethoxytrityl; DPPA for diphenylphosphoryl azide; EDC for N-(3-dimethylaminopropyl)-N'-ethylcarbodiimide; EDC HCl for N-(3-dimethylamino-propyl)-N'-ethylcarbodiimide hydrochloride; EtOAc for ethyl acetate; EtOH for ethanol; Et$_2$O for diethyl ether; Fmoc for 9-fluorenylmethoxycarbonyl; Grubbs-1 catalyst for benzylidene-bis(tricyclohexylphosphine)dichlororuthenium; HATU for O-(7-azabenzotriazol-1-yl)-N,N,N',N'-tetramethyluronium hexafluorophosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or —SO$_2$—CH$_3$; Ms$_2$O for methanesulfonic anhydride or mesyl-anhydride; NaBH$_4$ for sodium borohydride; NaBH$_3$CN for sodium cyanoborohydride; NaN(TMS)$_2$ for sodium bis(trimethylsilyl)amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$HCO$_3$ for ammonium bicarbonate; NH$_4$Cl for ammonium chloride; NMMO for N-methylmorpholine N-oxide; NaIO$_4$ for sodium periodate; Ni for nickel; OH for hydroxyl; OsO$_4$ for osmium tetroxide; Pd for palladium; Ph for phenyl; PMB for p-methoxybenzyl; POPd for dihydrogen dichlorobis(di-tert-butylphosphinito-κP)palladate(II); Pd$_2$(dba)$_3$ for tris(dibenzylidene-acetone)dipalladium (O); Pd(PPh$_3$)$_4$ for tetrakis(triphenylphosphine)palladium (0); PdCl$_2$(PPh$_3$)$_2$ for trans-dichlorobis(triphenyl-phosphine)palladium (II); Pt for platinum; Rh for rhodium; rt for romm temperature; Ru for ruthenium; SEM for (trimethylsilyl)ethoxymethyl; TBAF for tetrabutylammonium fluoride; TBS for tert-butyl dimethylsilyl; TEA or Et$_3$N for triethylamine; Teoc for 2-trimethylsilyl-ethoxy-carbonyl; TFA for trifluoroacetic acid; THF for tetrahydrofuran; TMEDA for N,N,N',N'-tetramethylethylenediamine; TPP or PPh$_3$ for triphenyl-phosphine; Troc for 2,2,2-trichloroethyl carbonyl; Ts for tosyl or —SO$_2$—C$_6$H$_4$CH$_3$; Ts$_2$O for tolylsulfonic anhydride or tosyl-anhydride; TsOH for p-tolylsulfonic acid; TMS for trimethylsilyl; TMSCl for trimethylsilyl chloride; or Zhan-1b catalyst for 1,3-bis(2,4,6-trimethylphenyl)-4,5-dihydroimidazol-2-ylidene[2-(iso-propoxy)-5-(N,N-dimethylaminosulfonyl)phenyl]methylene ruthenium(II) dichloride.

Synthetic Methods

The compounds and processes of the present invention will be better understood in connection with the following synthetic schemes that illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

The compounds of the present invention may be prepared via several different synthetic routes from a variety of 5/6-membered ring fused heteroaryl, 5-membered ring heteroaryl, and related intermediates. An exemplary method is shown in Schemes 1, 2, 3, and 4. A retro-synthesis of those title compounds include direct formation of a suitable heterocycle (5/6-membered ring fused heteroaryl or 5-membered ring heteroaryl) optionally with a suitable macrocyclic linkage, followed by attachment of a suitable capping group (such as C(O)R$^6$), plus some functional group manipulations in between and/or after. Various 5/6-membered ring fused heteroaryl or 5-membered ring heteroaryl intermediates are known to those skilled in the art, for example see the encyclopedic volumes edited by A. R. Katrizky, et al, "Comprehensive Heterocyclic Chemistry" 1984; "Comprehensive Heterocyclic Chemistry II" 1996; "Comprehensive Heterocyclic Chemistry III" 2008.

A general synthesis and further elaboration of some 6-membered ring fused with imidazole related intermediates are summarized in Scheme 1, in which T is N or CH.

The synthesis starts from the construction of an optionally substituted imidazopyridine or benzimidazole 1-2, which may be obtained by condensation of an amino acid or its derivatives 1-1.1 or 1-1.2 with 2,3-diaminopyridine or 1,2-diaminobenzene 1-1 under the conditions to those skilled in the art. The imidazole ring closure may be realized either in one pot by heat, optionally in the presence of an acid and/or with a dehydration reagent such as polyphosphoric acid; or in two steps: 1) amide formation between diamine 1-1 and amino acid 1-1.1 or 1-1.2 in the presence of a condensation reagent such as EDC.HCl, DCC or the like; or through mixed anhydride approach by reacting acid 1-1.1 or 1-1.2 with a chloroformate such as methyl chloroformate, isobutyl chloroformate, or the like, in the presence of a base such as TEA, DIPEA, DMAP, N-methylmorpholine, or the like, followed by treating the mixed anhydride with diamine 1-1; and 2) the heterocyclic ring closure in the presence of an acid such as acetic acid, sulfuric acid or the like or a dehydration reagent such as HATU or the like, optionally with heat. Other imidazopyridines or benzimidazoles with more substitution may be prepared similarly using the procedures described hereinwith.

Scheme 1

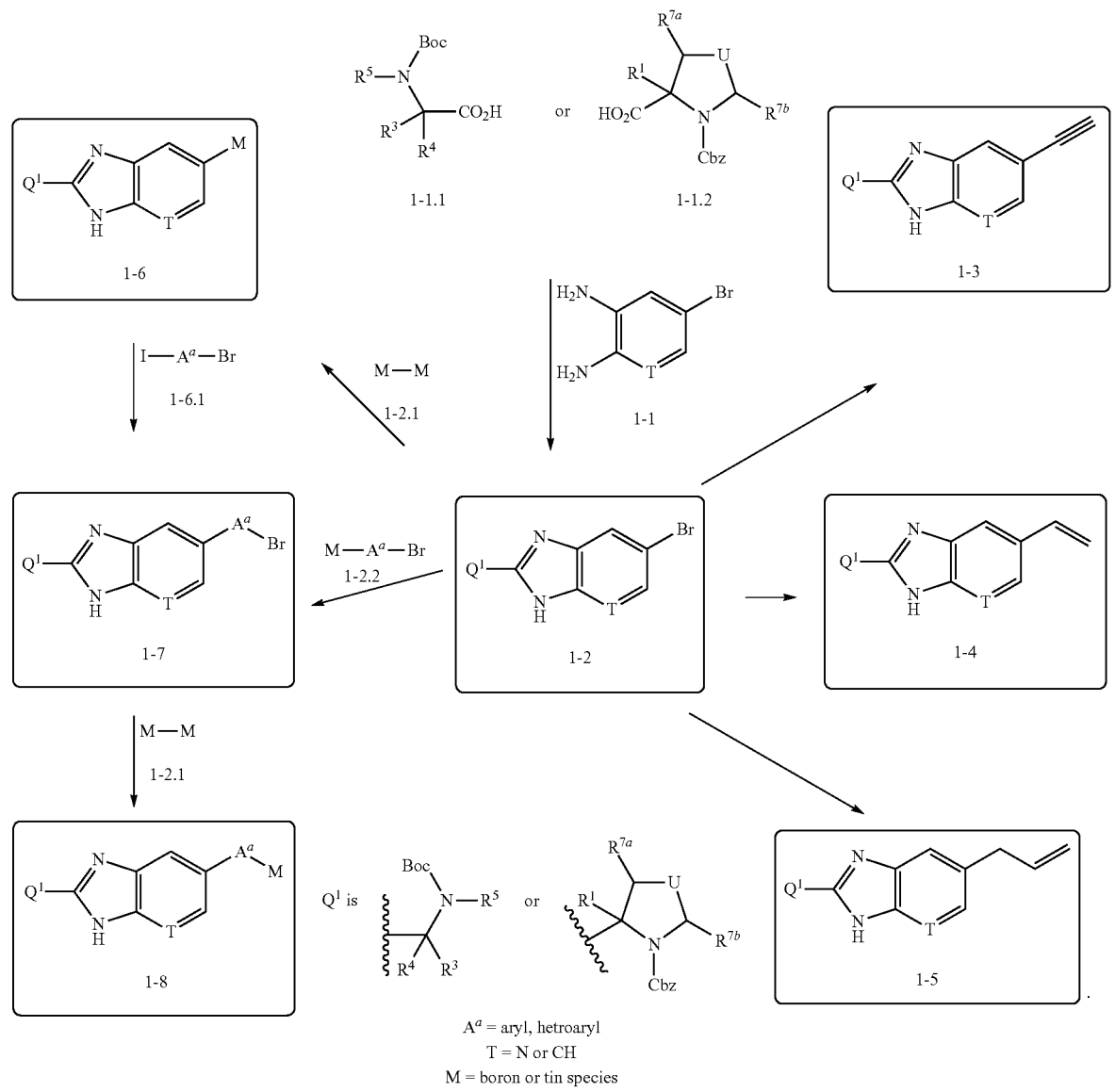

$A^a$ = aryl, hetroaryl
T = N or CH
M = boron or tin species

The imidazopyridine or benzimidazole 1-2 may be subjected to Suzuki, Stille or related coupling conditions known to those skilled in the art (see reviews: A. Suzuki, *Pure Applied Chem.*, 1991, 63, 419; A. Suzuki, *Handbook of Organopalladium Chemistry for Organic Synthesis*, 2002, 1, 249; A. Anastasia, et al, *Handbook of Organopalladium Chemistry for Organic Synthesis*, 2002, 1, 311; F. Bellina, et al, *Synthesis*, 2004, 2419; M. G. Organ, et al, *Synthesis* 2008, 2776; A. T. Lindhardt, et al, *Chem.—A European J.*, 2008, 14, 8756; E. A. B. Kantchev, et al, *Angew. Chem. Int. Ed.*, 2007, 46, 2768; V. Farina, et al, *Advances in Metal-Organic Chem.*, 1996, 5:1) with different coupling partners to provide a variety of key intermediates. For example, Sonogashira coupling between bromide 1-2 and trimethylsilylacetylene can generate alkyne 1-3 after removal of TMS by $K_2CO_3$ in MeOH. Alternatively, bromide 1-2 may be coupled with tributylvinylstanne through Stille reaction conditions known to those skilled in the art to provide alkene 1-4. Analogously, a key allyl Intermediate 1-5 may be prepared by Stille reaction from bromide 1-2 with an allylstanne such as allyltributylstanne.

Alternatively, bromide 1-2 may be converted to key intermediate 1-7 by selectively reacting with metallic reagent 1-2.2 under the Suzuki or Stille conditions which are known to those skilled in the art. Yet alternatively, intermediate 1-7 may be prepared by treating bromide 1-2 with dimetallic agent 1-2.1 to afford organometallic 1-6, followed by coupling with bromoiodoaryl compound 1-6.1, both may be under the previously described Suzuki or Stille reaction conditions. The bromide 1-7 may be further converted to organometallic 1-8 with dimetallic agent 1-2.1 using the conditions described above to prepare 1-6.

It should be noted that optionally the NH group of all the imidazopyridine or benzimidazole related intermediates listed above may be protected with an amino protecting group, such as SEM (i.e. SEM-Cl, NaH), Boc, Cbz, Teoc, Troc, or the like.

Scheme 2

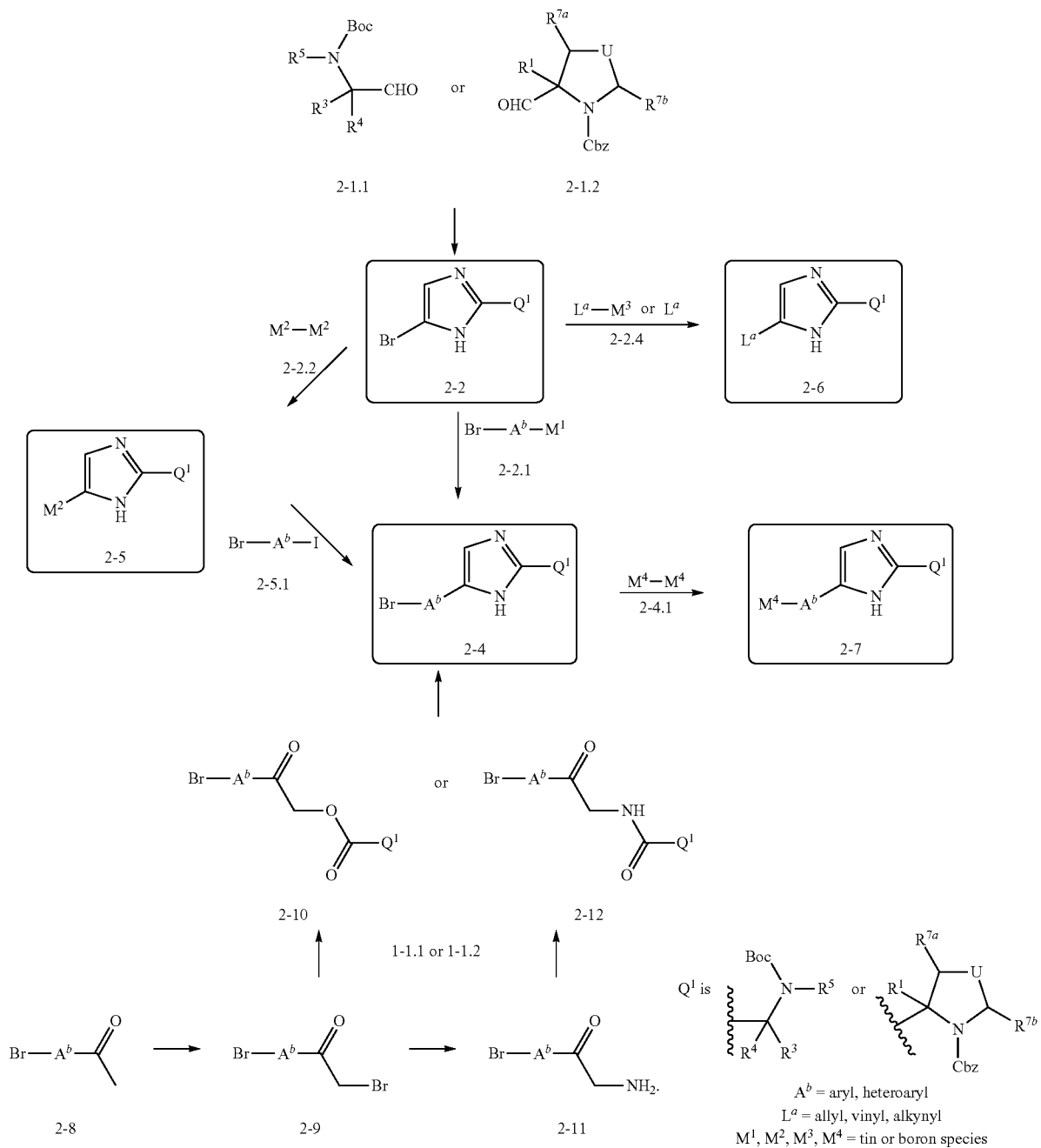

A typical synthesis of imidazole related intermediates are analogous to that of the imidazopyridine or benzimidazole intermediates. As shown in Scheme 2, bromo-imidazole 2-2 can be synthesized by condensation of amino acid derived aldehyde 2-1.1 or 2-1.2 and glyoxal in the presence of methanolic ammonia; followed by bromination of the imidazole ring under the conditions which are known to those skilled in the art. The bromination of the imidazole ring may be realized either in one pot by NBS, bromine, 2,4,4,6-tetrabromo-2,5-cyclohexadienone, or the like; or in two steps: 1) dibromide formation in the presence of excess bromination reagent such as NBS, bromine, 2,4,4,6-tetrabromo-2,5-cyclohexadienone, or the like, optionally with heat; and 2) reduction of the dibromide to monobromide in the presence of a reducing reagent such as $NaHSO_3$, $Na_2S_2O_3$, $Na_2SO_3$, or the like. Bromide 2-2 then may be served as a common intermediate further elaborable to many other imidazole derivatives using the chemistry discussed in Scheme 1. For example, bromide 2-2 may be coupled with allytin or vinyltin or TMS-acetylene to provide intermediate 2-6. Also, bromide 2-2 may be converted to key intermediate 2-4 by selectively reacting with metallic reagent 2-2.1 under the Suzuki or Stille conditions to provide key intermediate 2-4. Yet alternatively, intermediate 2-4 may be prepared by treating bromide 2-2 with dimetallic agent 2-2.2 to afford organometallic 2-5, followed by coupling with bromoiodo-aryl compound 2-5.1, both may be under the previously described Suzuki or Stille reaction conditions. The bromide 2-4 may be further converted to organometallic 2-7 with dimetallic agent 2-4.1 using the conditions described above for the preparation of intermediate 2-5.

Yet alternatively, aryl or heteroaryl bromide 2-4 may also be derived from bromoketone 2-9, which can be prepared from the corresponding ketone 2-8 in the presence of a bromination reagent such as NBS, bromine, or the like, optionally in the presence of an acid and/or with heating. Bromoketone 2-9 may be either converted to the corresponding amine 2-11 through azide substitution followed by reduction, or coupled with protected amino acid 1-1.1 or 1-1.2 in the presence of a base such as $Et_3N$ or DIPEA to afford keto-ester 2-10. Similarly, amine 2-11 may be converted to the corresponding keto-amide 2-12 via condensation with appropriate amino acid under standard amide formation conditions. Both 2-12 and 2-13 may be transformed to key intermediate 2-4 via heating with $NH_4OAc$ under thermal or microwave conditions.

Scheme 2a

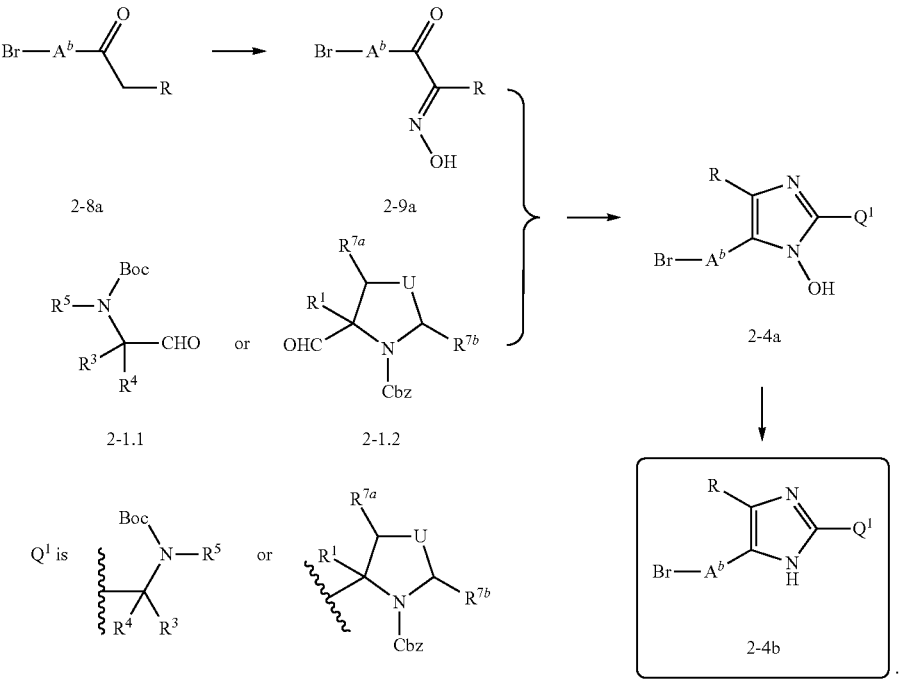

The synthesis of 4,5-disubstituted imidazole related intermediates are analogous to that described in Scheme 2. Alternatively, these imidazole intermediates can be synthesized from ketone 2-8a (Scheme 2a) through nitrosation (sodium nitrite, HCl) to ketoxime 2-9a, which can be cyclized with aldehyde 2-1.1 or 2-1.2 to 1-hydroxyimidazole 2-4a in the presence of ammonia or ammonium hydroxide. Reduction of 2-4a with a suitable reducing reagent such as triethyl phosphite can lead to the requisite imidazole 2-4b.

Scheme 3

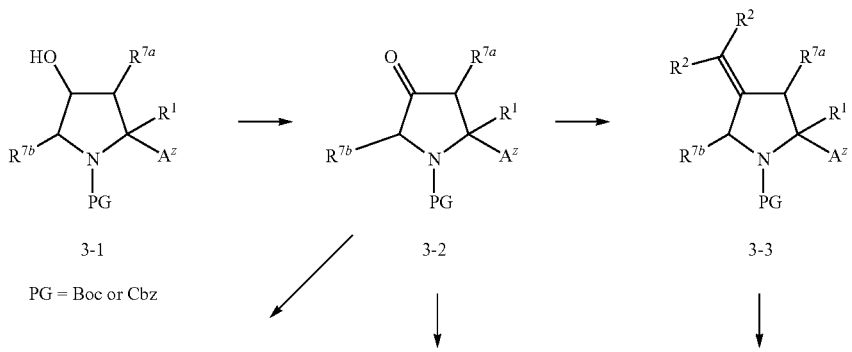

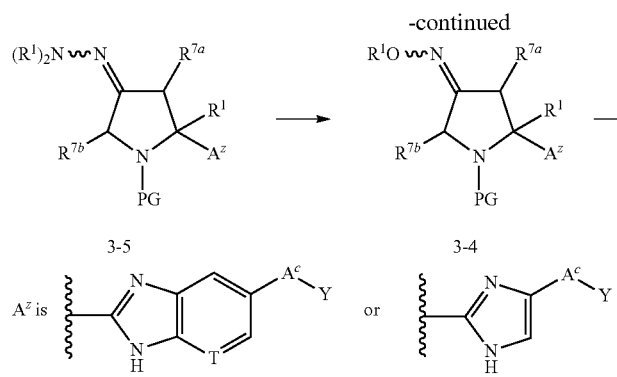

T = N or CH; Y = Br or I;
$A^c$ is absent, aryl or heteroaryl

As shown in Scheme 3, a compound 3-1 containing a hydroxy group substituted at the C4-position of the pyrrolidine ring may be illustrated by intermediates 1-2, 1-3, 1-4, 1-5, 1-7, 2-2, 2-4, and 2-6 when U is CH(OH) as shown in Schemes 1-2. Oxidation of 3-1 by a variety of oxidation agents such as Dess-Martin periodinane optionally in the presence of an acid such as acetic acid or camphorsulfonic acid may afford the ketone 3-2. More reagents and conditions for the oxidation of an alcohol to a ketone can be found in *Comprehensive Organic transformations*, R. C. Larock Ed., Wiley-RCH, 1999, page 1236-1249. 3-2 may then serve as a universal intermediate for further derivatization to olefin 3-3, oxime 3-4 and hydrazone 3-5. The olefination of 3-2 may be realized by various types of Wittig Reaction or Peterson Reaction, a more detailed reagents and conditions can be found in *Comprehensive Organic transformations*, R. C. Larock Ed., Wiley-RCH, 1999, page 327-350. The olefin 3-3 may be converted to cyclopropane 3-6 through the well-known Simmons-Smith cyclopropanation, a more detailed reagents and conditions can be found in *Name Reactions and Reagents in Organic Synthesis* B. P. Munday, et al Ed., Wiley, 2005, page 600 and J. C. Lorenz, et al, *J. Org. Chem.*, 2004, 69, 327 and references cited therein.

Scheme 3a

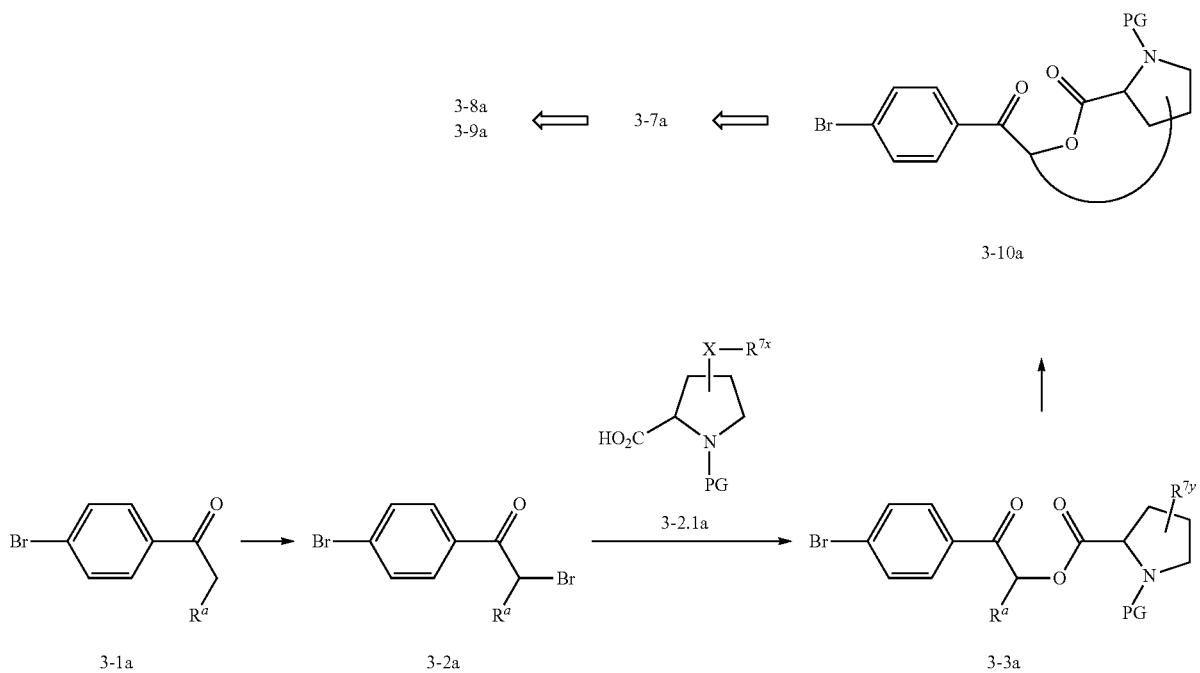

-continued

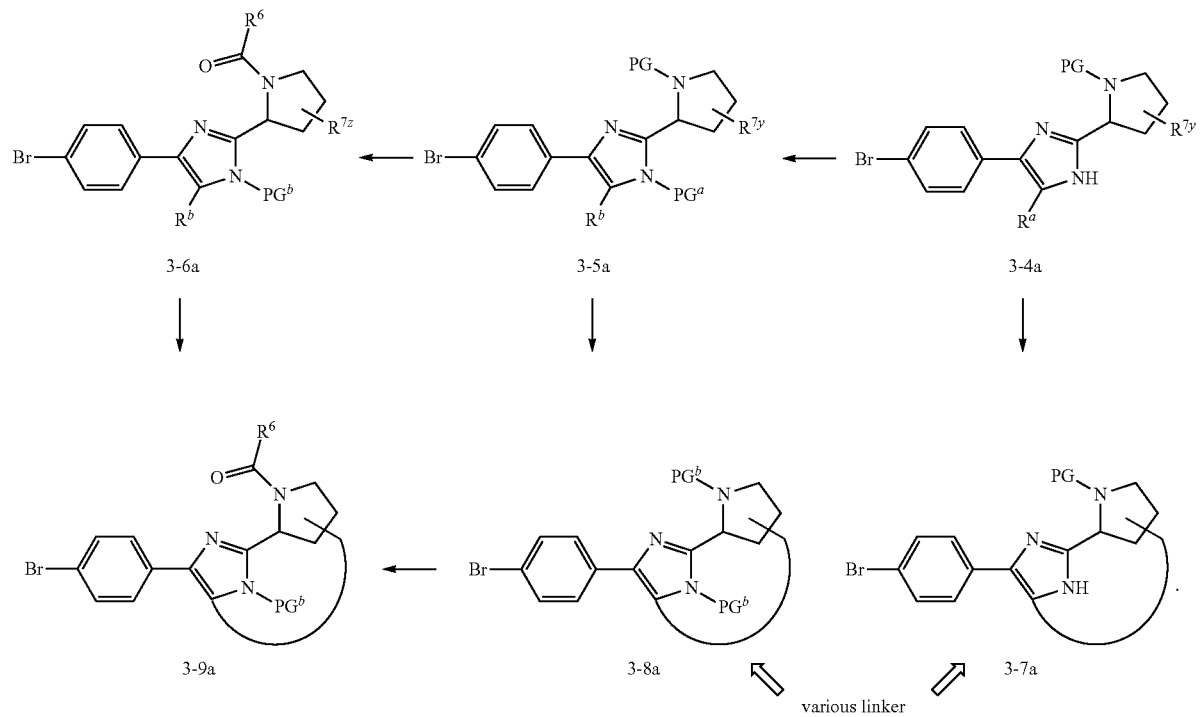

Suitably substituted analogs of intermediates 1-2, 2-4, 2-4b or the compounds in Scheme 3 may be used as precursors to make a macrocyclic derivative after suitable manipulations and transformations of functional groups or protection groups. As illustrated in Scheme 3a with phenylimidazole analogs. Bromination of ketone 3-1a (wherein $R^a$ is an optionally substituted alkyl, optionally substituted alkenyl, optionally substituted alkynyl, or alkoxycarbonyl), may lead to bromide 3-2a. The latter is then esterified with a protected proline derivative 3-2.1a (wherein PG is a protection group; X is absent, oxygen or substituted amino; $R^{7x}$ is derived from $R^1$, $R^{1a}$, $R^7$, $R^{7a}$, $R^{7aa}$, $R^{7b}$, or $R^{7ba}$; wherein $R^{7x}$ is not hydrogen and may be an optionally substituted alkyl, optionally substituted alkenyl, optionally substituted alkynyl, alkoxycarbonyl) prepared from the commercial available starting materials to afford ketoester 3-3a (wherein $R^{7y}$ is X—$R^{7x}$ or derived from X—$R^{7x}$ through functional group manipulation), which can be converted to imidazole 3-4a using the chemistry described in Scheme 2. The imidazole moiety in 3-4a may be optionally protected to 3-5a (wherein $PG^a$ is a protection group). The conversion from 3-4a to 3-5a may optionally involve one or more steps of functional group manipulation, thus $R^b$ in 3-5a may be the same as or different from $R^a$ as in 3-4a depending on the interchange of functional groups. These transformation step(s) may include, but not limited to alkylation, etherification, esterification, amidation, reduction, oxidation, olefination, halogenation, oximation, and/or hydroxylation. Compound 3-5a may be converted to 3-6a (wherein $PG^b$ is hydrogen or PO by two steps: 1) deprotection of the pyrrolidine PG group and optionally the imidazole protective $PG^a$ group in 3-5a, 2) the released pyrrolidine amine functionality may be acylated with a carboxylic acid ($R^6$COOH, wherein $R^6$ is as previously defined) under standard acylation conditions, for example, a coupling reagent such as HATU in combination with an organic base such as DIPEA can be used in this regard. Various carboxylic acids including amino acids in racemic or optical form are commercially available, and/or can be synthesized in racemic or optical form, see references cited in reviews by D. Seebach, et al, *Synthesis*, 2009, 1; C. Cativiela and M. D. Diaz-de-Villegas, *Tetrahedron: Asymmetry*, 2007, 18, 569; 2000, 11, 645; and 1998, 9, 3517; and experimental examples compiled in patent application WO 08/021927 A2 by C. Bachand, et al, from BMS, the contents of which are incorporated herein by reference. The conversion of 3-5a to 3-6a may optionally involve one or more steps of functional group manipulation, thus $R^{7z}$ in 3-6a may be the same as or different from $R^7$ as in 3-5a depending on the interchange of functional groups. A pair of two reactive groups in $R^a$ and $R^{7y}$ in 3-4a, $R^b$ and $R^{7y}$ in 3-5a and $R^b$ and $R^{7z}$ in 3-6a may undergo an intramolecular reaction to form a macrocyclic structure as seen in 3-7a, 3-8a and 3-9a under appropriate reaction conditions, optionally in the presence of catalyst(s) and/or promoter(s). The reaction that can be used to succeed this intramolecular cyclization may include, but not limited to etherification, ester formation, reductive amination, amide formation, carbamate formation, urea formation, ring-closure-metathesis, Pd-catalyzed selective cross-couplings, oximation, various types of Diels-Alder reaction, and/or radical cyclization. Optionally compounds 3-7a and 3-8a may be converted to 3-9a using similar chemistry described previously. Alternatively, a pair of two reactive groups in $R^a$ and $R^7$ in 3-4a may undergo an intramolecular macrocyclization at the ketoester stage as seen in 3-10a under appropriate reaction conditions described above.

Scheme 3b

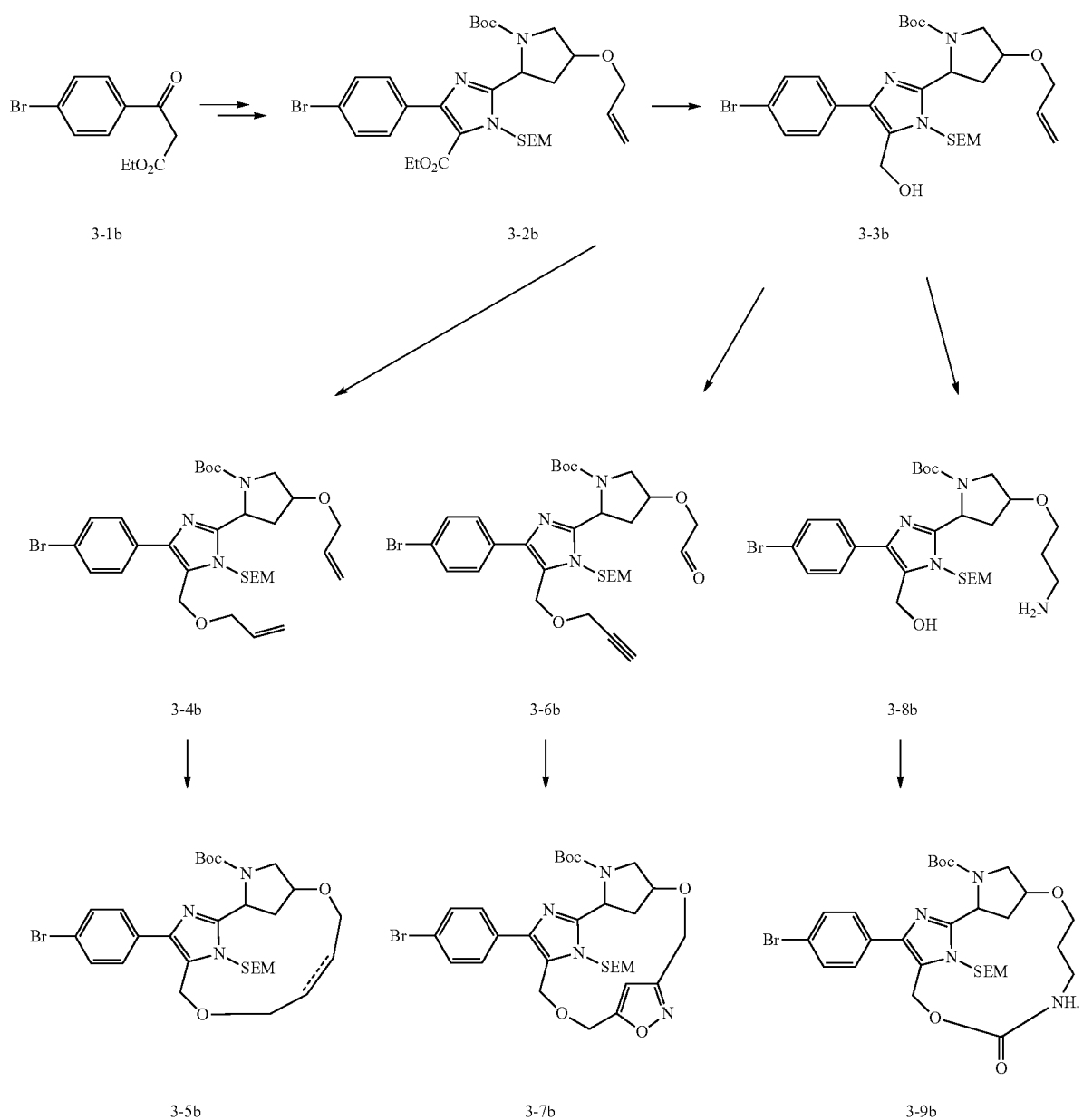

An example of strategies that may be used to form the macrocyclic structures are illustrated in Scheme 3b, wherein bromophenyl imidazole 3-2b can be obtained from ketone 3-1b using the procedures described above. 3-2b can be reduced by DIBAL-H to alcohol 3-3b, which is then served as a universal intermediate for further transformations. Thus, 3-4b may be obtained from 3-3b by allylation with allyl bromide and sodium hydride in DMF. The diene 3-4b can be converted to macrocyclic olefin 3-5b (wherein the dotted bond may be nil or a single bond) through metal-catalyzed ring-closure-metathesis (RCM), which is well-known to those-in-the-art. Similarly 3-3b can be alkylated with propargyl bromide, followed by oxidatively cleavage of the olefinic double bond to afford acetylenic aldehyde 3-6b. The aldehyde in 3-6b may be converted to oxime by hydroxylamine, which can be converted in situ to its nitrile oxide by NCS type reagent, and the latter may react with the triple bond to fulfil the "click" reaction to afford the macrocyclic isoxazole derivative 3-7b. Alternatively 3-3b can be converted to compound 3-8b in few steps: 1) protection of the hydroxy group as an acetate; 2) hydroboration with 9-BBN followed by sodium perborate oxidation to generate an alcohol; 3) conversion of the newly produced alcohol to an iodide with iodine and triphenylphosphine; 4) replacement of the iodide to azide by sodium azide; 5) deprotection of the acetate; and 6) reduction of the azide to amine. The free hydroxy and amino group in 3-8b may be united into a carbamate group by a reagent such as CDI, phosgene or the like to the macrocyclic carbamate 3-9b.

Scheme 3c

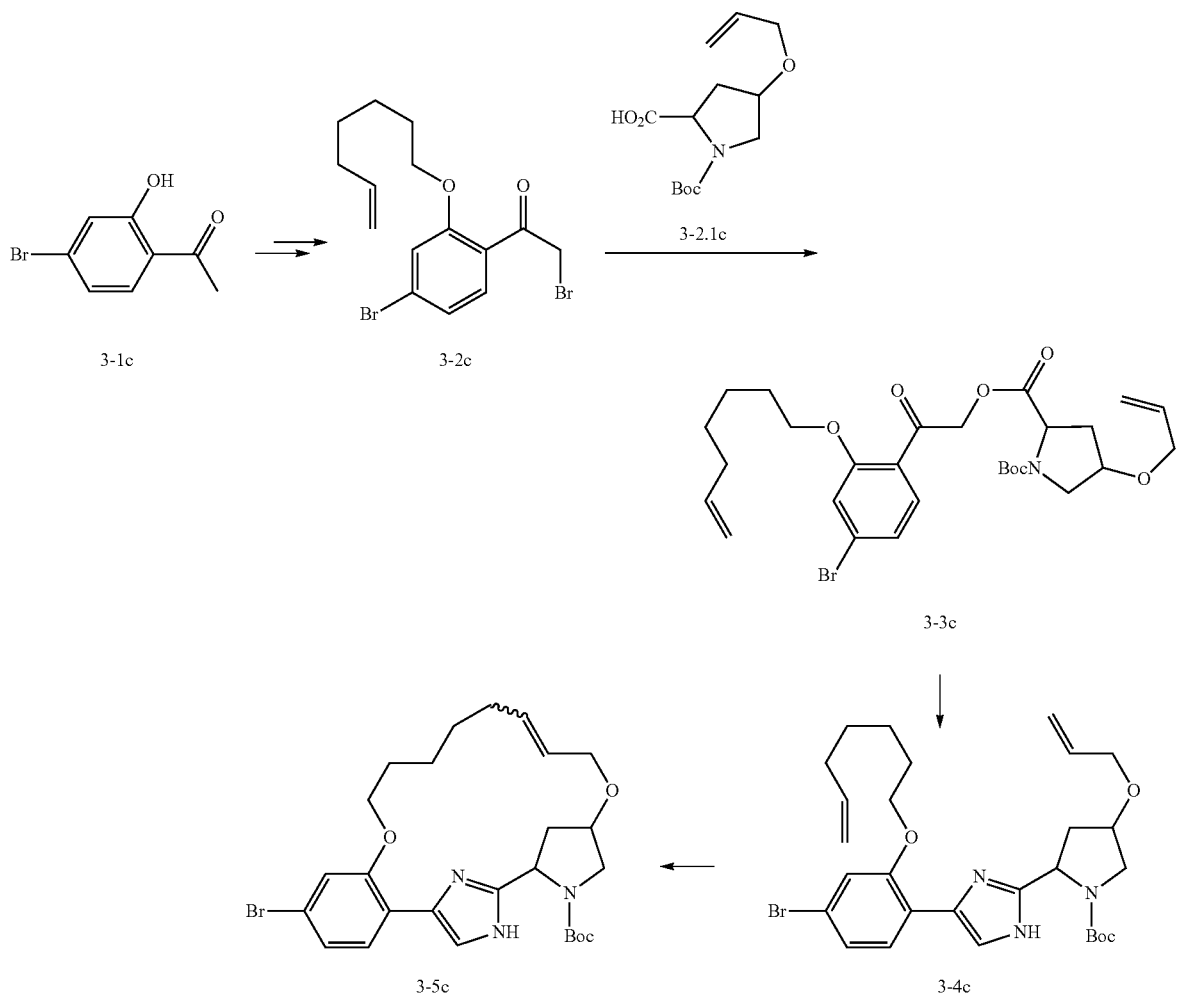

Similar strategies may be used to construct the macrocyclic moiety from attachment other than on imidazole. As illustrated in Scheme 3c, wherein the phenol in 3-1c can be alkylated with a bromide containing an olefinic double bond, such as 7-bromo-1-heptene, to give 3-2c. Intermediate 3-2c can be converted to macrocyclic 3-5c through intermediates, ketoester 3-3c and imidazole 3-4c, using similar chemistry described above.

With a variety of suitably substituted imidazopyridines, benzimidazoles and imidazoles such as those listed in Schemes 1-3, 2a, 3a, 3b and 3c in hand, the compounds of the present invention may be prepared through various coupling strategy or a combination of strategies to connect two fragments, optionally with a suitable cyclic or acyclic linker or formation of a cyclic or acyclic linker. The said strategy may include, but not limited to, Stille coupling, Suzuki coupling, Sonogashira coupling, Heck coupling, Buchwald amidation, Buchwald amination, amide coupling, ester bond formation, William etherification, Buchwald etherification, alkylation, pericyclic reaction with different variations, or the like.

Scheme 4

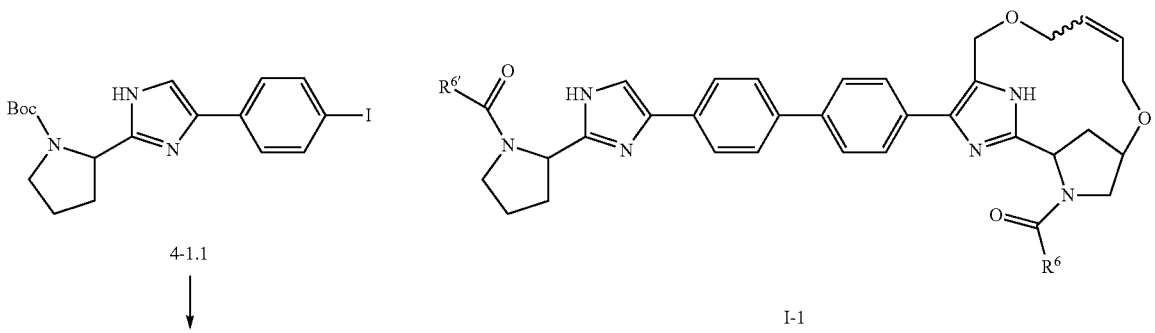

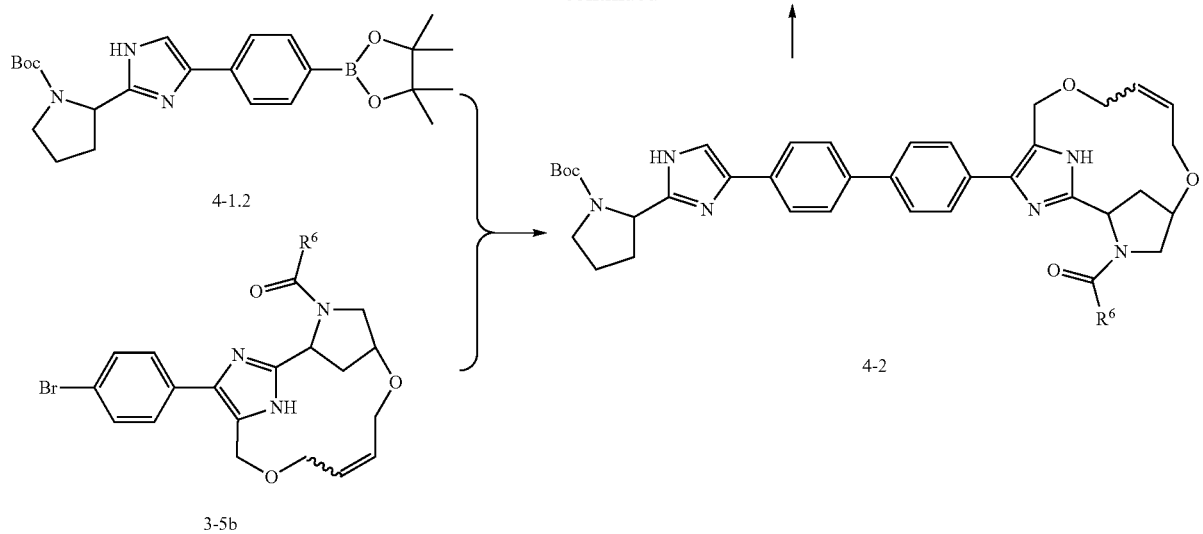

4-1.2

3-5b 4-2

An example of the strategies that may be used to prepare the compounds of the present invention is shown in Scheme 4. Both iodide 4-1.1 and its corresponding boronate derivative 4-1.2 can be prepared using similar procedures described previously. The bromide 3-5b can be coupled with boronate 4-1.2 under Suzuki condition in the presence of a Pd-catalyst to generate a core structure 4-2. Compound 4-2 then may be served as a common intermediate for further derivatizations to the title compounds I-1 using the procedures described above. Wherein the $R^{6'}$ has the same definition as $R^6$, but not necessary be identical.

Scheme 4a

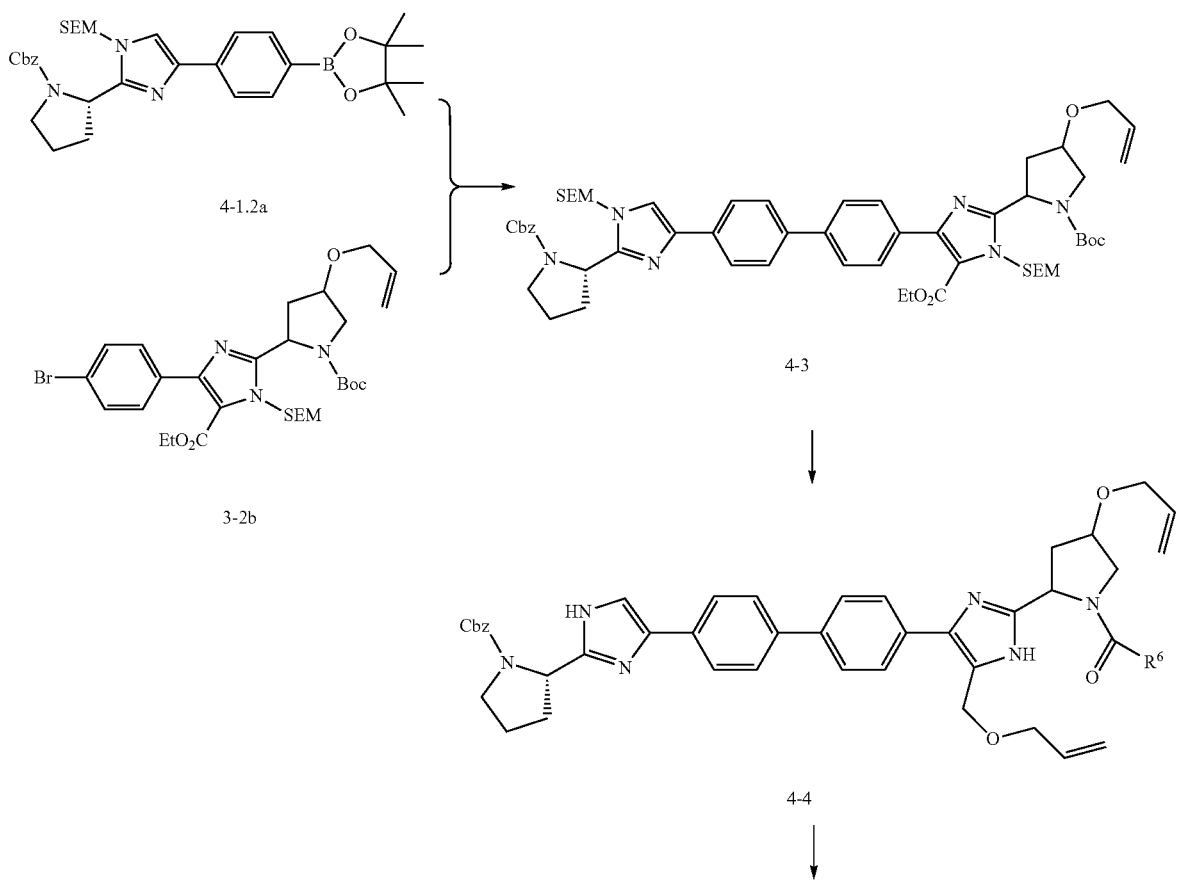

4-1.2a 3-2b 4-3

4-4

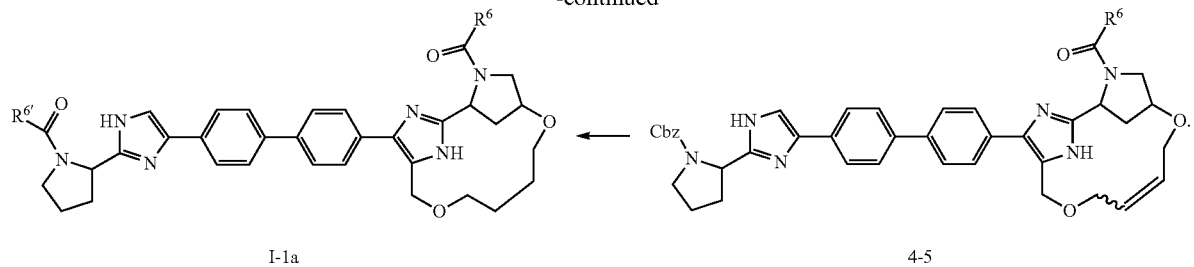

Yet alternatively, as shown in Scheme 4a, the compounds of the present invention (for example I-1a) may also be derived from key intermediate 4-3 after Suzuki coupling of 4-1.2a and 3-2b using the procedures described previously. Compound 4-3 can be converted to di-olefin 4-4 in a few steps: a) selectively reduced to alcohol; b) allylated to allylic ether; c) deprotected Boc and SEM; and d) capped with $R^6$, using the procedures described previously. As discussed earlier, the diene 4-4 can be converted to the title compound I-1a through RCM to macrocyclic intermediate 4-5 followed by de-Cbz under hydrogenation condition and capping with an acyl derivative all using the procedures described earlier.

3-5c can be coupled with boronate 4-1.2 under Suzuki condition in the presence of a Pd-catalyst to generate a core structure 5-1. Compound 5-1 then may be served as a common intermediate for further derivatizations to the title compounds 5-2.

The compounds of the present invention containing five-membered heteroaryl other than imidazole may be prepared using similar procedures described above in Schemes 1-4 and 4a. For example, some intermediates containing a desired, suitably substituted five-membered heteroaryl have

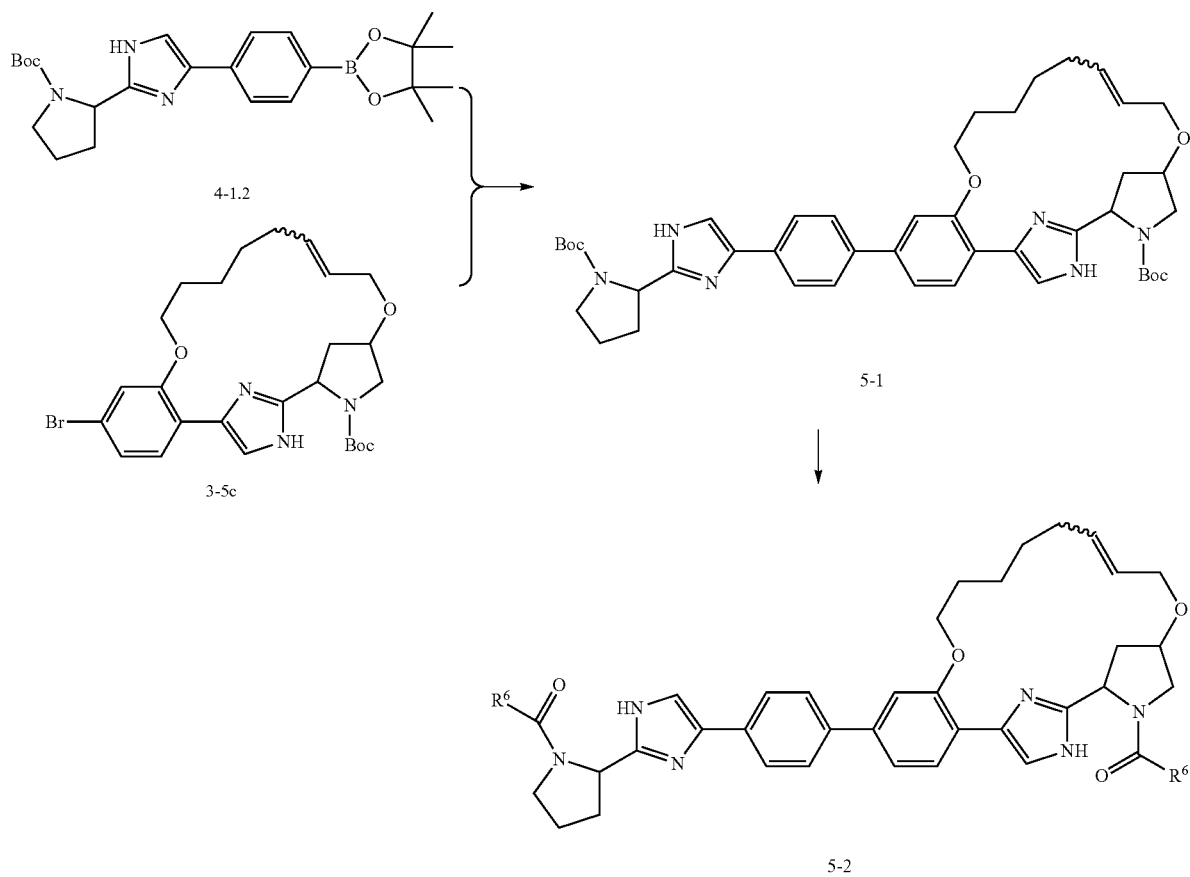

Still alternatively, similar coupling strategies may be applied to the macrocyclic moiety from attachment other than on imidazole. As showed in Scheme 5, the bromide been published in US 2008/0311075A1 by C. Bachand, et al from BMS. These intermediates are compiled in the following Table 13.

TABLE 13

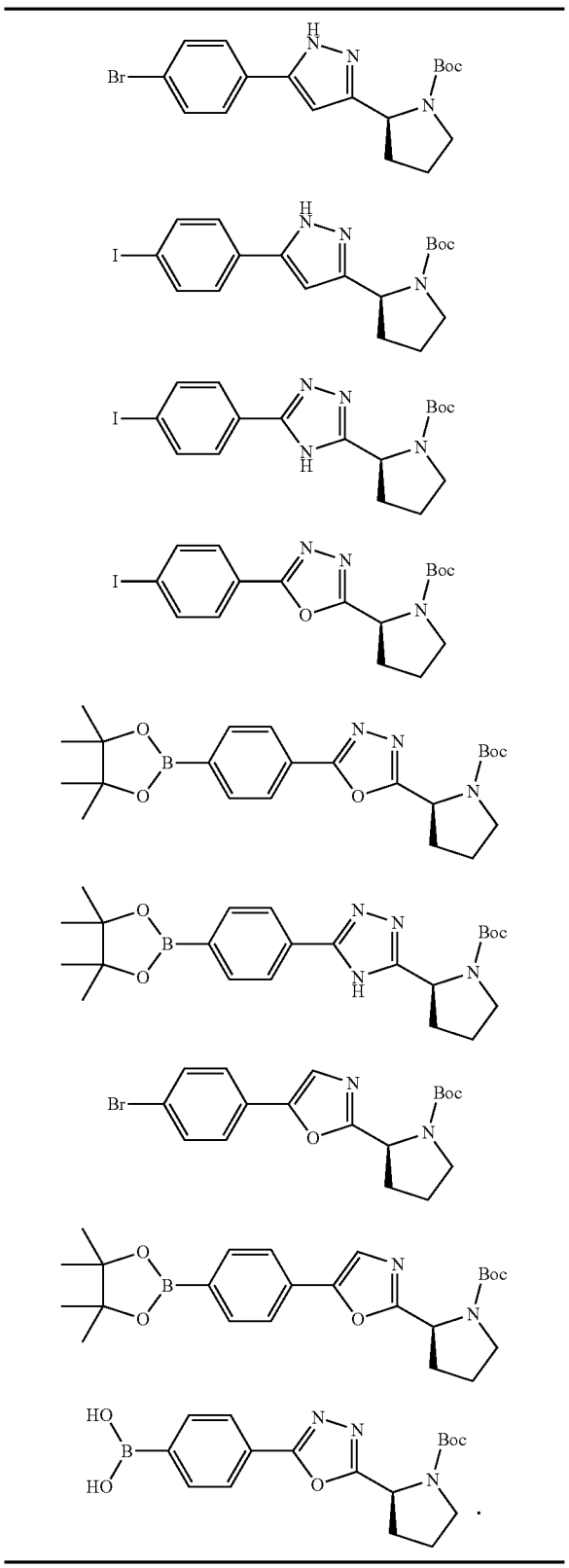

The synthesis of the compounds of the present invention involves 5/6-membered fused heteroaryl intermediates other than benzimidazoles, various 5/6-membered fused heteroaryl are known in the literature. The synthesis of other 5/6-membered fused heteroaryl intermediates depends on the chemical features of each structure. For example, a typical synthesis of indole intermediate is illustrated in Scheme 6. The commercially available bromoiodoaniline 6-1 may be coupled to the commercially available acetylene 6-1.1 under the Sonogashira conditions to give phenylacetylene 6-2. The latter may be cyclized to indole 6-3 under heat or microwave condition in the presence of a copper catalyst.

Scheme 6

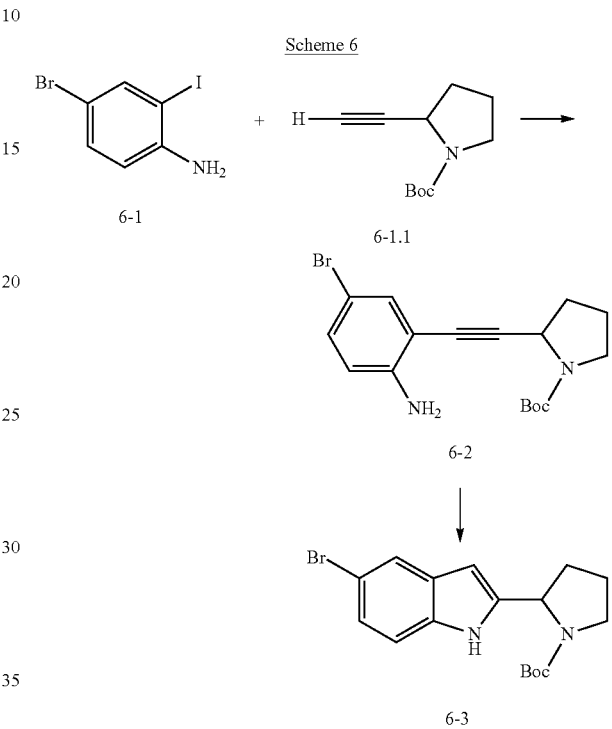

Some intermediates and/or precursors that may be used for the synthesis of the compounds of the present invention have also been disclosed in the following patent publications: WO 2009/102568A1; WO 2009/102633A1; WO 2010/065668A1; WO 2010/065674A1; WO 2010/065681A1; WO 2010/09677A1; WO 2010/111483A1; WO 2010/111534A1; WO 2010/111673A1; WO 2010/120935A1; WO 2010/132538A1A1; WO 2010/132601A1; WO 2010/138368A1; WO 2010/138488A1; WO 2010/138790A1; WO 2010/138791A1; WO 2010/144646A2; US 2010/0215618A1; WO 2011/004276A1; WO 2011/028596A1; WO 2011/060000A1; WO 2011/066241A1; WO 2011/075439A1; WO 2011/075615A1; WO 2011/091417A1; WO2011/112429; WO2011/119853; WO2011/119858; WO2011/119860; WO2011/119870; WO2011/127350; WO2011/149856; WO2011/150243; WO2011/153396; WO2011/154871; WO2011/156543; WO2011/156578; WO2011/156757A; WO2012/003642; WO2012/009394; WO2012/013643; WO2012/018325; WO2012/018534; WO2012/020036; WO2012/021591; WO2012/021704; WO2012/027712; WO2012/039717; WO2012/040389; WO2012/040923; WO2012/040924; WO2012/041014; WO2012/041227; WO2012/048421; WO2012/050848; WO2012/050850; WO2012050918; WO2012/051361; WO2012/061552; WO2012/068234; WO2012/074437; WO2012/083043; WO2012/083048; WO2012/083053; WO2012/083058; WO2012/083059; WO2012/083061; WO2012/083164; WO2012/083170; WO2012/087976; WO2012/109080; WO2012/116257; WO2012/

122716; WO2012/123298; and WO2012/125926, which are each incorporated by reference herein.

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 83

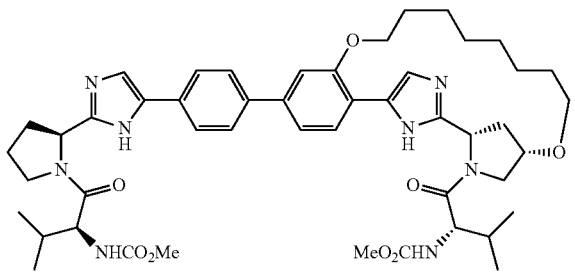

The title compound was prepared from the compounds from Example 345 (described below) using procedures similar to that described in step 338a (below). ESIMS m/z=881.66 [M+H]+.

Example 342

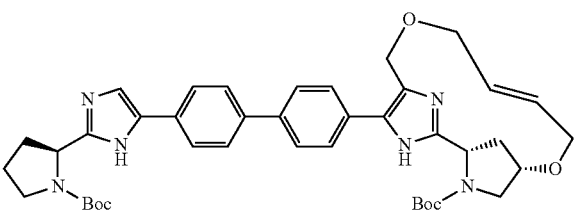 [SMILES: CC(C)(C)OC(=O)N1CCC[C@H]1c1ncc(-c2ccc(-c3ccc(-c4[nH]c5nc4COC/C=C/CO[C@H]4C[C@@H]5N(C(=O)OC(C)(C)C)C4)cc3)cc2)[nH]1]

Step 342a.

In to a solution of (2S,4S)-1-tert-butyl 2-methyl 4-hydroxypyrrolidine-1,2-dicarboxylate (2.0 g, 8.15 mmol) and allyl tert-butyl carbonate (2.57 g, 16.3 mmol) in THF (30 mL) was added the $Pd_2(dba)_3$ (149 mg, 0.163 mmol) and dppb (139 mg, 0.326 mmol). It was stirred at rt for 30 minutes before being heated at 75° C. for 2 hours. After cooling it was concentrated and chromatographied (silica) to give the desired product as a colorless oil (2.23 g, 96%). $^1$H NMR (CDCl$_3$, δ, ppm): 5.85 (m, 1H), 5.24 (dd, 1H), 5.18 (dd, 1H), 4.43 (m) and 4.27 (m) total 1H, 4.08 (m, 1H), 3.92 (m, 2H), 3.71 (s 3H), 3.63 (m) and 3.59 (m) total 1H, 3.49 (m, 1H), 2.28 (m, 2H), 1.43 (s) and 1.38 (s, totally 9H).

Step 342b.

Into a solution of the compound from step 342a (1 g, 3.5 mmol) in EtOH (10 mL) and water (10 mL) was added LiOH monohydrate (177 mg, 4.2 mmol). It was stirred at rt overnight before being concentrated. The crude was dissolved in water. It acidified to pH=2 by concentrated HCl and extracted with EtOAc (×3). The organic phase was dried and concentrated to give the desired compound as a light yellow oil (0.96 g, quantitative), which was used directly.

Step 342c.

A solution of ethyl 3-(4-bromophenyl)-3-oxopropanoate (5 g, 18.4 mmol) in 1,4-dioxane (20 mL) was treated with bromine (2.95 g, 18.5 mmol) at 0° C. for 1.5 hours. It was evaporated to give the crude desired product as a yellow oil (6.5 g, quantitative), which was used for the next step without further purification. $^1$H NMR (CDCl$_3$) 7.88 (d, 2H), 7.66 (d, 2H), 5.59 (s, 1H), 3.31 (q, 2H), 2.27 (t, 3H).

Step 342d.

Into a solution of the compound from step 342c (1.53 g, 4.4 mmol) in acetonitrile (20 mL) was added the compound from 342b (0.96 g, 3.5 mmol) and DIPEA (8 mL). The mixture was stirred at rt for 14 hours before the volatile were evaporated off. The crude was purified by chromatography (silica) to give a desired compound as a yellow oil (1.49 g, 80%). ESIMS m/z=540.11, 542.11 [M+H]+.

Step 342e.

Into the suspension of compound from step 342d (1.49 g, 2.75 mmol) in toluene (30 mL) was added ammonium acetate (3.9 g, 30.3 mmol). The mixture was stirred at 105° C. for 16 hours before being cooled and partitioned between aqueous NaHCO$_3$ and EtOAc. The organic phase was separated, dried (Na$_2$SO$_4$) and concentrated to afford a brown slurry, which was purified by chromatography (silica) to provide the desired compound as light yellow powder (635 mg, 44%). ESIMS m/z=520.15, 522.15 [M+H]+.

Step 342f.

Into a solution of the compound from 342e (635 mg, 1.22 mmol) in DMF (4 mL) was added sodium hydride (60% in mineral oil, 54 mg, 1.34 mmol). The mixture was stirred at rt for 1 hour before addition of 2-(trimethylsilyl)ethoxymethyl chloride (0.23 mL, 1.28 mmol). It was stirred at rt for another 3 hours before being partitioned between aqueous NaHCO$_3$ and EtOAc. The organic phase was separated, dried (Na$_2$SO$_4$) and concentrated to afford a brown slurry, which was purified by chromatography (silica, EtOAc-hexanes) to afford the desired compound as a light yellow oil (720 mg, 91%). ESIMS m/z=650.03, 652.03 [M+H]+.

Step 342g.

Into a solution of the compound from step 342f (464 mg, 0.713 mmol) in CH$_2$Cl$_2$ (6 mL) was added DIBAL-H solution (1M in hexane, 3.7 mL, 3.7 mmol) at −78° C. The resulting mixture was stirred at −78° C. for 3 hours. Aqueous sodium potassium tartrate (22 g in 20 ml, of water) was added dropwise before the mixture was partitioned between water and EtOAc. The organic phase was separated, dried (Na₂SO₄) and concentrated to afford a brown slurry, which was purified by chromatography (silica, EtOAc-hexanes) to afford the desired compound as a light yellow oil (304 mg, 70%). ESIMS m/z=608.30, 610.30 [M+H]⁺.

Step 342h.

Into a solution of the compound from step 342g (372 mg, 0.611 mmol) in DMF (3 mL) was added sodium hydride (60% in mineral oil, 49 mg, 1.22 mmol). The mixture was stirred for 15 minutes before allylbromide (0.21 mL, 2.44 mmol) was added. The mixture was stirred at rt for 3 hours before being partitioned between water and EtOAc. The organic phase was separated, dried (Na₂SO₄) and concentrated to afford a brown slurry, which was purified by chromatography (silica, EtOAc-hexanes) to afford the desired compound as a light yellow oil (331 mg, 84%). ESIMS m/z=648.24, 650.24 [M+H]⁺.

Step 342i.

Into a mixture of the compound from step 342h (145 mg, 0.223 mmol) in 1,4-dioxane (2 mL) was added hydrochloric acid (4M in 1,4-dioxane, 3 mL). The mixture was stirred at 50° C. for 12 hours before all volatiles were removed to afford the crude desired product as yellow powder, which was used directly for the next step without further purification. ESIMS m/z=418.03, 420.03 [M+H]⁺.

Step 342j.

A mixture of the crude compound from step 342i (0.223 mmol at most) and Boc₂O (59 mg, 0.268 mmol) in dioxane (3 mL) and water (3 mL) was treated with NaHCO₃ (84 mg, 1 mmol) 2 hour at rt before being partitioned between water and EtOAc. The organic phase was separated, dried (Na₂SO₄) and concentrated to afford a brown slurry, which was purified by chromatography (silica, EtOAc-hexanes) to afford the desired compound as a colorless oil (73 mg, 64% two steps). ESIMS m/z=518.11, 520.11 [M+H]⁺.

Step 342k.

Into a solution of the compound from step 342j (54 mg, 10.4 μmol) in toluene (40 mL) was added Zhan-1B catalyst (23 mg, 3.1 μmol). It was degassed and heated at 108° C. under N₂ for 16 hours before all volatiles were evaporated. The residue was purified by chromatography (silica, EtOAc-hexanes) three times to afford the desired compound as a yellow brown foam (16 mg, 31%). ESIMS m/z=490.12, 492.12 [M+H]⁺.

Step 342l.

To a mixture of 2,4'-dibromoacetophenone (5.00 g, 18.0 mmol) and N-Boc-L-proline (3.87 g, 18.0 mmol) in CH₃CN (60 mL) was added triethylamine (5.40 mL, 37.8 mmol) slowly. The mixture was stirred at rt until the disappearance of the starting material. The volatiles were evaporated and the residue was partitioned (EtOAc-water). The organics were washed with brine, dried (Na₂SO₄), filtered and evaporated. The residue was purified by chromatography (silica, hexanes-ethyl acetate) to give the desired compound as a light yellow foam (6.73 g, 91%). ¹H NMR (CDCl₃) 7.76 (t, J=8.0 Hz, 2H), 7.63 (dd, J=5.0, 8.5 Hz, 2H), 5.51, 5.16 (2d, J=16.0 Hz, 1H), 5.32, 5.28 (2d, J=16.5 Hz, 1H), 4.48, 4.40 (dd, J=5.0, 8.5 Hz, 1H), 3.56 (m, 1H), 3.43 (m, 1H), 2.30 (m, 2H), 2.06 (m, 1H), 1.92 (m, 1H), 1.46, 1.43 (2s, 9H).

Step 342m.

To a solution of the compound from step 342l (6.73 g, 16.3 mmol) in toluene (100 mL) was added ammonium acetate (25.1 g, 0.327 mol) and the mixture was heated at 100° C. for 14 hours. The volatiles were evaporated off and the residue was partitioned (EtOAc—aq. NaHCO₃). The organics were washed with brine, dried (Na₂SO₄), filtered and evaporated. The residue was purified by chromatography (silica, hexanes-ethyl acetate) to give the desired compound as a yellow foam (6.10 g, 95%). ESIMS m/z=392.24, 394.24 [M+H]⁺. ¹H NMR (CDCl₃) 7.57 (bs, 1H), 7.48 (m, 3H), 7.23 (s, 1H), 4.97 (m, 1H), 3.42 (m, 2H), 2.99 (m, 1H), 2.16 (m, 2H), 1.97 (m, 1H), 1.46 (s, 9H).

Step 342n.

To a mixture of the compound from step 342m (1.00 g, 2.55 mmol), bis(pinacolato)diboron (1.35 g, 5.33 mmol) and potassium acetate (0.640 g, 6.53 mmol) in 1,4-dioxane (20 mL) was added Pd(PPh₃)₄ (0.147 g, 0.128 mmol). The mixture was degassed and heated at 80° C. under N₂ for 14 hours. The volatiles were evaporated off and the residue was partitioned (EtOAc-water). The organics were washed with brine, dried (Na₂SO₄), filtered and evaporated. The residue was purified by chromatography (silica, hexanes-ethyl acetate) to give the desired compound as a light yellow solid (0.978 g, 87%). ESIMS m/z=440.39 [M+H]⁺. ¹H NMR (CDCl₃) 11.03, 10.55 (2s, 1H), 7.79 (m, 3H), 7.45 (m, 1H), 7.26 (m, 1H), 4.97 (m, 1H), 3.41 (m, 2H), 3.06, 2.91 (2m, 1H), 2.17 (m, 2H), 1.97 (m, 1H), 1.49 (s, 9H), 1.35 (s, 12H).

Step 342o.

Into the mixture of the compounds from step 342k (16 mg, 32.6 μmol), and 342n (36.3 mg, 82 μmol) and NaHCO₃ (14 mg, 0.167 mmol) in DME (2 mL) and H₂O (0.7 mL) was added Pd(PPh₃)₄ (7.5 mg, 6.5 μmol). The mixture were degassed and heated to 95° C. under N₂ for 3 hours. The volatiles were evaporated off and the residue was partitioned (EtOAc-H₂O). The organics were washed with brine, dried (Na₂SO₄), filtered and evaporated. The residue was purified by chromatography (silica, hexanes-ethyl acetate) to give the title compound as a light yellow solid (15 mg, 64%). ESIMS m/z=723.41 [M+H]⁺.

Example 343

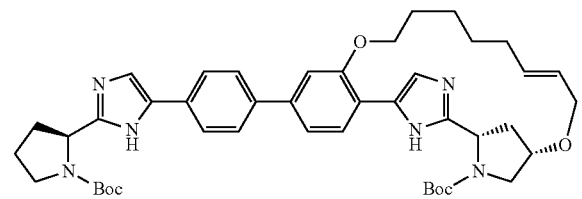 [SMILES: CC(C)(C)OC(=O)N1CCC[C@H]1c1ncc(-c2ccc(-c3ccc4c(c3)OCCCCC/C=C/CO[C@H]3C[C@@H](c5ncc-4[nH]5)N(C(=O)OC(C)(C)C)C3)cc2)[nH]1]

Step 343a.

Into a solution of 1-(4-bromo-2-hydroxyphenyl)ethanone (500 mg, 2.32 mmol) and 7-bromohept-1-ene (823 mg, 4.65 mmol) in DMF (1 mL) was added NaHCO₃ (590 g, 7 mmol). The mixture was stirred at 80° C. for 3 days before was partitioned (EtOAc/Hexanes (1:3)—H₂O). The organics were washed with water, brine, dried (Na₂SO₄), filtered and evaporated. The residue was purified by chromatography (silica, hexanes-ethyl acetate) to give the desired compound as a light yellow oil (497 mg, 66%). ¹H NMR (CDCl₃, δ, ppm) 7.61 (d, 1H), 7.12 (d, 1H), 7.10 (s, 1H), 5.80 (m, 1H), 4.98 (m, 2H), 4.04 (t, 2H), 2.60 (s, 3H), 2.09 (m, 2H), 1.85 (m, 2H), 1.49 (m, 4H).

Step 343b.

Into a solution of the compound from step 343a (479 mg, 1.54 mmol) in CH₂Cl₂ (6 mL) and TEA (2 mL) was added trimethylsilyl trifluoromethylsulfonate (0.56 mL, 3.08 mmol). The mixture was stirred at rt overnight before being partitioned (CHCl₃—H₂O). The organics were washed with water, brine, dried (Na₂SO₄), filtered and evaporated to give a brownish oil. It was dissolved in CCl₄ and was cooled to −15° C., bromine (246 mg, 1.54 mmol) was added dropwise.

Thirty minutes later, aqueous NaHSO₃ was added and partitioned. The aqueous phase was extracted with CH₂Cl₂ and the combined organic phase was dried (Na₂SO₄), filtered and evaporated to give an orange oil and was directly used in the next step.
Step 343c.

Into a solution of compound from steps 343b (1.54 mmol at the most) and 342b (440 mg 1.62 mmol) in acetonitrile (6 mL) was added DIPEA (1 mL). The mixture was stirred at rt overnight before was concentrated. The residue was purified by chromatography (silica, hexanes-ethyl acetate) to give the desired compound as a light yellow oil (256 mg, 29% three steps). ESIMS m/z=580.29, 582.29 [M+H]⁺.
Step 343d.

Into the suspension of compound from step 343c (255 mg, 0.44 mmol) in toluene (8 mL) was added ammonium acetate (375 mg, 4.83 mmol). The mixture was stirred at 105° C. for 16 hours before being cooled and partitioned between aqueous NaHCO₃ and EtOAc. The organic phase was separated, dried (Na₂SO₄) and concentrated to afford a brown slurry, which was purified by chromatography (silica) to provide the desired compound as light yellow oil (182 mg, 74%). ESIMS m/z=560.24, 562.24 [M+H]⁺.
Step 343e.

Into a solution of the compound from step 343d (180 mg, 0.32 mmol) in toluene (120 mL) was added Zhan-1B catalyst (24 mg, 0.032 mmol). The mixture were degassed and heated at 80° C. under N₂ for 2 hours when a second portion of Zhan-1B catalyst (12 mg, 0.016 mmol) was added. It was heated for another hour before the volatiles were evaporated off. The residue was purified by chromatography (silica, EtOAc-hexanes) to afford the desired compound as a yellow-brown foam (92 mg, 54%). ESIMS m/z=532.25, 534.24 [M+H]⁺.
Step 343f.

Into the mixture of the compounds from step 343e (92 mg, 0.172 mmol), and 342n (113 mg, 0.258 mmol) and NaHCO₃ (58 mg, 0.688 mmol) in DME (3 mL) and H₂O (1 mL) was added Pd(PPh₃)₄ (20.0 mg, 17.2 μmol). The mixture were degassed and heated to 95° C. under N₂ for 2 hours. The volatiles were evaporated and the residue was partitioned (EtOAc-H₂O). The organics were washed with brine, dried (Na₂SO₄), filtered and evaporated. The residue was purified by chromatography (silica, CH₂Cl₂-MeOH) to give the title compound as a light yellow solid (115 mg, 64%). ESIMS m/z=765.52 [M+H]'.

Example 344

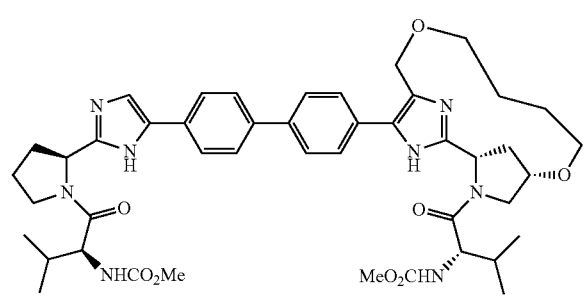

Step 344a.

Into a solution of the compound from Example 342 (15 mg, 20.7 μmol) in MeOH (16 mL) was added palladium hydroxide (20 wt % on carbon, 5.0 mg). The mixture was hydrogenated under 60 psi before filtration through Celite. The filtrate was concentrated and purified by chromatography (silica, CH₂Cl₂-MeOH) to give the desired compound as a light yellow solid (13.0 mg, 87%). ESIMS m/z=725.25 [M+H]⁺.

Step 344b.

A solution of the compound of step 344a (13 mg, 17.9 μmol) in 1,4-dioxane (0.5 mL) was treated with HCl in 1,4-dioxane (4 M, 1 mL) at rt for 1 hour. The volatiles were evaporated off to give the crude desired compound as a yellow solid, which was used directly in the next step.

Step 344c.

A mixture of the crude compound from step 344b (17.9 μmol at most) and (S)-2-(methoxycarbonylamino)-3-methylbutanoic acid (prepared according to WO 2008/021927, 6.5 mg, 37.1 μmol) in DMF (1 mL) was treated with HATU (13.5 mg, 35.5 μmol) in the presence of DIPEA (0.2 mL) for 30 minutes at rt and the volatiles were evaporated off. It was purified by chromatography (silica, CH₂Cl₂-MeOH) to give the title compound as a yellow solid (7.5 mg, 50% over 2 steps). ESIMS m/z=839.45 [M+H]⁺.

Example 345

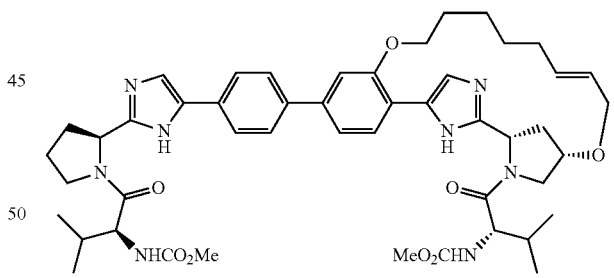

Step 345a.

The desired compound was prepared from the compound from Example 343 using procedures similar to that described in step 344b. ESIMS m/z=565.39 [M+H]⁺.

Step 345b.

The title compound was prepared from the compounds from step 341a using procedures similar to that described in step 344c. ESIMS m/z=879.59 [M+H]⁺.

The title compounds of examples 1-82 and 84-341 may be prepared using the chemistry described above.

TABLE 1

Compounds 1-219.

| Entry | R group structure |
|---|---|
| 1 | tert-butyl ester (OC(CH₃)₃-C(O)-) |
| 2 | methoxycarbonyl-NH-CH(Ph)-C(O)- |
| 3 | (CH₃)₂N-CH(Ph)-C(O)- |
| 4 | CH₃-CH(OH)-C(O)- |
| 5 | CH₃CH₂-CH(OH)-C(O)- |
| 6 | CH₃CH₂-C(O)- |
| 7 | CH₃O-CH₂-C(O)- |
| 8 | (CH₃)₂N-C(O)- |

TABLE 1-continued

Compounds 1-219.

| Entry | R—C(=O)— group |
|---|---|
| 9 | methyl ester (methoxycarbonyl): CH₃O–C(=O)– |
| 10 | CH₃–C(=O)–CH₂–CH₂–C(=O)– |
| 11 | (CH₃)₂CH–CH(OH)–C(=O)– |
| 12 | CH₂=CH–CH₂–CH₂–C(=O)– |
| 13 | cyclopropyl–C(=O)– |
| 14 | 1-(trifluoromethyl)cyclopropyl–C(=O)– |
| 15 | 1-hydroxycyclopropyl–C(=O)– |
| 16 | Ph–C(=O)– |

TABLE 1-continued

Compounds 1-219.

| Entry | R group |
|---|---|
| 17 | PhCH₂C(O)- |
| 18 | cyclopropyl-CH₂-C(O)- |
| 19 | Ph-C(CH₃)(OH)-C(O)- |
| 20 | Ph-CH(OMe)-C(O)- |
| 21 | Ph-CH(OH)-C(O)- |
| 22 | (pyridin-3-yl)-CH₂-C(O)- |
| 23 | (pyridin-4-yl)-CH₂-C(O)- |
| 24 | Ph-CH₂-CH(OH)-C(O)- |

TABLE 1-continued

Compounds 1-219.

| Entry | R group |
|---|---|
| 25 | (S)-tetrahydrofuran-2-yl carbonyl |
| 26 | (R)-tetrahydrofuran-2-yl carbonyl |
| 27 | tetrahydrofuran-3-yl carbonyl |
| 28 | 1-methylpiperidin-4-yl carbonyl |
| 29 | tetrahydropyran-4-yl carbonyl |
| 30 | morpholine-4-carbonyl |
| 31 | trans-4-(Boc-amino)cyclohexyl carbonyl |

TABLE 1-continued

Compounds 1-219.

| Entry | R group |
|---|---|
| 32 | 4-(Boc-amino)cyclohexyl-C(O)- |
| 33 | 1-Boc-piperidin-4-yl-C(O)- |
| 34 | 4-(diethylamino)cyclohexyl-C(O)- |
| 35 | 4-(methoxycarbonylamino)cyclohexyl-C(O)- |
| 36 | 4-methylpiperazin-1-yl-C(O)- |
| 37 | 2-(piperidin-1-ylmethyl)phenyl-CH2-C(O)- |

TABLE 1-continued
Compounds 1-219.
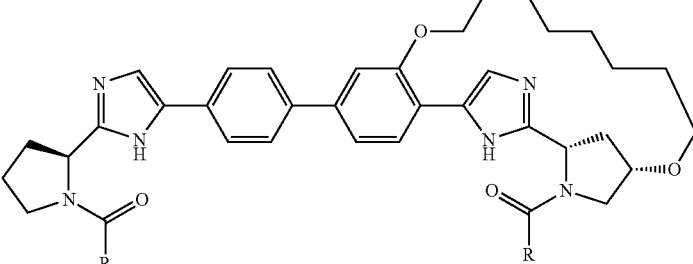
| Entry | |
|---|---|
| 38 | 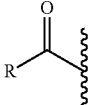 |
| 39 | 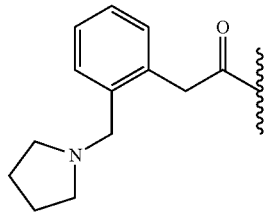 [SMILES: *C(=O)Cc1ccccc1CN1CCCC1] |
| 40 | 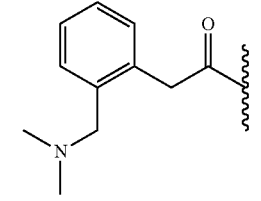 [SMILES: *C(=O)Cc1ccccc1CN(C)C] |
| 41 | 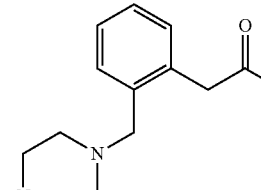 |
| 42 | 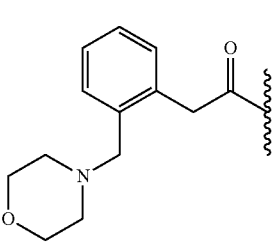 [SMILES: *C(=O)Cc1ccccc1CN1CCOCC1] |

TABLE 1-continued
Compounds 1-219.
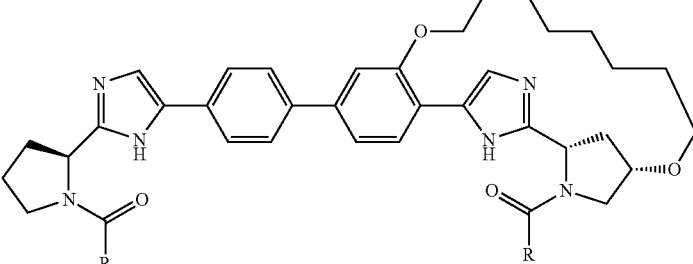
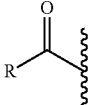
| Entry | |
|---|---|
| 43 | 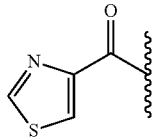 |
| 44 | 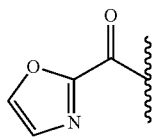 [SMILES: *C(=O)c1ncco1] |
| 45 | 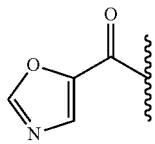 [SMILES: *C(=O)c1cnco1] |
| 46 | 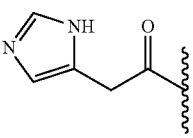 [SMILES: *C(=O)Cc1cnc[nH]1] |
| 47 | 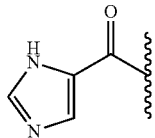 |
| 48 | 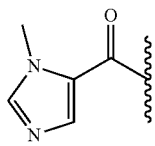 [SMILES: *C(=O)c1cncn1C] |
| 49 | 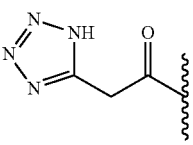 [SMILES: *C(=O)Cc1nnn[nH]1] |

TABLE 1-continued
Compounds 1-219.
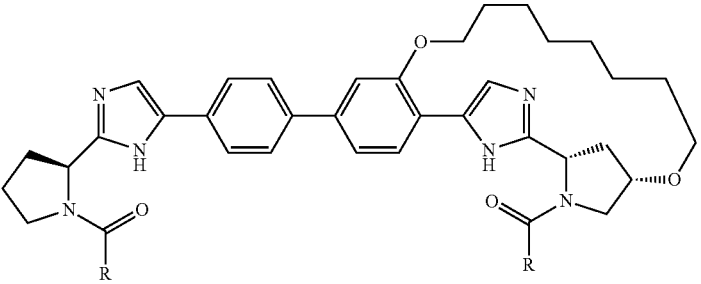
| Entry | 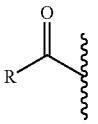 |
|---|---|
| 50 | 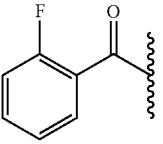 |
| 51 | 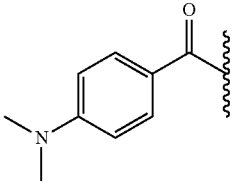 [SMILES: *C(=O)c1ccc(N(C)C)cc1] |
| 52 | 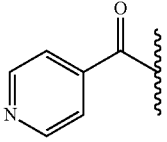 [SMILES: *C(=O)c1ccncc1] |
| 53 | 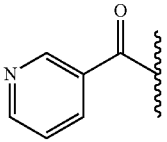 [SMILES: *C(=O)c1cccnc1] |
| 54 | 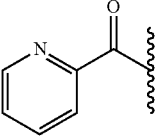 |
| 55 | 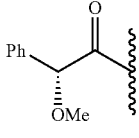 |
| 56 | 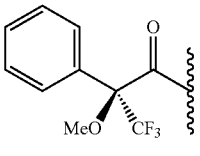 |

TABLE 1-continued
Compounds 1-219.
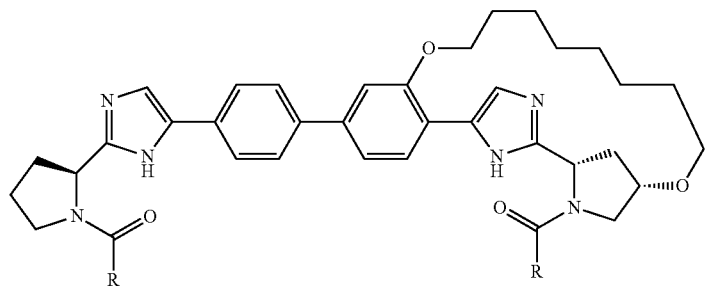
| Entry | |
|---|---|
| 57 | 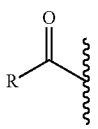 |
| 58 | 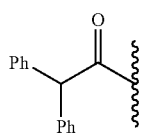 |
| 59 | 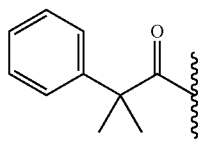 [SMILES: *C(=O)C(C)(C)c1ccccc1] |
| 60 | 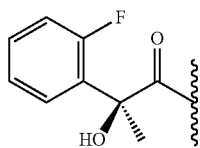 [SMILES: *C(=O)[C@@](C)(O)c1ccccc1F] |
| 61 | 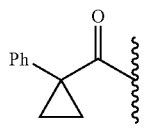 |
| 62 |  |
| 63 |  |

TABLE 1-continued

Compounds 1-219.

| Entry | R-C(=O)- group |
|---|---|
| 64 | (S)-tetrahydropyran-4-yl-O-C(=O)-NH-CH(CH₃)-C(=O)- |
| 65 | (R)-tetrahydropyran-4-yl-O-C(=O)-NH-CH(CH₃)-C(=O)- |
| 66 | MeO-C(=O)-NH-CH(CH₂OMe)-C(=O)- |
| 67 | MeO-C(=O)-NH-CH(CH₂CH₃)-C(=O)- |
| 68 | MeO-C(=O)-NH-CH(CH₂CH₃)-C(=O)- |
| 69 | MeO-C(=O)-NH-CH(CH₂CH₂OMe)-C(=O)- |

TABLE 1-continued

Compounds 1-219.

| Entry | R |
|---|---|
| 70 | methyl carbamate-NH-CH(CH(OH)CH₃)-C(O)- (threonine-like, one stereochem) |
| 71 | methyl carbamate-NH-CH(CH(OH)CH₃)-C(O)- (threonine-like, other stereochem) |
| 72 | methyl carbamate-NH-CH(CH(OH)CH₃)-C(O)- (threonine-like, another stereochem) |
| 73 | methyl carbamate-NH-CH(CH₂CH=CH₂)-C(O)- (allylglycine) |
| 74 | methyl carbamate-NH-CH(CH₂CH₂CH₃)-C(O)- (norvaline) |
| 75 | (CH₃)₂N-CH₂CH₂-CH(NH-Boc)-C(O)- |

TABLE 1-continued

Compounds 1-219.

| Entry | R group |
|---|---|
| 76 | methyl carbamate-NH-C(CH₃)₂-C(O)- |
| 77 | methyl carbamate-NH-CH(cyclopropyl)-C(O)- (S) |
| 78 | methyl carbamate-NH-CH(cyclopropyl)-C(O)- (R) |
| 79 | methyl carbamate-NH-CH(C(CH₃)₂OH)-C(O)- |
| 80 | methyl carbamate-NH-CH(CH₂CO₂Bn)-C(O)- |
| 81 | methyl carbamate-NH-CH(CH₂CONH₂)-C(O)- |
| 82 | methyl carbamate-NH-CH(CH(CH₃)₂)-C(O)- |

TABLE 1-continued
Compounds 1-219.
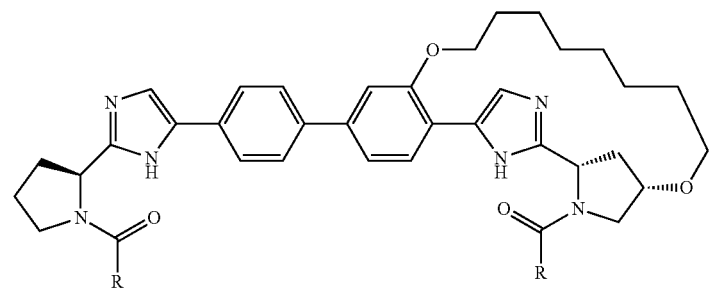
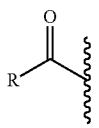
| Entry | |
|---|---|
| 83 | 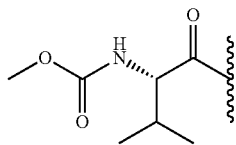 [SMILES: *C(=O)[C@@H](NC(=O)OC)C(C)C] |
| 84 | 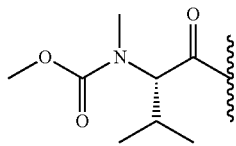 [SMILES: *C(=O)[C@H](C(C)C)N(C)C(=O)OC] |
| 85 | 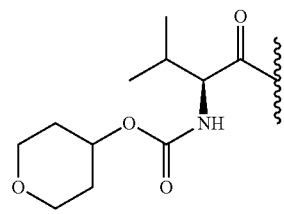 [SMILES: *C(=O)[C@@H](NC(=O)OC1CCOCC1)C(C)C] |
| 86 | 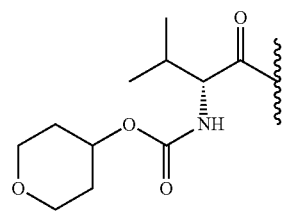 [SMILES: *C(=O)[C@H](NC(=O)OC1CCOCC1)C(C)C] |
| 87 | 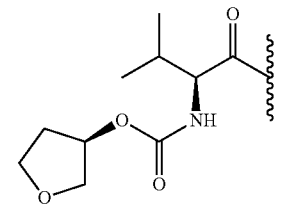 [SMILES: *C(=O)[C@@H](NC(=O)O[C@@H]1CCOC1)C(C)C] |

TABLE 1-continued
Compounds 1-219.
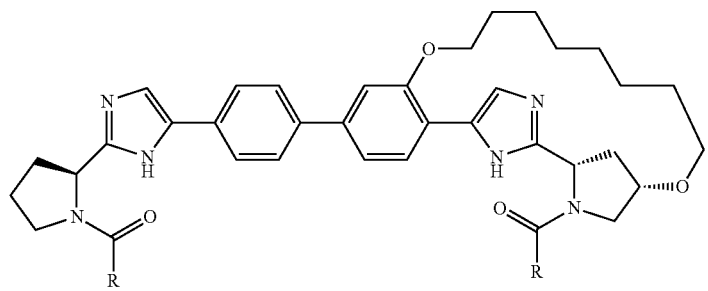
| Entry | 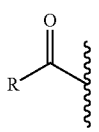 |
|---|---|
| 88 | 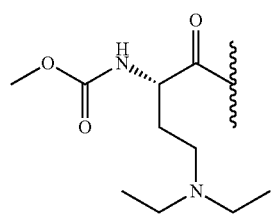 [SMILES: *C(=O)[C@H](CCN(CC)CC)NC(=O)OC] |
| 89 | 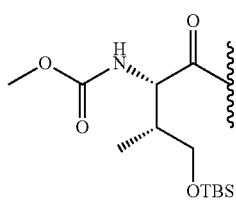 [SMILES: *C(=O)[C@@H](NC(=O)OC)[C@@H](C)CO[Si](C)(C)C(C)(C)C] |
| 90 | 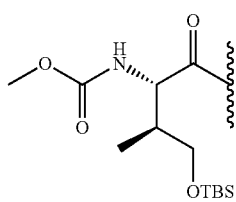 [SMILES: *C(=O)[C@@H](NC(=O)OC)[C@H](C)CO[Si](C)(C)C(C)(C)C] |
| 91 | 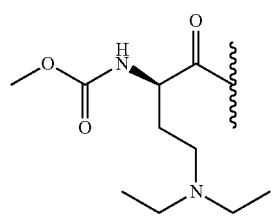 |
| 92 | 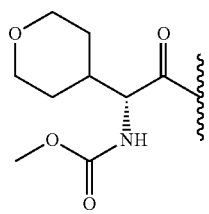 [SMILES: *C(=O)[C@H](NC(=O)OC)C1CCOCC1] |

TABLE 1-continued
Compounds 1-219.
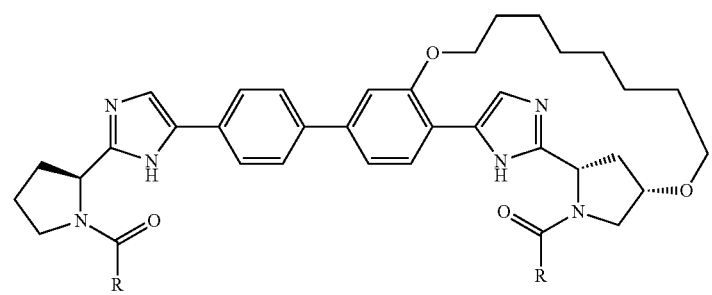
Entry 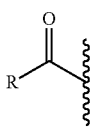
93 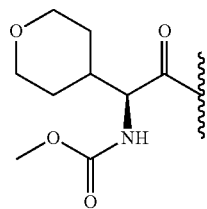 [SMILES: *C(=O)[C@@H](NC(=O)OC)C1CCOCC1]
94 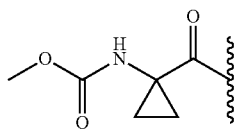 [SMILES: *C(=O)C1(NC(=O)OC)CC1]
95 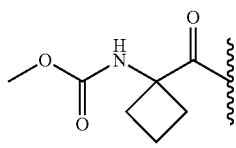 [SMILES: *C(=O)C1(NC(=O)OC)CCC1]
96 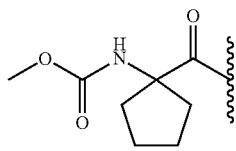 [SMILES: *C(=O)C1(NC(=O)OC)CCCC1]
97 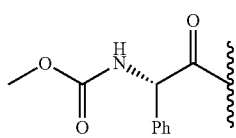 [SMILES: *C(=O)[C@@H](NC(=O)OC)c1ccccc1]
98 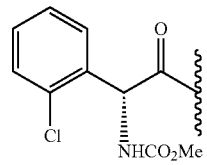

TABLE 1-continued

Compounds 1-219.

| Entry | R-C(O)- group |
|---|---|
| 99 | (S)-phenyl, NHAc |
| 100 | (S)-phenyl, NH-C(O)-NHMe |
| 101 | (S)-phenyl, NH-C(O)-NMe₂ |
| 102 | (S)-phenyl, NH-C(O)-NHEt |
| 103 | (S)-phenyl, NH-C(O)-NH-cyclopentyl |

TABLE 1-continued

Compounds 1-219.

| Entry | R group |
|---|---|
| 104 | MeO₂C-azetidine-C(O)- (2S) |
| 105 | Boc-azetidin-3-yl-C(O)- |
| 106 | 2-pyridylmethyl, NHCO₂Me (S) |
| 107 | 3-pyridylmethyl, NHCO₂Me (S) |
| 108 | 4-pyridylmethyl, NHCO₂Me (S) |
| 109 | (1-Bn-imidazol-4-yl)methyl, NHCO₂Me (S) |
| 110 | (1H-imidazol-4-yl)methyl, NHCO₂Me (S) |

TABLE 1-continued
Compounds 1-219.
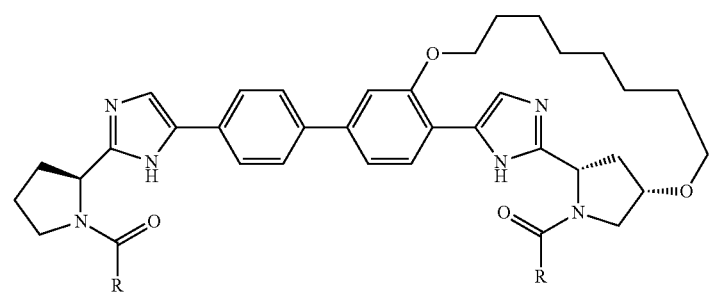
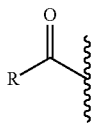
| Entry | |
|---|---|
| 111 | 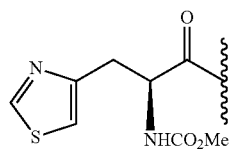 |
| 112 | 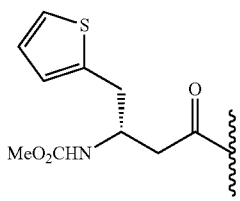 |
| 113 | 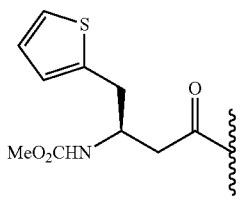 |
| 114 | 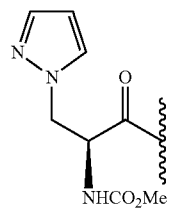 |
| 115 | 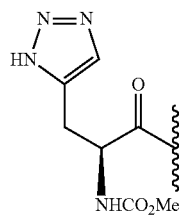 |

TABLE 1-continued
Compounds 1-219.
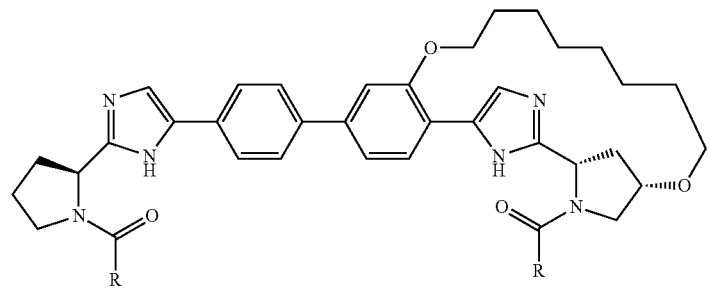
| Entry | 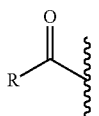 |
|---|---|
| 116 | 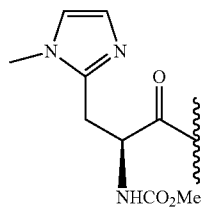 |
| 117 | 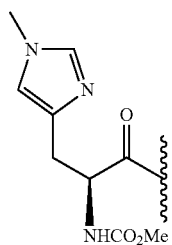 |
| 118 | 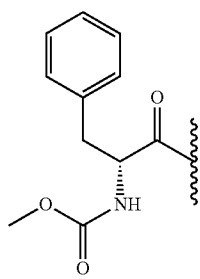 [SMILES: *C(=O)[C@@H](Cc1ccccc1)NC(=O)OC] |
| 119 | 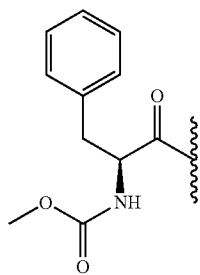 [SMILES: *C(=O)[C@H](Cc1ccccc1)NC(=O)OC] |

TABLE 1-continued

Compounds 1-219.

| Entry | R group structure |
|---|---|
| 120 | 4-(methyl hydrogen phosphate)-phenyl-CH₂-CH(NHCO₂Me)-C(O)- |
| 121 | indol-3-yl-CH₂-CH(NHCO₂Me)-C(O)- |
| 122 | 4-(OBn)-phenyl-CH₂-CH(NHCO₂Me)-C(O)- |
| 123 | 4-(CH₂NHFmoc)-phenyl-CH₂-CH(NHCO₂Me)-C(O)- |

US 9,676,802 B2
TABLE 1-continued
Compounds 1-219.
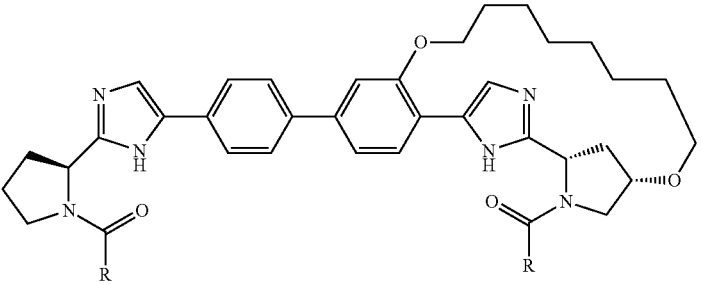
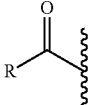
| Entry | |
|---|---|
| 124 | 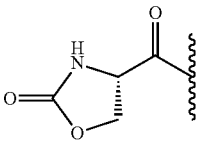 [SMILES: *C(=O)[C@@H]1COC(=O)N1] |
| 125 |  |
| 126 | 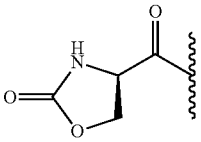 [SMILES: *C(=O)[C@H]1COC(=O)N1] |
| 127 |  |
| 128 | 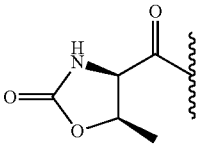 [SMILES: *C(=O)[C@@H]1NC(=O)O[C@@H]1C] |
| 129 |  |

TABLE 1-continued
Compounds 1-219.
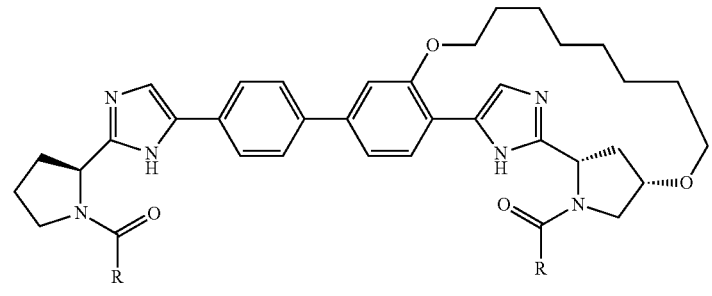
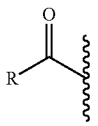
| Entry | |
|---|---|
| 130 | 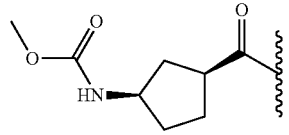 [SMILES: *C(=O)[C@H]1CC[C@@H](NC(=O)OC)C1] |
| 131 | 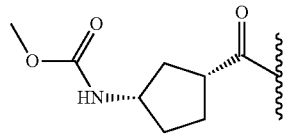 [SMILES: *C(=O)[C@@H]1CC[C@H](NC(=O)OC)C1] |
| 132 | 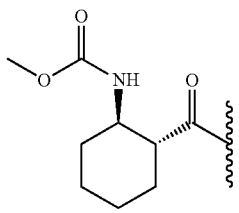 [SMILES: *C(=O)[C@@H]1CCCC[C@H]1NC(=O)OC] |
| 133 | 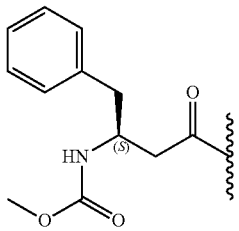 |
| 134 | 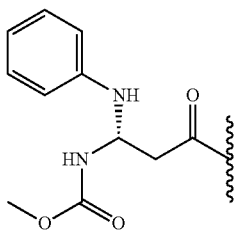 [SMILES: *C(=O)C[C@H](NC(=O)OC)Nc1ccccc1] |

TABLE 1-continued
Compounds 1-219.
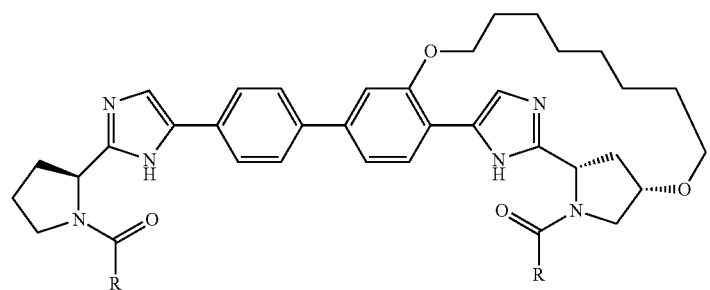
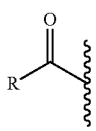
| Entry | |
|---|---|
| 135 | 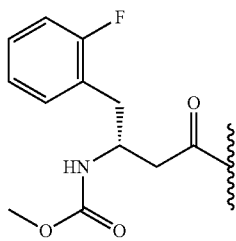 [SMILES: *C(=O)C[C@@H](Cc1ccccc1F)NC(=O)OC] |
| 136 | 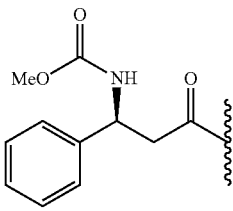 [SMILES: *C(=O)C[C@H](NC(=O)OC)c1ccccc1] |
| 137 | 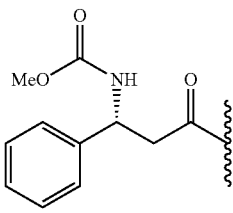 [SMILES: *C(=O)C[C@@H](NC(=O)OC)c1ccccc1] |
| 138 | 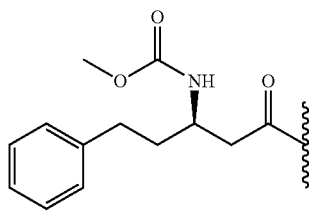 [SMILES: *C(=O)C[C@@H](CCc1ccccc1)NC(=O)OC] |
| 139 | 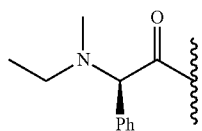 [SMILES: *C(=O)[C@@H](c1ccccc1)N(C)CC] |

TABLE 1-continued

Compounds 1-219.

| Entry | |
|---|---|
| 140 | |
| 141 | |
| 142 | |
| 143 | |
| 144 | |
| 145 | |

TABLE 1-continued
Compounds 1-219.
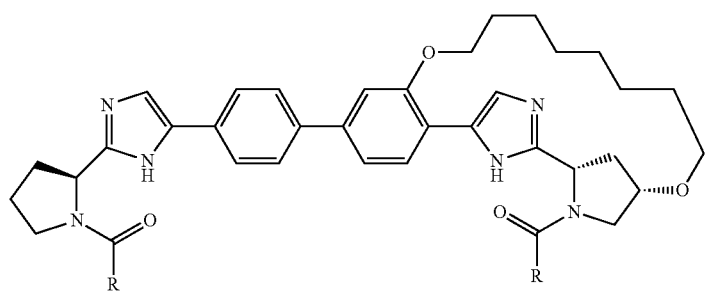
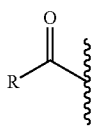
| Entry | |
|---|---|
| 146 | 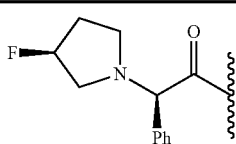 |
| 147 | 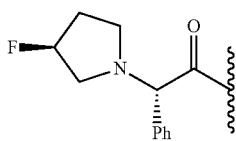 |
| 148 | 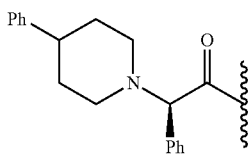 [SMILES: *C(=O)[C@@H](c1ccccc1)N1CCC(c2ccccc2)CC1] |
| 149 | 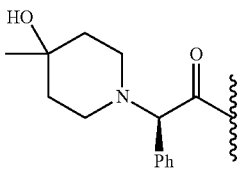 [SMILES: *C(=O)[C@@H](c1ccccc1)N1CCC(C)(O)CC1] |
| 150 | 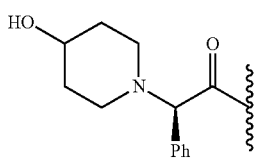 |
| 151 | 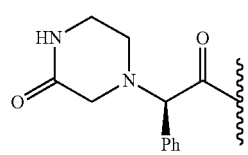 [SMILES: *C(=O)[C@@H](c1ccccc1)N1CCNC(=O)C1] |
| 152 | 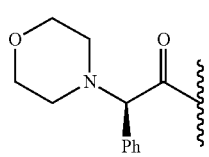 [SMILES: *C(=O)[C@@H](c1ccccc1)N1CCOCC1] |

TABLE 1-continued
Compounds 1-219.
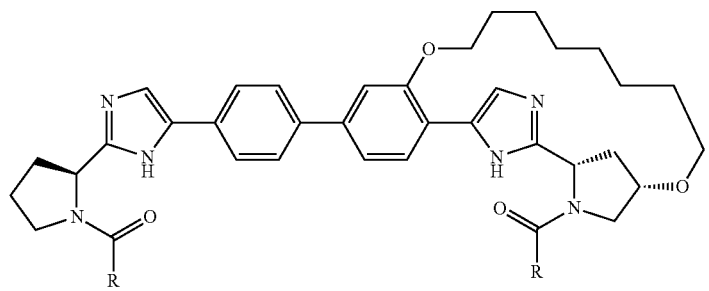
| Entry | |
|---|---|
| 153 | 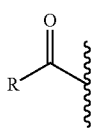 |
| 154 | 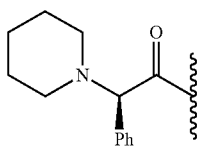 [SMILES: *C(=O)[C@@H](c1ccccc1)N1CCCCC1] |
| 155 | 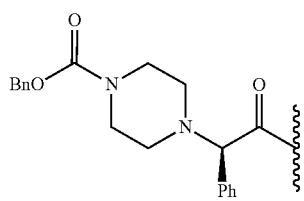 [SMILES: *C(=O)[C@@H](c1ccccc1)N1CCN(C(=O)OCc2ccccc2)CC1] |
| 156 | 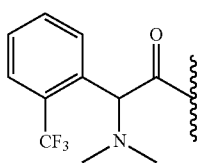 |
| 157 | 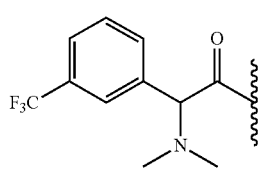 [SMILES: *C(=O)C(c1cccc(C(F)(F)F)c1)N(C)C] |
| 158 | 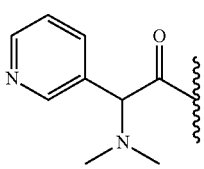 |

TABLE 1-continued
Compounds 1-219.
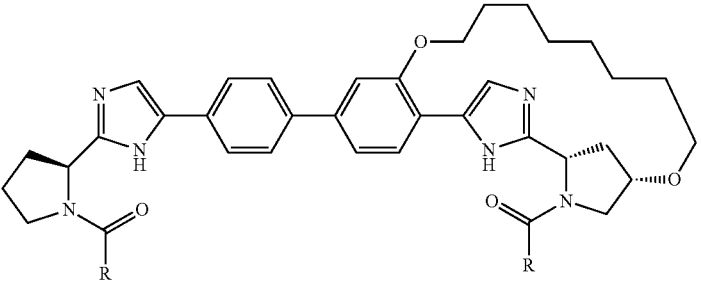
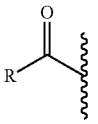
| Entry | |
|---|---|
| 159 | 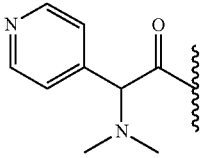 [SMILES: *C(=O)C(c1ccncc1)N(C)C] |
| 160 | 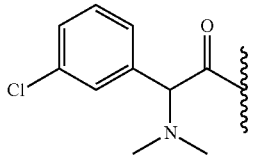 [SMILES: *C(=O)C(c1cccc(Cl)c1)N(C)C] |
| 161 | 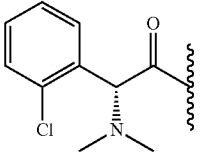 [SMILES: *C(=O)[C@@H](c1ccccc1Cl)N(C)C] |
| 162 | 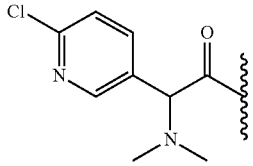 |
| 163 | 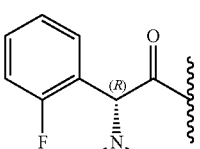 |
| 164 | 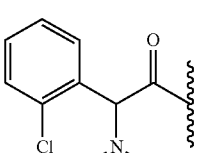 |

TABLE 1-continued
Compounds 1-219.
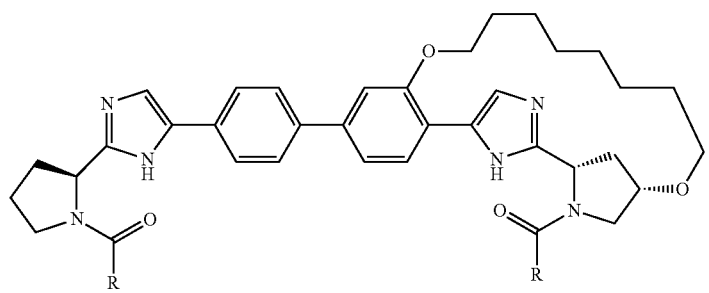
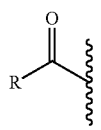
| Entry | |
|---|---|
| 165 | 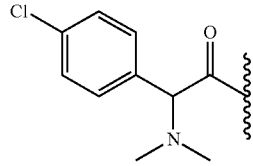 [SMILES: *C(=O)C(c1ccc(Cl)cc1)N(C)C] |
| 166 | 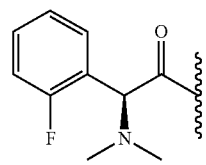 [SMILES: *C(=O)[C@H](c1ccccc1F)N(C)C] |
| 167 | 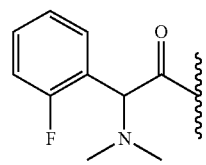 [SMILES: *C(=O)C(c1ccccc1F)N(C)C] |
| 168 | 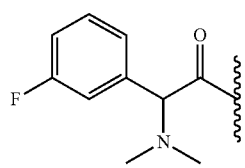 [SMILES: *C(=O)C(c1cccc(F)c1)N(C)C] |
| 169 | 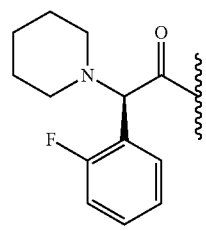 [SMILES: *C(=O)[C@@H](c1ccccc1F)N1CCCCC1] |
| 170 | 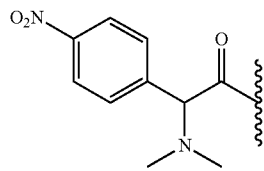 [SMILES: *C(=O)C(c1ccc([N+](=O)[O-])cc1)N(C)C] |

TABLE 1-continued
Compounds 1-219.
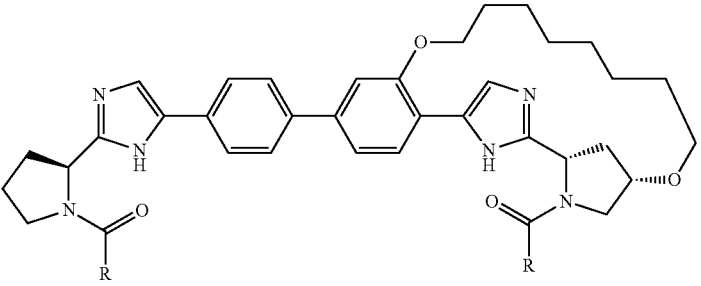
| Entry | |
|---|---|
| 171 | 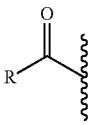 |
| 172 | 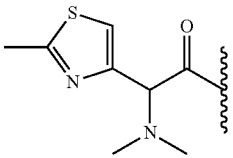 |
| 173 | 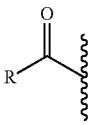 |
| 174 | 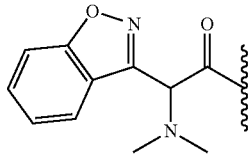 [SMILES: *C(=O)C(c1noc2ccccc12)N(C)C] |
| 175 | 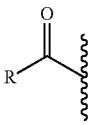 |
| 176 | 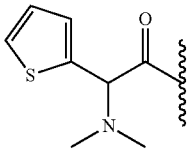 [SMILES: *C(=O)C(c1cccs1)N(C)C] |

TABLE 1-continued

Compounds 1-219.

| Entry | |
|---|---|
| 177 | 2-methylbenzothiazol-5-yl, N(CH3)2, C(=O) |
| 178 | PhCH2-N(CH3)-CH2-C(=O) |
| 179 | naphthalen-1-yl, N(CH3)2, C(=O) |
| 180 | pyrrolidin-1-yl-CH2-C(=O) |
| 181 | 4-methylpiperazin-1-yl-CH2-C(=O) |
| 182 | (CH3)2N-CH2-C(=O) |
| 183 | (Et)2N-CH(CH2OCH3)-C(=O) |

TABLE 1-continued

Compounds 1-219.

| Entry | R-C(O)- group |
|---|---|
| 184 | (S)-2-(N-benzyl-N-methylamino)propanoyl |
| 185 | (S)-2-(di-n-propylamino)propanoyl |
| 186 | (R)-2-(di-n-propylamino)propanoyl |
| 187 | (S)-2-(dimethylamino)propanoyl |
| 188 | (R)-2-(dimethylamino)propanoyl |
| 189 | (S)-2-acetamidopropanoyl |
| 190 | (S)-2-(diethylamino)propanoyl |

TABLE 1-continued
Compounds 1-219.
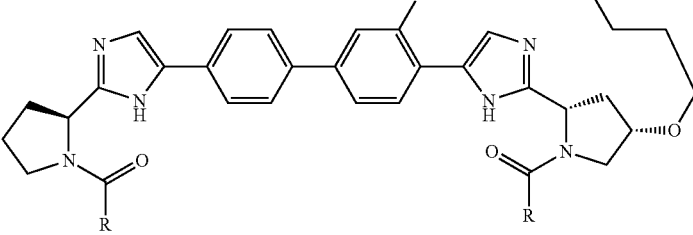
| Entry | |
|---|---|
| 191 | 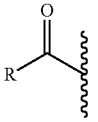 |
| 192 | 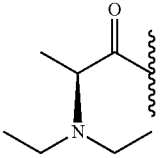 [SMILES: *C(=O)[C@H](C)N(CC)CC] |
| 193 | 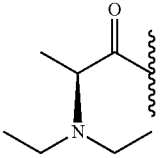 [SMILES: *C(=O)[C@H](C)N(CC)CC] |
| 194 | 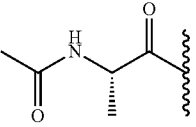 [SMILES: *C(=O)[C@H](C)NC(C)=O] |
| 195 | 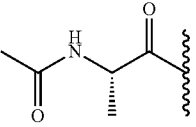 [SMILES: *C(=O)[C@H](C)NC(C)=O] |
| 196 | 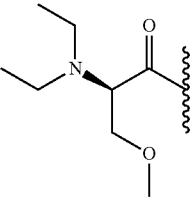 [SMILES: *C(=O)[C@@H](COC)N(CC)CC] |
| 197 | 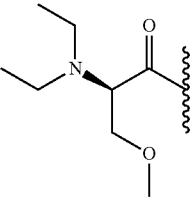 [SMILES: *C(=O)[C@@H](COC)N(CC)CC] |

TABLE 1-continued

Compounds 1-219.

| Entry | R-C(O)- group |
|---|---|
| 198 | (diethylamino)-CH(CH2C(O)NH2)-C(O)- |
| 199 | (diethylamino)-CH(iPr)-C(O)- |
| 200 | (4,5-dihydro-1H-imidazol-2-ylamino)-CH(iPr)-C(O)- |
| 201 | (4,5-dihydro-1H-imidazol-2-ylamino)-CH(iPr)-C(O)- |
| 202 | (1-methyl-4,5-dihydro-1H-imidazol-2-ylamino)-CH(iPr)-C(O)- |
| 203 | (5-amino-1-methyl-1H-1,2,4-triazol-3-ylamino)-CH(iPr)-C(O)- |

TABLE 1-continued

Compounds 1-219.

| Entry | |
|---|---|
| 204 | 2-thiazoline-NH-Val- |
| 205 | 5-amino-1H-1,2,4-triazol-3-yl-NH-Val- |
| 206 | pyridin-3-yl-NH-Val- |
| 207 | pyrimidin-4-yl-NH-Val- |
| 208 | 5-amino-1,2,4-oxadiazol-3-yl-NH-Val- |
| 209 | N,N-diethyl-tert-leucyl- |

TABLE 1-continued
Compounds 1-219.
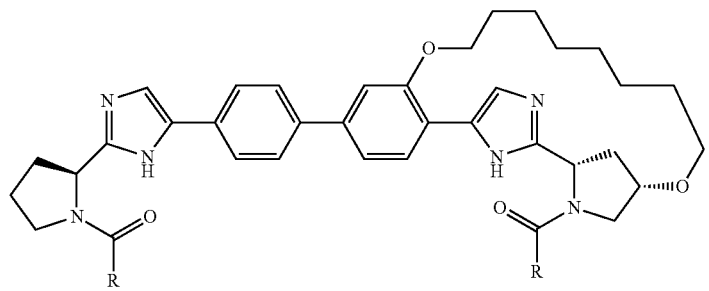
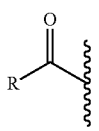
| Entry | |
|---|---|
| 210 | 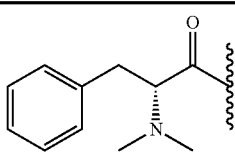 |
| 211 | 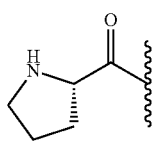 [SMILES: *C(=O)[C@@H]1CCCN1] |
| 212 | 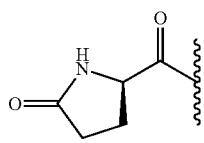 [SMILES: *C(=O)[C@H]1CCC(=O)N1] |
| 213 | 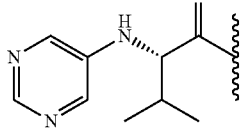 |
| 214 | 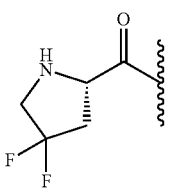 |
| 215 | 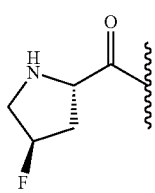 [SMILES: *C(=O)[C@@H]1C[C@@H](F)CN1] |
| 216 | 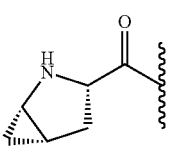 |

TABLE 1-continued
Compounds 1-219.
| Entry | |
|---|---|
| 217 | 1-methylpyrrolidine-2-carbonyl |
| 218 | 4-fluoro-1-methylpyrrolidine-2-carbonyl |
| 219 | 4-fluoropyrrolidine-2-carbonyl |
TABLE 2
Compounds 220-229.
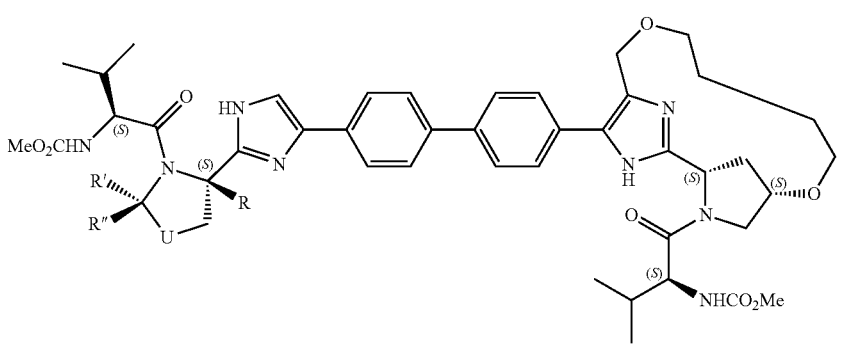
| Entry | R | R' | R" | U |
|---|---|---|---|---|
| 220 | Me | H | H | CH$_2$ |
| 221 | H | H | H | CF$_2$ |
| 222 | Me | H | H | S |

TABLE 2-continued

Compounds 220-229.

| Entry | R | R' | R" | U |
|---|---|---|---|---|
| 223 | H | H | H | CHF (H up, F down) |
| 224 | H | H | H | SiMe₂ |
| 225 | H | H | H | CHF (F up, H down) |
| 226 | H | Ph | H | CH₂ |
| 227 | H | H | H | C(H)(OH) (H up, OH down) |
| 228 | H | H | Ph | CH₂ |
| 229 | H | H | H | C(OH)(H) (OH up, H down) |

TABLE 3

Compounds 230-239.

| Entry | R | R' | R" |
|---|---|---|---|
| 230 | Me | H | H |
| 231 | H | CO₂Me | H |

TABLE 3-continued
Compounds 230-239.
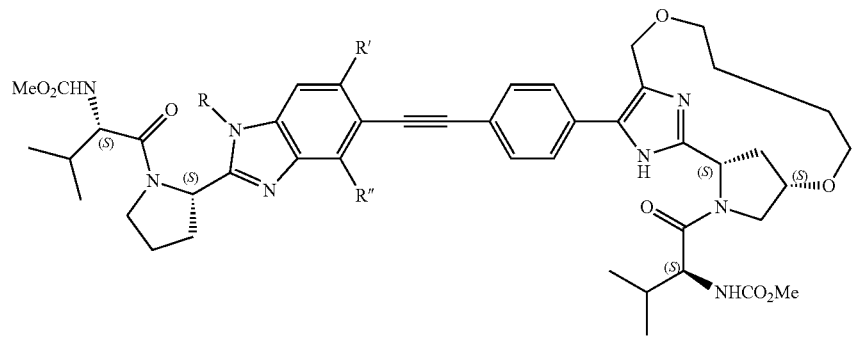
| Entry | R | R' | R" |
|---|---|---|---|
| 232 | H | F | H |
| 233 | H | H | CO₂Me |
| 234 | H | H | F |
| 235 | H | OMe | H |
| 236 | H | Cl | H |
| 237 | H | H | OMe |
| 238 | H | H | Cl |
| 239 | H | CF₃ | H |
TABLE 4
Compounds 240-253.
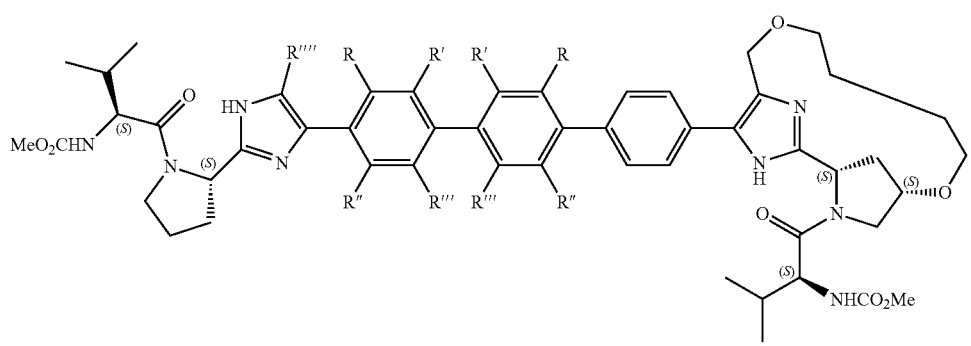
| Entry | R | R' | R" | R'" | R"" |
|---|---|---|---|---|---|
| 240 | F | H | H | H | H |
| 241 | F | F | H | H | H |
| 242 | Me | H | H | H | H |
| 243 | Me | Me | H | H | H |
| 244 | H | H | Me | Me | H |
| 245 | H | H | Et | Et | H |
| 246 | CF₃ | H | H | H | H |
| 247 | CF₃ | H | CF₃ | H | H |
| 248 | Cl | H | H | H | H |
| 249 | Cl | H | Cl | H | H |
| 250 | H | H | H | H | Br |
| 251 | H | H | H | H | Cl |
| 252 | H | H | H | H | F |
| 253 | H | H | H | H | CF₃ |

TABLE 5
Compounds 254-268.
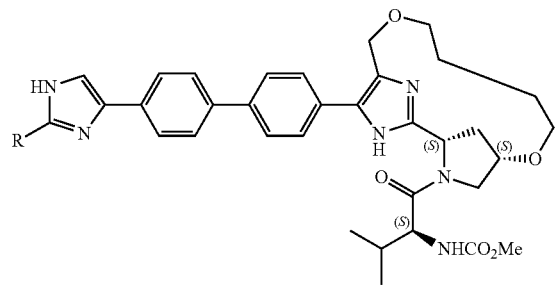
| Entry | R |
|---|---|
| 254 | 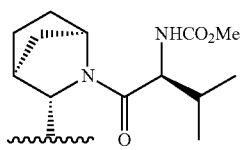 |
| 255 | 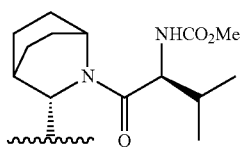 |
| 256 | 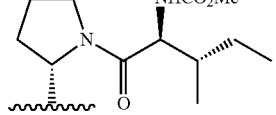 |
| 257 | 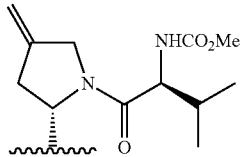 |
| 258 | 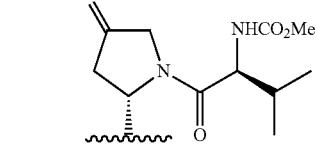 |
| 259 | 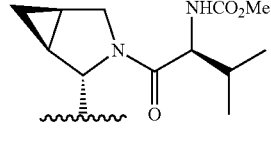 |
| 260 | 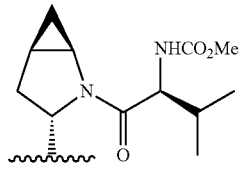 |
TABLE 5-continued
Compounds 254-268.
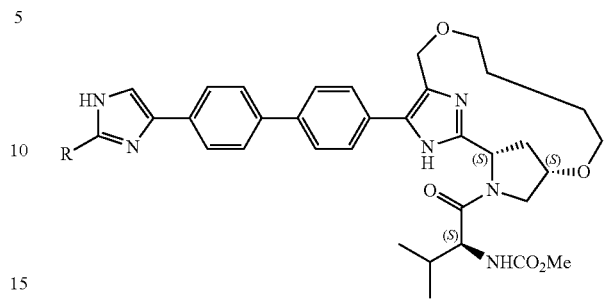
| Entry | R |
|---|---|
| 261 | 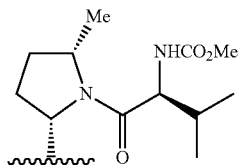 |
| 262 | 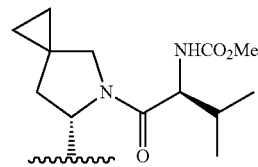 |
| 263 | 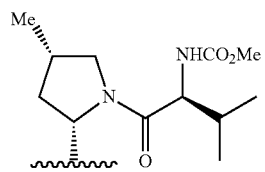 |
| 264 | 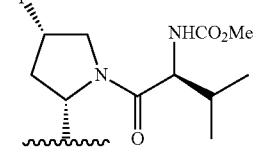 |
| 265 | 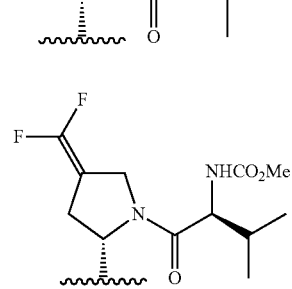 |
| 266 | 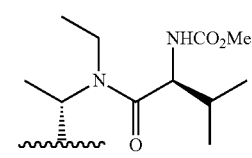 |

TABLE 5-continued
Compounds 254-268.
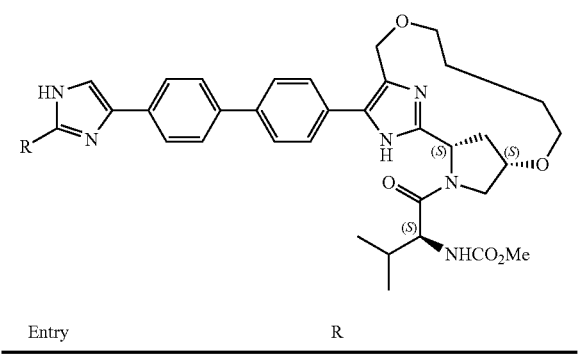
| Entry | R |
|---|---|
| 267 | 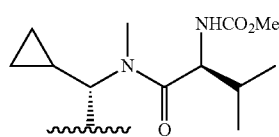 |
TABLE 5-continued
Compounds 254-268.
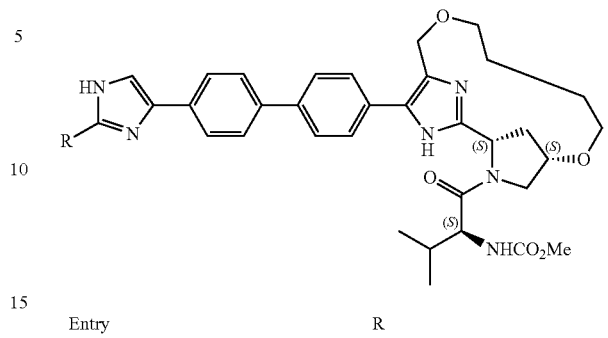
| Entry | R |
|---|---|
| 268 | 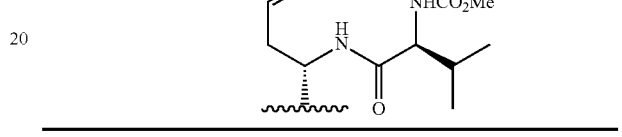 |
TABLE 6
Compounds 269-286.
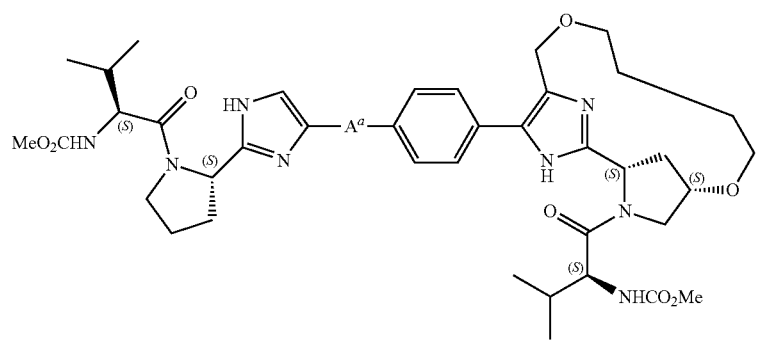
| Entry | $A^a$ |
|---|---|
| 269 | 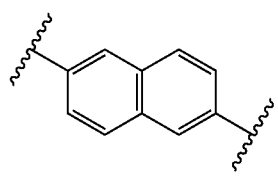 [SMILES: *c1ccc2cc(*)ccc2c1] |
| 270 | 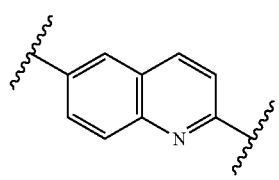 [SMILES: *c1ccc2nc(*)ccc2c1] |
| 271 | 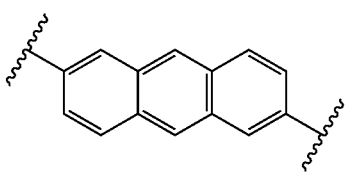 [SMILES: *c1ccc2cc3cc(*)ccc3cc2c1] |

TABLE 6-continued
Compounds 269-286.
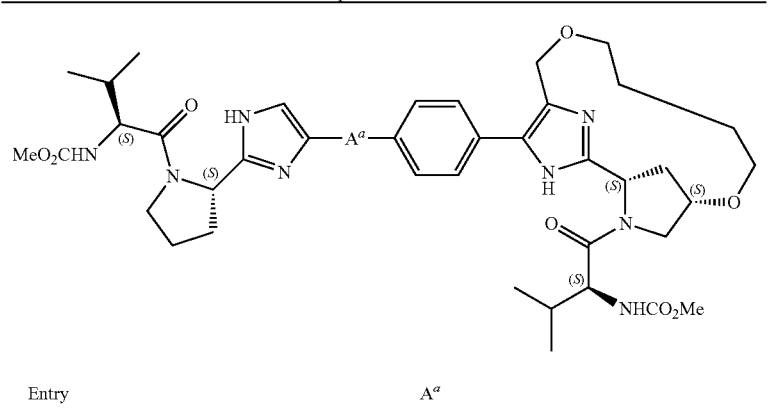
| Entry | $A^a$ |
|---|---|
| 272 | 6-naphthyl-phenyl linker |
| 273 | trans-CH=CH-phenyl linker |
| 274 | C≡C-phenyl linker |
| 275 | phenyl-cyclohexyl linker |
| 276 | piperazinyl-pyrimidinyl linker |
| 277 | pyrazolyl-pyridinyl linker |
| 278 | phenyl-pyridinyl linker |
| 279 | thienyl-phenyl linker |
| 280 | phenyl-CH=CH-phenyl linker |

TABLE 6-continued
Compounds 269-286.
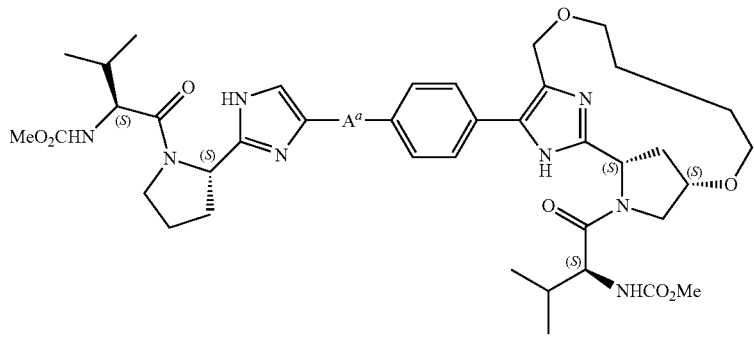
| Entry | $A^a$ |
|---|---|
| 281 | 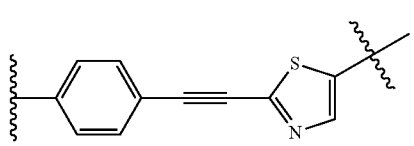 [SMILES: *c1ccc(C#Cc2ncc(*)s2)cc1] |
| 282 | 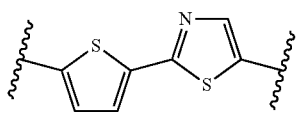 [SMILES: *c1ccc(-c2ncc(*)s2)s1] |
| 283 | 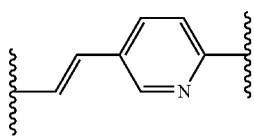 [SMILES: */C=C/c1ccc(*)nc1] |
| 284 | 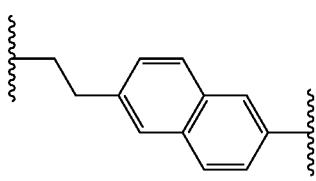 |
| 285 | 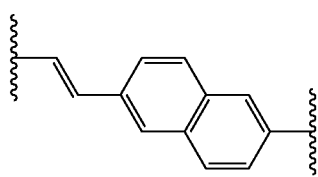 |
| 286 | 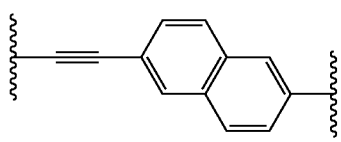 [SMILES: *C#Cc1ccc2cc(*)ccc2c1] |

TABLE 7
Compounds 287-307.
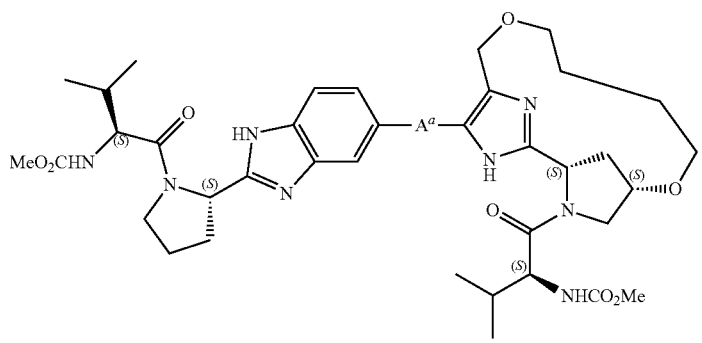
| Entry | $A^a$ |
|---|---|
| 287 | |
| 288 | |
| 289 | |
| 290 | |
| 291 | |
| 292 | |
| 293 | |
| 294 | |
| 295 | |

TABLE 7-continued
Compounds 287-307.
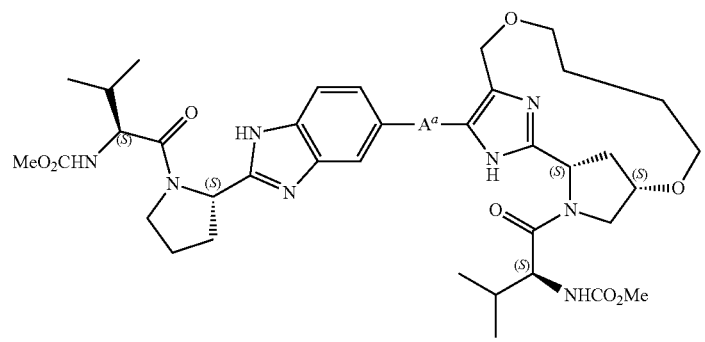
| Entry | $A^a$ |
|---|---|
| 296 | 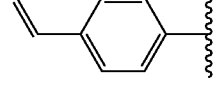 |
| 297 | 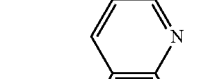 |
| 298 | 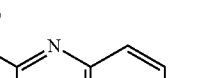 |
| 299 | 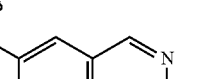 |
| 300 | 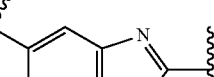 |
| 301 | 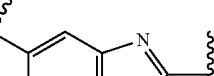 |
| 302 | 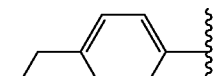 |

TABLE 7-continued
Compounds 287-307.
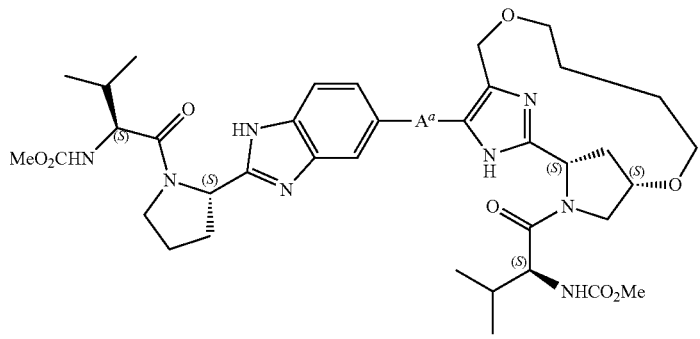
| Entry | $A^a$ |
|---|---|
| 303 | 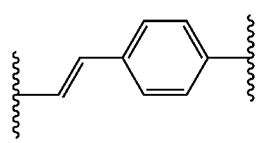 |
| 304 | 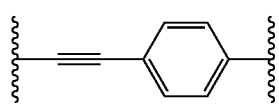 |
| 305 | 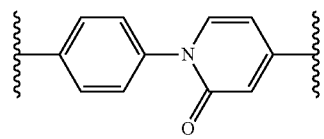 [SMILES: *c1ccc(-n2ccc(*)cc2=O)cc1] |
| 306 | 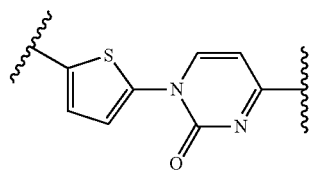 [SMILES: *c1ccn(-c2ccc(*)s2)c(=O)n1] |
| 307 | 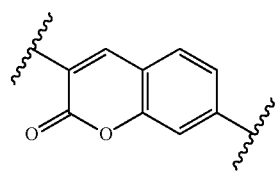 [SMILES: *c1ccc2cc(*)c(=O)oc2c1] |

TABLE 8
Compounds 308-319.
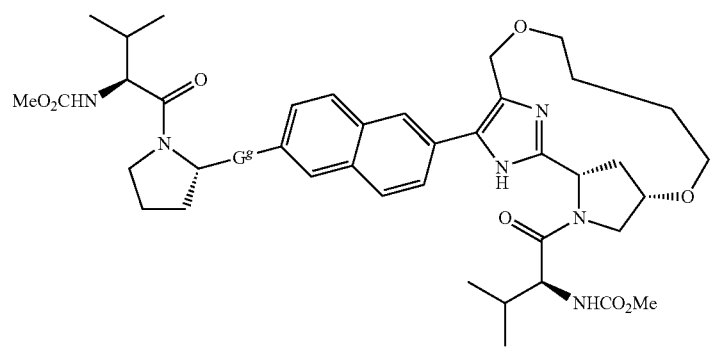
| Entry | A$^a$ |
|---|---|
| 308 | 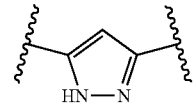 |
| 309 | 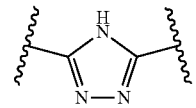 [SMILES: *c1nnc(*)[nH]1] |
| 310 | 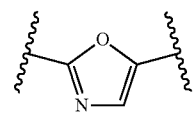 [SMILES: *c1cnc(*)o1] |
| 311 | 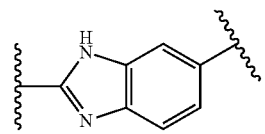 [SMILES: *c1ccc2nc(*)[nH]c2c1] |
| 312 | 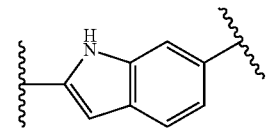 [SMILES: *c1ccc2cc(*)[nH]c2c1] |
| 313 | 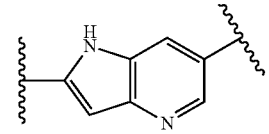 [SMILES: *c1cnc2cc(*)[nH]c2c1] |
| 314 | 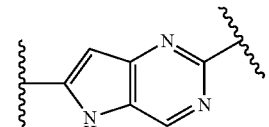 |
| 315 | 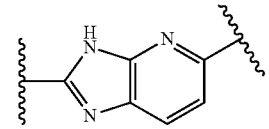 [SMILES: *c1ccc2nc(*)[nH]c2n1] |

TABLE 8-continued
Compounds 308-319.
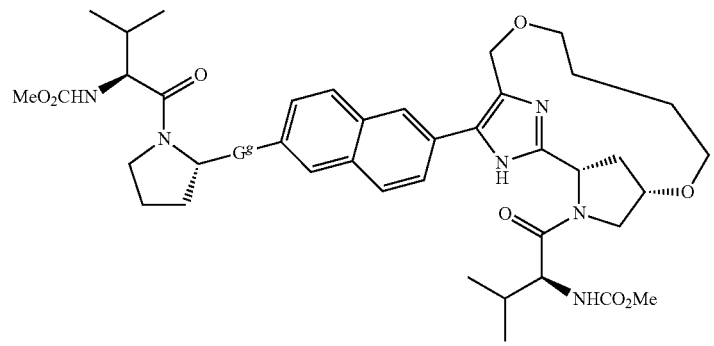
| Entry | $A^a$ |
|---|---|
| 316 | ![imidazopyridine] |
| 317 | ![imidazopyridine] |
| 318 | ![imidazopyrimidine] |
| 319 | ![indole] |
TABLE 9
Compounds 320-337.
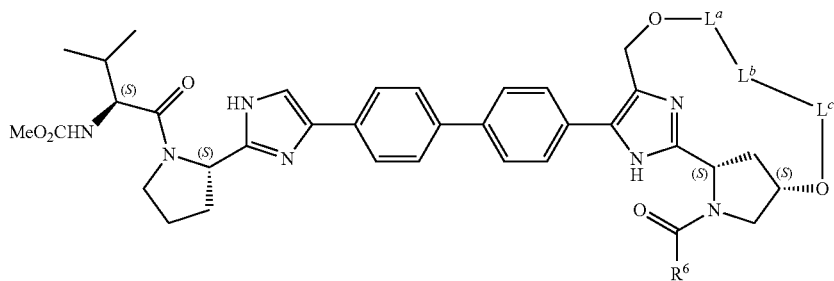
| Entry | $L^a$—$L^b$—$L^c$ |
|---|---|
| 320 | ![chain] |

TABLE 9-continued
Compounds 320-337.
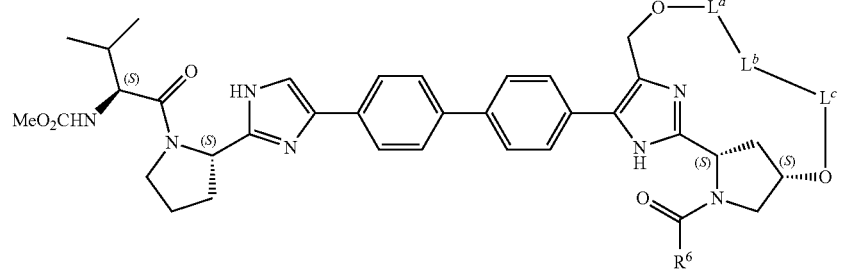
| Entry | $L^a$—$L^b$—$L^c$ |
|---|---|
| 321 | |
| 322 | |
| 323 | |
| 324 | |
| 325 | |
| 326 | |
| 327 | |
| 328 | |
| 329 | |
| 330 | |

TABLE 9-continued
Compounds 320-337.
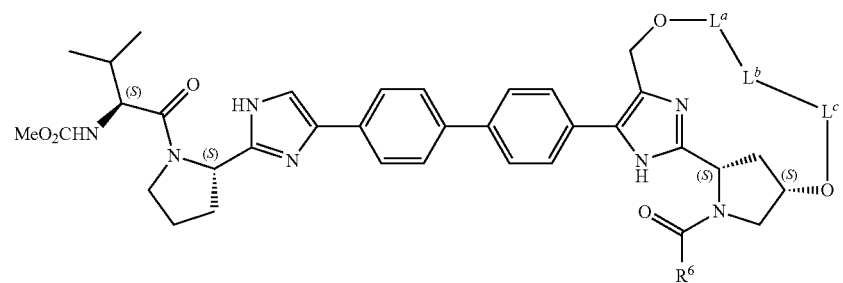
| Entry | $L^a$—$L^b$—$L^c$ |
|---|---|
| 331 | 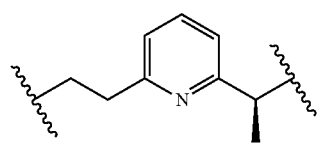 [SMILES: *CCc1cccc([C@@H](*)C)n1] |
| 332 | 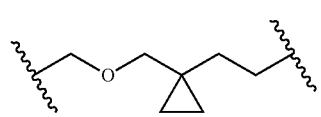 [SMILES: *CCC1(COC*)CC1] |
| 333 | 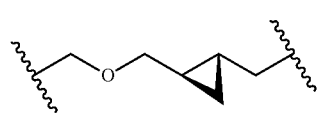 [SMILES: *COC[C@@H]1C[C@H]1C*] |
| 334 | 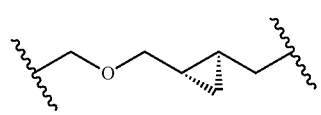 [SMILES: *COC[C@H]1C[C@@H]1C*] |
| 335 | 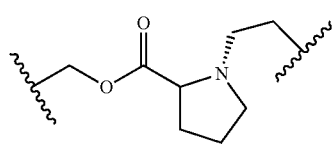 |
| 336 | 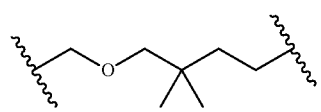 [SMILES: *CCC(C)(C)COC*] |
| 337 | 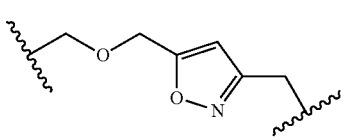 [SMILES: *COCc1cc(C*)no1] |

TABLE 10
Compounds 334-341.
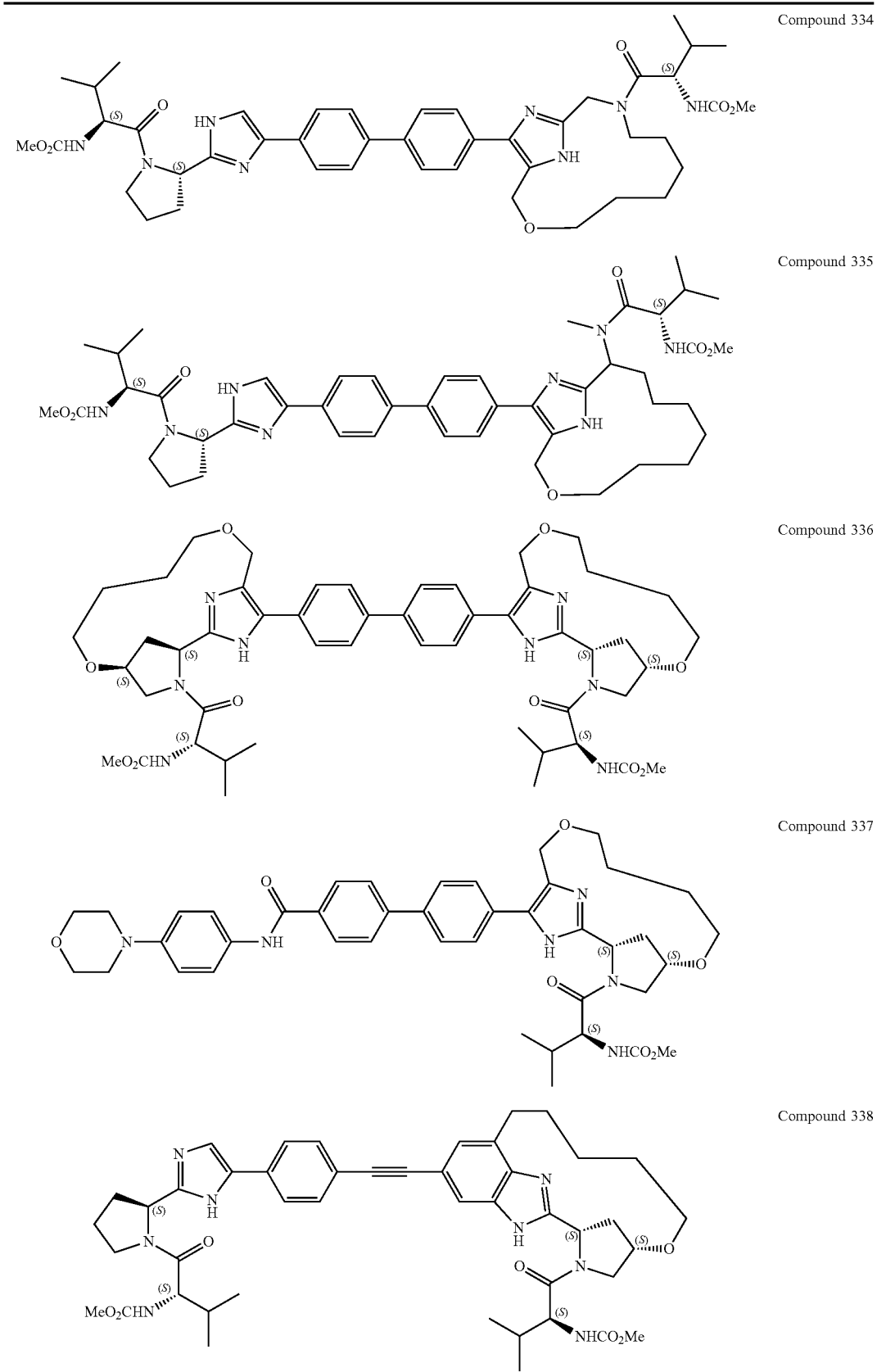
Compound 334
Compound 335
Compound 336
Compound 337
Compound 338

TABLE 10-continued

Compounds 334-341.

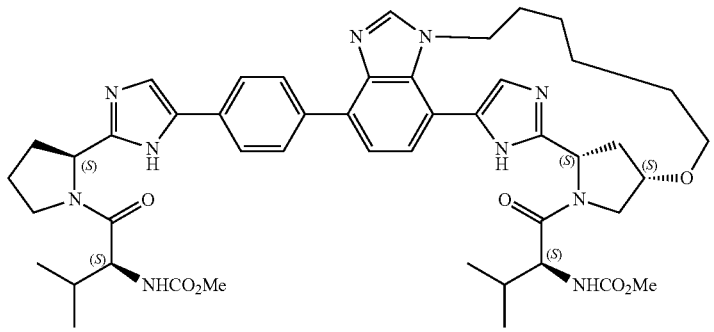

Compound 339

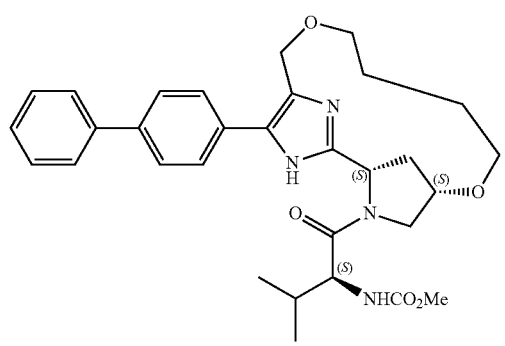

Compound 340

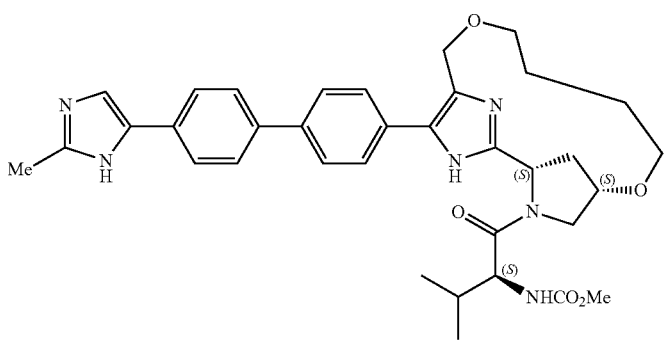

Compound 341

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

Q-G-A-L-B—Z—W    (I), or a pharmaceutically acceptable salt thereof, wherein:

A and B are each independently absent or a monocyclic or polycyclic group independently selected from the group consisting of aryl, heteroaryl, heterocyclic, $C_3$-$C_8$ cycloalkyl and $C_3$-$C_8$ cycloalkenyl, each optionally substituted;

L is absent or an aliphatic group;

wherein at least one of A, B and L is present;

Z is —C(O)NH—, an optionally substituted 5-membered heteroaryl containing one or more nitrogen atoms, or an optionally substituted 5-membered heteroaryl fused to a mono- or bicyclic ring, wherein the mono- or bicyclic ring is aromatic or non-aromatic, wherein the mono- or bicyclic ring is attached to one of groups A, L and B and wherein the 5-membered heteroaryl contains one or more nitrogen atoms;

G is absent, —C(O)NH—, an optionally substituted 5-membered heteroaryl containing one or more nitrogen atoms, or an optionally substituted 5-membered heteroaryl fused to a mono- or bicyclic ring, wherein the mono- or bicyclic ring is aromatic or non-aromatic, wherein the mono- or bicyclic ring is attached to one of groups A, L and B and wherein the 5-membered heteroaryl contains one or more nitrogen atoms;

W is

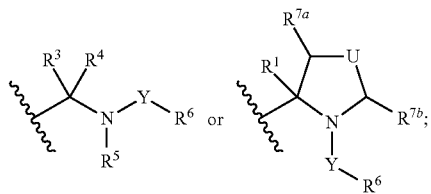

Q is hydrogen,

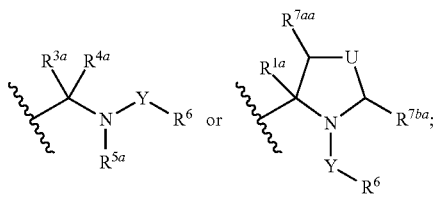

Y at each occurrence is independently C(O) or S(O)$_2$;
R$^1$ and R$^{1a}$ at each occurrence are independently hydrogen, hydroxy, O(C$_1$-C$_4$ alkyl) or optionally substituted C$_1$-C$_4$ alkyl;
R$^3$, R$^{3a}$, R$^4$ and R$^{4a}$ are each independently selected from the group consisting of hydrogen, optionally substituted C$_1$-C$_8$ alkyl, optionally substituted C$_2$-C$_8$ alkenyl, and optionally substituted C$_3$-C$_8$ cycloalkyl; alternatively, R$^3$ and R$^4$ or R$^{3a}$ and R$^{4a}$ can be taken together with the carbon atom to which they are attached to form optionally substituted C$_3$-C$_8$ cycloalkyl or optionally substituted heterocyclic;
R$^5$ and R$^{5a}$ are each independently hydrogen, optionally substituted C$_1$-C$_8$ alkyl, or optionally substituted C$_3$-C$_8$ cycloalkyl;
wherein one of R$^3$, R$^4$ and R$^5$ is connected to group Z via a linker of -L$^1$-L$^2$-L$^3$-; or alternatively one of R$^3$, R$^4$ and R$^5$ is connected to group B via a linker of -L$^1$-L$^2$-L$^3$-; wherein group B is present; alternatively, wherein one of R$^{3a}$, R$^{4a}$ and R$^{5a}$ is connected to group G via a linker of -L$^1$-L$^2$-L$^3$- wherein group G is present; or alternatively, one of R$^{3a}$, R$^{4a}$ and R$^{5a}$ is connected to group A via a linker of -L$^1$-L$^2$-L$^3$- wherein group A is present; yet alternatively, wherein one of R$^3$, R$^4$ and R$^5$ is connected to group Z or group B via a linker of -L$^1$-L$^2$-L$^3$- and one of R$^{3a}$, R$^{4a}$ and R$^{5a}$ is connected to group G or group A via a linker of -L$^1$-L$^2$-L$^3$;
L$^1$ and L$^3$ at each occurrence are each independently an aliphatic group, or one of L$^1$ and L$^3$ is absent and the other of L$^1$ and L$^3$ is an aliphatic group;
L$^2$ at each occurrence is independently absent, or selected from the group consisting of aryl, heteroaryl, heterocyclic, C$_3$-C$_8$ cycloalkyl, and C$_3$-C$_8$ cycloalkenyl, each optionally substituted;
wherein -L$^1$-L$^2$-L$^3$- together form a linker;
R$^6$ at each occurrence is independently selected from the group consisting of O(C$_1$-C$_8$ alkyl), amino, C$_1$-C$_8$ alkyl, C$_2$-C$_8$ alkenyl, C$_2$-C$_8$ alkynyl, C$_3$-C$_8$ cycloalkyl, C$_3$-C$_8$ cycloalkenyl, heterocyclic, aryl, and heteroaryl, each optionally substituted;
U and U$^a$ are each independently absent or each independently selected from O, S, S(O), SO$_2$, NC(O)—(C$_1$-C$_4$ alkyl), C(O), protected carbonyl, OCH$_2$, OCH$_2$CH$_2$, SCH$_2$, SCH$_2$CH$_2$, C(R$^7$)$_2$, Si(R$^7$)$_2$, C(R$^7$)$_2$C(R$^2$)$_2$, and C=C(R$^2$)$_2$;
R$^2$ at each occurrence is independently hydrogen, halogen, optionally substituted C$_1$-C$_4$ alkyl, optionally substituted aryl, or optionally substituted heteroaryl;
R$^7$ at each occurrence is independently selected from the group consisting of hydrogen, halogen, cyano, hydroxy, optionally substituted O(C$_1$-C$_4$ alkyl), S(C$_1$-C$_4$ alkyl), amino optionally substituted with one or two C$_1$-C$_4$ alkyl, optionally substituted aryl, optionally substituted heteroaryl, optionally substituted C$_1$-C$_4$ alkyl, and optionally substituted C$_3$-C$_8$ cycloalkyl;
alternatively two geminal R$^7$ groups are taken together with the carbon atom to which they are attached to form a spiro, optionally substituted 3- to 7-membered cyclic group selected from the group consisting of C$_3$-C$_7$ cycloalkyl, C$_3$-C$_7$ cycloalkenyl or 3- to 7-membered heterocyclic;
R$^{7a}$, R$^{7aa}$, R$^{7b}$, and R$^{7ba}$ at each occurrence are independently selected from the group consisting of hydrogen, optionally substituted aryl, optionally substituted C$_1$-C$_4$ alkyl, and optionally substituted C$_3$-C$_8$ cycloalkyl;
alternatively, CHR$^{7a}$—U, CHR$^{7b}$—U, CHR$^{7aa}$—U$^a$ or CHR$^{7ba}$—U$^a$ are taken together to form a group selected from CH=CH, fused and optionally substituted C$_3$-C$_8$ cycloalkyl, fused and optionally substituted aryl, or fused and optionally substituted heterocyclic; and
yet alternatively, U, R$^{7a}$, and R$^{7b}$ are taken together with the carbon atoms to which they are attached to form a bridged, optionally substituted 4- to 7-membered cyclic group selected from the group consisting of C$_4$-C$_7$ cycloalkyl, C$_4$-C$_7$ cycloalkenyl and 4- to 7-membered heterocyclic; and
wherein one of R$^{7a}$, R$^{7b}$ and U is connected to group Z via a linker of -L$^1$-L$^2$-L$^3$-; or alternatively one of R$^{7a}$, R$^{7b}$ and U is connected to group B via a linker of -L$^1$-L$^2$-L$^3$-; wherein group B is present; alternatively, wherein one of R$^{7aa}$, R$^{7ba}$, and U$^a$ is connected to group G via a linker of -L$^1$-L$^2$-L$^3$- wherein group G is present; or alternatively, one of R$^{7aa}$, R$^{7ba}$, and U$^a$ is connected to group A via a linker of -L$^1$-L$^2$-L$^3$- wherein group A is present; yet alternatively, wherein one of R$^{7a}$, R$^{7b}$ and U is connected to group Z or group B via a linker of -L$^1$-L$^2$-L$^3$- and one of R$^{7aa}$, R$^{7ba}$, and U$^a$ is connected to group G or group A via a linker of -L$^1$-L$^2$-L$^3$-; alternatively, U is connected to group R$^6$ via a linker of -L$^1$-L$^2$-L$^3$-; or
alternatively, U$^a$ is connected to group R$^6$ via a linker of -L$^1$-L$^2$-L$^3$.

2. The compound of claim 1, represented by Formula (Ia), (Ib), (Ic), (Id) or (Ie):

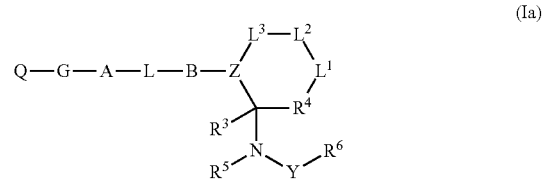

(Ia)

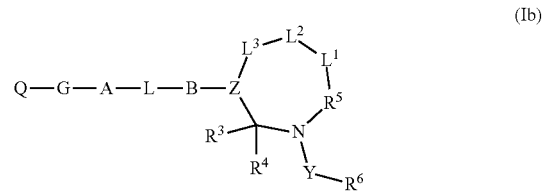

(Ib)

287
-continued

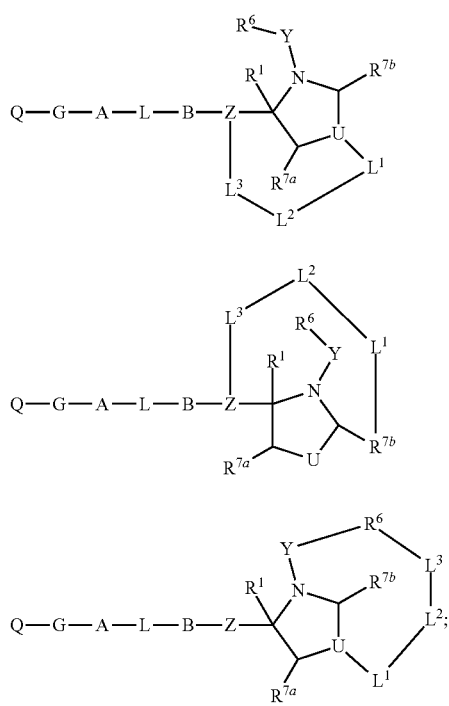

(Ic)

(Id)

(Ie)

or a pharmaceutically acceptable salt thereof.

3. The compound of claim 1, represented by Formula (IIa), (IIb), (IIc) or (IId):

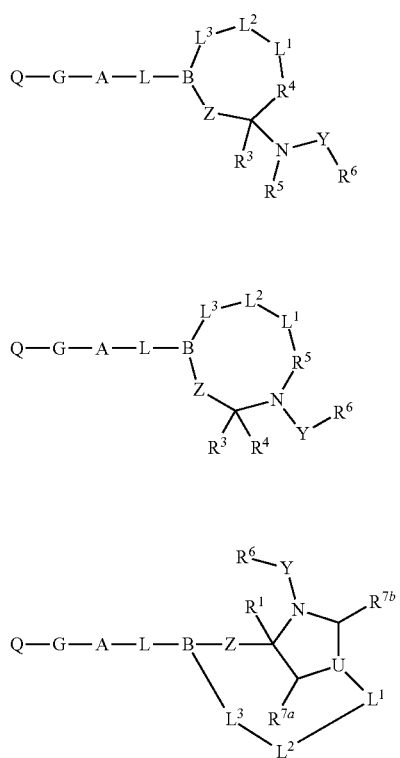

(IIa)

(IIb)

(IIc)

288
-continued

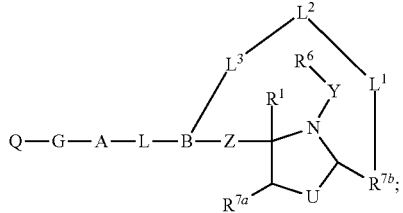

(IId)

or a pharmaceutically acceptable salt thereof.

4. The compound of claim 1, wherein:

$R^1$ and $R^{1a}$ are hydrogen;

Y is C(O);

L is absent or selected from the group consisting of O, —C(O)NH—, —($C_1$-$C_4$ alkyl)-NH—($C_1$-$C_4$ alkyl)-, heterocyclic, $C_2$-$C_4$ alkenyl, or $C_2$-$C_4$ alkynyl, each optionally substituted;

A and B are each independently absent, optionally substituted aryl, or optionally substituted heteroaryl; or alternatively A, L and B are taken together to form a linker selected from one of the groups illustrated below:

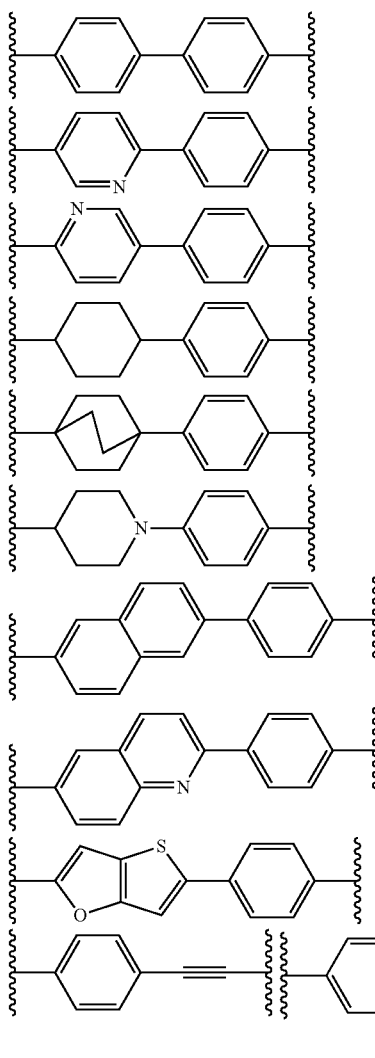

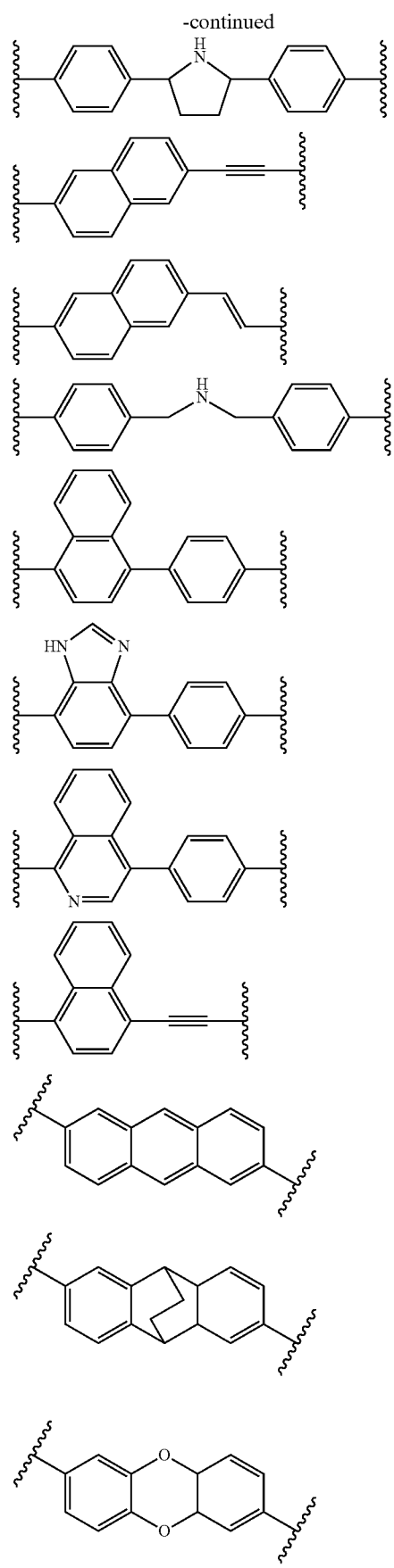
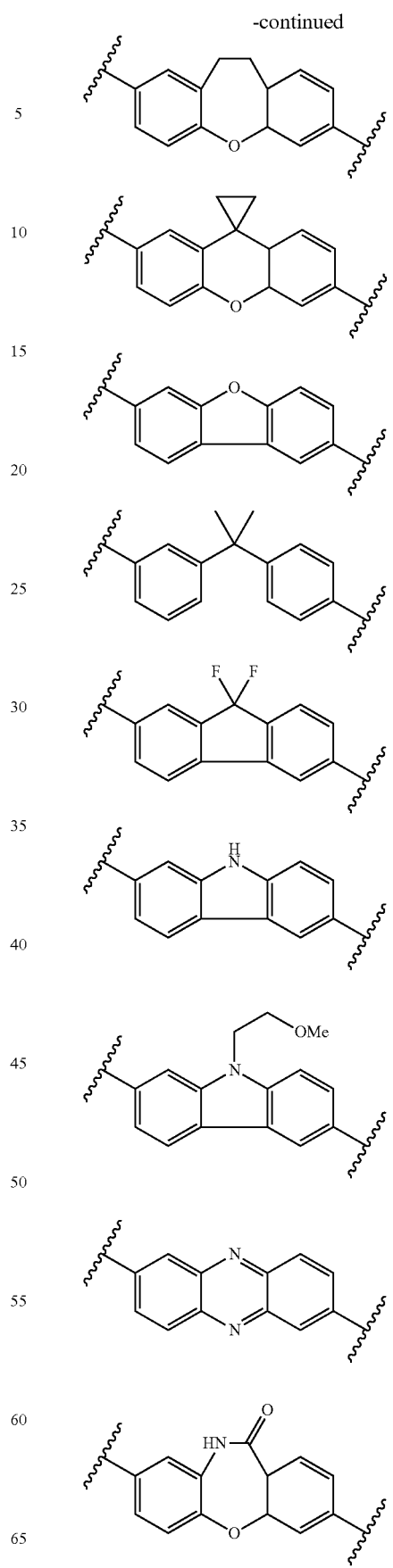

-continued

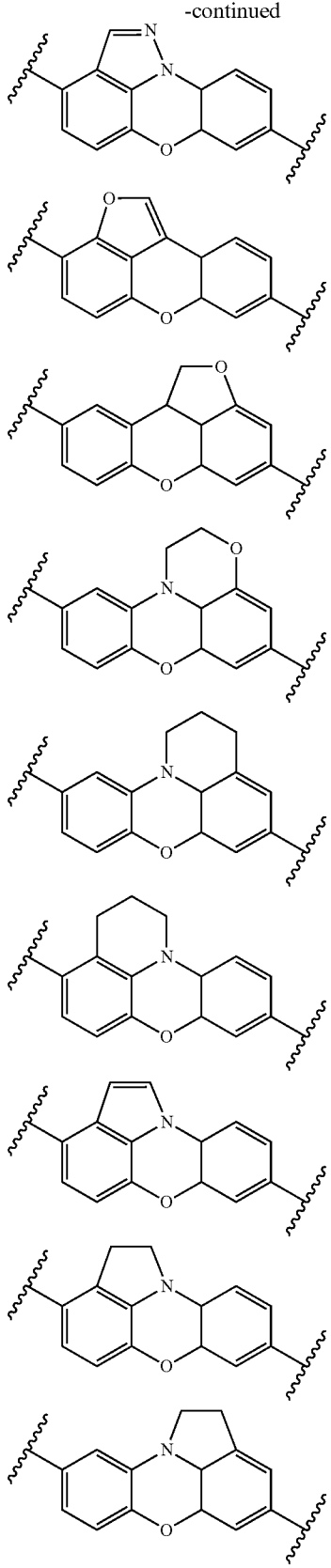

wherein each of the above shown groups is optionally substituted;

$L^1$ and $L^3$ at each occurrence are independently a linear aliphatic group, or one of $L^1$ and $L^3$ is a linear aliphatic group and the other one of $L^1$ and $L^3$ is absent;

wherein -$L^1$-$L^2$-$L^3$- together form a linker of from 8 to 14 bond lengths;

G and Z are each independently selected from the groups illustrated below:

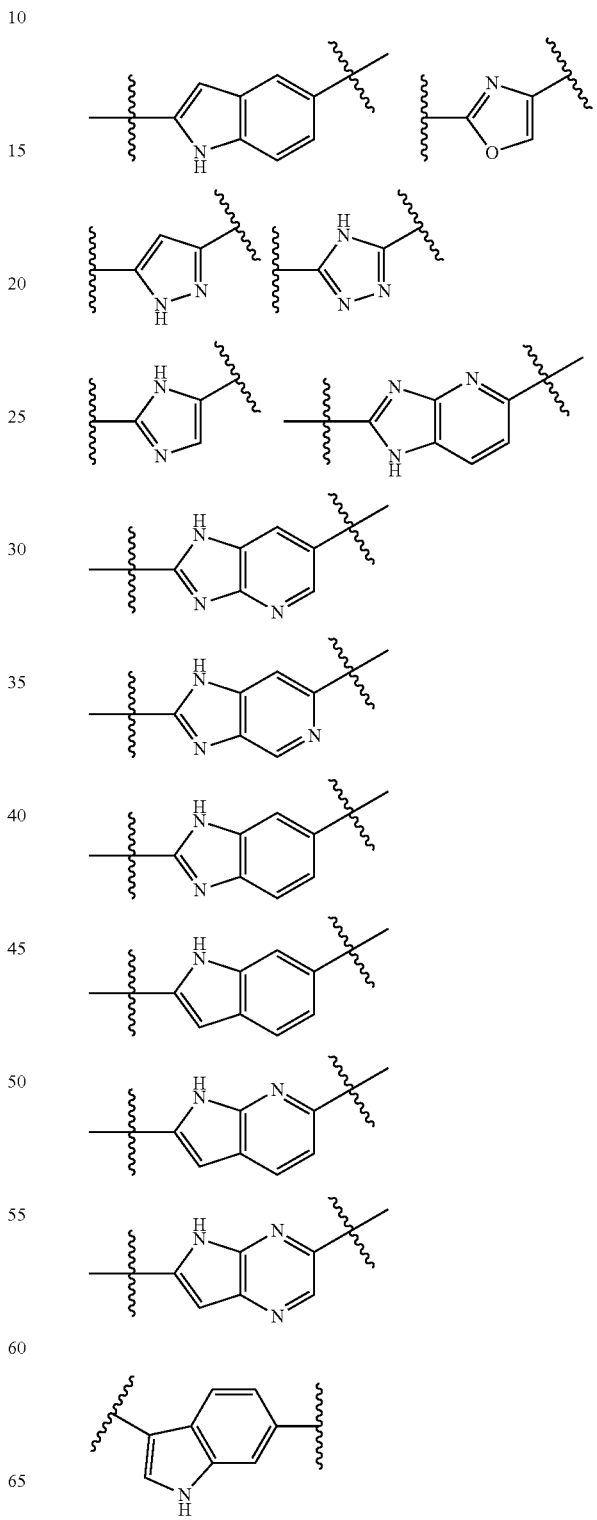

293
-continued
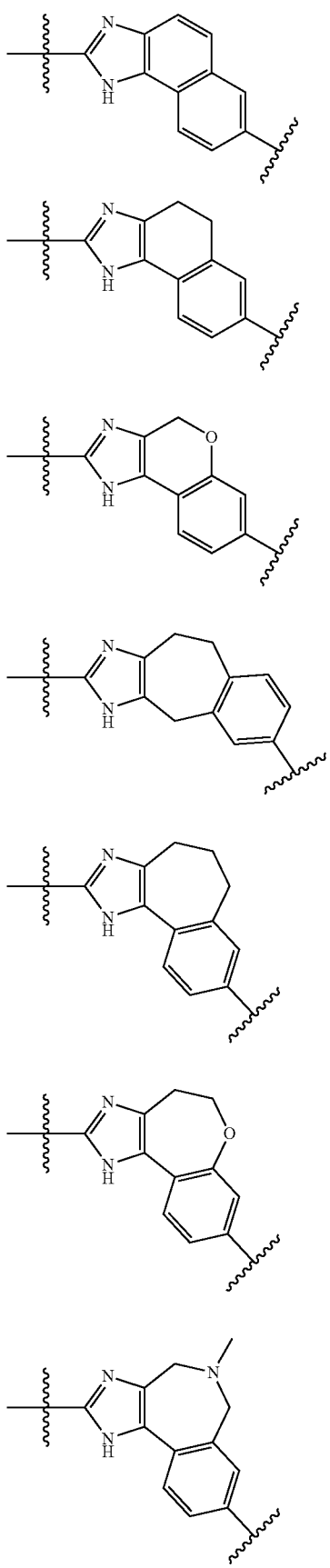
294
-continued
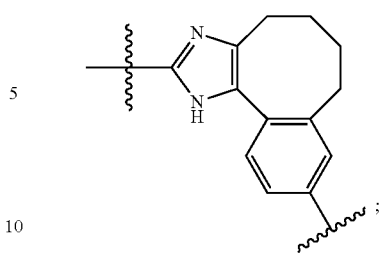
wherein each of the above shown heteroaryl groups is each optionally substituted; or a pharmaceutically acceptable salt thereof.
5. A compound of claim 1, represented by Formula (Ia-1), (Ia-2), (Ib-1), (Ib-2), (Ic-1), (Ic-2), (IIa-1), (IIa-2), (IIa-3), (IIa-4), (IIa-5), (IIa-6), (IIb-1), (IIb-2), (IIb-3), (IIb-4), (IIb-5), (IIc-1), (IIc-2), (IIc-3), (IIc-4), (IIc-5), or (IIc-6); or a pharmaceutically acceptable salt thereof:
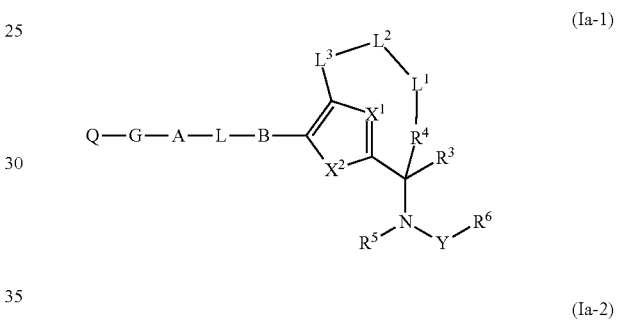
(Ia-1)
(Ia-2)
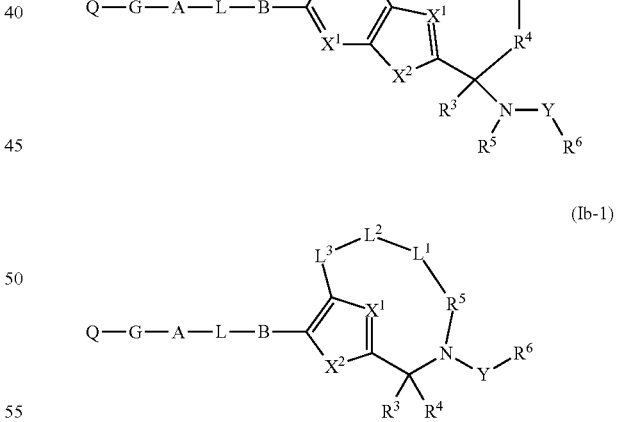
(Ib-1)
(Ib-2)
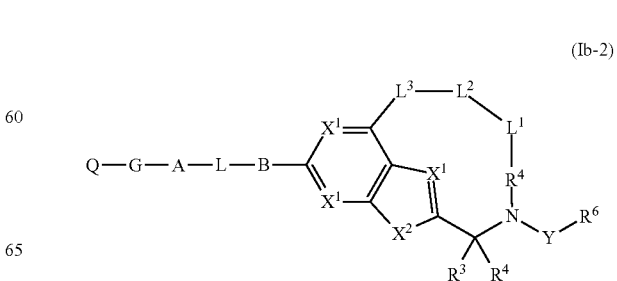

-continued
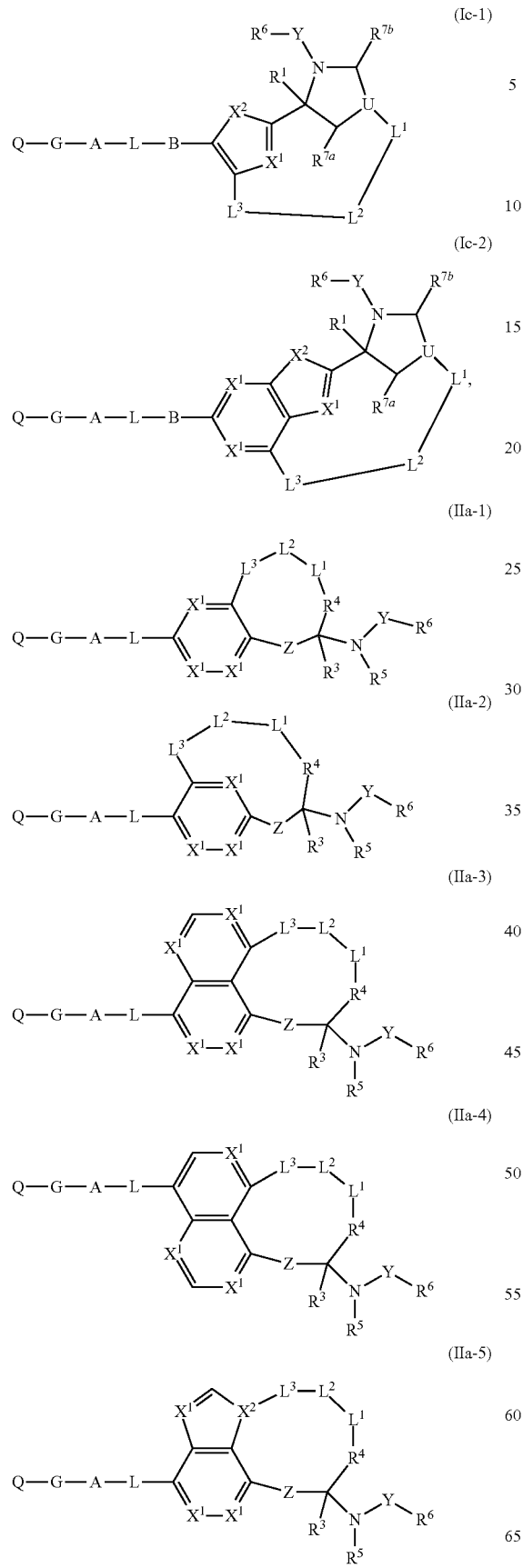
-continued
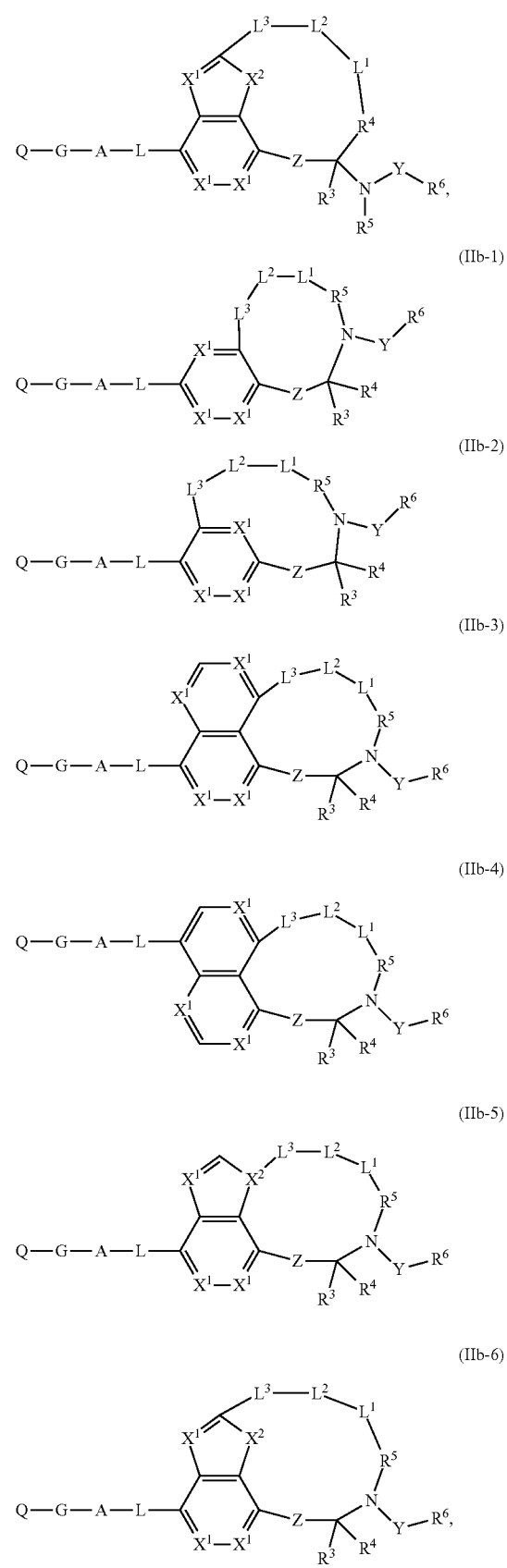

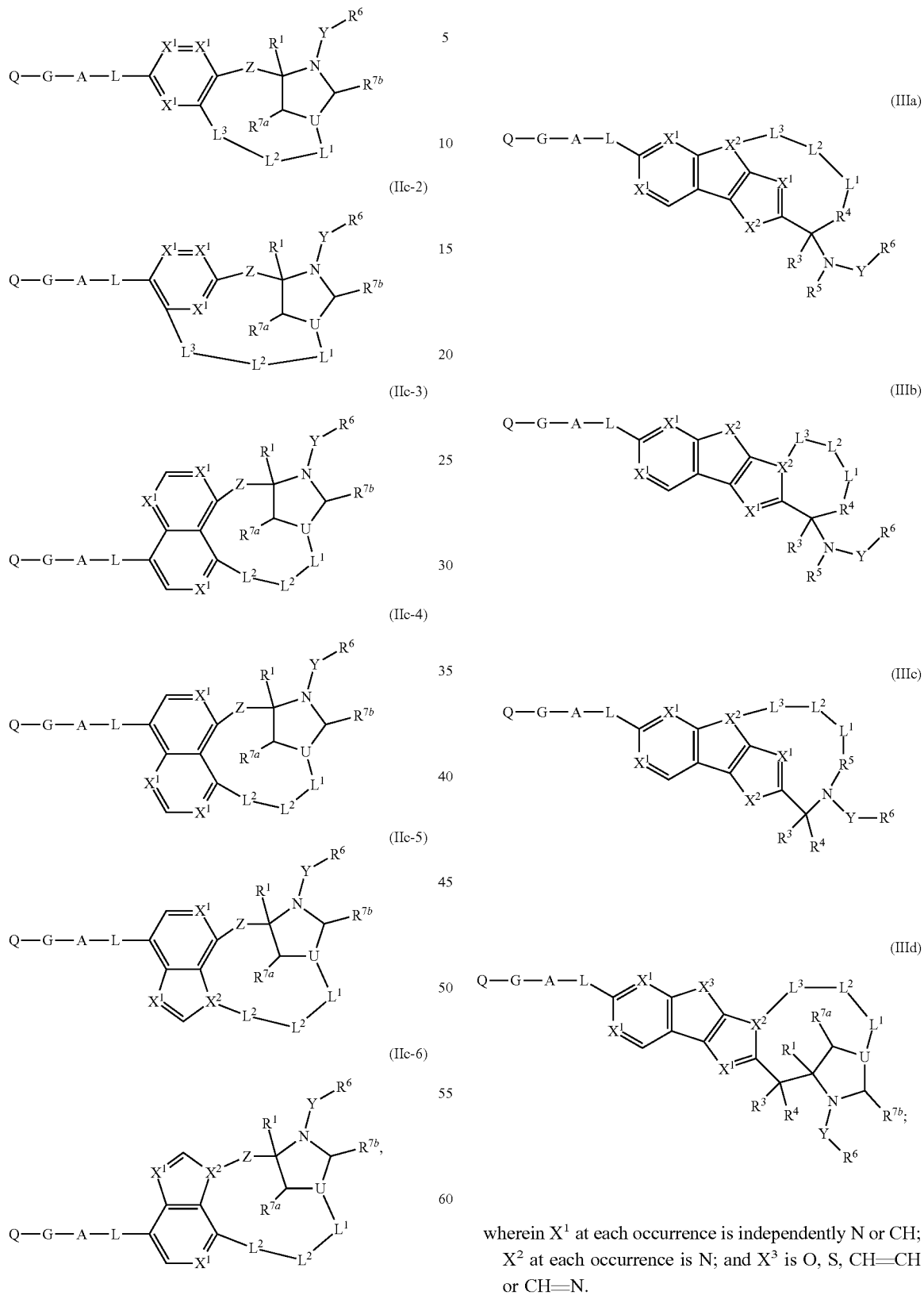

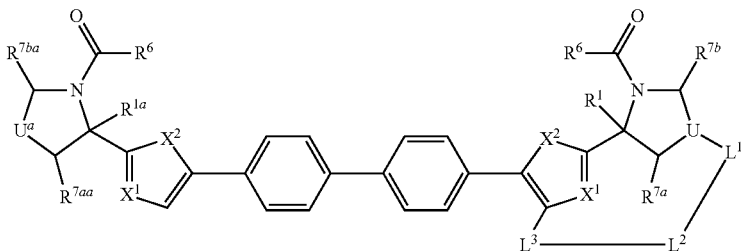 (VIa)
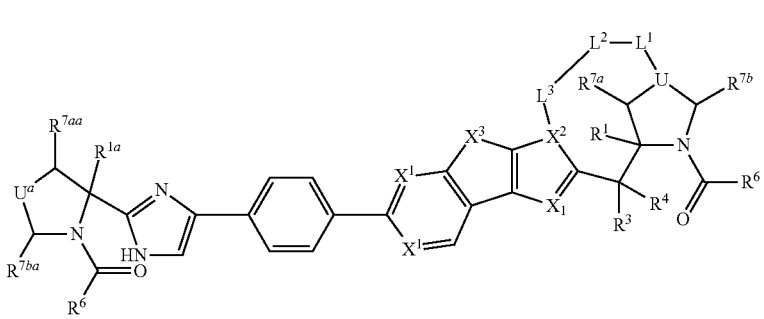 (VIb)
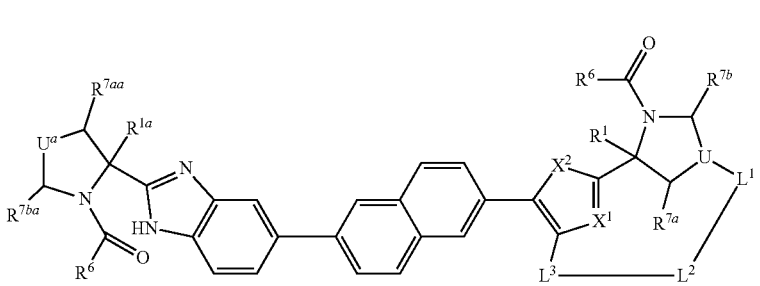 (VIc)
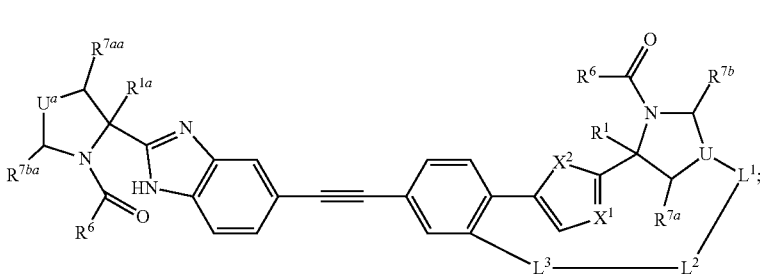 (VId)
wherein $X^1$ at each occurrence is independently N or CH; and $X^2$ at each occurrence is N; or a pharmaceutically acceptable salt thereof.
8. The compound of claim 1, wherein
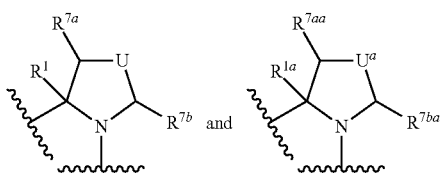
are independently selected from:
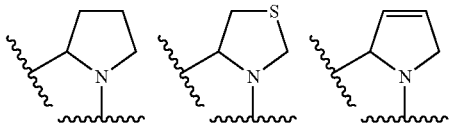
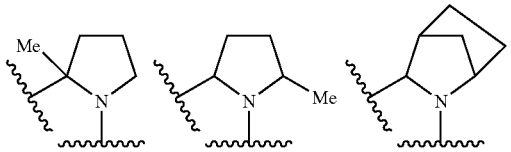

301
-continued
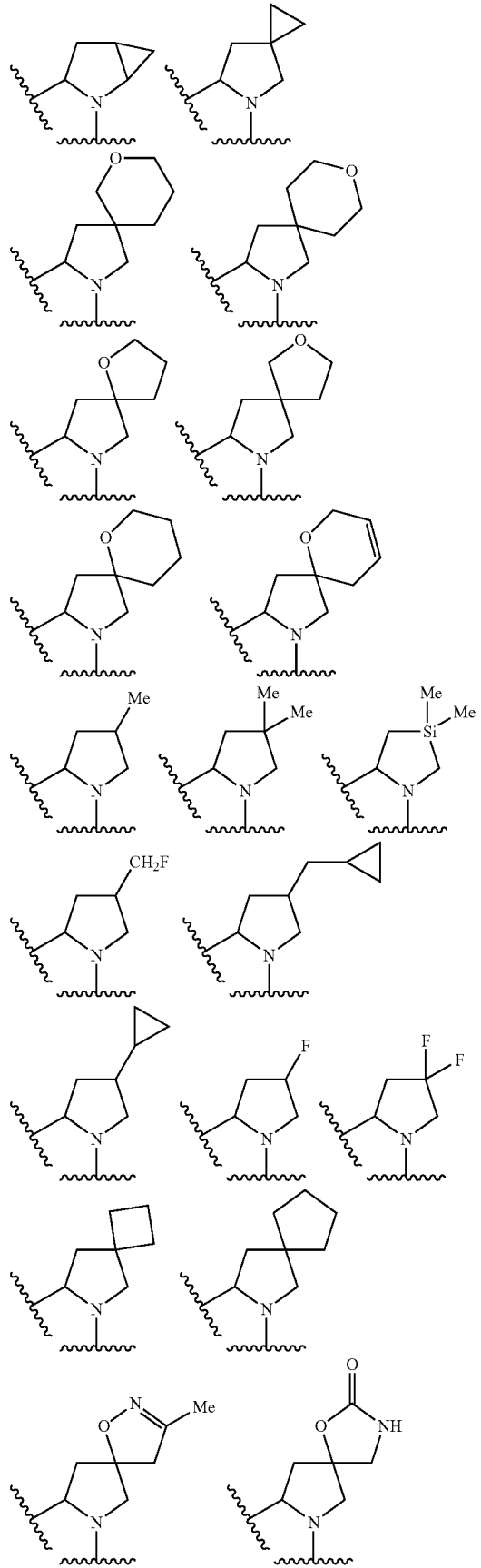
302
-continued
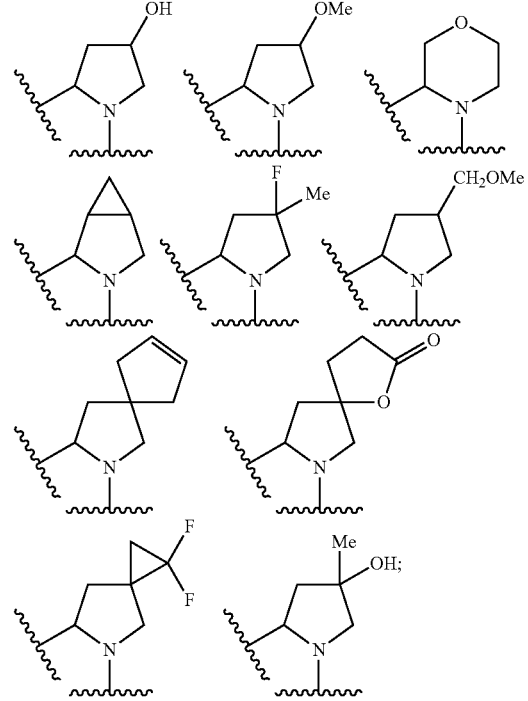
or a pharmaceutically acceptable salt thereof.
9. The compound of claim 1, wherein the linker -L$^1$-L$^2$-L$^3$- is selected from:
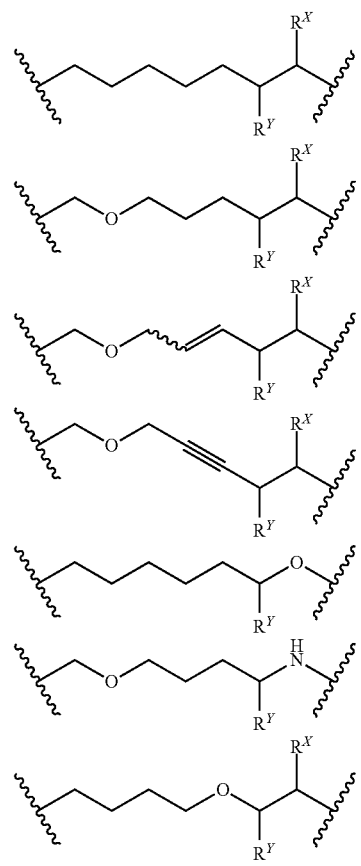

303
-continued

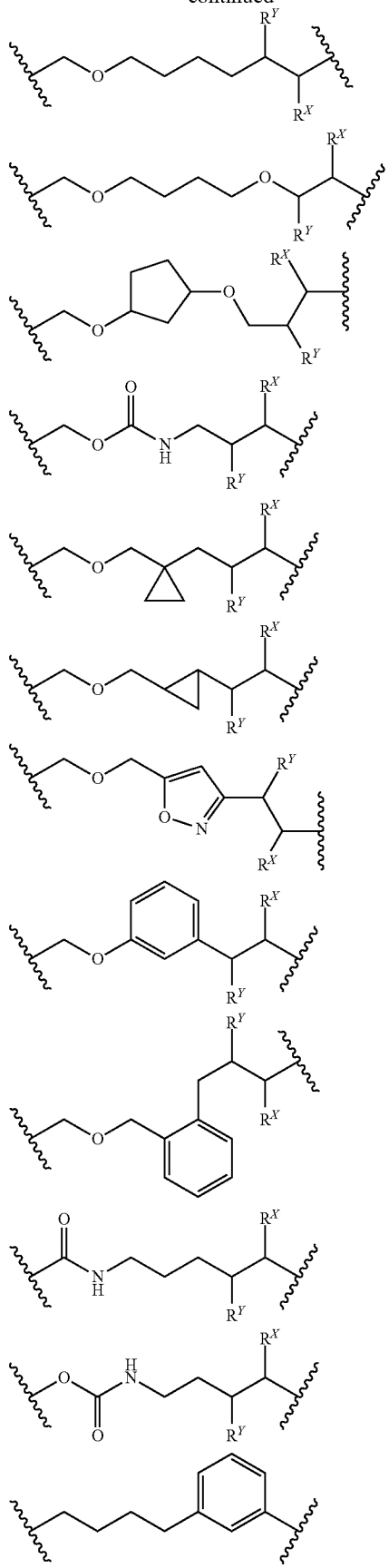

304
-continued

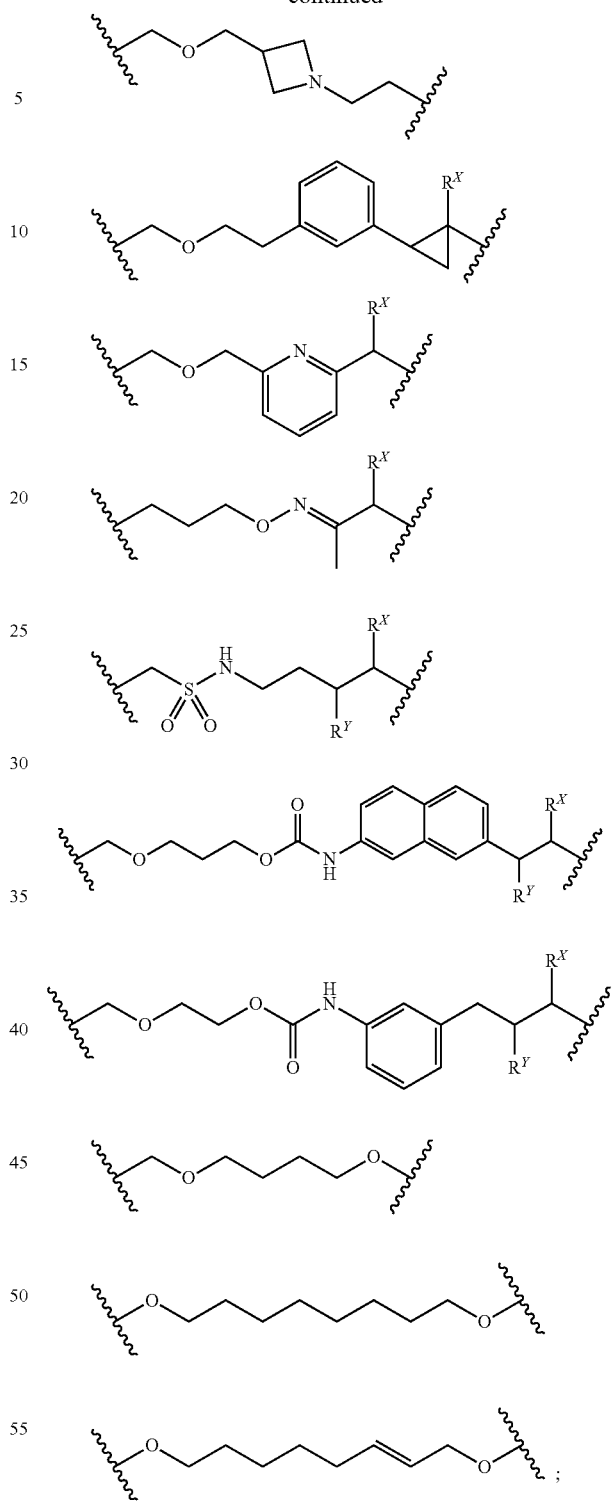

wherein $R^X$ is hydrogen, amino, hydroxy, protected amino or $O(C_1-C_4$ alkyl); $R^Y$ is hydrogen or optionally substituted $C_1-C_8$ alkyl; and each of the above shown groups is further optionally substituted; or a pharmaceutically acceptable salt thereof.

10. The compound of claim 1 selected from the group of compounds 1-345 compiled in the following tables:

Compounds 1-219
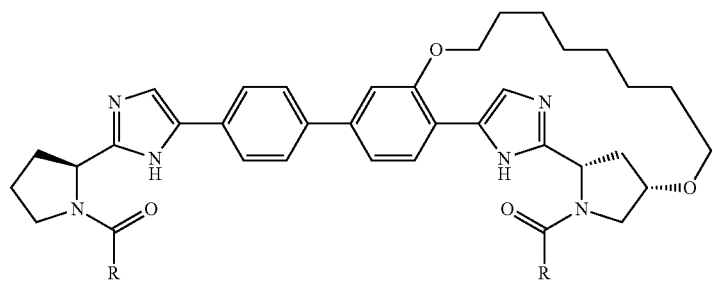
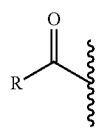
| Entry | |
|---|---|
| 1 | 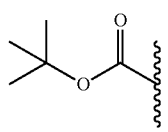 [SMILES: *C(=O)OC(C)(C)C] |
| 2 | 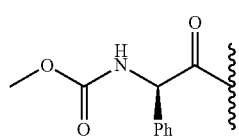 [SMILES: *C(=O)[C@H](NC(=O)OC)c1ccccc1] |
| 3 | 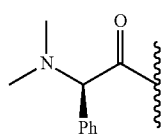 [SMILES: *C(=O)[C@@H](c1ccccc1)N(C)C] |
| 4 | 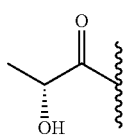 |
| 5 | 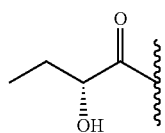 [SMILES: *C(=O)[C@H](O)CC] |
| 6 | 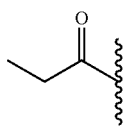 |
| 7 | 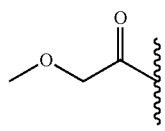 [SMILES: *C(=O)COC] |
| 8 | 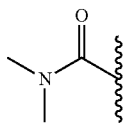 |

-continued
| Compounds 1-219 |
|---|
| 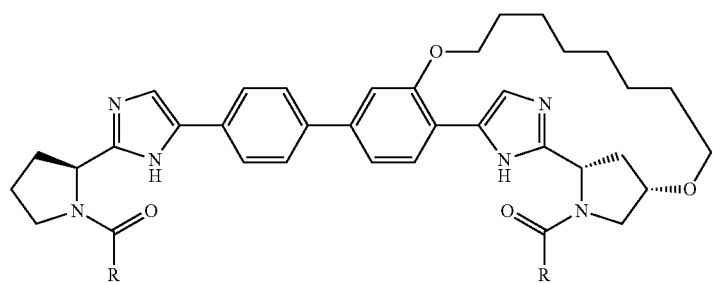 |
| 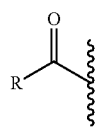 |
| Entry | |
|---|---|
| 9 | 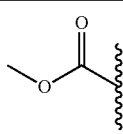 |
| 10 | 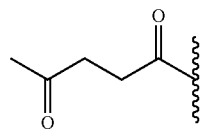 [SMILES: *C(=O)CCC(C)=O] |
| 11 | 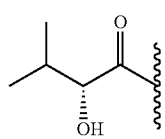 [SMILES: *C(=O)[C@H](O)C(C)C] |
| 12 | 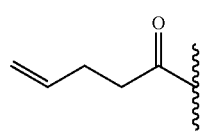 [SMILES: *C(=O)CCC=C] |
| 13 | 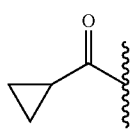 [SMILES: *C(=O)C1CC1] |
| 14 | 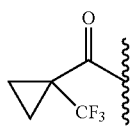 |
| 15 | 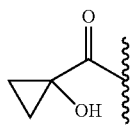 [SMILES: *C(=O)C1(O)CC1] |
| 16 | 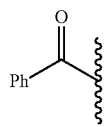 |

Compounds 1-219
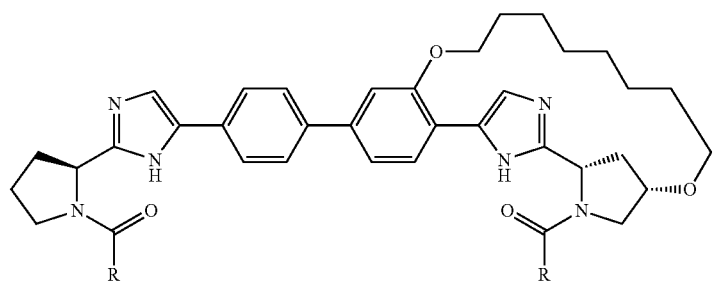
| Entry | R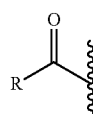 |
|---|---|
| 17 | 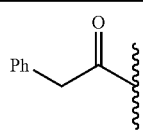 |
| 18 | 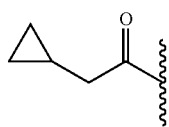 [SMILES: *C(=O)CC1CC1] |
| 19 | 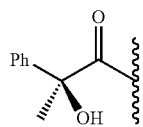 [SMILES: *C(=O)[C@@](C)(O)c1ccccc1] |
| 20 | 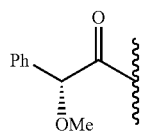 [SMILES: *C(=O)[C@H](OC)c1ccccc1] |
| 21 | 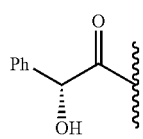 [SMILES: *C(=O)[C@H](O)c1ccccc1] |
| 22 | 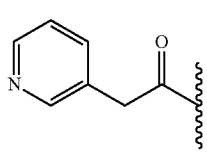 [SMILES: *C(=O)Cc1cccnc1] |
| 23 | 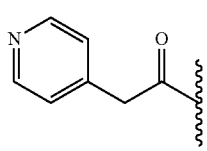 [SMILES: *C(=O)Cc1ccncc1] |
| 24 | 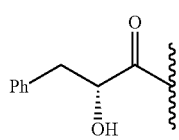 |

-continued
Compounds 1-219
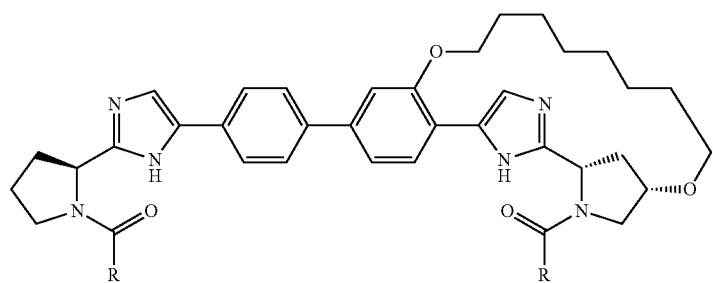
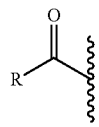
| Entry | |
|---|---|
| 25 | 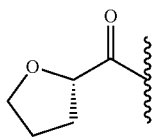 |
| 26 | 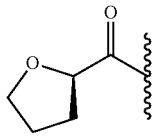 [SMILES: *C(=O)[C@H]1CCCO1] |
| 27 | 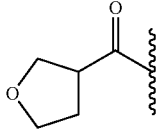 [SMILES: *C(=O)C1CCOC1] |
| 28 | 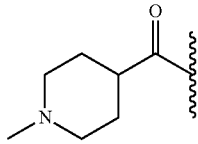 [SMILES: *C(=O)C1CCN(C)CC1] |
| 29 | 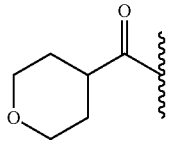 [SMILES: *C(=O)C1CCOCC1] |
| 30 | 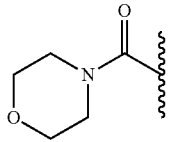 [SMILES: *C(=O)N1CCOCC1] |
| 31 | 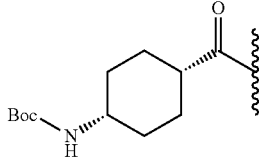 [SMILES: *C(=O)[C@H]1CC[C@@H](NC(=O)OC(C)(C)C)CC1] |

-continued
Compounds 1-219
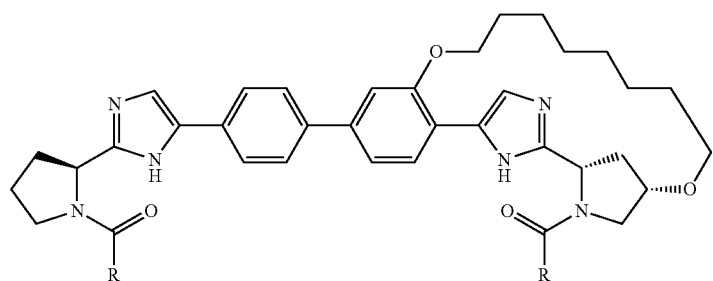
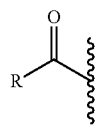
| Entry | |
|---|---|
| 32 | 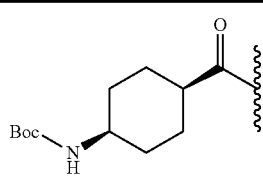 |
| 33 | 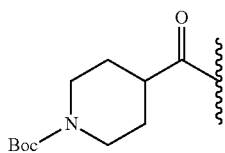 [SMILES: *C(=O)C1CCN(C(=O)OC(C)(C)C)CC1] |
| 34 | 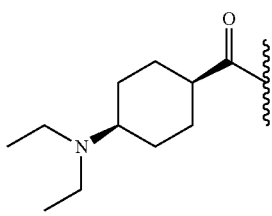 [SMILES: *C(=O)[C@H]1CC[C@@H](N(CC)CC)CC1] |
| 35 | 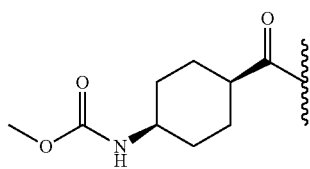 [SMILES: *C(=O)[C@H]1CC[C@@H](NC(=O)OC)CC1] |
| 36 | 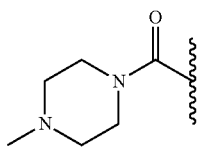 [SMILES: *C(=O)N1CCN(C)CC1] |
| 37 | 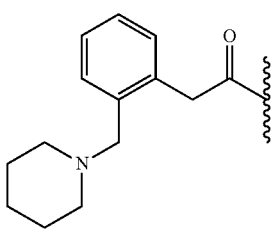 [SMILES: *C(=O)Cc1ccccc1CN1CCCCC1] |

Compounds 1-219
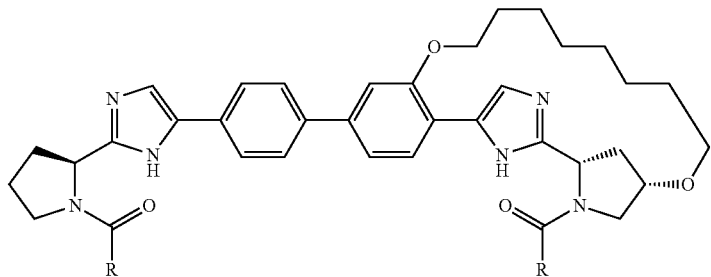
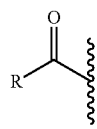
| Entry | |
|---|---|
| 38 | 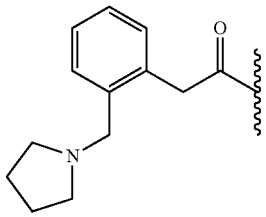 [SMILES: *C(=O)Cc1ccccc1CN1CCCC1] |
| 39 | 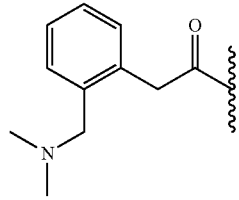 [SMILES: *C(=O)Cc1ccccc1CN(C)C] |
| 40 | 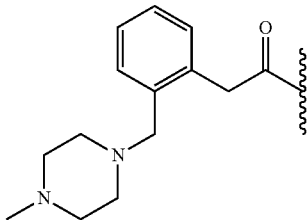 [SMILES: *C(=O)Cc1ccccc1CN1CCN(C)CC1] |
| 41 | 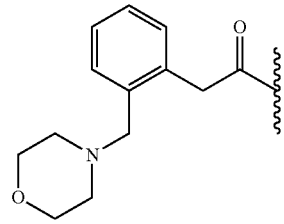 [SMILES: *C(=O)Cc1ccccc1CN1CCOCC1] |
| 42 | 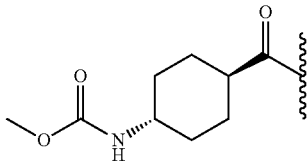 [SMILES: *C(=O)[C@H]1CC[C@H](NC(=O)OC)CC1] |

-continued
Compounds 1-219
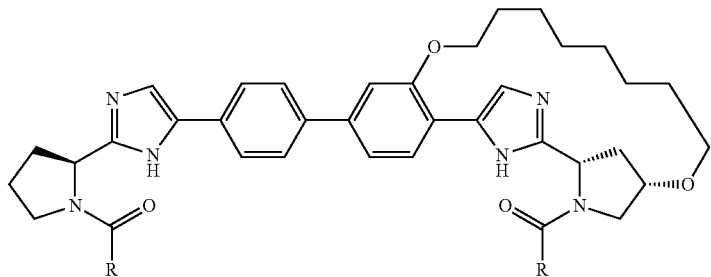
| Entry | 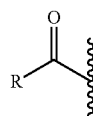 |
|---|---|
| 43 | 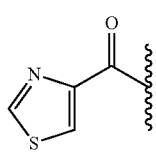 [SMILES: *C(=O)c1cscn1] |
| 44 | 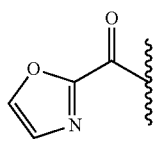 [SMILES: *C(=O)c1ncco1] |
| 45 | 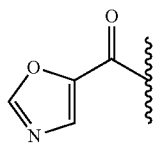 [SMILES: *C(=O)c1cnco1] |
| 46 | 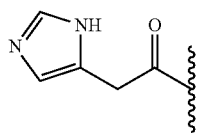 |
| 47 | 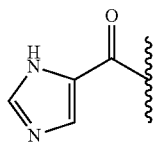 [SMILES: *C(=O)c1cnc[nH]1] |
| 48 | 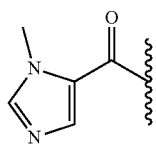 [SMILES: *C(=O)c1cncn1C] |
| 49 | 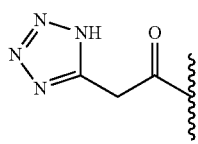 [SMILES: *C(=O)Cc1nnn[nH]1] |

-continued
Compounds 1-219
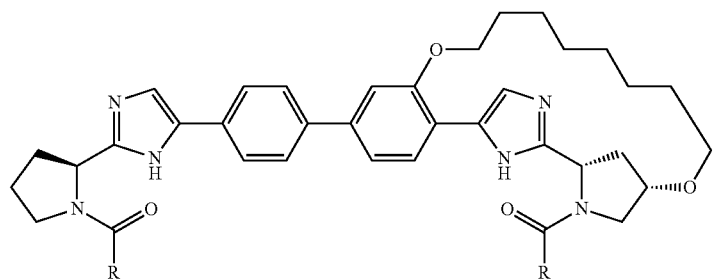
| Entry | R‒C(O)‒ |
|---|---|
| 50 | 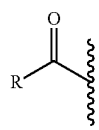 |
| 51 | 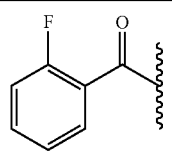 |
| 52 | 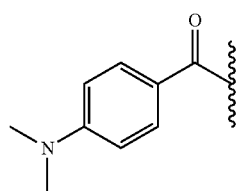 [SMILES: *C(=O)c1ccc(N(C)C)cc1] |
| 53 | 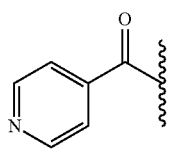 |
| 54 | 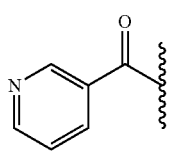 |
| 55 | 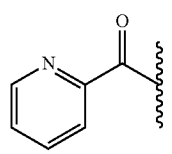 [SMILES: *C(=O)c1ccccn1] |
| 56 | 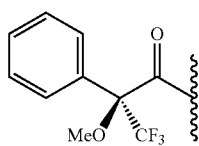 [SMILES: *C(=O)[C@@](OC)(c1ccccc1)C(F)(F)F] |

-continued
| Compounds 1-219 |
|---|
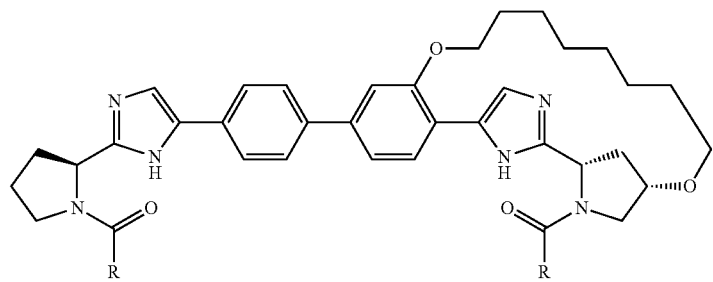
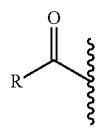
| Entry | |
|---|---|
| 57 | 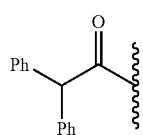 [SMILES: *C(=O)C(c1ccccc1)c1ccccc1] |
| 58 | 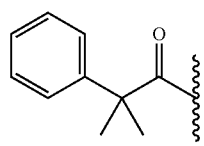 [SMILES: *C(=O)C(C)(C)c1ccccc1] |
| 59 | 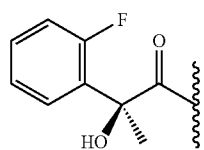 [SMILES: *C(=O)[C@@](C)(O)c1ccccc1F] |
| 60 | 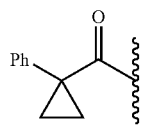 [SMILES: *C(=O)C1(c2ccccc2)CC1] |
| 61 | 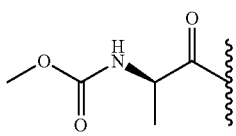 |
| 62 | 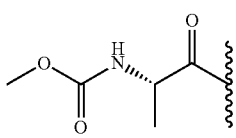 |
| 63 | 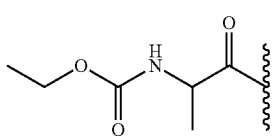 [SMILES: *C(=O)C(C)NC(=O)OCC] |

Compounds 1-219
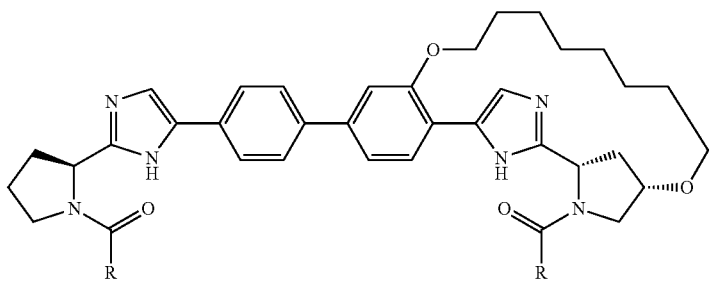
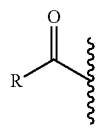
| Entry | |
|---|---|
| 64 | 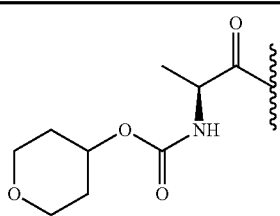 |
| 65 | 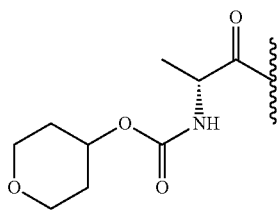 [SMILES: *C(=O)[C@@H](C)NC(=O)OC1CCOCC1] |
| 66 | 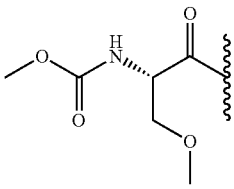 [SMILES: *C(=O)[C@H](COC)NC(=O)OC] |
| 67 | 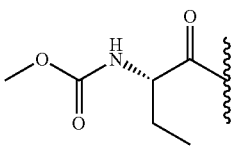 [SMILES: *C(=O)[C@H](CC)NC(=O)OC] |
| 68 | 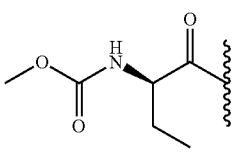 [SMILES: *C(=O)[C@@H](CC)NC(=O)OC] |
| 69 | 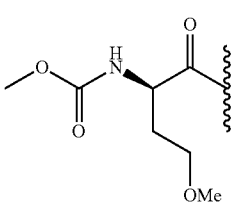 [SMILES: *C(=O)[C@@H](CCOC)NC(=O)OC] |

-continued
Compounds 1-219
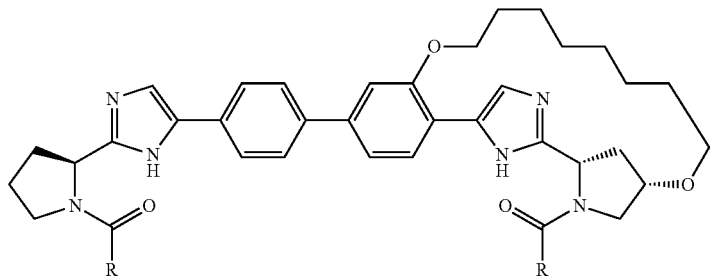
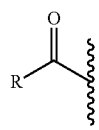
| Entry | |
|---|---|
| 70 | 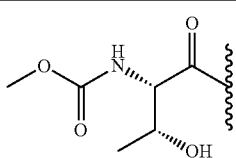 |
| 71 | 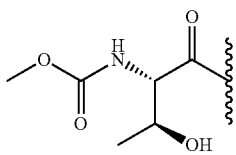 [SMILES: *C(=O)[C@@H](NC(=O)OC)[C@H](C)O] |
| 72 | 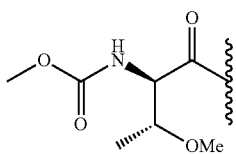 [SMILES: *C(=O)[C@H](NC(=O)OC)[C@@H](C)OC] |
| 73 | 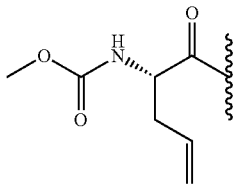 |
| 74 | 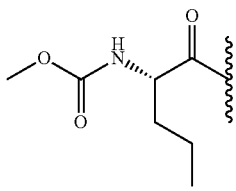 [SMILES: *C(=O)[C@H](CCC)NC(=O)OC] |
| 75 | 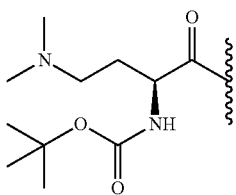 [SMILES: *C(=O)[C@H](CCN(C)C)NC(=O)OC(C)(C)C] |

Compounds 1-219
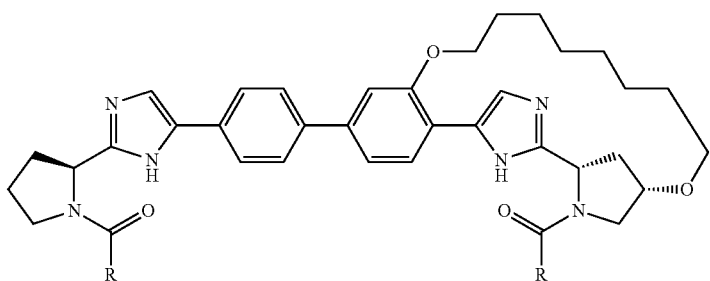
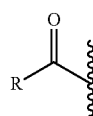
| Entry | |
|---|---|
| 76 | 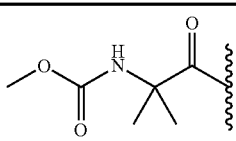 |
| 77 | 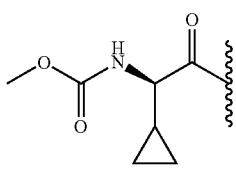 [SMILES: *C(=O)[C@H](NC(=O)OC)C1CC1] |
| 78 | 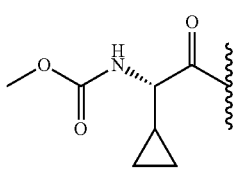 |
| 79 | 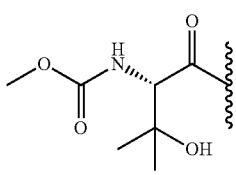 |
| 80 | 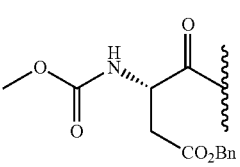 [SMILES: *C(=O)[C@H](CC(=O)OCc1ccccc1)NC(=O)OC] |
| 81 | 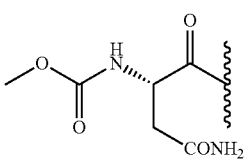 [SMILES: *C(=O)[C@H](CC(N)=O)NC(=O)OC] |
| 82 | 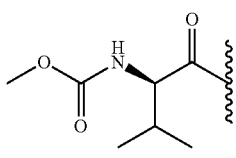 [SMILES: *C(=O)[C@H](NC(=O)OC)C(C)C] |

-continued
Compounds 1-219
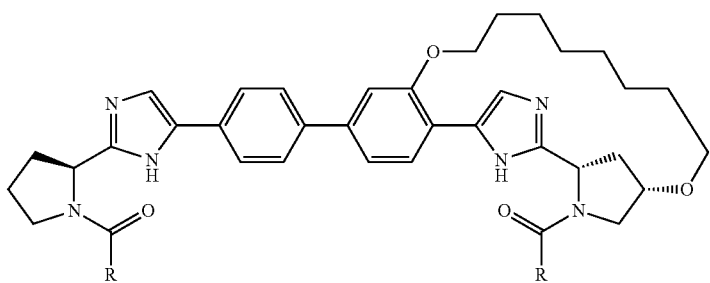
| Entry | 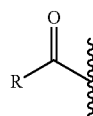 |
|---|---|
| 83 | 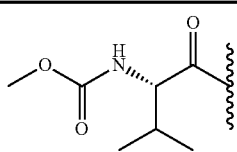 |
| 84 | 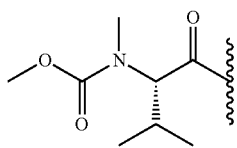 |
| 85 | 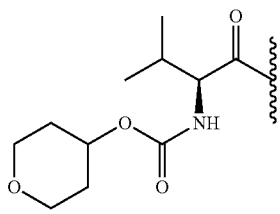 [SMILES: *C(=O)[C@@H](NC(=O)OC1CCOCC1)C(C)C] |
| 86 | 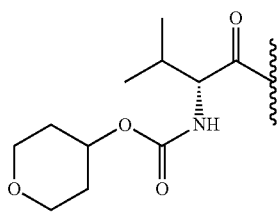 [SMILES: *C(=O)[C@H](NC(=O)OC1CCOCC1)C(C)C] |
| 87 | 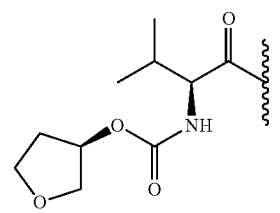 [SMILES: *C(=O)[C@@H](NC(=O)O[C@@H]1CCOC1)C(C)C] |
| 88 | 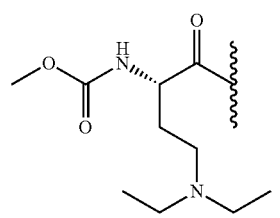 [SMILES: *C(=O)[C@H](CCN(CC)CC)NC(=O)OC] |

-continued
Compounds 1-219
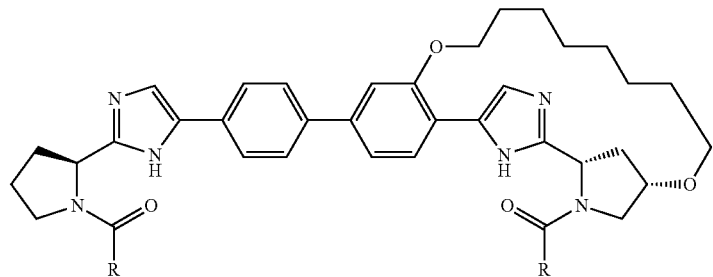
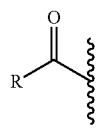
| Entry | |
|---|---|
| 89 | 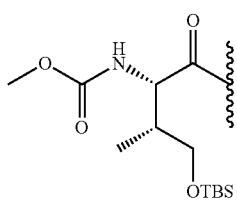 [SMILES: *C(=O)[C@@H](NC(=O)OC)[C@@H](C)CO[Si](C)(C)C(C)(C)C] |
| 90 | 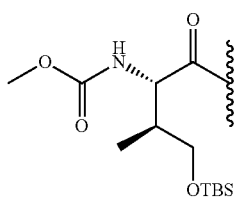 [SMILES: *C(=O)[C@@H](NC(=O)OC)[C@H](C)CO[Si](C)(C)C(C)(C)C] |
| 91 | 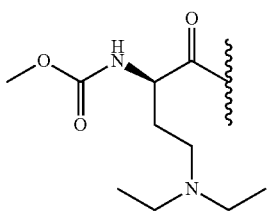 [SMILES: *C(=O)[C@@H](CCN(CC)CC)NC(=O)OC] |
| 92 | 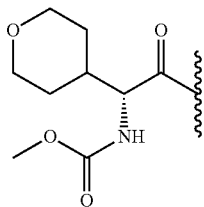 [SMILES: *C(=O)[C@H](NC(=O)OC)C1CCOCC1] |
| 93 | 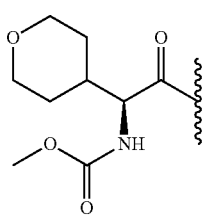 [SMILES: *C(=O)[C@@H](NC(=O)OC)C1CCOCC1] |

-continued
Compounds 1-219
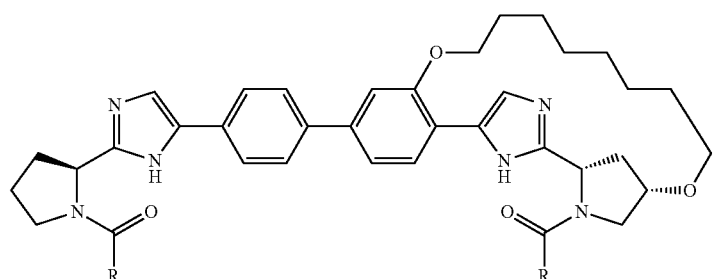
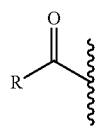
| Entry | |
|---|---|
| 94 | 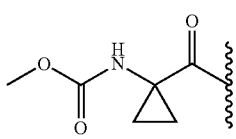 [SMILES: *C(=O)C1(NC(=O)OC)CC1] |
| 95 | 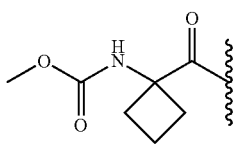 [SMILES: *C(=O)C1(NC(=O)OC)CCC1] |
| 96 | 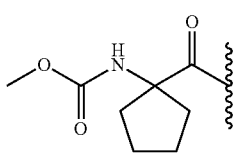 [SMILES: *C(=O)C1(NC(=O)OC)CCCC1] |
| 97 | 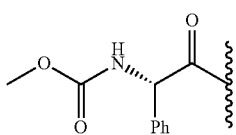 [SMILES: *C(=O)[C@@H](NC(=O)OC)c1ccccc1] |
| 98 | 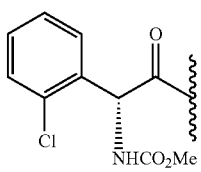 |
| 99 | 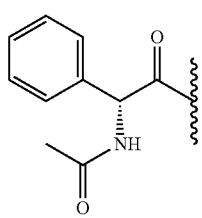 [SMILES: *C(=O)[C@H](NC(C)=O)c1ccccc1] |

-continued
Compounds 1-219
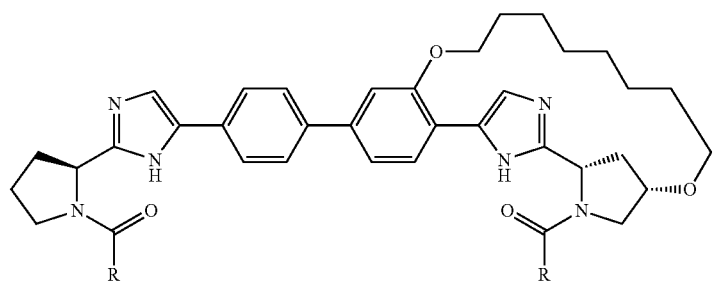
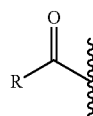
| Entry | |
|---|---|
| 100 | 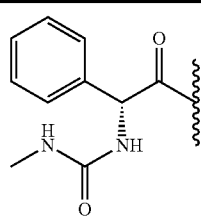 |
| 101 | 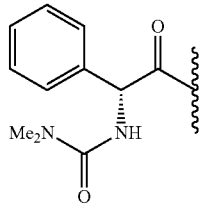 [SMILES: *C(=O)[C@H](NC(=O)N(C)C)c1ccccc1] |
| 102 | 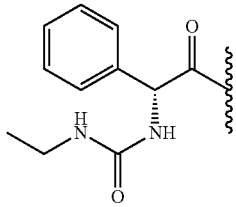 [SMILES: *C(=O)[C@H](NC(=O)NCC)c1ccccc1] |
| 103 | 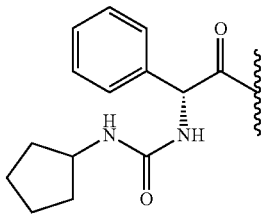 [SMILES: *C(=O)[C@H](NC(=O)NC1CCCC1)c1ccccc1] |
| 104 | 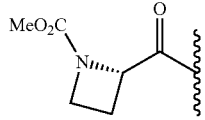 |
| 105 | 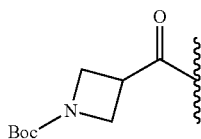 [SMILES: *C(=O)C1CN(C(=O)OC(C)(C)C)C1] |

-continued
Compounds 1-219
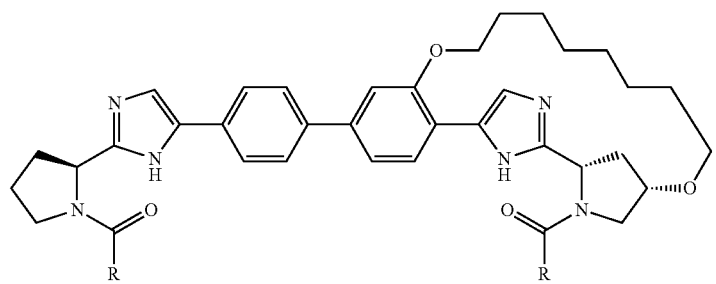
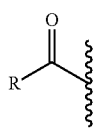
| Entry | |
|---|---|
| 106 | 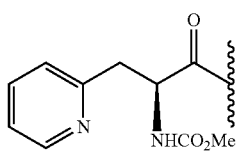 |
| 107 | 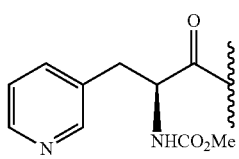 |
| 108 | 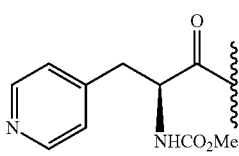 |
| 109 | 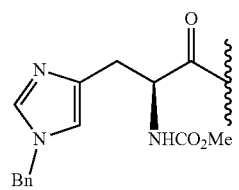 |
| 110 | 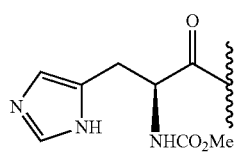 |
| 111 | 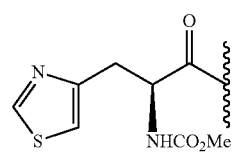 |

-continued
Compounds 1-219
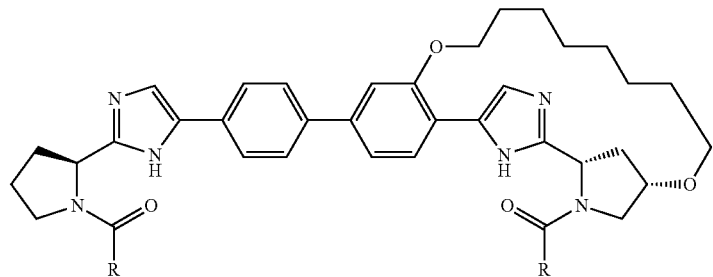
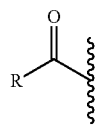
| Entry | |
|---|---|
| 112 | 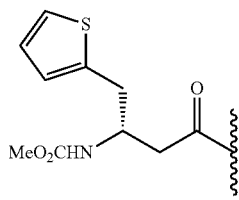 |
| 113 | 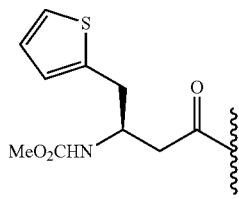 |
| 114 | 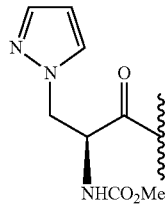 |
| 115 | 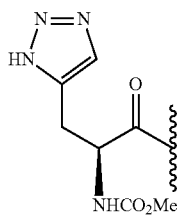 |
| 116 | 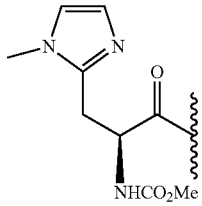 |

-continued
Compounds 1-219
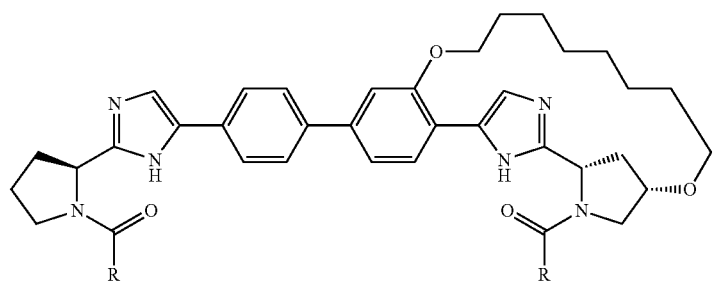
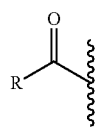
| Entry | |
|---|---|
| 117 | 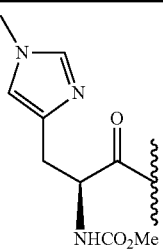 |
| 118 | 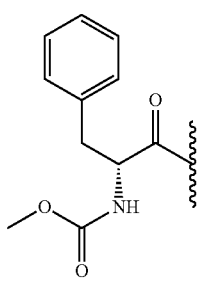 [SMILES: *C(=O)[C@@H](Cc1ccccc1)NC(=O)OC] |
| 119 | 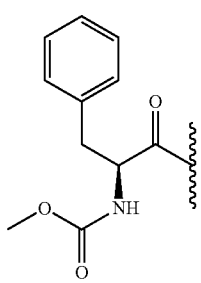 [SMILES: *C(=O)[C@H](Cc1ccccc1)NC(=O)OC] |
| 120 | 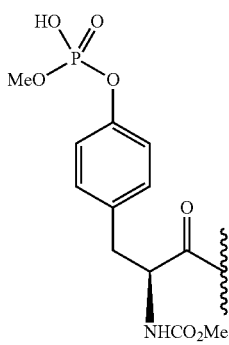 |

-continued
Compounds 1-219
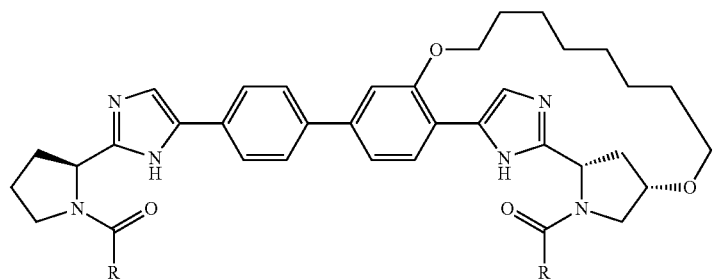
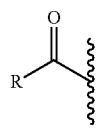
| Entry | |
|---|---|
| 121 | 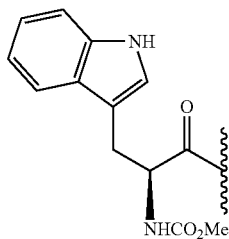 |
| 122 | 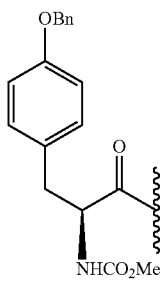 |
| 123 | 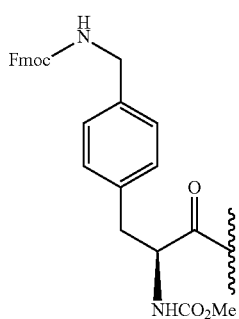 |
| 124 | 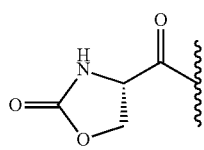 |
| 125 | 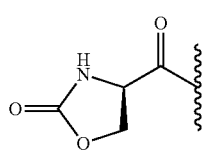 |

-continued
| Compounds 1-219 |
|---|
| 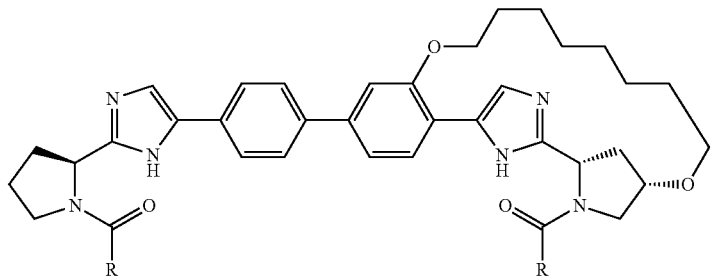 |
| Entry |
126 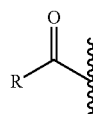
127 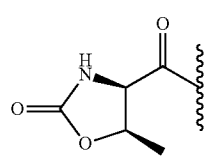 [SMILES: *C(=O)[C@@H]1NC(=O)O[C@@H]1C]
128 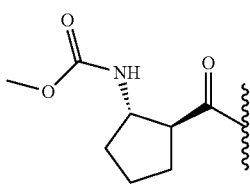 [SMILES: *C(=O)[C@H]1CCC[C@@H]1NC(=O)OC]
129 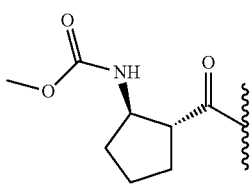 [SMILES: *C(=O)[C@@H]1CCC[C@H]1NC(=O)OC]
130 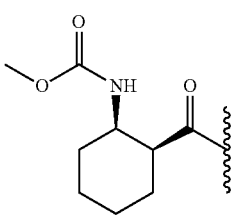 [SMILES: *C(=O)[C@H]1CCCC[C@H]1NC(=O)OC]
131 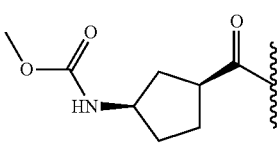 [SMILES: *C(=O)[C@H]1CC[C@@H](NC(=O)OC)C1]

Compounds 1-219
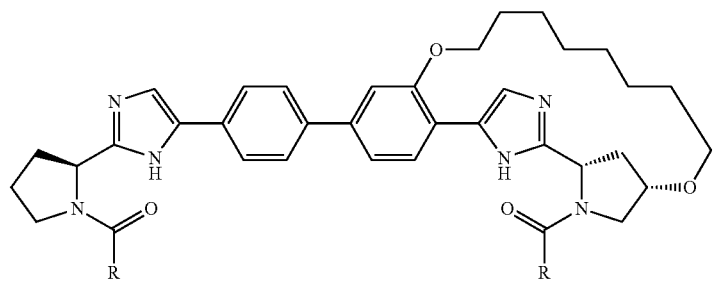
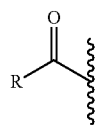
| Entry | |
|---|---|
| 132 | 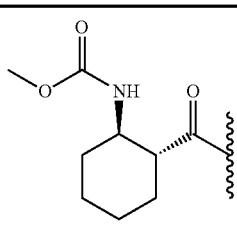 |
| 133 | 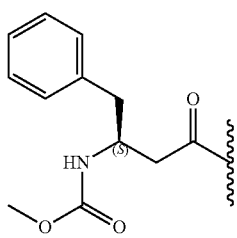 |
| 134 | 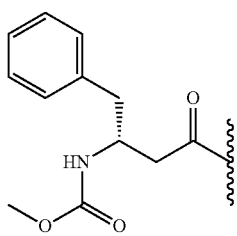 [SMILES: *C(=O)C[C@@H](Cc1ccccc1)NC(=O)OC] |
| 135 | 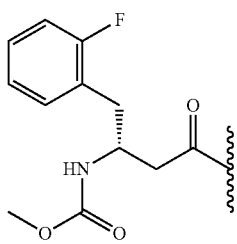 [SMILES: *C(=O)C[C@@H](Cc1ccccc1F)NC(=O)OC] |
| 136 | 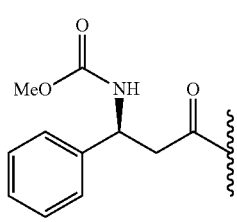 [SMILES: *C(=O)C[C@H](NC(=O)OC)c1ccccc1] |

-continued
Compounds 1-219
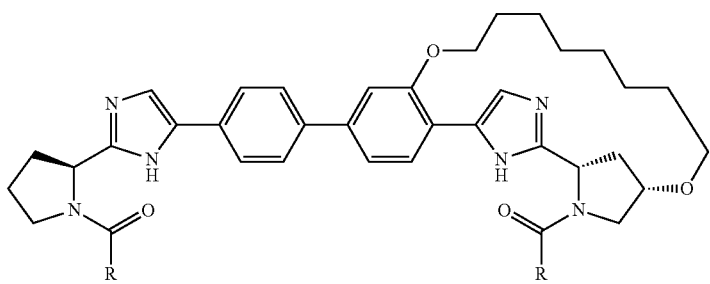
| Entry | |
|---|---|
| 137 | 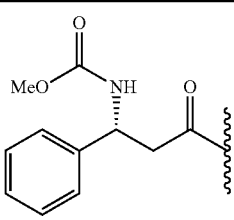 |
| 138 | 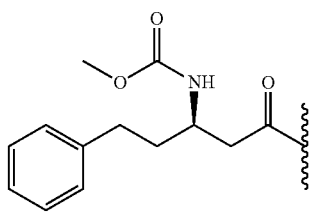 [SMILES: *C(=O)C[C@@H](CCc1ccccc1)NC(=O)OC] |
| 139 | 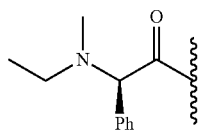 [SMILES: *C(=O)[C@@H](c1ccccc1)N(C)CC] |
| 140 | 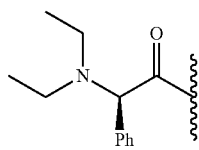 [SMILES: *C(=O)[C@@H](c1ccccc1)N(CC)CC] |
| 141 | 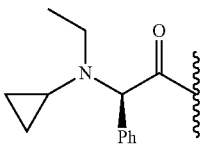 [SMILES: *C(=O)[C@@H](c1ccccc1)N(CC)C1CC1] |
| 142 | 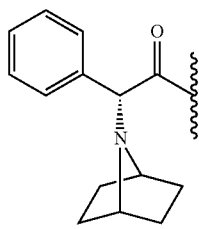 [SMILES: *C(=O)[C@@H](c1ccccc1)N1C2CCC1CC2] |
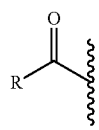

-continued
Compounds 1-219
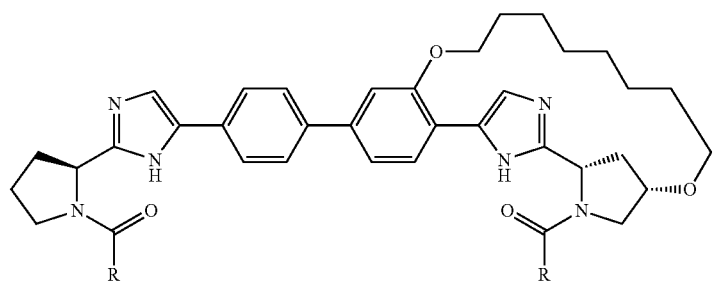
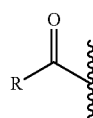
| Entry | |
|---|---|
| 143 | 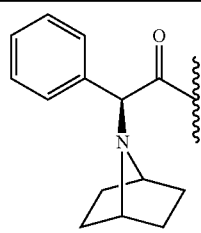 |
| 144 | 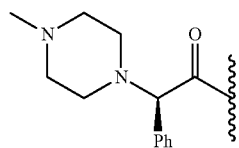 [SMILES: *C(=O)[C@@H](c1ccccc1)N1CCN(C)CC1] |
| 145 | 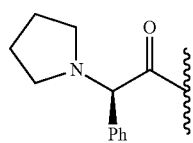 [SMILES: *C(=O)[C@@H](c1ccccc1)N1CCCC1] |
| 146 | 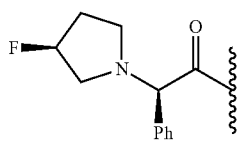 |
| 147 | 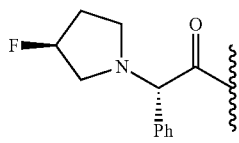 |
| 148 | 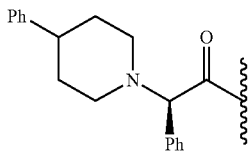 |
| 149 | 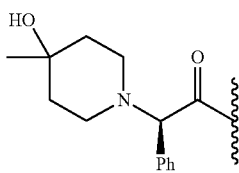 |

-continued
Compounds 1-219
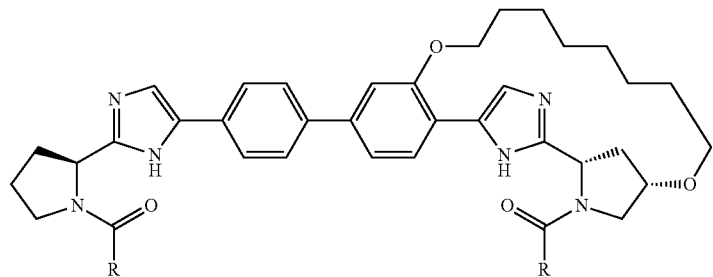
| Entry | 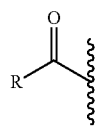 |
|---|---|
| 150 | 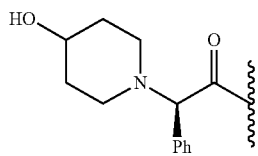 [SMILES: *C(=O)[C@@H](c1ccccc1)N1CCC(O)CC1] |
| 151 | 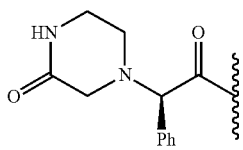 [SMILES: *C(=O)[C@@H](c1ccccc1)N1CCNC(=O)C1] |
| 152 | 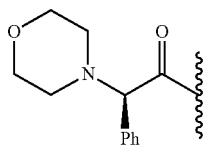 [SMILES: *C(=O)[C@@H](c1ccccc1)N1CCOCC1] |
| 153 | 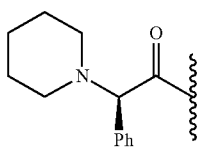 [SMILES: *C(=O)[C@@H](c1ccccc1)N1CCCCC1] |
| 154 | 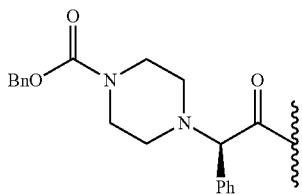 [SMILES: *C(=O)[C@@H](c1ccccc1)N1CCN(C(=O)OCc2ccccc2)CC1] |
| 155 | 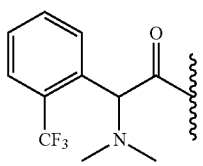 |

-continued
Compounds 1-219
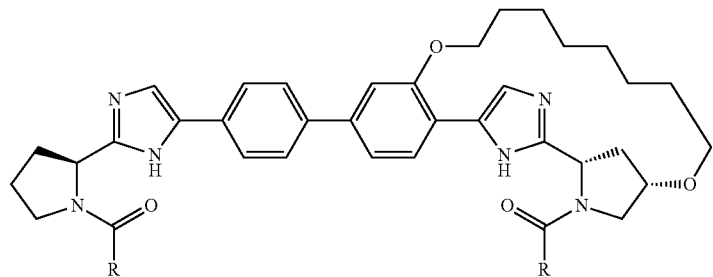
| Entry | 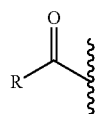 |
|---|---|
| 156 | 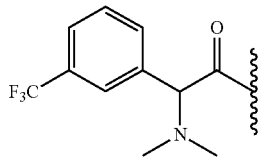 [SMILES: *C(=O)C(c1cccc(C(F)(F)F)c1)N(C)C] |
| 157 | 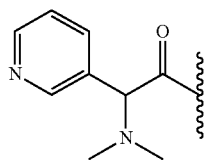 [SMILES: *C(=O)C(c1cccnc1)N(C)C] |
| 158 | 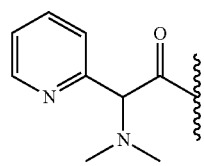 [SMILES: *C(=O)C(c1ccccn1)N(C)C] |
| 159 | 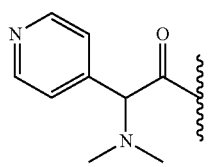 [SMILES: *C(=O)C(c1ccncc1)N(C)C] |
| 160 | 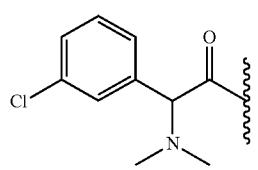 [SMILES: *C(=O)C(c1cccc(Cl)c1)N(C)C] |
| 161 | 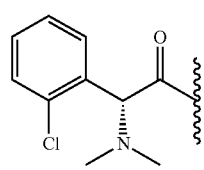 |

-continued
Compounds 1-219
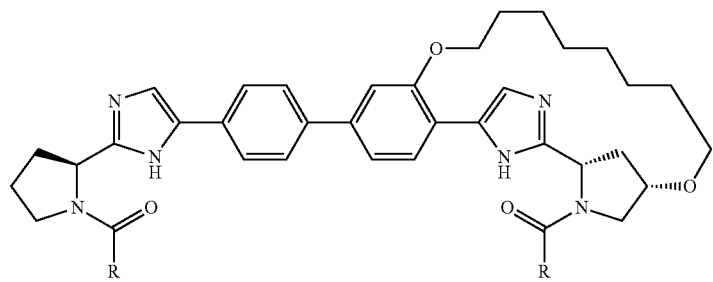
| Entry | R |
|---|---|
| 162 | 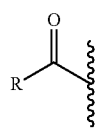 |
| 163 | 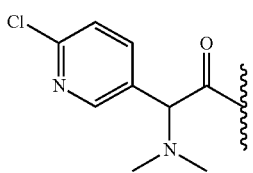 [SMILES: *C(=O)C(c1ccc(Cl)nc1)N(C)C] |
| 164 | 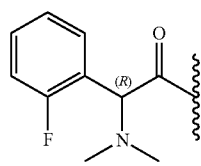 |
| 165 | 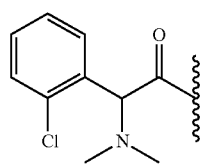 [SMILES: *C(=O)C(c1ccccc1Cl)N(C)C] |
| 166 | 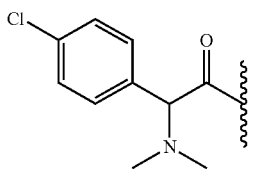 [SMILES: *C(=O)C(c1ccc(Cl)cc1)N(C)C] |
| 167 | 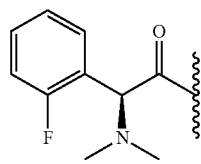 [SMILES: *C(=O)[C@H](c1ccccc1F)N(C)C] |

-continued
Compounds 1-219
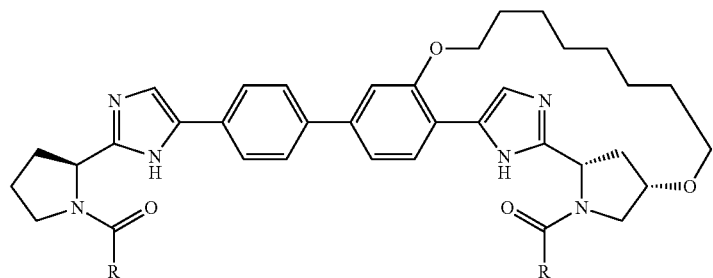
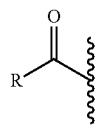
| Entry | |
|---|---|
| 168 | 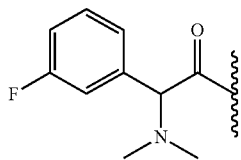 [SMILES: *C(=O)C(c1cccc(F)c1)N(C)C] |
| 169 | 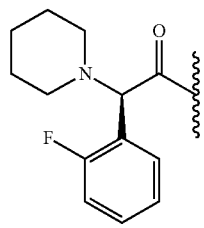 [SMILES: *C(=O)[C@@H](c1ccccc1F)N1CCCCC1] |
| 170 | 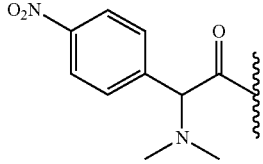 [SMILES: *C(=O)C(c1ccc([N+](=O)[O-])cc1)N(C)C] |
| 171 | 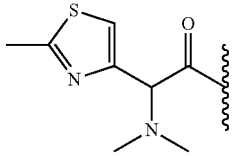 [SMILES: *C(=O)C(c1csc(C)n1)N(C)C] |
| 172 | 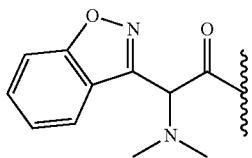 [SMILES: *C(=O)C(c1noc2ccccc12)N(C)C] |
| 173 | 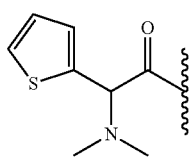 [SMILES: *C(=O)C(c1cccs1)N(C)C] |

-continued
Compounds 1-219
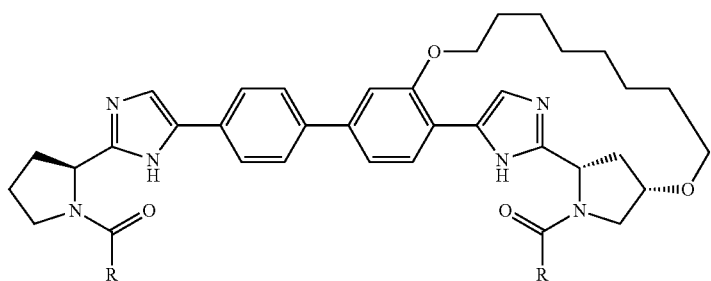
| Entry | R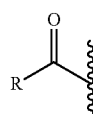 |
|---|---|
| 174 | 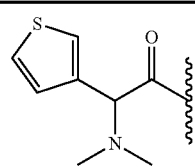 |
| 175 | 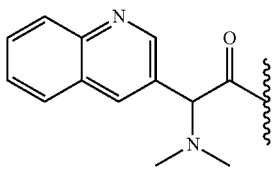 [SMILES: *C(=O)C(c1cnc2ccccc2c1)N(C)C] |
| 176 | 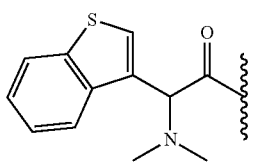 [SMILES: *C(=O)C(c1csc2ccccc12)N(C)C] |
| 177 | 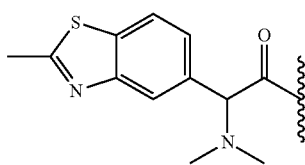 [SMILES: *C(=O)C(c1ccc2sc(C)nc2c1)N(C)C] |
| 178 | 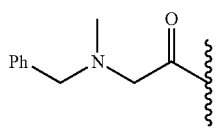 [SMILES: *C(=O)CN(C)Cc1ccccc1] |
| 179 | 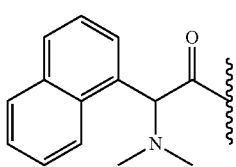 [SMILES: *C(=O)C(c1cccc2ccccc12)N(C)C] |
| 180 | 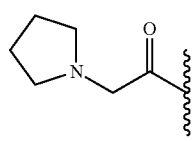 [SMILES: *C(=O)CN1CCCC1] |

-continued
Compounds 1-219
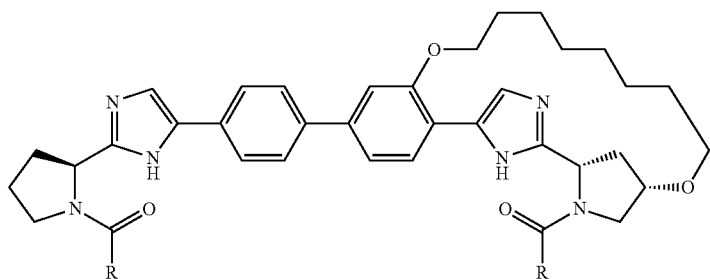
| Entry | |
|---|---|
| 181 | 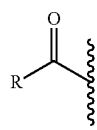 |
| 182 | 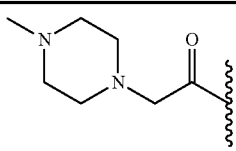 |
| 183 | 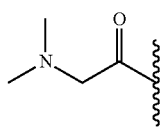 [SMILES: *C(=O)CN(C)C] |
| 184 | 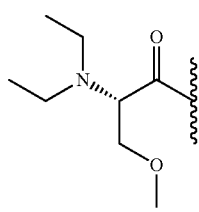 [SMILES: *C(=O)[C@H](COC)N(CC)CC] |
| 185 | 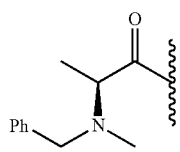 |
| 186 | 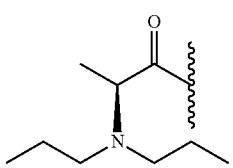 [SMILES: *C(=O)[C@H](C)N(CCC)CCC] |
| 187 | 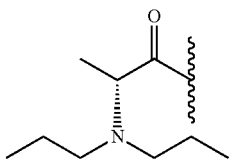 [SMILES: *C(=O)[C@@H](C)N(CCC)CCC] |

-continued
Compounds 1-219
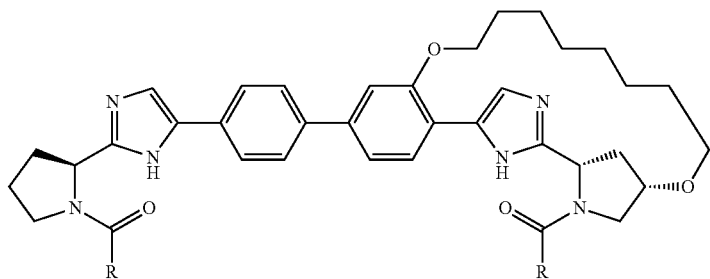
| Entry | 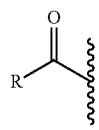 (R group structure header) |
|---|---|
| 188 | 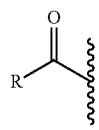 |
| 189 | 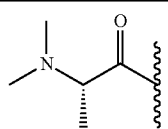 |
| 190 | 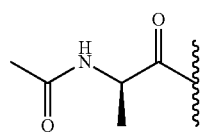 [SMILES: *C(=O)[C@@H](C)NC(C)=O] |
| 191 | 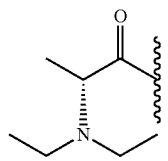 [SMILES: *C(=O)[C@@H](C)N(CC)CC] |
| 192 | 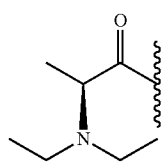 [SMILES: *C(=O)[C@H](C)N(CC)CC] |
| 193 | 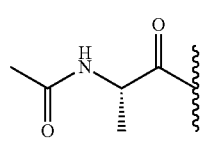 [SMILES: *C(=O)[C@H](C)NC(C)=O] |
| 194 | 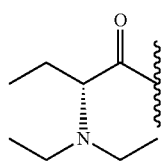 [SMILES: *C(=O)[C@@H](CC)N(CC)CC] |

-continued
Compounds 1-219
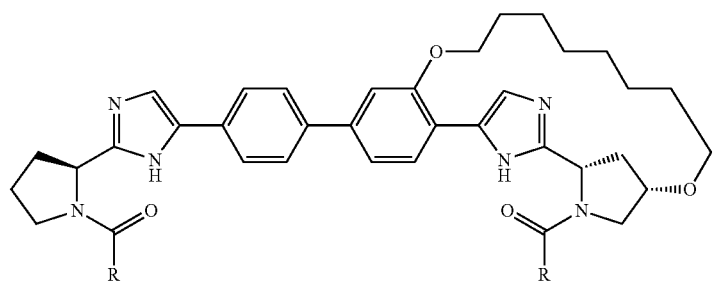
R⏜O⏜⌇
| Entry | |
|---|---|
| 195 | 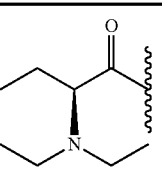 |
| 196 | 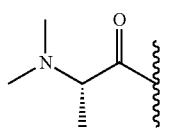 [SMILES: *C(=O)[C@H](C)N(C)C] |
| 197 | 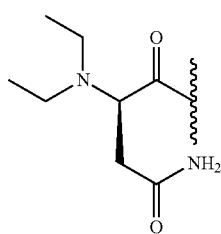 [SMILES: *C(=O)[C@@H](CC(N)=O)N(CC)CC] |
| 198 | 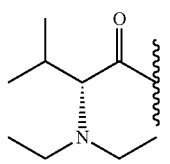 [SMILES: *C(=O)[C@@H](C(C)C)N(CC)CC] |
| 199 | 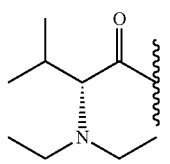 [SMILES: *C(=O)[C@@H](C(C)C)N(CC)CC] |
| 200 | 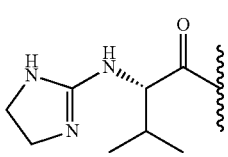 [SMILES: *C(=O)[C@@H](NC1=NCCN1)C(C)C] |
| 201 | 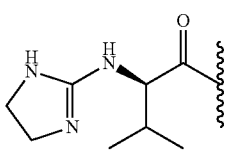 [SMILES: *C(=O)[C@H](NC1=NCCN1)C(C)C] |

Compounds 1-219
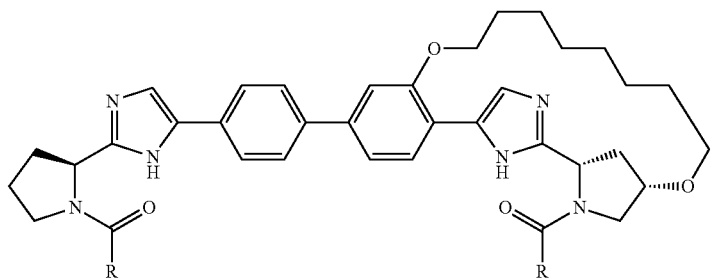
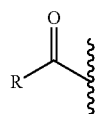
| Entry | |
|---|---|
| 202 | 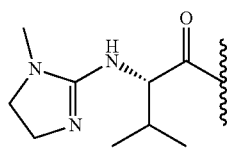 [SMILES: *C(=O)[C@@H](NC1=NCCN1C)C(C)C] |
| 203 | 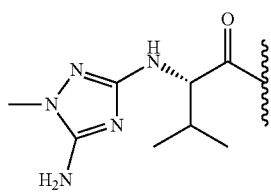 [SMILES: *C(=O)[C@@H](Nc1nc(N)n(C)n1)C(C)C] |
| 204 | 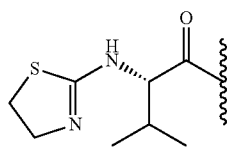 [SMILES: *C(=O)[C@@H](NC1=NCCS1)C(C)C] |
| 205 | 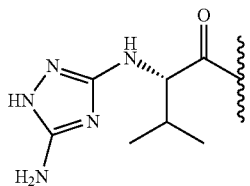 [SMILES: *C(=O)[C@@H](Nc1n[nH]c(N)n1)C(C)C] |
| 206 | 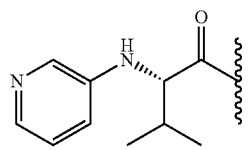 [SMILES: *C(=O)[C@@H](Nc1cccnc1)C(C)C] |
| 207 | 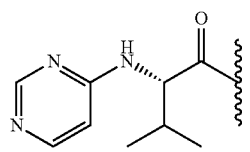 [SMILES: *C(=O)[C@@H](Nc1ccncn1)C(C)C] |

-continued
Compounds 1-219
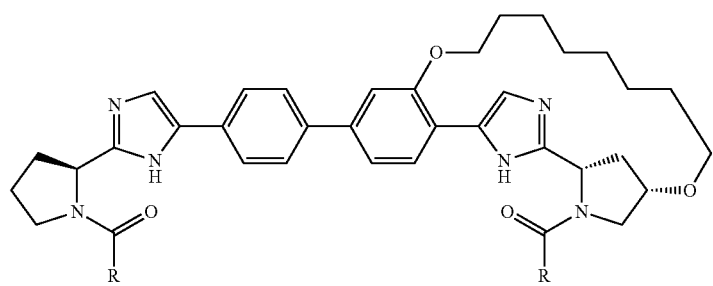
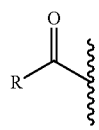
Entry
208
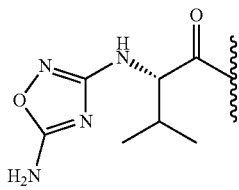 [SMILES: *C(=O)[C@@H](Nc1noc(N)n1)C(C)C]
209
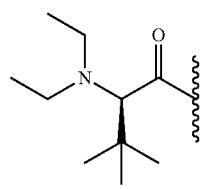 [SMILES: *C(=O)[C@H](N(CC)CC)C(C)(C)C]
210
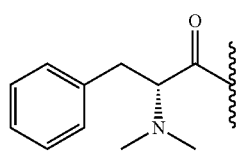 [SMILES: *C(=O)[C@@H](Cc1ccccc1)N(C)C]
211
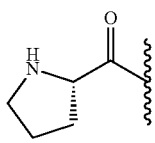
212
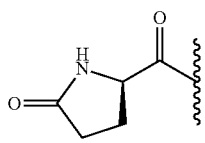
213
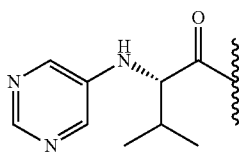 [SMILES: *C(=O)[C@@H](Nc1cncnc1)C(C)C]

-continued
Compounds 1-219
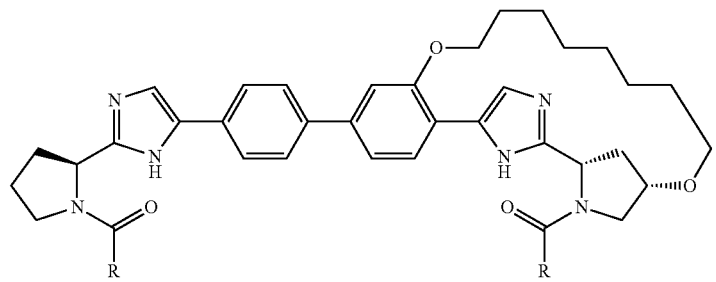
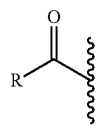
| Entry | |
|---|---|
| 214 | 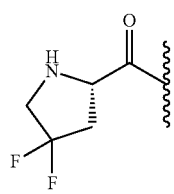 [SMILES: *C(=O)[C@@H]1CC(F)(F)CN1] |
| 215 | 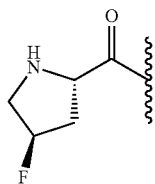 [SMILES: *C(=O)[C@@H]1C[C@@H](F)CN1] |
| 216 | 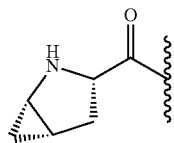 [SMILES: *C(=O)[C@@H]1C[C@@H]2C[C@@H]2N1] |
| 217 | 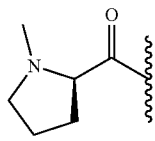 [SMILES: *C(=O)[C@H]1CCCN1C] |
| 218 | 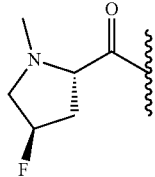 [SMILES: *C(=O)[C@@H]1C[C@@H](F)CN1C] |
| 219 | 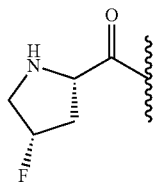 [SMILES: *C(=O)[C@@H]1C[C@H](F)CN1] |

Compounds 220-229
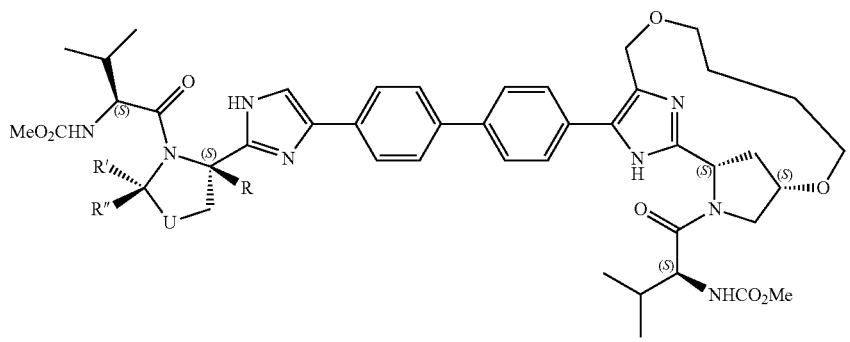
| Entry | R | R' | R" | U |
|---|---|---|---|---|
| 220 | Me | H | H | CH$_2$ |
| 221 | H | H | H | CF$_2$ |
| 222 | Me | H | H | S |
| 223 | H | H | H | 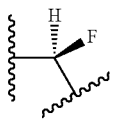 |
| 224 | H | H | H | SiMe$_2$ |
| 225 | H | H | H | 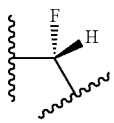 |
| 226 | H | Ph | H | CH$_2$ |
| 227 | H | H | H | 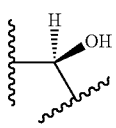 |
| 228 | H | H | Ph | CH$_2$ |
| 229 | H | H | H | 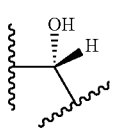 |

| Compounds 220-229 |
|---|
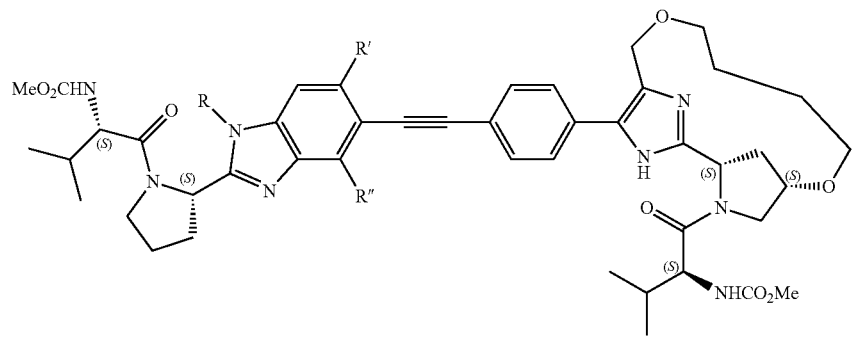
| Entry | R | R' | R" |
|---|---|---|---|
| 230 | Me | H | H |
| 231 | H | CO$_2$Me | H |
| 232 | H | F | H |
| 233 | H | H | CO$_2$Me |
| 234 | H | H | F |
| 235 | H | OMe | H |
| 236 | H | Cl | H |
| 237 | H | H | OMe |
| 238 | H | H | Cl |
| 239 | H | CF$_3$ | H |
| Compounds 240-253 |
|---|
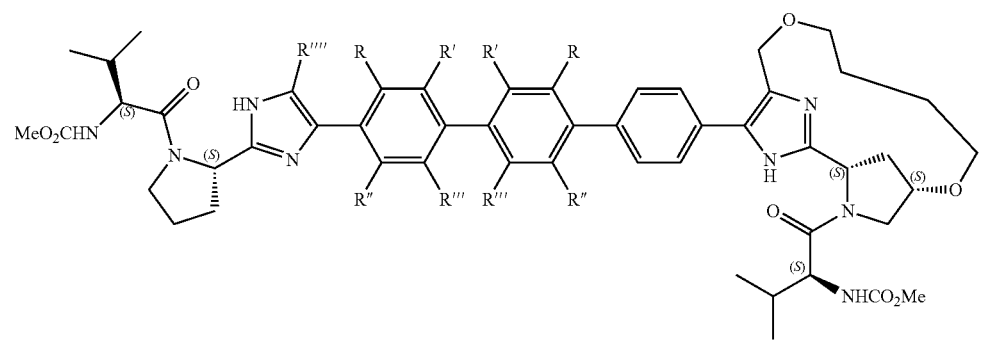
| Entry | R | R' | R" | R''' | R'''' |
|---|---|---|---|---|---|
| 240 | F | H | H | H | H |
| 241 | F | F | H | H | H |
| 242 | Me | H | H | H | H |
| 243 | Me | Me | H | H | H |
| 244 | H | H | Me | Me | H |
| 245 | H | H | Et | Et | H |
| 246 | CF$_3$ | H | H | H | H |
| 247 | CF$_3$ | H | CF$_3$ | H | H |
| 248 | Cl | H | H | H | H |
| 249 | Cl | H | Cl | H | H |
| 250 | H | H | H | H | Br |
| 251 | H | H | H | H | Cl |
| 252 | H | H | H | H | F |
| 253 | H | H | H | H | CF$_3$ |

| Compounds 254-268 | |
|---|---|
| 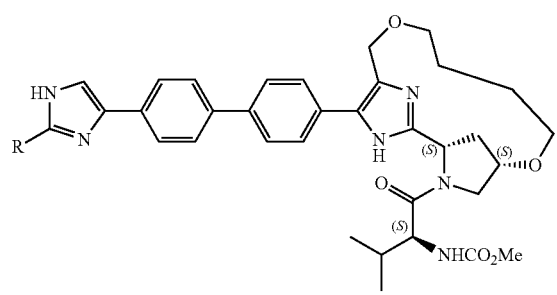 | |
| Entry | R |
| 254 | 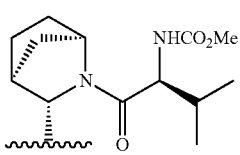 |
| 255 | 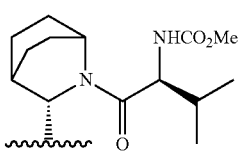 |
| 256 | 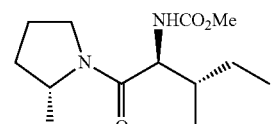 |
| 257 | 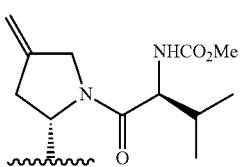 |
| 258 | 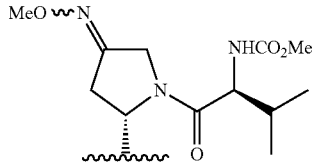 |
| 259 | 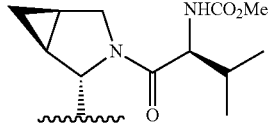 |
| 260 | 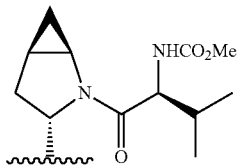 |
-continued
| Compounds 254-268 | |
|---|---|
| 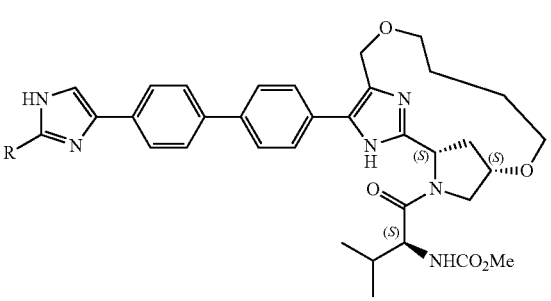 | |
| Entry | R |
| 261 | 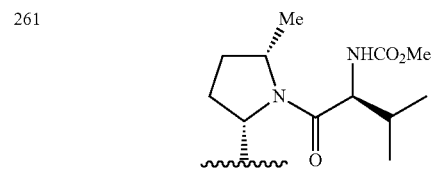 |
| 262 | 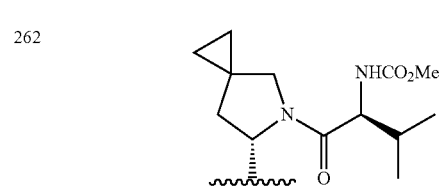 |
| 263 | 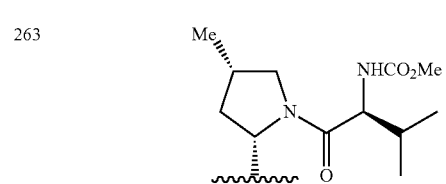 |
| 264 | 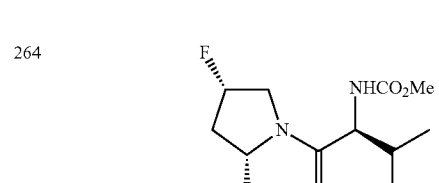 |
| 265 | 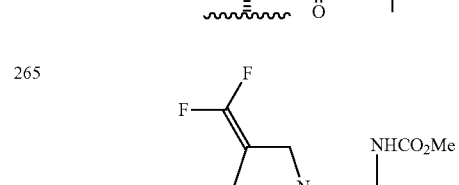 |
| 266 | 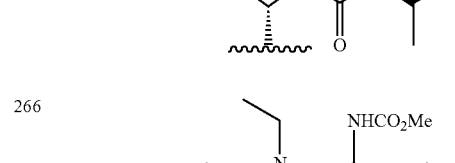 |

Compounds 254-268
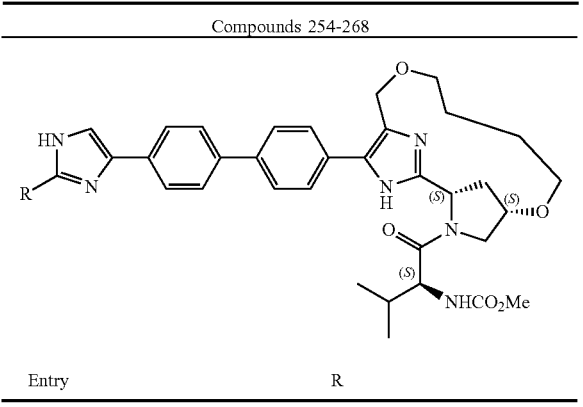
| Entry | R |
|---|---|
| 267 | 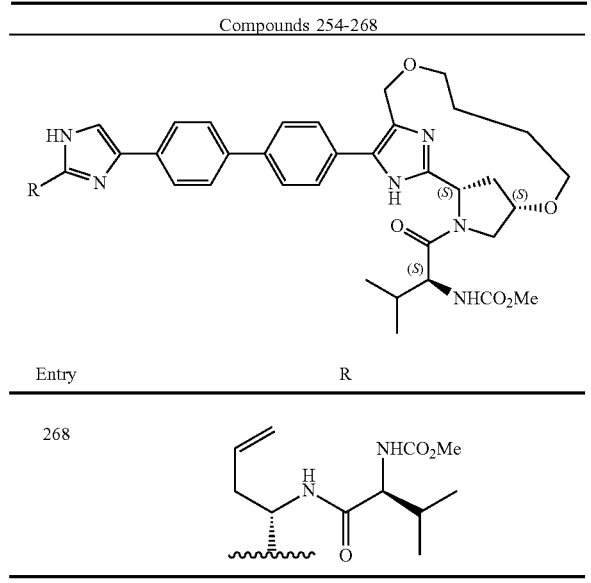 |
| 268 | |
Note: Entry 268's R group appears on the right column.
Compounds 269-286
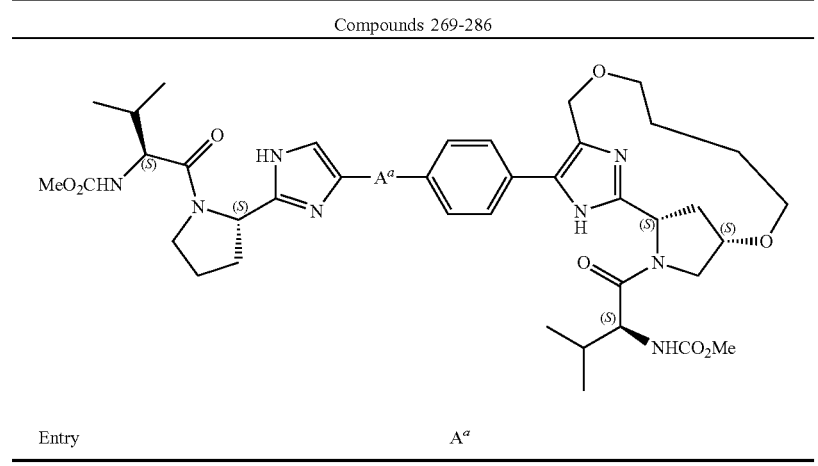
| Entry | $A^a$ |
|---|---|
| 269 | (2,6-naphthalenediyl) |
| 270 | (quinoline-2,6-diyl) |
| 271 | (2,6-anthracenediyl) |
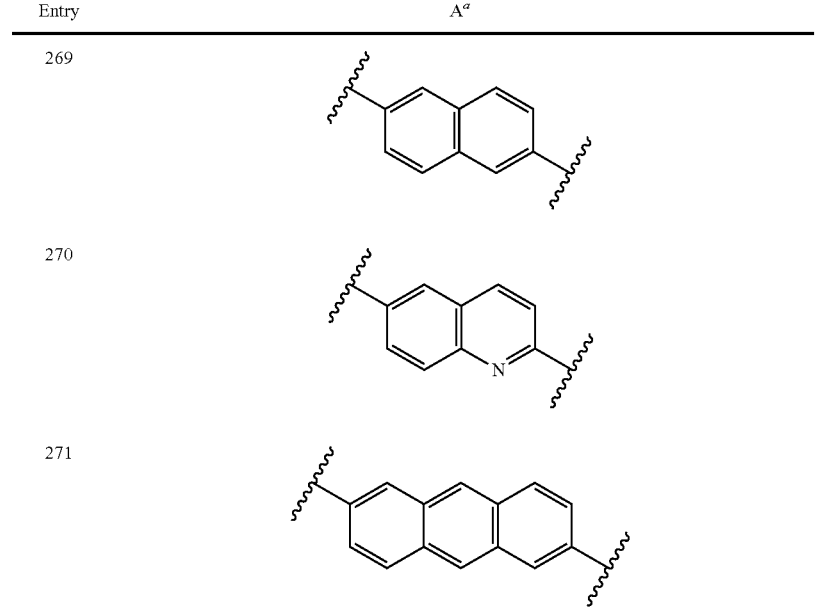

Compounds 269-286
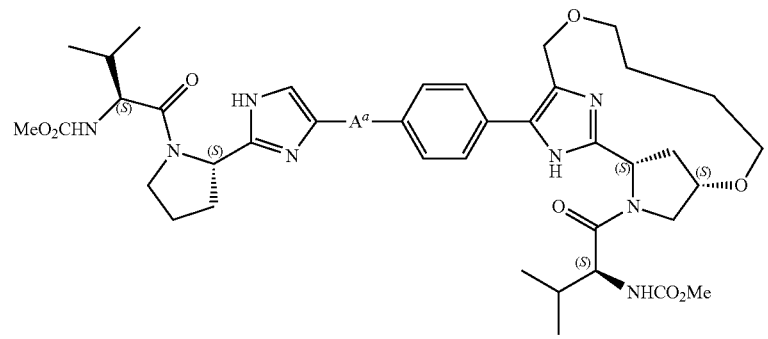
| Entry | $A^a$ |
|---|---|
| 272 | 6-naphthyl-phenyl linker |
| 273 | trans-CH=CH-phenyl linker |
| 274 | C≡C-phenyl linker |
| 275 | phenyl-cyclohexyl linker |
| 276 | piperazine-pyrimidine linker |
| 277 | pyrazole-pyridine linker |
| 278 | phenyl-pyridine linker |
| 279 | thiophene-phenyl linker |
| 280 | phenyl-CH=CH-phenyl linker |

-continued
Compounds 269-286
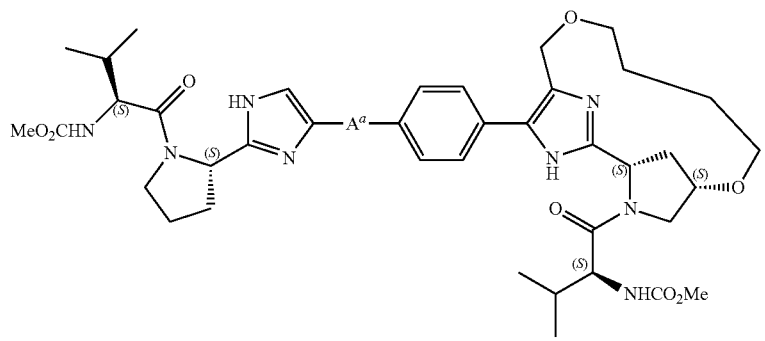
| Entry | $A^a$ |
|---|---|
| 281 | 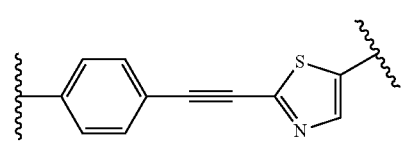 |
| 282 | 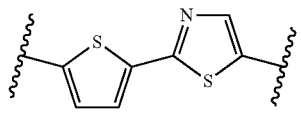 [SMILES: *c1ccc(-c2ncc(*)s2)s1] |
| 283 | 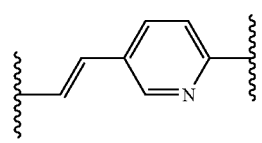 [SMILES: */C=C/c1ccc(*)nc1] |
| 284 | 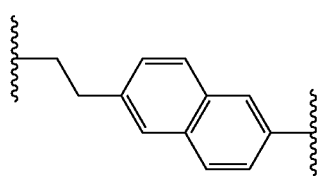 |
| 285 | 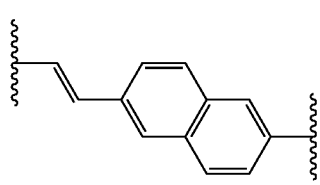 [SMILES: */C=C/c1ccc2cc(*)ccc2c1] |
| 286 | 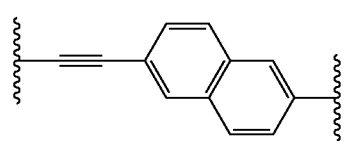 |

| Compounds 287-307 |
|---|
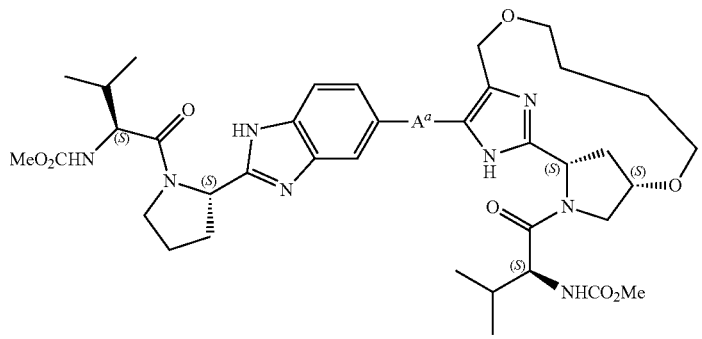
| Entry | $A^a$ |
|---|---|
| 287 | 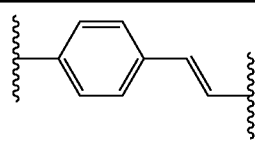 |
| 288 | 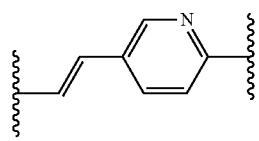 [SMILES: */C=C/c1ccc(*)nc1] |
| 289 | 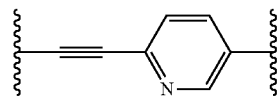 |
| 290 | 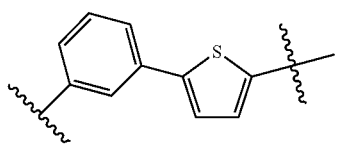 [SMILES: *c1cccc(-c2ccc(*)s2)c1] |
| 291 | 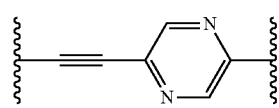 |
| 292 | 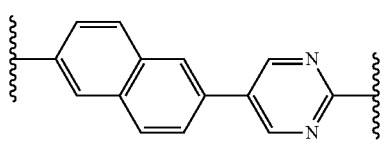 |
| 293 | 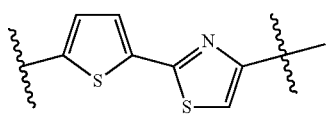 [SMILES: *c1csc(-c2ccc(*)s2)n1] |
| 294 | 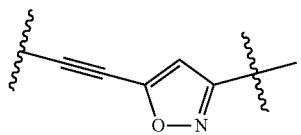 [SMILES: *C#Cc1cc(*)no1] |
| 295 | 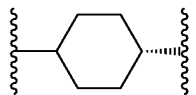 |

-continued
Compounds 287-307
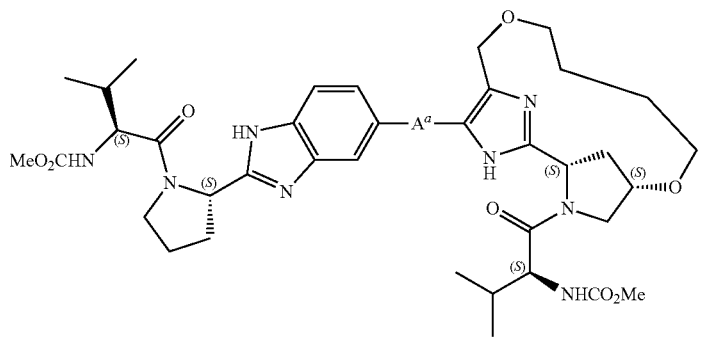
| Entry | $A^a$ |
|---|---|
| 296 | |
| 297 | |
| 298 | |
| 299 | |
| 300 | |
| 301 | |
| 302 | |

Compounds 287-307
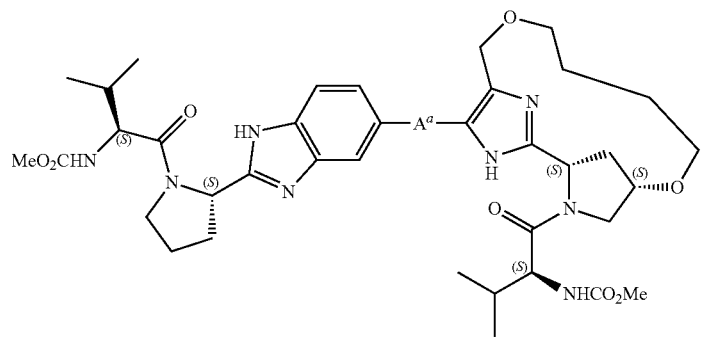
| Entry | $A^a$ |
|---|---|
| 303 | 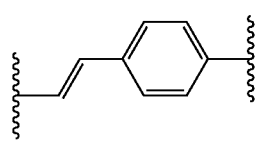 |
| 304 | 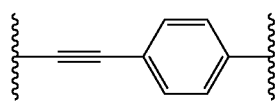 |
| 305 | 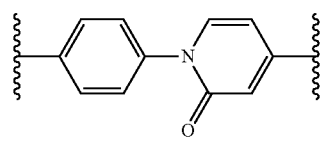 [SMILES: *c1ccc(-n2ccc(*)cc2=O)cc1] |
| 306 | 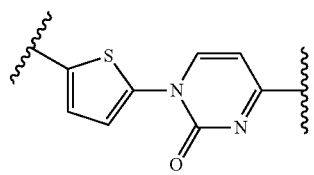 [SMILES: *c1ccn(-c2ccc(*)s2)c(=O)n1] |
| 307 | 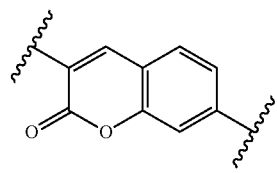 [SMILES: *c1ccc2cc(*)c(=O)oc2c1] |

Compounds 308-319
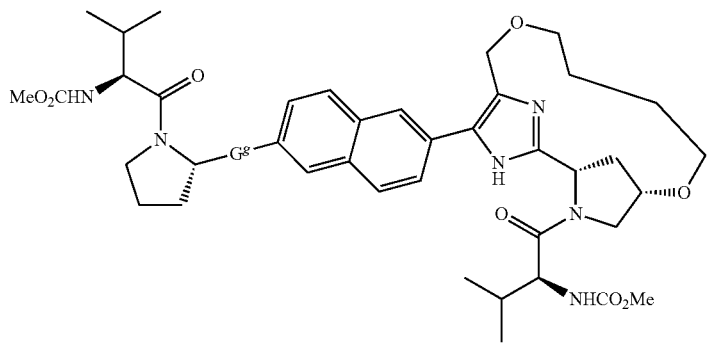
| Entry | G^g |
|---|---|
| 308 | 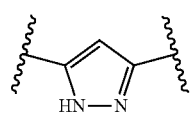 [SMILES: *c1cc(*)[nH]n1] |
| 309 | 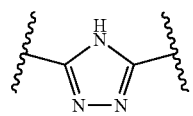 [SMILES: *c1nnc(*)[nH]1] |
| 310 | 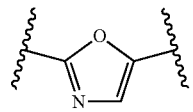 |
| 3117 | 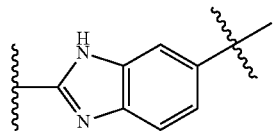 [SMILES: *c1ccc2nc(*)[nH]c2c1] |
| 312 | 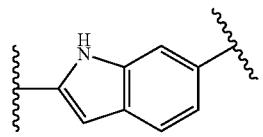 [SMILES: *c1ccc2cc(*)[nH]c2c1] |
| 313 | 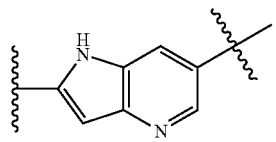 [SMILES: *c1cnc2cc(*)[nH]c2c1] |
| 314 | 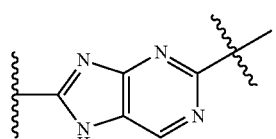 |
| 315 | 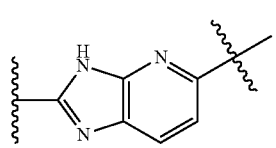 [SMILES: *c1ccc2nc(*)[nH]c2n1] |

Compounds 308-319
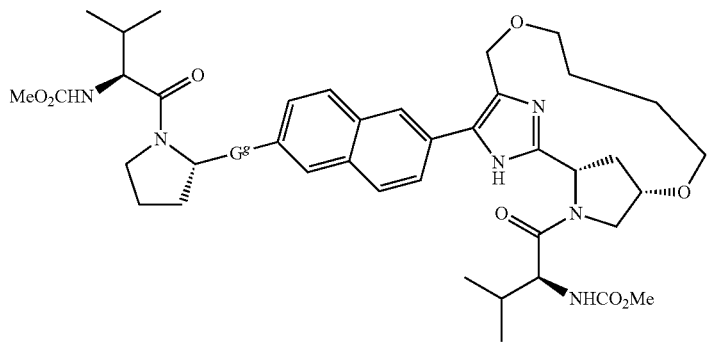
| Entry | $G^g$ |
|---|---|
| 316 |  |
| 317 | 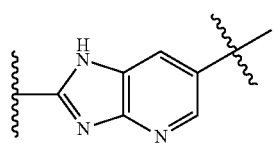 [SMILES: *c1cnc2nc(*)[nH]c2c1] |
| 318 | 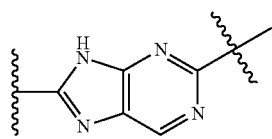 [SMILES: *c1ncc2nc(*)[nH]c2n1] |
| 319 | 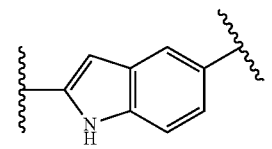 [SMILES: *c1ccc2[nH]c(*)cc2c1] |
Compounds 320-337
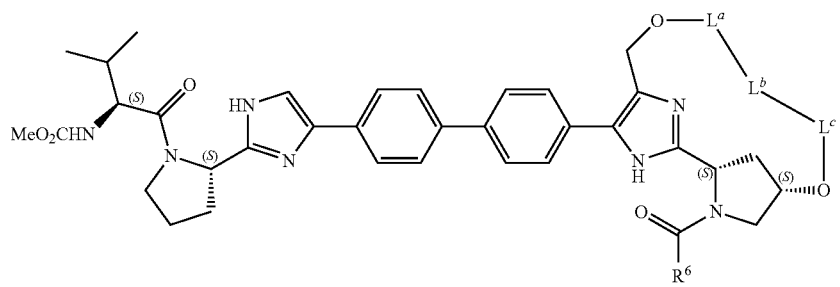
| Entry | $L^a$—$L^b$—$L^c$ |
|---|---|
| 320 | 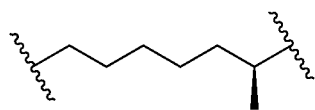 [SMILES: *CCCCC[C@@H](*)C] |

Compounds 320-337
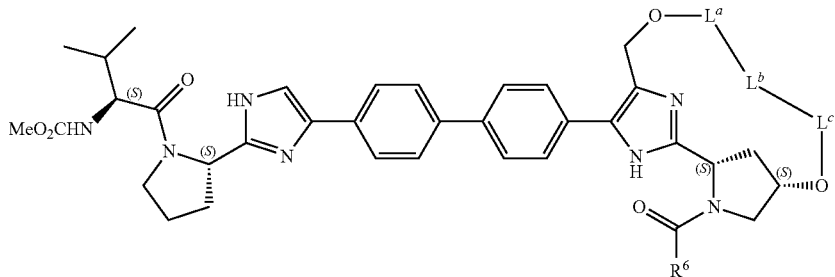
| Entry | $L^a$—$L^b$—$L^c$ |
|---|---|
| 321 | 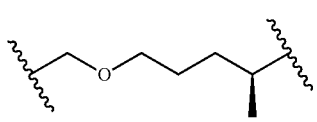 [SMILES: *COCCC[C@@H](*)C] |
| 322 | 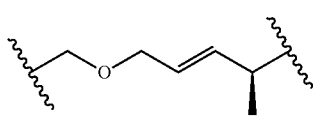 [SMILES: *COC/C=C/[C@@H](*)C] |
| 323 | 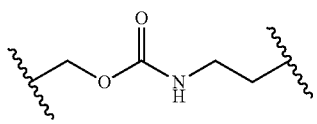 [SMILES: *CCNC(=O)OC*] |
| 324 | 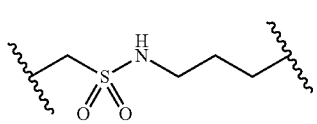 [SMILES: *CCCNS(=O)(=O)C*] |
| 325 | 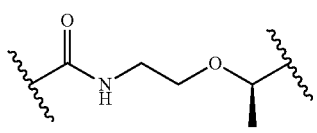 [SMILES: *C(=O)NCCO[C@@H](*)C] |
| 326 | 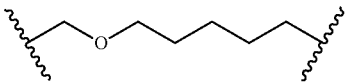 [SMILES: *CCCCCOC*] |
| 327 | 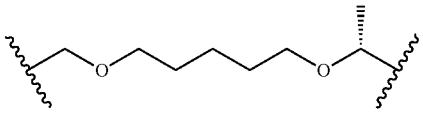 [SMILES: *COCCCCCO[C@@H](*)C] |
| 328 | 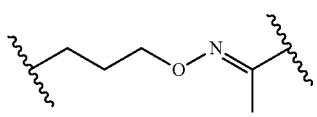 [SMILES: *CCCO/N=C(/*)C] |
| 329 | 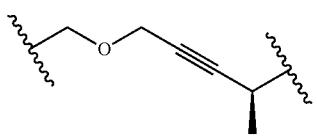 [SMILES: *COCC#C[C@@H](*)C] |

-continued
Compounds 320-337
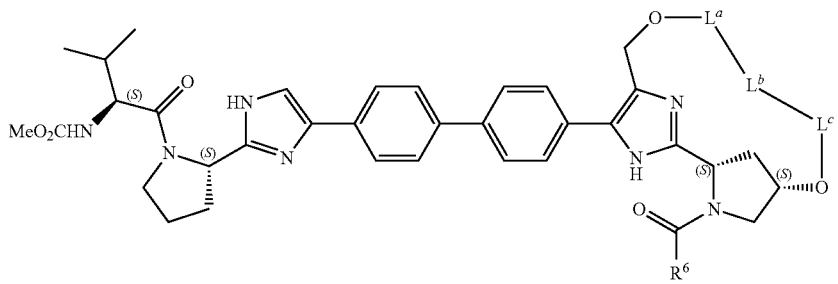
| Entry | $L^a$—$L^b$—$L^c$ |
|---|---|
| 330 | 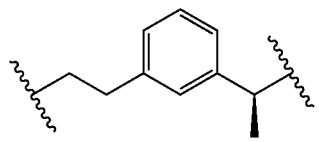 [SMILES: *CCc1cccc([C@@H](*)C)c1] |
| 331 | 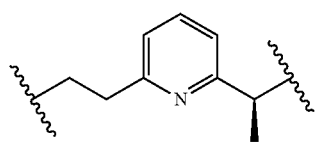 [SMILES: *CCc1cccc([C@@H](*)C)n1] |
| 332 | 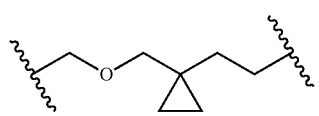 [SMILES: *CCC1(COC*)CC1] |
| 333 | 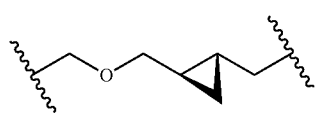 [SMILES: *COC[C@@H]1C[C@H]1C*] |
| 334 | 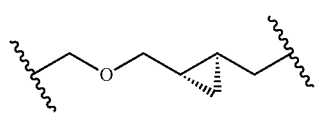 [SMILES: *COC[C@H]1C[C@@H]1C*] |
| 335 | 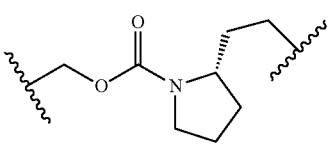 [SMILES: *CC[C@@H]1CCCN1C(=O)OC*] |
| 336 | 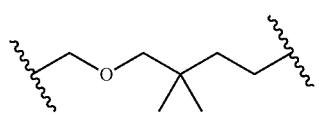 [SMILES: *CCC(C)(C)COC*] |
| 337 | 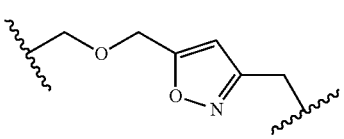 [SMILES: *COCc1cc(C*)no1] |

Compounds 334-341
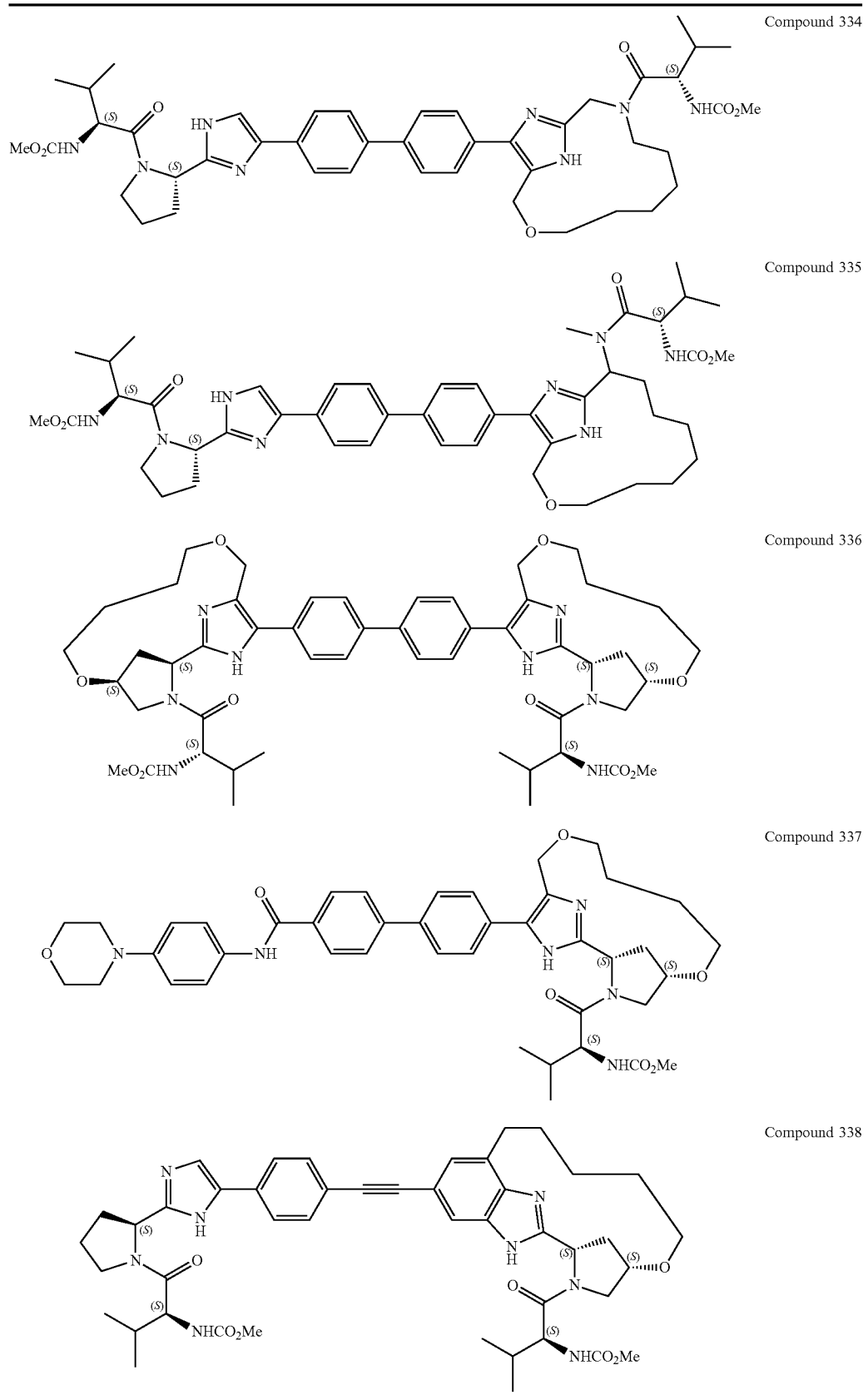
Compound 334
Compound 335
Compound 336
Compound 337
Compound 338

-continued
| Compounds 334-341 | |
|---|---|
| 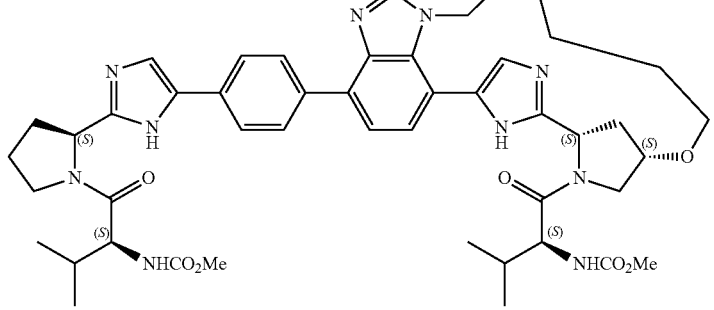 | Compound 339 |
| 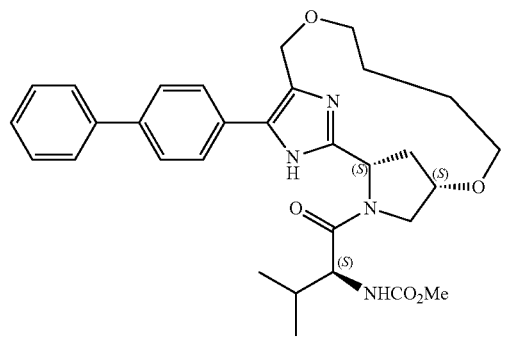 | Compound 340 |
| 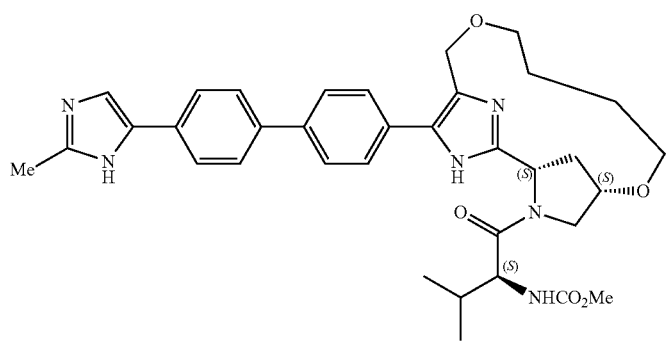 | Compound 341 |
| Compounds 342-346 | |
|---|---|
| 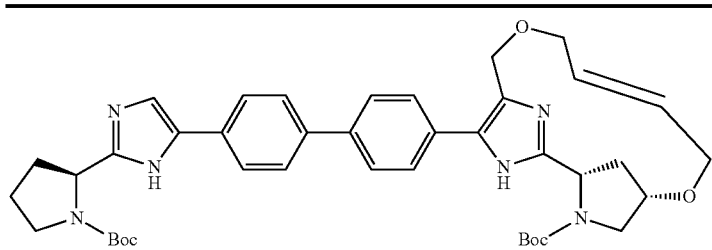 | Compound 342 |
| 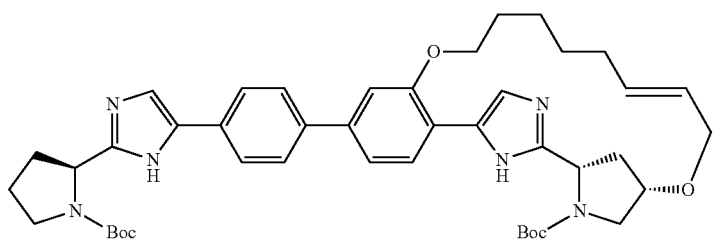 [SMILES: CC(C)(C)OC(=O)N1CCC[C@H]1c1ncc(-c2ccc(-c3ccc4c(c3)OCCCCC/C=C/CO[C@H]3C[C@@H](c5ncc-4[nH]5)N(C(=O)OC(C)(C)C)C3)cc2)[nH]1] | Compound 343 |

-continued

Compounds 342-346

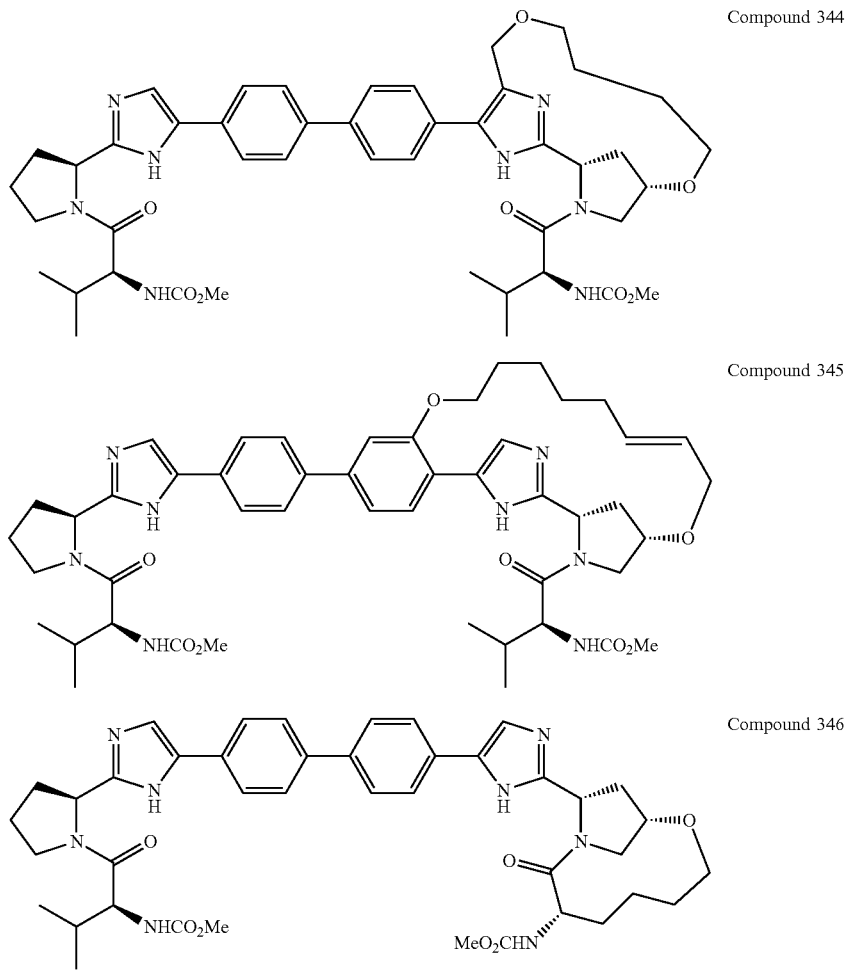

Compound 344

Compound 345

Compound 346 or a pharmaceutically acceptable salt thereof.

11. A pharmaceutical composition comprising a compound or a combination of compounds according to claim 1 or a pharmaceutically acceptable salt thereof, in combination with a pharmaceutically acceptable carrier or excipient.

12. A method of inhibiting the replication of an RNA-containing virus comprising contacting said virus with a therapeutically effective amount of a compound or combination of compounds of claim 1, or a pharmaceutically acceptable salt thereof.

13. A method of treating or preventing infection caused by an RNA-containing virus comprising administering to a patient in need of such treatment a therapeutically effective amount of a compound or combination of compounds of claim 1, or a pharmaceutically acceptable salt thereof.

14. The method of claim 13, wherein the RNA-containing virus is hepatitis C virus.

15. The method of claim 13, further comprising the step of administering to the patient one or more agents selected from the group consisting of a host immune modulator and an antiviral agent, or a combination thereof.

16. The method of claim 15, wherein the host immune modulator is selected from the group consisting of interferon-alpha, pegylated-interferon-alpha, interferon-beta, interferon-gamma, consensus interferon, a cytokine, and a vaccine.

17. The method of claim 15, wherein the antiviral agents inhibit replication of HCV by inhibiting host cellular functions associated with viral replication.

18. The method of claim 15, wherein the antiviral agents inhibit the replication of HCV by targeting proteins of the viral genome.

19. The method of claim 15, wherein said antiviral agent is an inhibitor of a HCV viral protein, a replication process or a combination thereof, wherein said targeting protein or replication process is selected from the group consisting of helicase, protease, polymerase, metalloprotease, NS4A, NS4B, NS5A, assembly, entry, and IRES.

20. The method of claim 13, further comprising the step of administering to the patient an agent or combination of agents that treat or alleviate a symptom of HCV infection selected from cirrhosis and inflammation of the liver.

21. The method of claim 13, further comprising the step of administering to the patient one or more anti-HBV agents.

22. The method of claim 13, further comprising the step of administering to the patient one or more anti-HIV agents.

23. The pharmaceutical composition of claim 11, further comprising an agent selected from interferon, pegylated interferon, ribavirin, amantadine, an HCV protease inhibitor, an HCV polymerase inhibitor, an HCV helicase inhibitor, or an internal ribosome entry site inhibitor.

24. The composition of claim 11, further comprising a cytochrome P450 monooxygenase inhibitor or a pharmaceutically acceptable salt thereof.

25. The composition of claim 24, wherein the cytochrome P450 mooxygenase inhibitor is ritonavir.

26. A method of treating hepatitis C infection in a subject in need thereof comprising co-administering to said subject a cytochrome P450 monooxygenase inhibitor or a pharmaceutically acceptable salt thereof, and a compound of claim 1 or a pharmaceutically acceptable salt thereof.

27. The compound of claim 2,
or a pharmaceutically acceptable salt thereof;
wherein -$L^1$-$L^2$-$L^3$- together form a linker of from 6 to 10 bond lengths.

28. The compound of claim 1, or a pharmaceutically acceptable salt thereof, wherein L is selected from the group consisting of O, —NH—, —C(O)—, —C(O)NH—, $C_1$-$C_4$ alkyl, $C_2$-$C_4$ alkenyl, $C_2$-$C_4$ alkynyl, —($C_1$-$C_4$ alkyl)-N(R)—($C_1$-$C_4$ alkyl)- and heterocyclic, each optionally substituted.

29. The compound of claim 1, or a pharmaceutically acceptable salt thereof, wherein Z is optionally substituted imidazolyl, optionally substituted benzimidazolyl or optionally substituted imidazopyridyl.

30. The compound of claim 1, or a pharmaceutically acceptable salt thereof, wherein $R^3$, $R^{3a}$, $R^4$ and $R^{4a}$ are each independently hydrogen or optionally substituted $C_1$-$C_4$ alkyl.

31. The compound of claim 1, or a pharmaceutically acceptable salt thereof, wherein $L^1$ and $L^3$ at each occurrence are independently a linear aliphatic group, or one of $L^1$ and $L^3$ is absent and the other of $L^1$ and $L^3$ is a linear aliphatic group.

* * * * *

UNITED STATES PATENT AND TRADEMARK OFFICE
CERTIFICATE OF CORRECTION

PATENT NO. : 9,676,802 B2
APPLICATION NO. : 14/254265
DATED : June 13, 2017
INVENTOR(S) : Yao-Ling Qiu et al.

It is certified that error appears in the above-identified patent and that said Letters Patent is hereby corrected as shown below:

At Column 285
In Claim 1, at Lines 5 through 10, after the word or, delete

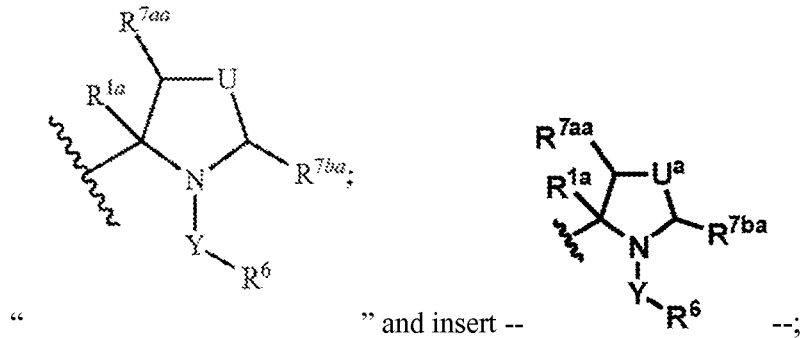

" and insert -- --;

At Column 298
In Claim 6, at Lines 21 through 30, structure (IIIb), delete

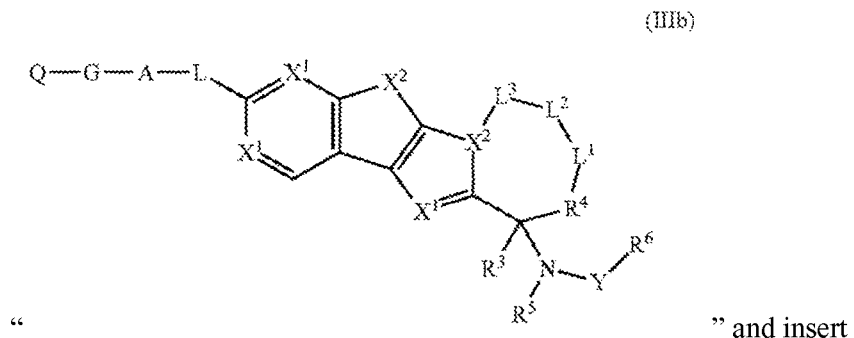

" and insert

Signed and Sealed this
Third Day of April, 2018

Andrei Iancu
*Director of the United States Patent and Trademark Office*

CERTIFICATE OF CORRECTION (continued)
U.S. Pat. No. 9,676,802 B2

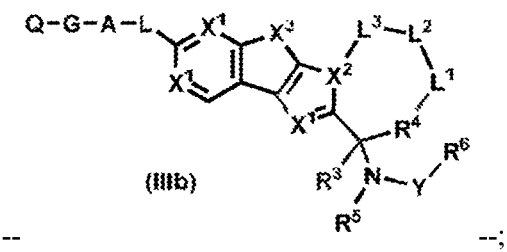

(IIIb)

-- --;

At Column 302
In Claim 9, at Lines 57 through 62, delete

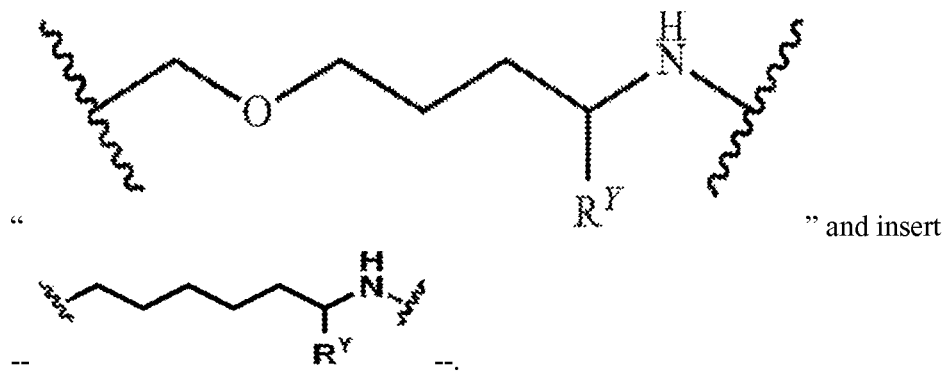

" " and insert

-- --.